(12) United States Patent
Flint et al.

(10) Patent No.: US 8,652,823 B2
(45) Date of Patent: Feb. 18, 2014

(54) STRAIN FOR BUTANOL PRODUCTION WITH INCREASED MEMBRANE UNSATURATED TRANS FATTY ACIDS

(75) Inventors: Dennis Flint, Newark, DE (US); Tina K. Van Dyk, Wilmington, DE (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 681 days.

(21) Appl. No.: 12/625,593

(22) Filed: Nov. 25, 2009

(65) Prior Publication Data

US 2010/0136641 A1  Jun. 3, 2010

Related U.S. Application Data

(60) Provisional application No. 61/119,451, filed on Dec. 3, 2008.

(51) Int. Cl.

| | |
|---|---|
| C12N 1/21 | (2006.01) |
| C12P 7/16 | (2006.01) |
| C12N 15/00 | (2006.01) |
| C12P 21/00 | (2006.01) |
| C07H 21/00 | (2006.01) |

(52) U.S. Cl.
USPC ............. 435/252.3; 435/252.9; 435/160; 435/320.1; 435/69.1; 536/23.2

(58) Field of Classification Search
USPC ............... 435/252.3, 252.31, 252.32, 252.33, 435/252.34, 160
See application file for complete search history.

(56) References Cited

U.S. PATENT DOCUMENTS

| | | | |
|---|---|---|---|
| 4,683,202 | A | 7/1987 | Mullis et al. |
| 5,192,673 | A | 3/1993 | Jain et al. |
| 6,358,717 | B1 | 3/2002 | Blaschek et al. |
| 6,960,465 | B1 | 11/2005 | Papoutsakis et al. |
| 8,518,678 | B2 | 8/2013 | Flint et al. |
| 2007/0031918 | A1 | 2/2007 | Dunson et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2009/0305370 | A1 | 12/2009 | Grady et al. |
| 2011/0097773 | A1 | 4/2011 | Grady et al. |
| 2011/0195505 | A1 | 8/2011 | Euler et al. |
| 2011/0312053 | A1 | 12/2011 | Burlew et al. |

FOREIGN PATENT DOCUMENTS

| | | |
|---|---|---|
| WO | 0061740 | 10/2000 |
| WO | 03089621 | 10/2003 |
| WO | 2007041269 | 4/2007 |
| WO | 2007146377 | 12/2007 |
| WO | 2008073406 | 6/2008 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
International Search Report filed in corresponding patent application PCT/US2009/066327 mailed Mar. 1, 2010.
Alegre et al., FEMS Microbiology Letters 241:73-77 (2004).
Altschul, S. F., et al., J. Mol. Biol., 215:403 410 (1993).
Arthur et al., Antimicrob. Agents Chemother. 38:1899-1903 (1994).
Bieszkiewicz et al., Acta Microbiologica Polonica 36(3):259-265 (1987).
Bligh et al., Can. J. Biochem. Physiol. (1959) 37:911-17.
Bringel et al., Appl. Microbiol. Biotechnol. 33: 664-670 (1990).
Cruz-Rodz et al. Molecular Genetics and Genomics 224:1252-154 (1990).
Eichenbaum et al. Appl. Environ. Microbiol. 64(8):2763-2769 (1998).
Durre, Appl. Microbiol. Biotechnol. 49:639-648 (1998).
Ferain et al., J. Bacteriol. 176:596-601 (1994).
Frohman et al., PNAS USA 85:8998 (1988).
Fujimoto et al., Appl. Environ. Microbiol. 67:1262-1267 (2001).
Girbal et al., Trends in Biotechnology 16:11-16 (1998).
Groot et al., Process. Biochem. 27:61-75 (1992).
Hols et al. (Appl. Environ. Microbiol. 60:1401-1413 (1994).
Jang et al. Micro. Lett. 24:191-195 (2003).
Junker et al., (1999) J. Bacteriol. 181:5693-5700.
Kleerebezem et al., Appl. Environ. Microbiol. 63:4581-4584 (1997).
Loh et al., Science 243:217 (1989).
Maguin et al., J. Bacteriol. 174(17):5633-5638 (1992).
Moreira et al. (BMC Microbiol. 5:15 (2005).
Ohara et al., PNAS USA 86:5673 (1989).
O'Sullivan et al., Gene 137:227-231 (1993).
Quratulain et al., Folia Microbiologica (Prague) 40(5):467-471 (1995).
Renault et al., Gene 183:175-182 (1996).
Rud et al., Microbiology 152:1011-1019 (2006).
Sardessai et al., Current Science 82(6):622-623 (2002).
Scott et al., Plasmid 50(1):74-79 (2003).
Shrago et al., Appl. Environ. Micro. 52: 574-576 (1986).
Soucaille et al., Current Microbiology 14(5):295-299 (1987).
Tabor, S. et al., Proc. Acad. Sci. USA 82:1074 (1985).
Tanimoto et al., J. Bacteriol. 184:5800-5804 (2002).
Tomas et al., Appl. Environ. Microbiol. 69(8):4951-4965 (2003).
van Kranenburg et al., Appl. Environ. Microbiol. Mar. 2005; 71(3): 1223-1230.
Van Ness et al., Nucl. Acids Res. 19:5143 5151 (1991).
Walker, et al., Proc. Natl. Acad. Sci. U.S.A., 89:392 (1992).
Wyckoff et al. Appl. Environ. Microbiol. 62:1481-1486 (1996).
Aukrust, T.W., et al. In: Electroporation Protocols for Microorganisms; Nickoloff, J.A., Ed.; Methods in Molecular Biology, vol. 47; Humana Press, Inc., Totowa, NJ, 1995, pp. 201-208.

(Continued)

*Primary Examiner* — Delia Ramirez
(74) *Attorney, Agent, or Firm* — Christine M. Lhulier

(57) ABSTRACT

Bacteria that are not natural butanol producers were found to have increased tolerance to butanol when the membrane content of unsaturated trans fatty acids was increased. Feeding cells with unsaturated trans fatty acids increased their concentration in the membrane, which may also be accomplished by expressing a fatty acid cistrans isomerase.

6 Claims, No Drawings

(56) References Cited

OTHER PUBLICATIONS

Ausubel, F. M. et al., In Current Protocols in Molecular Biology, published by Greene Publishing and Wiley-Interscience, 1987.
Biocomputing: Informatics and Genome Projects (Smith, D. W., Ed.) Academic: NY (1993).
Thomas D. Brock in Biotechnology: A Textbook of Industrial Microbiology, Second Edition (1989) Sinauer Associates, Inc., Sunderland, MA.
Deshpande, Appl. Biochem. Biotechnol., 36:227 (1992).
Computational Molecular Biology (Lesk, A. M., Ed.) Oxford University: NY (1988).
Computer Analysis of Sequence Data, Part I (Griffin, A. M., and Griffin, H. G., Eds.) Humania: NJ (1994).
Kuhn and Linden, Biotechnology and Bioengineering Symposium 17(Symp. Biotechnol. Fuels Chem., 8th, 1986), 197-207.
W. R. Pearson, Comput. Methods Genome Res., [Proc. Int. Symp.] (1994), Meeting Date 1992, 111 20. Editor(s): Suhai, Sandor. Plenum: New York, NY).
Rychlik, W., In Methods in Molecular Biology, White, B. A. Ed., (1993) vol. 15, pp. 31 39, PCR Protocols: Current Methods and Applications. Humania: Totowa, NJ.
Sambrook, J., Fritsch, E. F. and Maniatis, T. Molecular Cloning: A Laboratory Manual, 3rd ed., Cold Spring Harbor Laboratory: Cold Spring Harbor, NY (2001), particularly Chapter 11 and Table 11.1.
Ramos et al., Annual Review of Microbiology, Annual Reviews, vol. 56, Jan. 1, 2002, pp. 743-768.
Sequence Analysis in Molecular Biology (von Heinje, G., Ed.) Academic (1987).
Sequence Analysis Primer (Gribskov, M. and Devereux, J., Eds.) Stockton: NY (1991).
Silhavy, T. J., Bennan, M. L. and Enquist, L. W. Experiments with Gene Fusions; Cold Spring Harbor Laboratory: Cold Spring Harbor, New York, 1984.
Thein and Wallace, "The use of oligonucleotides as specific hybridization probes in the diagnosis of genetic disorders", in Human Genetic Diseases: A Practical Approach, K. E. Davis Ed., (1986) pp. 33 50, IRL: Herndon, VA.
Endo et al., J. Gen. Appl. Microbioil. 52, pp. 29-35 (2006).
Weeks et al., The Journal of Biological Chemistry, vol. 245, No. 8, Issue of Apr. 23, pp. 1913-1921 (1970).

\* cited by examiner

STRAIN FOR BUTANOL PRODUCTION WITH INCREASED MEMBRANE UNSATURATED TRANS FATTY ACIDS

CROSS REFERENCE TO RELATED APPLICATIONS

This application is related to and claims the benefit of priority to U.S. Provisional Application No. 61/119,451 filed Dec. 3, 2008, the entirety of which is herein incorporated by reference.

FIELD OF THE INVENTION

The invention relates to the field of microbiology and tolerance of microorganisms to butanol. More specifically, increased membrane trans fatty acid composition was found to play a role in butanol tolerance in bacteria which are not natural butanol producers.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Butanol may be made through chemical synthesis or by fermentation. The most popular fermentation process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway (U.S. Patent Application Publication No. US20080182308A1), a 2-butanol biosynthetic pathway (U.S. Patent Application Publication Nos. US20070259410A1 and US 20070292927A1), and an isobutanol biosynthetic pathway (U.S. Patent Application Publication No. US 20070092957) have been described. However, biological production of butanols is believed to be limited by butanol toxicity to the host microorganism used in the fermentation.

Bacteria of the genus *Clostridium* naturally produce butanol. Strains of *Clostridium* with increased tolerance to 1-butanol have been isolated by chemical mutagenesis (U.S. Pat. No. 5,192,673; and U.S. Pat. No. 6,358,717), overexpression of certain classes of genes such as those that express stress response proteins (U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., *Current Microbiology* 14(5):295-299 (1987)). Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) has been described.

It has been reported that in *Pseudomonas putida*, that cis unsaturated fatty acids are converted to the trans confirmation when cells are stressed with chemicals such as toluene. The increased trans fatty acid in the cell membrane plays a role in the toluene tolerance of *P. putida* (Junker and Ramos (1999) J. Bacteriol. 181:5693-5700).). In contrast, it has been reported that feeding a trans fatty acid to *Clostridium acetobutylicum* did not lead to improved butanol tolerance (Kuhn and Linden, Biotechnology and Bioengineering Symposium 17(Symp. Biotechnol. Fuels Chem., 8$^{th}$, 1986), 197-207).

There is a need, therefore, for bacterial host strains which do not naturally produce butanol but can be engineered to express a butanol biosynthetic pathway to be more tolerant to these chemicals. In addition there is a need for methods of producing butanols using bacterial host strains engineered for butanol production that are more tolerant to these chemicals.

SUMMARY OF THE INVENTION

Provided herein are butanol tolerant bacterial cells comprising an engineered butanol biosynthetic pathway and having an increased concentration of membrane unsaturated trans fatty acids as compared with a wildtype cell. In some embodiments, the concentration of at least one unsaturated trans fatty acid selected from the group consisting of elaidic acid, vaccenic acid, and C16:1 trans fatty acid is increased. In some embodiments, the cell is a member of a genus selected from the group consisting of *Zymomonas*, *Escherichia*, *Salmonella*, *Rhodococcus*, *Pseudomonas*, *Bacillus*, *Lactobacillus*, *Enterococcus*, *Pediococcus*, *Alcaligenes*, *Klebsiella*, *Paenibacillus*, *Arthrobacter*, *Corynebacterium*, *Leuconostoc*, and *Brevibacterium*. In some embodiments, the cell is a member of the genus *Lactobacillus* and the growth yield of the cell is at least about 1.6 to about 3.5-fold higher in 2.5% isobutanol than when the cell does not have an increased concentration of membrane unsaturated trans fatty acids. In some embodiments, the cell is a member of the genus *Lactobacillus* and the growth yield of the cell is at least about 1.6 to about 3.0-fold higher in 2.25% 1-butanol than when the cell does not have an increased concentration of membrane unsaturated trans fatty acids. In some embodiments, the cell is a member of the genus *Lactobacillus* the growth yield of the cell is at least about 2.2 to about 4-fold higher in 4.0% 2-butanol than when the cell does not have an increased concentration of membrane unsaturated trans fatty acids. In some embodiments, the membrane content of at least one unsaturated trans fatty acid is about 44 fold higher as compared with a wildtype cell.

In some embodiments, the butanol tolerant bacterial cells comprise at least one gene encoding fatty acid cistrans isomerase. In some embodiments, the at least one gene encoding cistrans isomerase has an amino acid sequence which is at least 95% identical to an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 136 based on the Clustal W method of alignment using the default parameters of GAP PENALTY=10, GAP LENGTH PENALTY=0.1, and Gonnet 250 series of protein weight matrix.

In some embodiments, the butanol biosynthetic pathway is selected from the group consisting of: a) 1-butanol biosynthetic pathway; b) a 2-butanol biosynthetic pathway; and c) an isobutanol biosynthetic pathway.

Further, provided herein are methods for the production of a butanol producing butanol tolerant bacterial cell comprising: a) providing a bacterial cell comprising an engineered butanol biosynthetic pathway; and b) feeding the bacterial cell of step (a) at least one trans fatty acid under conditions wherein the concentration of trans unsaturated fatty acids in the membrane of the cell are increased. In one embodiment, the at least one fatty acid is selected from the group consisting of elaidic acid, vaccenic acid and C16:1 trans fatty acid.

Provided herein are methods for the production of a butanol producing butanol tolerant bacterial cell comprising: a) providing a bacterial cell comprising an engineered butanol biosynthetic pathway and at least one gene encoding a fatty acid cistrans isomerase; and b) expressing the at least one gene encoding a fatty acid cistrans isomerase whereby the concentration of unsaturated trans fatty acids in the membrane of the cell are increased. In some embodiments, the at least one gene encoding cistrans isomerase has an amino acid sequence that is at least 95% identical to an amino acid sequence selected from the group consisting of SEQ ID NO: 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, and 136, based on the Clustal W method of alignment using the default parameters of GAP PENALTY=10, GAP LENGTH PENALTY=0.1, and Gonnet 250 series of protein weight matrix.

Provided herein are methods for the production of isobutanol comprising: a) providing a bacterial cell comprising an engineered isobutanol biosynthetic pathway; b) feeding the bacterial cell of step (a) at least one trans fatty acid under conditions wherein the concentration of unsaturated trans fatty acids in the membrane of the cell are increased; and c) growing the bacterial cell of step (b) under conditions wherein isobutanol is produced.

Provided herein are methods for the production of isobutanol comprising: a) providing a bacterial cell comprising an engineered isobutanol biosynthetic pathway and at least one gene encoding cistrans isomerase; b) expressing the at least one gene encoding fatty acid cistrans isomerase whereby the concentration of unsaturated trans fatty acids in the membrane of the cell are increased; and c) growing the bacterial cell of step (b) under conditions wherein isobutanol is produced.

In some embodiments, methods provided herein for the production of isobutanol comprise an isobutanol pathway wherein the isobutanol biosynthetic pathway comprises: a) at least one gene encoding acetolactate synthase; b) at least one gene encoding acetohydroxy acid isomeroreductase; c) at least one gene encoding acetohydroxy acid dehydratase; d) at least one gene encoding a branched-chain keto acid decarboxylase; and e) at least one gene encoding branched-chain alcohol dehydrogenase Sequence Descriptions The various embodiments of the invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID Numbers for Examples of Coding Regions and Proteins for 1-Butanol Biosynthetic Pathway

| Description | SEQ ID NO: Nucleic acid | SEQ ID NO: Peptide |
| --- | --- | --- |
| Acetyl-CoA acetyltransferase thlA from Clostridium acetobutylicum ATCC 824 | 1 | 2 |
| Acetyl-CoA acetyltransferase thlB from Clostridium acetobutylicum ATCC 824 | 3 | 4 |
| 3-Hydroxybutyryl-CoA dehydrogenase from Clostridium acetobutylicum ATCC 824 | 5 | 6 |
| Crotonase from Clostridium acetobutylicum ATCC 824 | 7 | 8 |
| Putative trans-enoyl CoA reductase from Clostridium acetobutylicum ATCC 824 | 9 | 10 |
| Euglena gracilis butyryl-CoA dehydrogenase/trans-2-enoyl-CoA reductase codon optimized lacking mitochondrial presequence. | 39 | 40 |
| Butyraldehyde dehydrogenase from Clostridium beijerinckii NRRL B594 | 11 | 12 |
| 1-Butanol dehydrogenase bdhB from Clostridium acetobutylicum ATCC 824 | 13 | 14 |
| 1-Butanol dehydrogenase bdhA from Clostridium acetobutylicum ATCC 824 | 15 | 16 |

TABLE 2

SEQ ID Numbers for Examples of Coding Regions and Proteins for 2-Butanol Biosynthetic Pathway

| Description | SEQ ID NO: Nucleic acid | SEQ ID NO: Peptide |
| --- | --- | --- |
| budA, acetolactate decarboxylase from Klebsiella pneumoniae ATCC 25955 | 17 | 18 |
| budB, acetolactate synthase from Klebsiella pneumoniae ATCC 25955 | 19 | 20 |
| budC, butanediol dehydrogenase from Klebsiella pneumoniae IAM1063 | 21 | 22 |
| pddA, butanediol dehydratase alpha subunit from Klebsiella oxytoca ATCC 8724 | 23 | 24 |
| pddB, butanediol dehydratase beta subunit from Klebsiella oxytoca ATCC 8724 | 25 | 26 |
| pddC, butanediol dehydratase gamma subunit from Klebsiella oxytoca ATCC 8724 | 27 | 28 |
| sadH, 2-butanol dehydrogenase from Rhodococcus ruber 219 | 29 | 30 |

TABLE 3

SEQ ID Numbers for Examples of Coding Regions and Proteins for Isobutanol Biosynthetic Pathway

| Description | SEQ ID NO: Nucleic acid | SEQ ID NO: Peptide |
| --- | --- | --- |
| Klebsiella pneumoniae budB (acetolactate synthase) | 19 | 20 |
| E. coli ilvC (acetohydroxy acid reductoisomerase) | 31 | 32 |
| B. subtilis ilvC (acetohydroxy acid reductoisomerase) | 41 | 42 |
| E. coli ilvD (acetohydroxy acid dehydratase) | 33 | 34 |
| Lactococcus lactis kivD (branched-chain α-keto acid decarboxylase), codon optimized | 35 | 36 |
| E. coli yqhD (branched-chain alcohol dehydrogenase) | 37 | 38 |

TABLE 4

Representative fatty acid cistrans isomerase coding regions and encoded proteins

| Organism | SEQ ID NO: nucleic acid | SEQ ID NO: amino acid |
| --- | --- | --- |
| *Shewanella* sp. MR-4 | 43 | 44 |
| *Shewanella* sp. MR-7 | 45 | 46 |
| *Vibrio vulnificus* YJ016 | 47 | 48 |
| *Colwellia psychrerythraea* 34H | 49 | 50 |
| *Saccharophagus degradans* 2-40 | 51 | 52 |
| *Pseudomonas fluorescens* Pf-5 | 53 | 54 |
| *Pseudomonas aeruginosa* PAO1 | 55 | 56 |
| *Vibrio vulnificus* CMCP6 | 57 | 58 |
| *Pseudomonas aeruginosa* UCBPP-PA14 | 59 | 60 |
| *Pseudomonas fluorescens* PfO-1 | 61 | 62 |
| *Methylococcus capsulatus* str. Bath | 63 | 64 |
| *Pseudomonas syringae* pv. tomato str. DC3000 | 65 | 66 |
| *Vibrio parahaemolyticus* RIMD 2210633 | 67 | 68 |
| *Nitrosomonas europaea* ATCC 19718 | 69 | 70 |
| *Vibrio cholerae* O1 biovar eltor str. N16961 | 71 | 72 |
| *Pseudomonas syringae* pv. *phaseolicola* 1448A | 73 | 74 |
| *Bdellovibrio bacteriovorus* HD100 | 75 | 76 |
| *Vibrio fischeri* ES114 | 77 | 78 |
| *Photobacterium profundum* SS9 | 79 | 80 |
| *Pseudoalteromonas haloplanktis* TAC125 | 81 | 82 |
| *Pseudoalteromonas atlantica* T6c | 83 | 84 |
| *Azotobacter vinelandii* AvOP | 85 | 86 |
| *Pseudomonas entomophila* L48 | 87 | 88 |
| *Alcanivorax borkumensis* SK2 | 89 | 90 |
| *Vibrio cholerae* V51 | 91 | 92 |
| *Vibrio cholerae* MO10 | 93 | 94 |
| *Vibrio cholerae* O395 | 95 | 96 |
| *Shewanella baltica* OS155 | 97 | 98 |
| *Vibrio cholerae* RC385 | 99 | 100 |
| *Pelobacter propionicus* DSM 2379 | 101 | 102 |
| *Pseudomonas aeruginosa* C3719 | 103 | 104 |
| *Pseudomonas aeruginosa* 2192 | 105 | 106 |
| *Vibrio* sp. Ex25 | 107 | 108 |
| *Vibrio cholerae* V52 | 109 | 110 |
| *Shewanella* sp. ANA-3 | 111 | 112 |
| *Pseudomonas putida* F1 | 113 | 114 |
| *Vibrio splendidus* 12B01 | 115 | 116 |
| *Congregibacter litoralis* KT71 | 117 | 118 |
| *Pseudoalteromonas tunicata* D2 | 119 | 120 |
| *Vibrio* sp. MED222 | 121 | 122 |
| *Vibrio alginolyticus* 12G01 | 123 | 124 |
| *Photobacterium profundum* 3TCK | 125 | 126 |
| *Pseudomonas aeruginosa* PA7 | 127 | 128 |
| *Oceanobacter* sp. RED65 | 129 | 130 |
| *Shewanella baltica* OS195 | 131 | 132 |
| *Pseudomonas aeruginosa* PACS2 | 133 | 134 |
| *Pseudomonas putida* KT2440 | 135 | 136 |

SEQ ID NO:137 is the nucleotide sequence of the *L. Plantarum* atpB promoter.

SEQ ID NOs:138 and 139 are primers for PCR amplification of the *L. Plantarum* atpB promoter.

SEQ ID NOs:140 and 141 are primers for PCR amplification of a DNA fragment from *Lactobacillus plantarum* (Genbank NC_004567) with homology to IdhL.

SEQ ID NO:142 is the integration vector pFP988.

SEQ ID NOs:143 and 144 are primers for PCR amplification of the Cm resistance gene with its promoter from pC194 (GenBank NC_002013).

SEQ ID NOs:145 and 146 are oligonucleotides for constructing the P11 promoter.

SEQ ID NOs:147 and 148 are primers for PCR amplification of the *L. plantarum* IdhL promoter.

SEQ ID NOs:149 and 150 are oligonucleotides for constructing the P11 promoter.

SEQ ID NOs:151 and 152 are primers for PCR amplification of the *L. plantarum* IdhL promoter.

SEQ ID NOs:153 and 154 are primers for PCR amplification of the fatty acid cistrans isomerase coding region from *P. putida* KT2440 (ATCC#47054 D-5).

SEQ ID NOs:155 and 156 are primers for PCR amplification of a trc promoter-cti gene fragment.

DETAILED DESCRIPTION

The invention provides a recombinant bacterial cell which does not naturally produce butanol at detectable levels, but which is engineered to express a butanol biosynthetic pathway, that is modified to have increased concentration of unsaturated trans fatty acid in the cell membrane fatty acid composition as compared with a corresponding membrane fatty acid unmodified bacterial cell. Such cells have an increased tolerance to butanol as compared with cells that lack the membrane fatty acid modification. Increase in membrane unsaturated trans fatty acid may be accomplished by feeding the cell with an unsaturated trans fatty acid or by genetically modifying the cell to increase expression of at least one gene involved in unsaturated trans fatty acid synthesis, such as one encoding fatty acid cistrans isomerase. The present cells may be used to produce butanol, which may be used as an alternative energy source to fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The terms "butanol tolerant bacterial strain" and "tolerant" when used to describe a modified bacterial strain of the invention, refers to a modified bacterium that shows better growth in the presence of butanol than the parent strain from which it is derived.

The term "wildtype" as it applies to a butanol tolerant bacterial cell of the invention refers to a cell which has not been modified or altered to increase butanol tolerance with respect to the concentration of unsaturated fatty acids in the membrane.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and H₂O. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (Gen Bank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417-484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence, L04470 NCBI nucleotide sequence), *Klebsiella terrigena* (Gen Bank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product.

S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417-484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual*, 3rd ed., Cold Spring Harbor Laboratory: Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are at least about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data*, Part I (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Butanol Tolerance in Butanol Non-Producing Bacteria—Membrane Composition

The invention relates to the discovery that an increase in the unsaturated trans fatty acid content of the membrane of a bacterial cell that does not naturally produce butanol increases butanol tolerance of the cell. The discovery came from results of studies on feeding butanol non-producing bacterial cells with different fatty acids followed by analysis of butanol tolerance. Any bacteria that does not naturally produce butanol may have butanol tolerance increased through increase in membrane unsaturated trans fatty acid composition. Examples include, but are not limited to, bacterial cells of *Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Leuconostoc,* and *Brevibacterium*. Examples of specific bacterial cells include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis,* and *Bacillus subtilis*.

Increasing Membrane Unsaturated Trans Fatty Acids

In the bacterial cells of the present invention, the amount of unsaturated trans fatty acids in the membrane may be increased with respect to the amounts of other types of fatty acids by any method. Examples of methods that may be used include feeding the cells a fatty acid that will result in an increase in membrane unsaturated trans fatty acid and making a genetic modification that results in increasing the membrane unsaturated trans fatty acid composition. Fatty acids that may be fed to cells to increase membrane unsaturated fatty acid composition include, for example, elaidic acid (C18:1 trans-9; IUPAC name: (E)-octadec-9-enoic acid), vaccenic acid (18:1 trans-11; IUPAC name: (E)-11-octadecenoic acid) and C16:1 trans fatty acid.

Genetic modifications that increase membrane unsaturated fatty acid composition include expression of at least one gene whose encoded enzyme is able to convert unsaturated cis fatty acids to unsaturated trans fatty acids. One example is the enzyme fatty acid cistrans isomerase. Modification of any bacterial cell, that does not naturally make butanol, for expression of any fatty acid cistrans isomerase may be used to prepare cells of the present invention. Examples of amino acid sequences and the encoding DNA sequences for representative fatty acid cistrans isomerases are given in Table 4 as SEQ ID NOs: 43-136. Additional fatty acid cistrans isomerases that may be used in the present bacterial cells may be identified by one skilled in the art through bioinformatics methods as described above. Additional proteins that have at least about 40%-45%, 45%-50%, 50%-55%, 55%-60%, 60%-65%, 65%-70%, 70%-75%, 75%-80%, 80-85%, 85%-90%, 90%-95% or at least about 98% sequence identity to any of SEQ ID NOs:even numbers 44-136 and having fatty acid cistrans isomerase activity may be used. Identities are based on the Clustal W method of alignment using the default parameters of GAP PENALTY=10, GAP LENGTH PENALTY=0.1, and Gonnet 250 series of protein weight matrix.

In addition to using protein or coding region sequence and bioinformatics methods to identify additional fatty acid cistrans isomerases, the sequences described herein or those recited in the art may be used to experimentally identify other homologs in nature. For example each of the fatty acid cistrans isomerase encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the fatty acid cistrans isomerase encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described fatty acid cistrans isomerase encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For expression of a fatty acid citrans isomerase, a coding region for a fatty acid cistrans isomerase is introduced into a bacterial cell and is expressed from a plasmid or is integrated into the cell genome. Typically the coding region is operably linked to regulatory sequences, which may be native to the gene including the coding region or heterologous to the coding region. More typically, a promoter that is not native to the gene and known to be active in the host bacterial cell is operably linked to the fatty acid cistrans isomerase coding region for expression. Examples of promoters and plasmids (vectors) that may be used for transfer and expression of fatty acid cistrans isomerase genes in bacteria such as *E. coli*, *Lactobacillus*, and *Pseudomonas* are the same as those described below for expression of butanol pathway genes.

It may be desirable to codon-optimize a heterologous coding region for optimal expression in a particular bacterial cell. Methods for codon-optimization are well known in the art.

Butanol Tolerance of Increased Membrane Unsaturated Trans Fatty Acid Strain

A bacterial cell of the present invention modified for increased membrane unsaturated trans fatty acid composition has improved tolerance to butanol. The increased tolerance may be assessed by assaying growth in concentrations of butanol that are detrimental to growth of the parental strain (prior to modification for increased membrane unsaturated trans fatty acid composition). Improved tolerance is to butanol compounds including 1-butanol, isobutanol, and 2-butanol. The amount of tolerance improvement will vary depending on the inhibiting chemical and its concentration, growth conditions and the specific modified cell. For example, as shown in Example 2 herein, cells of *L. plantarum* having increased membrane unsaturated trans fatty acid composition had a growth yield in 2.5% to 3.5% (w.v) isobutanol that was between 1.6 and 3.5-fold higher than *L. plantarum* cells without increased membrane unsaturated trans fatty acid composition. In Example 3 herein is shown that cells of *L. plantarum* having increased membrane unsaturated trans fatty acid composition had a growth yield in 2.25% to 3.0% (w/v) 1-butanol that was between 1.6 and 3-fold higher than *L. plantarum* cells without increased membrane unsaturated trans fatty acid composition. In Example 4 herein is shown that cells of *L. plantarum* having increased membrane unsaturated trans fatty acid composition had a growth yield in 4.0% to 4.9% (w/v) 2-butanol that was between 2.2 and 4-fold higher than *L. plantarum* cells without increased membrane unsaturated trans fatty acid composition.

Butanol Biosynthetic Pathway

In the present invention, a modification conferring increased unsaturated trans fatty acid in the membrane is made in a bacterial cell that does not naturally produce butanol, but that has an engineered butanol biosynthetic pathway. Either modification may take place prior to the other.

The butanol biosynthetic pathway may be a 1-butanol, 2-butanol, or isobutanol biosynthetic pathway. Particularly suitable bacterial hosts for the production of butanol and modification for increased butanol tolerance include, but are not limited to, members of the genera *Escherichia*, *Rhodococcus*, *Pseudomonas*, *Bacillus*, *Lactobacillus*, and *Enterococcus*. Preferred hosts include: *Escherichia coli*, *Pseudomonas putida*, *Lactobacillus plantarum*, *Enterococcus faecium*, and *Enterococcus faecalis*.

1-Butanol Biosynthetic Pathway

A suitable biosynthetic pathway for the production of 1-butanol is described by Donaldson et al. in U.S. Patent Application Publication No. US20080182308A1 incorporated herein by reference. This biosynthetic pathway comprises the following substrate to product conversions:

a) acetyl-CoA to acetoacetyl-CoA, as catalyzed for example by acetyl-CoA acetyltransferase (which may be encoded, for example, by the genes given as SEQ ID NO:1 or 3);

b) acetoacetyl-CoA to 3-hydroxybutyryl-CoA, as catalyzed for example by 3-hydroxybutyryl-CoA dehydrogenase (which may be encoded, for example, by the gene given as SEQ ID NO:5);

c) 3-hydroxybutyryl-CoA to crotonyl-CoA, as catalyzed for example by crotonase (which may be encoded, for example, by the gene given as SEQ ID NO:7);

d) crotonyl-CoA to butyryl-CoA, as catalyzed for example by butyryl-CoA dehydrogenase (which may be encoded, for example, by the gene given as SEQ ID NO:9);

e) butyryl-CoA to butyraldehyde, as catalyzed for example by butyraldehyde dehydrogenase (which may be encoded, for example, by the gene given as SEQ ID NO:11); and f) butyraldehyde to 1-butanol, as catalyzed for example by 1-butanol dehydrogenase (which may be encoded, for example, by the genes given as SEQ ID NO:13 or 15).

The pathway requires no ATP and generates $NAD^+$ and/or $NADP^+$, thus, it balances with the central, metabolic routes that generate acetyl-CoA.

Other suitable biosynthetic pathways for the production of 1-butanol will be apparent to those of skill in the art.

2-Butanol Biosynthetic Pathway

Suitable biosynthetic pathways for the production of 2-butanol are described by Donaldson et al. in U.S. Patent Application Publication Nos. US20070259410A1 and US 20070292927A1, both incorporated herein by reference. One 2-butanol biosynthetic pathway comprises the following substrate to product conversions:

a) pyruvate to alpha-acetolactate, as catalyzed for example by acetolactate synthase (which may be encoded, for example, by the gene given as SEQ ID NO:19);

b) alpha-acetolactate to acetoin, as catalyzed for example by acetolactate decarboxylase (which may be encoded, for example, by the gene given as SEQ ID NO:17);

c) acetoin to 2,3-butanediol, as catalyzed for example by butanediol dehydrogenase (which may be encoded, for example, by the gene given as SEQ ID NO:21);

d) 2,3-butanediol to 2-butanone, catalyzed for example by butanediol dehydratase (which may be encoded, for example, by genes given as SEQ ID NOs:23, 25, and 27); and e) 2-butanone to 2-butanol, as catalyzed for example by 2-butanol dehydrogenase (which may be encoded, for example, by the gene given as SEQ ID NO:29).

Other suitable biosynthetic pathways for the production of 2-butanol will be apparent to those of skill in the art.

Isobutanol Biosynthetic Pathway

Suitable biosynthetic pathways for the production of isobutanol are described by Maggio-Hall et al. in U.S. Patent Application Publication No. US20070092957 A1, incorporated herein by reference. One isobutanol biosynthetic pathway comprises the following substrate to product conversions:

a) pyruvate to acetolactate, as catalyzed for example by acetolactate synthase (which may be encoded, for example, by the gene given as SEQ ID NO:19);

b) acetolactate to 2,3-dihydroxyisovalerate, as catalyzed for example by acetohydroxy acid isomeroreductase (which may be encoded, for example, by the gene given as SEQ ID NO:31);

c) 2,3-dihydroxyisovalerate to α-ketoisovalerate, as catalyzed for example by acetohydroxy acid dehydratase (which may be encoded, for example, by the gene given as SEQ ID NO:33);

d) α-ketoisovalerate to isobutyraldehyde, as catalyzed for example by a branched-chain keto acid decarboxylase (which may be encoded, for example, by the gene given as SEQ ID NO:35); and e) isobutyraldehyde to isobutanol, as catalyzed for example by a branched-chain alcohol dehydrogenase (which may be encoded, for example, by the gene given as SEQ ID NO:37).

Other suitable biosynthetic pathways for the production of isobutanol will be apparent to those of skill in the art.

Construction of Bacterial Strains for Butanol Production

Any bacterial strain that is modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods well known to one skilled in the art, are introduced into a bacterial host. Representative coding and amino acid sequences for pathway enzymes that may be used are given in Tables 1, 2, and 3, with SEQ ID NOs:1-38, and 39-42. Typically BLAST (described above) searching of publicly available databases with the provided amino acid sequences is used to identify homologs and their encoding sequences that may be used in butanol biosynthetic pathways in the present cells. For example, proteins having amino acid sequence identities of at least about 70-75%, 75%-80%, 80-85%, 85%-90%, 90%-95% or 98% sequence identity to any of the proteins in Tables 1, 2, or 3 and having the noted activities may be identified. Identities are based on the Clustal W method of alignment using the default parameters of GAP PENALTY=10, GAP LENGTH PENALTY=0.1, and Gonnet 250 series of protein weight matrix. In addition to using protein or coding region sequence and bioinformatics methods to identify additional homologs, the sequences described herein or those recited in the art may be used to experimentally identify other homologs in nature as described above for fatty acid cistrans isomerase.

Methods described in U.S. Patent Application Publication Nos. US20080182308A1, US20070259410A1, US 20070292927A1, and US20070092957 A1 (all incorporated herein by reference) may be used to engineer bacteria for expression of a butanol biosynthetic pathway. Vectors or plasmids useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically, the vector or plasmid contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, IPL, IPR, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression Gram-positive bacteria, Eichenbaum et al. *Appl. Environ. Microbiol.* 64(8): 2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633-5638 (1992)).

Expression of a Butanol Biosynthetic Pathway in *E. Coli*

Vectors useful for the transformation of *E. coli* are common and commercially available from the companies listed above. For example, the genes of an isobutanol, 1-butanol, or 2-butanol biosynthetic pathway may be isolated from various sources, as described above, cloned onto a modified pUC19 vector and transformed into *E. coli* host cells. Alternatively, the genes encoding a butanol biosynthetic pathway may be divided into multiple operons, cloned onto expression vectors, and transformed into various *E. coli* strains.

Construction of *Lactobacillus* Strains for Butanol Production

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAM61 and derivatives thereof (Renault et al., *Gene* 183:175-182 (1996); and O'Sullivan et al., *Gene* 137:227-

231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. *Appl. Environ. Microbiol.* 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other Gram-positive organisms. A non-limiting example is the nisA promoter from *Lactococcus*. Termination control regions may also be derived from various genes native to the preferred hosts or related bacteria.

The various genes for a butanol biosynthetic pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224: 1252-154 (1990)), Bringel and Hubert (*Appl. Microbiol. Biotechnol.* 33: 664-670 (1990)), and Teresa Alegre, Rodriguez and Mesas (*FEMS Microbiology letters* 241:73-77 (2004)). Plasmids can also be introduced to *Lactobacillus plantatrum* by conjugation (Shrago, Chassy and Dobrogosz *Appl. Environ. Micro.* 52: 574-576 (1986)). The butanol biosynthetic pathway genes can also be integrated into the chromosome of *Lactobacillus* using integration vectors (Hols et al. *Appl. Environ. Micro.* 60:1401-1403 (1990); Jang et al. *Micro. Lett.* 24:191-195 (2003)).

Fermentation of Butanol Tolerant Bacteria for Butanol Production

The present cells with increased membrane unsaturated trans fatty acid composition and having a butanol biosynthesis pathway may be used for fermentation production of butanol.

Fermentation media for the production of butanol must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Sucrose may be obtained from feedstocks such as sugar cane, sugar beets, cassava, and sweet sorghum, and mixtures thereof. Glucose and dextrose may be obtained through saccharification of starch based feedstocks including grains such as corn, wheat, rye, barley, and oats, and mixtures thereof. Other fermentable sugars from algae (macroalgae or microalgae).

In addition, fermentable sugars may be obtained from cellulosic and lignocellulosic biomass through processes of pretreatment and saccharification, as described, for example, in US Patent Application Publication US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

Although it is contemplated that all of the above mentioned carbon substrates and mixtures thereof are suitable in the present invention, preferred carbon substrates are glucose, fructose, and sucrose or mixtures of these with C5 sugars such as xylose and/or arabinose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Typically cells are grown at a temperature in the range of about 25° C. to about 40° C. in an appropriate medium. Suitable growth media are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Butanol may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Butanol may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol may be practiced using either batch, fed-batch or continuous processes and that any known mode of fermentation would be suitable. Additionally, it is contemplated that cells may be immobilized on a substrate as whole cell catalysts and subjected to fermentation conditions for butanol production.

Methods for Butanol Isolation from the Fermentation Medium

Bioproduced butanol may be isolated from the fermentation medium using methods known in the art, such as the methods for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "kb" means kilobase(s), "min" means minute(s), "h" or "hr" means hour(s), "sec' means second(s), "d" means day(s), "nl" means nanoliter(s), "µl" means microliter(s), "ml" means milliliter(s), "L" means liter(s), "nm" means nanometer(s), "mm" means millimeter(s), "cm" means centimeter(s), "µm" means micrometer(s), "µM" means micromolar, "mM" means millimolar, "M" means molar, "mmol" means millimole(s), "µmole" means micromole(s), "g" means gram(s), "ng" means nanogram(s), "µg" means microgram(s), "mg" means milligram(s), "rpm" means revolutions per minute, "w/v" means weight/volume, "Cm" means chloramphenicol, "OD" means optical density, and "OD600" means optical density measured at a wavelength of 600 nm.

General Methods

Growth medium was semi-synthetic LAB medium, pH7, with bovine serum albumin (BSA) used as a carrier. In general, the presence of BSA resulted in a medium with little to no cloudiness when fatty acids were added. The composition of this medium is as follows:
0.01 M Ammonium Sulfate
0.005 M Potassium Phosphate, pH 7.0
0.05 M MOPS, pH 7.0
1% S10 Metal Mix
0.01 M Glucose
0.2% Yeast Extract
0.01% Casamino Acids
5 g/l BSA The composition of S10 Metal Mix is:
200 mM $MgCl_2$
70 mM $CaCl_2$
5 mM $MnCl_2$
0.1 mM $FeCl_3$
0.1 mM $ZnCl_2$
0.2 mM Thiamine Hydrochloride
172 µM $CuSO_4$
253 µM $CoCl_2$
242 µM $Na_2MoO_4$ All medium ingredients were purchased from Sigma Chemical Company (St. Louis, Mo.) except yeast extract and casamino acids, which were purchased from Beckton, Dickinson and Co (Sparks, Md.). Free fatty acids, added to a final concentration of 50 mg/ml from 1% ethanol stock solutions (stored at −20° C.), were purchased from Sigma Chemical Company (St Louis, Mo.), Isobutanol, 1-butanol, 2-butanol, and methyl ethyl ketone (MEK) were purchased from Sigma Chemical Company (St. Louis, Mo.).

A working stock of *Lactobacillus plantarum* PN0512 (ATCC # PTA-7727) was prepared to use as a consistent source of inoculum. Cultures were grown in MRS medium (Acumedia Manufacturers, Inc. Lansing, Mich.) at 30° C. overnight. Glycerol was added to a final concentration of 12.5% and aliquots were frozen at −80° C. One aliquot was thawed at room temperature and used to inoculate all tubes in an experiment and then discarded.

For preparation of samples for fatty acid methyl ester analysis (FAME), the working stock was used to inoculate 40 ml of medium containing free fatty acids and the cultures were grown overnight. The cell pellet was harvested by centrifugation and was washed twice with phosphate buffered saline (PBS, Bio-Rad Laboratories, Hercules, Calif.) and 5 g/l BSA, then two more times with PBS. Cell pellets were stored at −80° C. until analyzed by FAME using a transesterification protocol, which quantifies fatty acids that have been incorporated in membrane lipids, but not free fatty acids associated with the cell membrane.

Lipid Extraction

The membrane lipids were extracted by modified Bligh and Dyer protocol (Can. J. Biochem. Physiol. (1959) 37:911-17). The cell pellet prepared as described above was suspended in a mixture of 0.5 ml $CHCl_3$ and 1 ml $CH_3OH$, and transferred to a 13×100 mm tube with a screw top cap. The cap was screwed on about ¾ of the way (i.e., not tight), and the tube was incubated at 40° C. for 30 min. The tube was cooled and an additional 0.5 ml $CHCl_3$ and 1 ml $H_2O$ were added the mixture. This results in the formation of two phases. The two phases were equilibrated by vortexing. The two phases were allowed to separate; then the lower $CHCl_3$ layer was removed and transferred to another 13×100 mm tube with a screw top cap. With the cap removed, the $CHCl_3$ was evaporated under a stream of $N_2$. Methyl esters of the fatty acids in the residue were then formed using one of the following procedures.

Formation of Fatty Acid Methyl Esters by Transesterification Using $CH_3ONa$ in $CH_3OH$ 1 ml freshly made 1.0 M $CH_3ONa$ in $CH_3OH$ was added to the tubes containing lipid samples extracted by the Bligh and Dyer method as described above. The caps were placed on tubes, screwed on about ¾ of the way (i.e., not tight), then the tubes were heated at 60° C. for 30 minutes. The mixture was chilled in ice bath and 1 ml of 1.0 N HCl was added to the solution in the tubes. The pH of the resulting solution was checked with pH paper to make sure a pH of 7 or lower had been reached. 0.5 ml hexane was added into the test tube and mixed well by vortexing. The tubes were allowed to sit for a few minutes until two phases formed. The top hexane layer was removed and placed in a separate tube for storage until analysis, which was done by GC/FID and/or GC/MS. 2 µl of the hexane layer was injected into an Agilent GC (model 6890)/MS (model 5973). For routine samples a Supelco Equity-1 column (15 m×0.25 mm×0.25 um film thickness; catalog #28045-U) was used with an FID detector (GC/FID). When an unknown peak needed to be identified, the same column was used with an Agilent MSD detector (GC/MS). When samples requiring difficult separations that were impossible to achieve on a 15 m column were analyzed (e.g., the separation of oleic from elaidic acid), a Supelco S-2380 column (100 m×0.25 mm×0.25 um film thickness; catalog #24317) was used.

Growth Analysis

For growth yield experiments, 5 ml of medium with fatty acids and several concentrations of 1-butanol, isobutanol, 2-butanol, or MEK in 15 ml screw cap tubes was inoculated with 12.5 µl of the working stock giving an initial OD600 of 0.012. The caps were tightly sealed and incubated at 30° C. on a roller drum for 20 to 26 hours, at which time 1.0 ml was removed and OD600 was measured with a blank of medium amended with the fatty acid. All solvent concentrations are reported as % (w/v).

Methods for Determining Isobutanol Concentration in Culture Media

The concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

Methods for Determining 2-Butanol Concentration in Culture Media

The concentration of 2-butanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Under the conditions used, 2-butanol had a retention time of 44.3 min. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of 2-butanol was 5.03 min.

Methods for Determining 1-Butanol Concentration in Culture Media

The concentration of 1-butanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. 1-Butanol had a retention time of 52.8 min under the conditions used. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of 1-butanol was 5.4 min. A similar GC method using a Varian CP-WAX 58(FFAP) CB column (25 m×0.25 mm id×0.2 µm film thickness, Varian, Inc., Palo Alto, Calif.) was also used.

Example 1

Incorporation of Fed Fatty Acids into Membrane Lipids of *L. plantarum* PN0512

Cultures of *Lactobacillus plantarum* PN0512 were grown in media containing either oleic acid (cis) or elaidic acid (trans), or no added fatty acid, as described in General Methods, and membrane composition was analyzed also as described in General Methods. The results of FAME analyses shown in Table 1 indicate that when elaidic acid or oleic acid was added to the growth medium of PN0512 these were incorporated into the cell membrane so that the amount of the fed fatty acid was substantially increased in the cell membrane.

TABLE 1

Effect of feeding free fatty acids on membrane composition of *L. plantarum* PN0512; amounts are in weight %.

| | fatty acid in growth medium | | |
|---|---|---|---|
| membrane fatty acid | None | Oleic (C18:1, 9-cis) | Elaidic (C18:1, 9-trans) |
| C14:0 | <0.1 | <0.1 | 1.8 |
| C16:0 | 27.1 | 19.1 | 16.4 |
| C16:1 | 5.8 | 2 | 5.6 |
| C18:0 | 4.1 | 1.5 | 1.5 |
| C18:1, 9-cis | nd* | 42.7 | nd |
| C18:1, 9-trans | nd | nd | 44 |
| C18:1, 11-cis | 42.4 | 14.4 | 18.3 |
| cyc-C19:0-9-(cyclopropane derived from 9-cis) | nd | 13.3 | nd |
| cyc-C19:0-11-(cyclopropane derived from 11-cis) | 16.4 | 7.2 | 12.3 |

*nd means not detected

Oleic, elaidic, and dihydrosterculic (cyc-C19:0, 9-) acids are not normally found in the cell membrane of *L. plantarum*. When elaidic or oleic acids were fed, each increased from 0% to high levels in the cell membrane of strain PN0512. Dihydrosterculic is present when PN0512 is fed oleic acid because cyclopropane fatty acid synthase in PN0512 converts the cis double bond in oleic acid to cyclopropane. Thus these growth conditions yield cell cultures with substantially different cell membranes that were used to determine the effect of elevated trans fatty acid in the membrane lipids on butanol tolerance.

Example 2

Improved Tolerance to Isobutanol with Increased Trans Unsaturated Fatty Acids in the Cell Membrane Oleic acid (cis) and elaidic acid (trans) differ only in the conformation of the double bond. As shown in Example 1, feeding *L. plantarum* cells either oleic or elaidic acid resulted in membranes containing an increased amount of the fed fatty acid. Growth in the presence of these fatty acids and various concentrations of isobutanol was tested. Cultures were prepared as described in General Methods. Table 6 displays the average of two independent experiments comparing the growth yield of elaidic acid and oleic acid fed cultures of PN0512 after 20 hours of incubation at 30° C. in different amounts of isobutanol.

TABLE 2

Growth yield of oleic acid and elaidic acid fed *L. plantarum* PN0512 in the presence of isobutanol.

| [Isobutanol] % w/v | OD600 Oleic fed | OD600 Elaidic fed |
|---|---|---|
| 0 | 1.340 | 1.280 |
| 1.0 | 1.190 | 1.210 |
| 1.5 | 1.110 | 1.145 |
| 2.0 | 1.130 | 1.100 |
| 2.5 | 0.519 | 0.922 |
| 2.7 | 0.387 | 0.606 |
| 2.9 | 0.095 | 0.281 |
| 3.1 | 0.063 | 0.122 |
| 3.3 | 0.035 | 0.072 |
| 3.5 | 0.015 | 0.042 |

These results show that at concentrations greater than 2% isobutanol, the growth yield of the elaidic acid fed cultures was greater than the growth yield of the oleic acid fed cultures. For example, for cultures grown in 2.5% w/v isobutanol, the growth yield was 78% higher in the elaidic acid fed cultures than in the oleic acid fed cultures. These results are consistent with greater isobutanol tolerance of the culture with a high trans unsaturated fatty acid in the membrane as compared with the culture with high cis unsaturated fatty acid.

Example 3

Improved Tolerance to 1-Butanol with Increased Trans Unsaturated Fatty Acids in the Cell Membrane Growth of PN0512 in the presence of oleic acid or elaidic acid and various concentrations of 1-butanol was tested. Cultures were prepared as described in General Methods. Table 7 shows the results, giving the average of the OD600 of biological replicates for each culture after overnight growth at 30° C. in different amounts of 1-butanol.

TABLE 7

Growth yield of oleic acid and elaidic acid fed *L. plantarum* PN0512 in the presence of 1-butanol.

| [1-Butanol] % (w/v) | OD600 oleic fed | OD600 elaidic fed |
|---|---|---|
| 0 | 1.509 | 1.508 |
| 2.0 | 1.026 | 1.039 |
| 2.25 | 0.611 | 1.003 |
| 2.5 | 0.161 | 0.559 |
| 2.75 | 0.061 | 0.095 |
| 3.0 | 0.003 | 0.009 |

These results show that at concentrations greater than 2% 1-butanol, the growth yield of the elaidic acid fed cultures was greater than the growth yield of the oleic acid fed cultures. For example, for cultures grown in 2.5% w/v 1-butanol, the growth yield was greater than 3 fold higher in the elaidic acid fed cultures than in the oleic acid fed cultures. These results are consistent with greater 1-butanol tolerance of the culture with a high trans unsaturated fatty acid in the membrane as compared with the culture with high cis unsaturated fatty acid.

Example 4

Improved Tolerance to 2-Butanol with Increased Trans Unsaturated Fatty Acids in the Cell Membrane Growth of PN0512 in the presence of oleic acid or elaidic acid and various concentrations of 2-butanol was tested. Cultures were prepared as described in General Methods. Table 8 shows the results giving the average of the OD600 of biological replicates for each culture after overnight growth at 30° C. in different amounts of 2-butanol.

TABLE 8

Growth yield of oleic acid and elaidic acid fed *L. plantarum* PN0512 in the presence of 2-butanol.

| [2-butanol] % w/v | OD600 Oleic fed | OD600 Elaidic fed |
|---|---|---|
| 0 | 1.480 | 1.490 |
| 2.0 | 1.410 | 1.430 |
| 3.0 | 1.130 | 1.270 |
| 4.0 | 0.431 | 1.030 |
| 4.5 | 0.100 | 0.400 |
| 4.7 | 0.067 | 0.186 |
| 4.9 | 0.040 | 0.088 |
| 5.1 | 0.030 | 0.038 |
| 5.3 | 0.004 | 0.030 |
| 5.5 | 0.004 | 0.008 |

As was observed with isobutanol and 1-butanol, the elaidic acid fed culture demonstrated improved tolerance to 2-butanol when compared to the oleic acid fed culture. For example, for cultures grown in 4.5% w/v 2-butanol, the growth yield was 4 fold higher in the elaidic acid fed cultures than in the oleic acid fed cultures.

Example 5

Specificity of Tolerance Improvements with Increased Trans Unsaturated Fatty Acids in the Cell Membrane Growth of PN0512 in the presence of oleic acid or elaidic acid and various concentrations of methyl ethyl ketone (MEK) was tested. Cultures were prepared as described in General Methods. Table 9 shows the results, giving the average of the OD600 of biological replicates after overnight growth at 30° C. in different amounts of MEK.

TABLE 9

Growth yield of oleic and elaidic fed *L. plantarum* PN0512 in the presence of MEK

| [MEK], % (w/v) | OD600 oleic fed | OD600 elaidic fed |
|---|---|---|
| 0 | 1.53895 | 1.548 |
| 3.5 | 1.00155 | 1.0041 |
| 4.0 | 0.9446 | 0.91055 |
| 4.5 | 0.942 | 0.88705 |
| 5.0 | 0.6828 | 0.32345 |
| 5.5 | 0.50045 | 0.14765 |

In contrast to the results with isobutanol, 2-butanol, and 1-butanol, elaidic acid fed cultures of PN0512 did not have improved tolerance to MEK as compared with oleic acid fed cultures. Thus, there was specificity in that elevated trans fatty acids improved tolerance to 4 carbon alcohols, but not to a 4 carbon ketone.

Example 6

Genetic Implementation of Elevated Trans Fatty Acids in Cell Membrane (Prophetic)

It may not be desirable for a biological process of butanol production to rely on exogenously added fatty acids to alter membrane properties of a production organism. Thus, genetic changes to the production organism resulting in altered membrane composition can be made. Expression of an enzyme that converts cis unsaturated fatty acids to the trans conformation will increase the levels of trans fatty acids in bacterial cells that do not normally have trans fatty acids. Such an enzyme is the esterified fatty acid cistrans isomerase (cti) of *Pseudomonas putida* KT2440, encoded by cti (PP_2376; protein with SEQ ID NO:136, coding region with SEQ ID NO:135).

For expression, the coding region of the cti gene is amplified by PCR and cloned into an expression vector. For example, expression in *Escherichia coli* is accomplished using the pTrcHis2-TOPO vector (Invitrogen Inc., Carlsbad, Calif.). The cti coding region is obtained by PCR amplification using genomic DNA from *P. putida* KT2440 (ATCC#47054D-5) as a template and the following sense and antisense primers, respectively:

(SEQ ID NO: 153)
5' ACAGGAGAATGAATTCATGGTGCATCGTATCCTTGCC 3'

(SEQ ID NO: 154)
5' TCAGAGGTTCTCGTAGCGGT 3'

The sense primer includes an extension that provides a ribosome binding site and eliminates the short N-terminal fusion in the pTrcHis2-TOPO vector by generating an in-frame termination codon in the primer. The antisense primer includes the stop codon for the coding region, so that the native protein will be expressed in *E. coli*. Cloning of this fragment into the pTrcHis2-TOPO vector is done following the manufacturer's protocol. Orientation of the cloned insert and verification of the cloned sequence is done by DNA sequence analysis. A plasmid with the cti coding region in the correct orientation for expression controlled by the trc promoter is saved and is named pTrcCti. Transformed *E. coli* MG1655 (ATCC#700926) cells carrying this plasmid are grown in LB medium (Teknova, Inc. Half Moon Bay, Calif.) at 30° C. or 37° C. Cells harvested and analyzed by FAME are expected to show the presence of trans monounsaturated fatty acids in membrane lipids. Increased tolerance to isobutanol, 1-butanol, and 2-butanol is expected to be evident in growth yield assays of these cells done at 30° C. or 37° C. as described in Examples 2, 3, and 4.

Example 7

Prophetic

Producing Isobutanol Using *E. coli* Strain with Expression of cti

*E. coli* strains engineered to express an isobutanol biosynthetic pathway are described in US Patent Application Publication No. US20070092957A1, Examples 9-15, which are herein incorporated by reference. Strain BL21 (DE) 1.5GI yqhD/pTrc99a::budB-ilvC-ilvD-kivD was derived from BL21 (DE3) (Invitrogen) and was engineered to contain an operon expressed from the trc promoter that includes the *Klebsiella pneumoniae* budB coding region for acetolactate synthase, the *E. coli* ilvC coding region for acetohydroxy acid reductoisomerase, the *E. coli* ilvD coding region for acetohydroxy acid dehydratase and the *Lactococcus lactis* kivD coding region for branched chain α-keto acid decarboxylase. In addition, in this strain the native promoter of the yqhD gene (encoding 1,3-propanediol dehydrogenase) was replaced with the 1.5GI promoter (WO 2003/089621). The same promoter replacement was made in *E. coli* strain MG1655 to create MG1655 1.5GI-yqhD::Cm, and the same plasmid was introduced resulting in strain MG655 1.5/GI yqhD/pTrc99A::budB-ilvC-ilvD-kivD.

These isobutanol pathway containing strains are engineered for butanol tolerance by introducing a compatible plasmid for expression of a cti gene. Such a compatible plasmid is constructed by amplifying the region from plasmid pTrcCti described in Example 6 with the trc promoter and the *E. coli* cti gene. Both of the primers for amplification (SEQ ID NOs:155 and 156) also have a BsrD I restriction site. Sense primer:    5'-GCAATGGTTTGACAGCTTATCATCGAC-3' Antisense primer: 5'-GCAATGGAGGTTCTCGTAGCGGT-TCA-3' The PCR product is partially digested with BsrD I and the largest fragment is ligated into BsrD I digested vector pACYC184 (New England Biolabs, Beverly, Mass.). Transformants of *E. coli* TOP10 are selected for tetracycline resistance and screened for sensitivity to chloroamphenicol. Plasmid DNA is isolated from tetracycline resistant and chloramphenicol sensitive transformants. The presence of the trc promoter and the cti gene are verified by DNA sequence analysis. This plasmid having the *P. putida* KT2440 cti coding region expressed from the trc promoter in the pACYC184 vector backbone is named pACYCtrcCti and is used to transform strains BL21 (DE) 1.5GI yqhD/pTrc99a::budB-ilvC-ilvD-kivD and MG655 1.5/GI yqhD/pTrc99A::budB-ilvC-ilvD-kivD selecting for ampicillin resistance and tetracycline resistance.

These strains are analyzed for butanol production. The cells from cultures of each strain are used to inoculate shake flasks (approximately 175 mL total volume) containing 50 or 170 mL of TM3a/glucose medium (with appropriate antibiotics) to represent high and low oxygen conditions, respectively. TM3a/glucose medium contains (per liter): glucose (10 g), $KH_2PO_4$ (13.6 g), citric acid monohydrate (2.0 g), $(NH_4)_2SO_4$ (3.0 g), $MgSO_4.7H_2O$ (2.0 g), $CaCl_2.2H_2O$ (0.2 g), ferric ammonium citrate (0.33 g), thiamine.HCl (1.0 mg), yeast extract (0.50 g), and 10 mL of trace elements solution. The pH was adjusted to 6.8 with $NH_4OH$. The trace elements solution contains: citric acid.$H_2O$ (4.0 g/L), $MnSO_4H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L).

The flasks are inoculated at a starting $OD_{600}$ of ≤0.01 units and incubated at 34° C. with shaking at 300 rpm. The flasks containing 50 mL of medium are closed with 0.2 µm filter caps; the flasks containing 150 mL of medium are closed with sealed caps. IPTG is added to a final concentration of 0.04 mM when the cells reach an $OD_{600}$ of ≥0.4 units. Approximately 18 h after induction, an aliquot of the broth is analyzed by HPLC (Shodex Sugar SH1011 column (Showa Denko America, Inc. NY) with refractive index (RI) detection) and GC (Varian CP-WAX 58(FFAP) CB, 0.25 mm×0.2 µm×25 m (Varian, Inc., Palo Alto, Calif.) with flame ionization detection (FID)) for isobutanol content, as described in the General Methods section. No isobutanol is detected in control strains. Molar selectivities and titers of isobutanol produced by strains carrying pTrc99A::budB-ilvC-ilvD-kivD are obtained. In preferred embodiments, higher titers of isobutanol are obtained in the cultures of the strains with the cti plasmid than in the parental strains.

Example 8

Prophetic

Producing 2-Butanol Using *E. coli* Strain with Expression of cti

The engineering of *E. coli* for expression of a 2-butanol biosynthetic pathway is described in US Patent Application Publication No. US20070259410A1, Examples 6 and 7, which are herein incorporated by reference. Construction is described of two plasmids for upper and lower pathway expression. In pBen-budABC, an NPR promoter (*Bacillus amyloliquefaciens* neutral protease promoter) directs expression of *Klebsiella pneumoniae* budABC coding regions for acetolactate decarboxylase, acetolactate synthase, and butanediol dehydrogenase. In pBen-pdd-sadh an NPR promoter directs expression of *Klebsiella oxytoca* pddABC coding regions for butanediol dehydratase alpha subunit, butanediol dehydratase beta subunit, and butanediol dehydratase gamma subunit, and the *Rhodococcus ruber* sadh coding region for butanol dehydrogenase. Plasmid p2BOH is described containing both operons, and strain NM522/p2BOH containing this plasmid for 2-butanol pathway expression is described.

The NM522/p2BOH strain is engineered for butanol tolerance by introducing the cti overexpression plasmid pACYCtrcCti (described in Example 7). *E. coli* NM522/p2BOH with and without the cti plasmid are inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 µM; $CoCl_2$, 253 µM; and $Na_2MoO_4$, 242 µM.

After 18 h, 2-butanol is detected by HPLC or GC analysis using methods that are well known in the art, for example, as described in the General Methods section above. In preferred embodiments, higher titers are obtained from the strain with the cti plasmid.

Example 9

Prophetic

Producing 1-Butanol Using *E. coli* Strain with Expression of cti

*E. coli* strains engineered to express a 1-butanol biosynthetic pathway are described in US Patent Application Publication No. US20080182308A1, Example 13, which is herein incorporated by reference. Two plasmids were constructed that carry genes encoding the 1-butanol pathway. Plasmid pBHR T7-ald contains a gene for expression of butyraldehyde dehydrogenase (ald). Plasmid pTrc99a-E-C-H-T contains a four gene operon comprising the upper pathway, for expression of acetyl-CoA acetyltransferase (thlA), 3-hydroxybutyryl-CoA dehydrogenase (hbd), crotonase (crt), and butyryl-CoA dehydrogenase (trans-2-enoyl-CoA reductase, EgTER(opt)) (EgTER(opt), crt, hbd and thlA). In addition, in this strain the native promoter of the yqhD gene (encoding 1,3-propanediol dehydrogenase) was replaced with the 1.5GI promoter (WO 2003/089621).

The 1-butanol producing strain is engineered for butanol tolerance by introducing the cti expression plasmid pACYC-trcCti (described in Example 7).

The parental strain and the transformant with the cti expression plasmid are used to inoculate shake flasks (approximately 175 mL total volume) containing 15, 50 and 150 mL of TM3a/glucose medium (with appropriate antibiotics) to represent high, medium and low oxygen conditions, respectively. TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine.HCl, 0.50 g yeast extract, and 10 mL trace elements solution, adjusted to pH 6.8 with $NH_4OH$. The solution of trace elements contains: citric acid.$H_2O$ (4.0 g/L), $MnSO_4H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks are inoculated at a starting $OD_{600}$ of ≤0.01 units and incubated at 34° C. with shaking at 300 rpm. The flasks containing 15 and 50 mL of medium are capped with vented caps; the flasks containing 150 mL, are capped with non-vented caps to minimize air exchange. IPTG is added to a final concentration of 0.04 mM; the $OD_{600}$ of the flasks at the time of addition is ≥0.4 units. Approximately 15 h after induction, an aliquot of the broth is analyzed by HPLC (Shodex Sugar SH1011 column) with refractive index (RI) detection and GC (Varian CP-WAX 58(FFAP) CB column, 25 m×0.25 mm id×0.2 µm film thickness) with flame ionization detection (FID) for 1-butanol content, as described in the General Methods section. In preferred embodiments, titers of 1-butanol are found to be higher in the strain harboring the cti expression plasmid.

Example 10

Prophetic

Expression of an Isobutanol Biosynthetic Pathway in *Lactobacillus plantarum* with Increased Expression of cti The purpose of this prophetic Example is to describe how to express an isobutanol biosynthetic pathway in a *Lactoba-*

*cillus plantarum* strain that expresses cti. The five genes of the isobutanol pathway, encoding five enzyme activities, are divided into two operons for expression. The budB, ilvD and kivD genes, encoding the enzymes acetolactate synthase, acetohydroxy acid dehydratase, and branched-chain α-keto acid decarboxylase, respectively, are integrated into the chromosome of *Lactobacillus plantarum* by homologous recombination using the method described by Hols et al. (*Appl. Environ. Microbiol.* 60:1401-1413 (1994)). The remaining two genes of the isobutanol biosynthetic pathway (ilvC and bdhB, encoding the enzymes acetohydroxy acid reductoisomerase and butanol dehydrogenase, respectively) and the cti gene are cloned into an expression plasmid and transformed into the *Lactobacillus* strain carrying the integrated isobutanol genes. *Lactobacillus plantarum* is grown in MRS medium (Difco Laboratories, Detroit, Mich.) at 37° C., and chromosomal DNA is isolated as described by Moreira et al. (*BMC Microbiol.* 5:15 (2005)).

Integration

The budB-ilvD-kivD cassette under the control of the synthetic P11 promoter (Rud et al., *Microbiology* 152:1011-1019 (2006)) is integrated into the chromosome of *Lactobacillus plantarum* ATCC BAA-793 (NCIMB 8826) at the ldhL1 locus by homologous recombination. To build the ldhL integration targeting vector, a DNA fragment from *Lactobacillus plantarum* (Genbank NC_004567) with homology to ldhL is PCR amplified with primers LDH EcoRV F (SEQ ID NO:140) and LDH AatIIR (SEQ ID NO:141). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988 (a *Bacillus* integration vector that contains an *E. coli* replicon from pBR322, an ampicillin antibiotic marker for selection in *E. coli* and two sections of homology to the sacB gene in the *Bacillus* chromosome that directs integration of the vector and intervening sequence by homologous recombination; given as SEQ ID NO:142) is digested with HindIII and treated with Klenow DNA polymerase to blunt the ends. The linearized plasmid is then digested with AatII and the 2931 bp vector fragment is gel purified. The EcoRV/AatII ldhL1 fragment is ligated with the pFP988 vector fragment and transformed into *E. coli* Top10 cells. Transformants are selected on LB agar plates containing ampicillin (100 μg/mL) and are screened by colony PCR to confirm construction of pFP988-ldhL.

To add a selectable marker to the integrating DNA, the Cm resistance gene with its promoter is PCR amplified from pC194 (GenBank NC_002013) with primers Cm F (SEQ ID NO:143) and Cm R (SEQ ID NO:144), amplifying a 836 bp PCR product. This PCR product is cloned into pCR4Blunt-TOPO and transformed into *E. coli* Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel purified. The ldhL-homology containing integration vector pFP988-ldhL is digested with MluI and SwaI and the 4740 bp vector fragment is gel purified. The Cm cassette fragment is ligated with the pFP988-ldhL vector creating pFP988-DldhL::Cm.

Finally the budB-ilvD-kivD cassette which includes the *Klebsiella pneumoniae* budB coding region (SEQ ID NO:19), the *E. coli* ilvD coding region (SEQ ID NO:33), and the codon optimized *Lactococcus lactis* kivD coding region (SEQ ID NO:35) from pFP988DssPspac-budB-ilvD-kivD (described in Examples 1, 4, 9, 10, 11, 12, 14, and 20 of US 2007-0092957 A1) is modified to replace the amylase promoter with the synthetic P11 promoter. Then, the whole operon is moved into pFP988-DldhL::Cm. The P11 promoter is built by oligonucleotide annealing with primers P11 F-StuI (SEQ ID NO:145) and P11 R-SpeI (SEQ ID NO:146). The annealed oligonucleotide is gel-purified on a 6% Ultra PAGE gel (Embi Tec, San Diego, Calif.). The plasmid pFP988DssPspac-budB-ilvD-kivD, containing the amylase promoter, is digested with StuI and SpeI and the resulting 10.9 kbp vector fragment is gel-purified. The isolated P11 fragment is ligated with the digested pFP988DssPspac-budB-ilvD-kivD to create pFP988-P11-budB-ilvD-kivD. Plasmid pFP988-P11-budB-ilvD-kivD is then digested with StuI and BamHI and the resulting 5.4 kbp P11-budB-ilvD-kivD fragment is gel-purified. pFP988-DldhL::Cm is digested with HpaI and BamHI and the 5.5 kbp vector fragment isolated. The budB-ilvD-kivD operon is ligated with the integration vector pFP988-DldhL::Cm to create pFP988-DldhL-P11-budB-ilvD-kivD::Cm.

Integration of pFP988-DldhL-P11-budB-ilvD-kivD::Cm into *L. plantarum* BAA-793 to Form *L. plantarum* ldhL1::budB-ilvD-kivD::Cm Comprising Exogenous budB, ilvD, and kivD Genes.

Electrocompetent cells of *L. plantarum* are prepared as described by Aukrust, T. W., et al. (In: *Electroporation Protocols for Microorganisms*; Nickoloff, J. A., Ed.; Methods in Molecular Biology, Vol. 47; Humana Press, Inc., Totowa, N.J., 1995, pp 201-208). After electroporation, cells are outgrown in MRSSM medium (MRS medium supplemented with 0.5 M sucrose and 0.1 M MgCl$_2$) as described by Aukrust et al. supra for 2 h at 37° C. without shaking. Electroporated cells are plated for selection on MRS plates containing chloramphenicol (10 μg/mL) and incubated at 37° C. Transformants are initially screened by colony PCR amplification to confirm integration, and initial positive clones are then more rigorously screened by PCR amplification with a battery of primers.

Plasmid Expression of ilvC, bdhB and cti1 Genes.

The remaining two isobutanol genes and cti1 under the control of the *L. plantarum* ldhL promoter (Ferain et al., *J. Bacteriol.* 176:596-601 (1994)) are expressed from plasmid pTRKH3 (O'Sullivan D J and Klaenhammer T R, *Gene* 137:227-231 (1993)). The ldhL promoter is PCR amplified from the genome of *L. plantarum* ATCC BAA-793 using primers PldhL F-HindIII (SEQ ID NO:147) and PldhL R-BamHI (SEQ ID NO:148). The 411 bp PCR product is cloned into pCR4Blunt-TOPO and sequenced. The resulting plasmid, pCR4Blunt-TOPO-PldhL is digested with HindIII and BamHI releasing the PldhL fragment. The cti coding region is PCR amplified from *Pseudomonas putida* KT240 genomic DNA using primers SEQ ID NOs:153 and 154 from Ex 6). The PCR product is cloned into pCR4Blunt-TOPO and sequenced. The resulting plasmid, pCR4Blunt-TOPO-cti, is digested with SphI releasing the fragment with the cti coding region.

Plasmid pTRKH3 is digested with SphI and partially digested with HindIII. The gel-purified approximately 7 Kb vector fragment is ligated with the PldhL fragment and the gel-purified 2.4 kbp BamHI/SphI fragment containing ilvC (B.s.)-bdhB, which includes the *Bacillus subtilis* ilvC coding region (SEQ ID NO:41) and the *Clostridium acetobutylicum* bdhB coding region (SEQ ID NO:13) from a *Bacillus* expression plasmid pBDPgroE-ilvC(B.s.)-bdhB (described in Example 20 of US 2007-0092957 A1) in a three-way ligation. The ligation mixture is transformed into *E. coli* Top 10 cells and transformants are grown on Brain Heart Infusion (BHI, Difco Laboratories, Detroit, Mich.) plates containing erythromycin (150 mg/L). Transformants are screened by PCR to confirm construction. The resulting plasmid, pTRKH3-ilvC (B.s.)-bdhB, is digested with SphI, treated with calf intestinal alkaline phosphatase, and ligated with the cti coding region fragment. The ligation mixture is transformed into E. coli Top 10 cells and transformants are grown on Brain Heart Infusion (BHI, Difco Laboratories, Detroit, Mich.) plates containing erythromycin (150 mg/L). The transformants are screened by PCR and one with the cti gene in the same orientation as ilvC and bdhB is retained and named pTRKH3-ilvC(B.s.)-bdhB-cti. This plasmid and plasmid pTRKH3-ilvC(B.s.)-bdhB are transformed into L. plantarum ΔldhL1::budB-ilvD-kivD::Cm by electroporation, as described above.

L. plantarum ΔldhL1::budB-ilvD-kivD::Cm containing pTRKH3-ilvC(B.s.)-bdhB-cti or containing pTRKH3-ilvC (B.s.)-bdhB are inoculated into a 250 mL shake flask containing 50 mL of MRS medium plus erythromycin (10 μg/mL) and grown at 37° C. for 18 to 24 h without shaking, after which isobutanol is detected by HPLC or GC analysis. In preferred embodiments, higher titers of isobutanol are obtained from the strain with the cti gene on the plasmid.

Example 11

Prophetic

Expression of the 1-Butanol Biosynthetic Pathway in Lactobacillus plantarum with Expression of cti The purpose of this prophetic Example is to describe how to express the 1-butanol biosynthetic pathway in a Lactobacillus plantarum strain that expresses cti. The six genes of the 1-butanol pathway, encoding six enzyme activities, are divided into two operons for expression. The first three genes of the pathway (thl, hbd, and crt, encoding the enzymes acetyl-CoA acetyltransferase, 3-hydroxybutyryl-CoA dehydrogenase, and crotonase, respectively) are integrated into the chromosome of Lactobacillus plantarum by homologous recombination using the method described by Hols et al. (Appl. Environ. Microbiol. 60:1401-1413 (1994)). The last three genes of the 1-butanol pathway (EgTER, ald, and bdhB, encoding the enzymes butyryl-CoA dehydrogenase, butyraldehyde dehydrogenase and butanol dehydrogenase, respectively) and cti are cloned into an expression plasmid and transformed into the Lactobacillus strain carrying the integrated upper pathway 1-butanol genes. Lactobacillus is grown in MRS medium (Difco Laboratories, Detroit, Mich.) at 37° C. Chromosomal DNA is isolated from Lactobacillus plantarum as described by Moreira et al. (BMC Microbiol. 5:15 (2005)).

Integration

The thl-hbd-crt cassette under the control of the synthetic P11 promoter (Rud et al., Microbiology 152:1011-1019 (2006)) is integrated into the chromosome of Lactobacillus plantarum ATCC BAA-793 (NCIMB 8826) at the ldhL1 locus by homologous recombination. To build the ldhL integration targeting vector, a DNA fragment from Lactobacillus plantarum (Genbank NC_004567) with homology to ldhL is PCR amplified with primers LDH EcoRV F (SEQ ID NO:140) and LDH AatIIR (SEQ ID NO:141). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988, described in Example 10, is digested with HindIII and treated with Klenow DNA polymerase to blunt the ends. The linearized plasmid is then digested with AatII and the 2931 bp vector fragment is gel-purified. The EcoRV/AatII ldhL1 fragment is ligated with the pFP988 vector fragment and transformed into E. coli Top10 cells. Transformants are selected on LB agar plates containing ampicillin (100 μg/mL) and are screened by colony PCR to confirm construction of pFP988-IdhL.

To add a selectable marker to the integrating DNA, the Cm gene with its promoter is PCR amplified from pC194 (Genbank NC_002013) with primers Cm F (SEQ ID NO:143) and Cm R (SEQ ID NO:144), amplifying a 836 bp PCR product. The amplicon is cloned into pCR4Blunt-TOPO and transformed into E. coli Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel-purified. The IdhL-homology containing integration vector pFP988-IdhL is digested with MluI and SwaI and the 4740 bp vector fragment is gel-purified. The Cm cassette fragment is ligated with the pFP988-IdhL vector creating pFP988-DldhL::Cm.

Finally the thl-hbd-crt cassette from pFP988Dss-T-H-C (described in WO2007041269 Examples 13 and 14, which are herein incorporated by reference) including the Clostridium acetobutylicum thlA, hbd, and crt coding regions (SEQ ID NOs:1, 5, and 7 respectively) is modified to replace the amylase promoter with the synthetic P11 promoter. Then, the whole operon is moved into pFP988-DldhL::Cm. The P11 promoter is built by oligonucleotide annealing with primer P11 F (SEQ ID NO:149) and P11 R (SEQ ID NO:150). The annealed oligonucleotide is gel-purified on a 6% Ultra PAGE gel (Embi Tec, San Diego, Calif.). The plasmid pFP988Dss-T-H-C is digested with XhoI and SmaI and the 9 kbp vector fragment is gel-purified. The isolated P11 fragment is ligated with the digested pFP988Dss-T-H-C to create pFP988-P11-T-H-C. Plasmid pFP988-P11-T-H-C is digested with XhoI and BamHI and the 3034 bp P11-T-H-C fragment is gel-purified. pFP988-DldhL::Cm is digested with XhoI and BamHI and the 5558 bp vector fragment isolated. The upper pathway operon is ligated with the integration vector to create pFP988-DldhL-P11-THC::Cm.

Integration of pFP988-DldhL-P11-THC::Cm into L. plantarum BAA-793 to Form L. plantarum ΔldhL1::T-H-C::Cm Comprising Exogenous thl, hbd, and crt Genes Electrocompetent cells of L. plantarum are prepared as described by Aukrust, T. W., et al. (In: Electroporation Protocols for Microorganisms; Nickoloff, J. A., Ed.; Methods in Molecular Biology, Vol. 47; Humana Press, Inc., Totowa, N.J., 1995, pp 201-208). After electroporation, cells are outgrown in MRSSM medium (MRS medium supplemented with 0.5 M sucrose and 0.1 M $MgCl_2$) as described by Aukrust et al. supra for 2 h at 37° C. without shaking. Electroporated cells are plated for selection on MRS plates containing chloramphenicol (10 μg/mL) and incubated at 37° C. Transformants are initially screened by colony PCR amplification to confirm integration, and initial positive clones are then more rigorously screened by PCR amplification with a battery of primers.

Plasmid Expression of EgTER, ald, and bdhB Genes.

The three remaining 1-butanol genes under the control of the L. plantarum ldhL promoter (Ferain et al., J. Bacteriol. 176:596-601 (1994)). and cti under control of the atpB promoter are expressed from plasmid pTRKH3 (O'Sullivan D J and Klaenhammer T R, Gene 137:227-231 (1993)). The ldhL promoter is PCR amplified from the genome of L. plantarum ATCC BAA-793 with primers PldhL F (SEQ ID NO:151) and PldhL R (SEQ ID NO:152). The 369 bp PCR product is cloned into pCR4Blunt-TOPO and sequenced. The resulting plasmid, pCR4Blunt-TOPO-PldhL is digested with SacI and BamHI releasing the 359 bp PldhL fragment.

pHT01-ald-EB (described in WO2007041269 Examples 9, 13 and 14) including the *Clostridium beijerinckii* ald coding region, the *Clostridium acetobutylicum* bdhB and a codon optimized *Euglena gracilis* TER fragment (SEQ ID NOs:11, 13, and 39 respectively) is digested with SacI and BamHI and the 10503 bp vector fragment is recovered by gel purification. The PldhL fragment and vector are ligated creating pHT01-Pldhl-ald-EB.

To subclone the IdhL promoter-ald-EgTER-bdh cassette, pHT01-Pldhl-ald-EB is digested with MluI and the ends are treated with Klenow DNA polymerase. The linearized vector is digested with SalI and the 4270 bp fragment containing the PldhL-AEB fragment is gel-purified. Plasmid pTRKH3 is digested with SalI and EcoRV and the gel-purified vector fragment is ligated with the PldhL-AEB fragment. The ligation mixture is transformed into *E. coli* Top 10 cells and transformants are plated on Brain Heart Infusion (BHI, Difco Laboratories, Detroit, Mich.) plates containing erythromycin (150 mg/L). Transformants are screened by PCR to confirm construction of pTRKH3-ald-E-B.

The cti gene is amplified from *Pseudomonas putida* KT2440 genomic DNA as described in example 6. The PCR product is cloned into pCR4Blunt-TOPO and sequenced. The resulting plasmid, pCR4Blunt-TOPO-cti, is digested with NruI and XhoI releasing the fragment with the cti coding region.

The plasmid pTRKH3-ald-E-B is digested with NruI and XhoI and the large fragment is gel purified and ligated with the cti fragment. The ligation mixture is transformed into *E. coli* Top 10 cells and transformants are grown on Brain Heart Infusion (BHI, Difco Laboratories, Detroit, Mich.) plates containing erythromycin (150 mg/L). Transformants are screened by PCR to confirm construction of plasmid pTRKH3-ald-E-B-cti, where cti is expressed from the same promoter as ald-E-b.

Plasmids pTRKH3-ald-E-B and pTRKH3-ald-E-B-cti are transformed into *L. plantarum* ΔldhL1::T-H-C::Cm by electroporation, as described above.

*L. plantarum* ΔIdhL1::T-H-C::Cm containing pTRKH3-ald-E-B or containing pTRKH3-ald-E-B-PatpB-cti are inoculated into a 250 mL shake flask containing 50 mL of MRS medium plus erythromycin (10 μg/mL) and grown at 37° C. for 18 to 24 h without shaking. After 18 h to 24, 1-butanol is detected by HPLC or GC analysis. In preferred embodiments, higher titers of 1-butanol are obtained from the strain with the cti gene on the plasmid.

What is claimed is:

1. An isobutanol tolerant *Lactobacillus* bacterial cell comprising:
   (a) an engineered isobutanol biosynthetic pathway, wherein the *Lactobacillus* bacterial cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:
      (i) pyruvate to acetolactate catalyzed by the acetolactate synthase,
      (ii) acetolactate to 2,3-dihydroxyisovalerate catalyzed by the acetohydroxy acid isomeroreductase,
      (iii) 2,3-dihydroxyisovalerate to α-ketoisovalerate catalyzed by the acetohydroxy acid dehydratase or dihydroxyacid dehydratase,
      (iv) α-ketoisovalerate to isobutyraldehyde catalyzed by the branched-chain keto acid decarboxylase, and
      (v) isobutyraldehyde to isobutanol catalyzed by the branched-chain alcohol dehydrogenase; and
   (b) at least one gene encoding a heterologous fatty acid cistrans isomerase, wherein the isobutanol tolerant *Lactobacillus* bacterial cell has increased concentration of membrane unsaturated trans fatty acids as compared with that of the corresponding *Lactobacillus* bacterial cell that lacks the at least one gene encoding a heterologous fatty acid cistrans isomerase.

2. The isobutanol tolerant *Lactobacillus* bacterial cell of claim 1, wherein the concentration of at least one unsaturated trans fatty acid selected from the group consisting of elaidic acid, vaccenic acid, and C16:1 trans fatty acid is increased as compared with that of the corresponding *Lactobacillus* bacterial cell that lacks the at least one gene encoding a heterologous fatty acid cistrans isomerase.

3. The isobutanol tolerant *Lactobacillus* bacterial cell of claim 1, wherein said cell produces isobutanol and the growth yield of the cell is at least 1.6 to about 3.5-fold higher in a culture medium comprising 2.5% isobutanol than the corresponding *Lactobacillus* bacterial cell that lacks the at least one gene encoding a heterologous fatty acid cistrans isomerase.

4. The isobutanol tolerant *Lactobacillus* bacterial cell of claim 1, wherein the concentration of at least one membrane unsaturated trans fatty acid is about 44-fold higher than that of the corresponding *Lactobacillus* bacterial cell that lacks the at least one gene encoding a heterologous fatty acid cistrans isomerase.

5. A method for the production of isobutanol comprising:
   (I) providing an isobutanol tolerant *Lactobacillus* bacterial cell that comprises:
      (a) an engineered isobutanol biosynthetic pathway, wherein the *Lactobacillus* bacterial cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:
         (i) pyruvate to acetolactate catalyzed by the acetolactate synthase,
         (ii) acetolactate to 2,3-dihydroxyisovalerate catalyzed by the acetohydroxy acid isomeroreductase,
         (iii) 2,3-dihydroxyisovalerate to α-ketoisovalerate catalyzed by the acetohydroxy acid dehydratase or dihydroxyacid dehydratase,
         (iv) α-ketoisovalerate to isobutyraldehyde catalyzed by the branched-chain keto acid decarboxylase, and
         (v) isobutyraldehyde to isobutanol catalyzed by the branched-chain alcohol dehydrogenase; and
      (b) at least one gene encoding a heterologous fatty acid cistrans isomerase, wherein the isobutanol tolerant *Lactobacillus* bacterial cell has increased concentration of membrane unsaturated trans fatty acids as compared with that of the corresponding *Lactobacillus* bacterial cell that lacks the at least one gene encoding a heterologous fatty acid cistrans isomerase;

(II) feeding the *Lactobacillus* bacterial cell of step (I) at least one trans fatty acid under conditions wherein the concentration of unsaturated trans fatty acids in the membrane of the cell are increased; and (III) growing the *Lactobacillus* bacterial cell of step (II) under conditions wherein isobutanol is produced.

6. A method for the production of isobutanol comprising:

(I) providing an isobutanol tolerant *Lactobacillus* bacterial cell that comprises:

(a) an engineered isobutanol biosynthetic pathway, wherein the *Lactobacillus* bacterial cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:

(i) pyruvate to acetolactate catalyzed by the acetolactate synthase, (ii) acetolactate to 2,3-dihydroxyisovalerate catalyzed by the acetohydroxy acid isomeroreductase, (iii) 2,3-dihydroxyisovalerate to α-ketoisovalerate catalyzed by the acetohydroxy acid dehydratase or dihydroxyacid dehydratase, (iv) α-ketoisovalerate to isobutyraldehyde catalyzed by the branched-chain keto acid decarboxylase, and (v) isobutyraldehyde to isobutanol catalyzed by the branched-chain alcohol dehydrogenase; and (b) at least one gene encoding a heterologous fatty acid cistrans isomerase, wherein the isobutanol tolerant *Lactobacillus* bacterial cell has increased concentration of membrane unsaturated trans fatty acids as compared with that of the corresponding *Lactobacillus* bacterial cell that lacks the at least one gene encoding a heterologous fatty acid cistrans isomerase; and (II) growing the *Lactobacillus* bacterial cell of step (I) under conditions wherein isobutanol is produced.

* * * * *

SEQUENCE LISTING

<160> NUMBER OF SEQ ID NOS: 156

<210> SEQ ID NO 1
<211> LENGTH: 1179
<212> TYPE: DNA
<213> ORGANISM: Clostridium acetobutylicum

<400> SEQUENCE: 1

```
atgaaagaag ttgtaatagc tagtgcagta agaacagcga ttggatctta tggaaagtct      60
cttaaggatg taccagcagt agatttagga gctacagcta taaaggaagc agttaaaaaa     120
gcaggaataa aaccagagga tgttaatgaa gtcattttag gaaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa tatgtctaga     360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaaagctga agaagctata aaatcaggtc aatttaaaga tgaaatagtt     600
cctgtagtaa ttaaaggcag aaagggagaa actgtagttg atacagatga gcaccctaga     660
tttggatcaa ctatagaagg acttgcaaaa ttaaaacctg ccttcaaaaa agatggaaca     720
gttacagctg gtaatgcatc aggattaaat gactgtgcag cagtacttgt aatcatgagt     780
gcagaaaaag ctaaagagct tggagtaaaa ccacttgcta agatagtttc ttatggttca     840
gcaggagttg acccagcaat aatgggatat ggacctttct atgcaacaaa agcagctatt     900
gaaaaagcag gttggacagt tgatgaatta gatttaatag aatcaaatga agcttttgca     960
gctcaaagtt tagcagtagc aaaagattta aaatttgata tgaataaagt aaatgtaaat    1020
ggaggagcta ttgcccttgg tcatccaatt ggagcatcag gtgcaagaat actcgttact    1080
cttgtacacg caatgcaaaa aagagatgca aaaaaaggct tagcaacttt atgtataggt    1140
```
ggcggacaag gaacagcaat attgctagaa aagtgctag                                    1179

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
```

```
                370                 375                 380
Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatg tacctgcaac agagttagga gctatagtaa taaaggaagc tgtaagaaga     120
gctaatataa atccaaatga gattaatgaa gttattttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg tatggaaaaa tatgtctaga     360
tcaccatatt tgattaacaa tcagagatgg ggtcaaagaa tgggagatag tgaattagtt     420
gatgaaatga taaaggatgg tttgtgggat gcatttaatg gatatcatat gggagtaact     480
gcagaaaata ttgcagaaca atggaatata caagagaag agcaagatga attttcactt     540
atgtcacaac aaaagctga aaagccatt aaaaatggag aatttaagga tgaaatagtt     600
cctgtattaa taaagactaa aaaaggtgaa atagtctttg atcaagatga atttcctaga     660
ttcggaaaca ctattgaagc attaagaaaa cttaaaccta ttttcaagga aaatggtact     720
gttacagcag gtaatgcatc cggattaaat gatggagctg cagcactagt aataatgagc     780
gctgataaag ctaacgctct cggaataaaa ccacttgcta agattacttc ttacggatca     840 tatgggtag atccatcaat aatgggatat ggagcttttt atgcaactaa agctgcctta     900
gataaaatta tttaaaaacc tgaagactta gatttaattg aagctaacga ggcatatgct     960
tctcaaagta tagcagtaac tagagattta aatttagata tgagtaaagt taatgttaat    1020
ggtggagcta tagcacttgg acatccaata ggtgcatctg gtgcacgtat tttagtaaca    1080
ttactatacg ctatgcaaaa aagagattca aaaaaaggtc ttgctactct atgtattggt    1140
ggaggtcagg gaacagctct cgtagttgaa agagactaa                           1179

<210> SEQ ID NO 4
<211> LENGTH: 392
<212> TYPE: PRT
<213> ORGANISM: Clostridium acetobutylicum

<400> SEQUENCE: 4

Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
                20                  25                  30

Val Ile Lys Glu Ala Val Arg Arg Ala Asn Ile Asn Pro Asn Glu Ile
            35                  40                  45

Asn Glu Val Ile Phe Gly Asn Val Leu Gln Ala Gly Leu Gly Gln Asn
        50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
```

|       |     |     |     |     | 100 |     |     |     |     | 105 |     |     |     |     | 110 |     |     |
|-------|-----|-----|-----|-----|-----|-----|-----|-----|-----|-----|-----|-----|-----|-----|-----|-----|-----|

Gly Gly Met Glu Asn Met Ser Arg Ser Pro Tyr Leu Ile Asn Asn Gln
            115                 120                 125

Arg Trp Gly Gln Arg Met Gly Asp Ser Glu Leu Val Asp Glu Met Ile
130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
            195                 200                 205

Gly Glu Ile Val Phe Asp Gln Asp Glu Phe Pro Arg Phe Gly Asn Thr
            210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
                260                 265                 270

Ala Lys Ile Thr Ser Tyr Gly Ser Tyr Gly Val Asp Pro Ser Ile Met
            275                 280                 285

Gly Tyr Gly Ala Phe Tyr Ala Thr Lys Ala Ala Leu Asp Lys Ile Asn
            290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Leu Tyr Ala Met Gln Lys Arg
            355                 360                 365

Asp Ser Lys Lys Gly Leu Ala Thr Leu Cys Ile Gly Gly Gly Gln Gly
            370                 375                 380

Thr Ala Leu Val Val Glu Arg Asp
385                 390

```
<210> SEQ ID NO 5
<211> LENGTH: 849
<212> TYPE: DNA
<213> ORGANISM: Clostridium acetobutylicum

<400> SEQUENCE: 5
atgaaaaagg tatgtgttat aggtgcaggt actatgggtt caggaattgc tcaggcattt     60
gcagctaaag gatttgaagt agtattaaga gatattaaag atgaatttgt tgatagagga    120
ttagatttta tcaataaaaa tctttctaaa ttagttaaaa aaggaaagat agaagaagct    180
actaaagttg aaatcttaac tagaattcc ggaacagttg accttaatat ggcagctgat    240
tgcgatttag ttatagaagc agctgttgaa agaatggata ttaaaaagca gatttttgct    300
gacttagaca atatatgcaa gccagaaaca attcttgcat caaatacatc atcactttca    360
ataacagaag tggcatcagc aactaaaaga cctgataagg ttataggtat gcatttcttt    420
aatccagctc ctgttatgaa gcttgtagag gtaataagag gaatagctac atcacaagaa    480
```

```
actttgatg cagttaaaga gacatctata gcaataggaa agatcctgt agaagtagca      540 gaagcaccag gatttgttgt aaatagaata ttaataccaa tgattaatga agcagttggt   600
atattagcag aaggaatagc ttcagtagaa gacatagata aagctatgaa acttggagct   660
aatcacccaa tgggaccatt agaattaggt gattttatag gtcttgatat atgtcttgct   720
ataatggatg ttttatactc agaaactgga gattctaagt atagaccaca tacattactt   780
aagaagtatg taagagcagg atggcttgga agaaaatcag gaaaaggttt ctacgattat   840
tcaaaataa                                                            849
```

<210> SEQ ID NO 6
<211> LENGTH: 282
<212> TYPE: PRT
<213> ORGANISM: Clostridium acetobutylicum

<400> SEQUENCE: 6

```
Met Lys Lys Val Cys Val Ile Gly Ala Gly Thr Met Gly Ser Gly Ile
 1               5                  10                  15

Ala Gln Ala Phe Ala Ala Lys Gly Phe Glu Val Val Leu Arg Asp Ile
             20                  25                  30

Lys Asp Glu Phe Val Asp Arg Gly Leu Asp Phe Ile Asn Lys Asn Leu
         35                  40                  45

Ser Lys Leu Val Lys Lys Gly Lys Ile Glu Glu Ala Thr Lys Val Glu
     50                  55                  60

Ile Leu Thr Arg Ile Ser Gly Thr Val Asp Leu Asn Met Ala Ala Asp
 65                  70                  75                  80

Cys Asp Leu Val Ile Glu Ala Ala Val Glu Arg Met Asp Ile Lys Lys
                 85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280
```

<210> SEQ ID NO 7
<211> LENGTH: 786
<212> TYPE: DNA

<213> ORGANISM: Clostridium acetobutylicum

<400> SEQUENCE: 7

```
atggaactaa acaatgtcat ccttgaaaag gaaggtaaag ttgctgtagt taccattaac    60
agacctaaag cattaaatgc gttaaatagt gatacactaa agaaatgga ttatgttata   120
ggtgaaattg aaaatgatag cgaagtactt gcagtaattt taactggagc aggagaaaaa   180
tcatttgtag caggagcaga tatttctgag atgaaggaaa tgaataccat tgaaggtaga   240
aaattcggga tacttggaaa taaagtgttt agaagattag aacttcttga aaagcctgta   300
atagcagctg ttaatggttt tgctttagga ggcggatgcg aaatagctat gtcttgtgat   360
ataagaatag cttcaagcaa cgcaagattt ggtcaaccag aagtaggtct cggaataaca   420
cctggttttg gtggtacaca agactttca agattagttg aatgggcat ggcaaagcag    480
cttatattta ctgcacaaaa tataaaggca gatgaagcat taagaatcgg acttgtaaat   540
aaggtagtag aacctagtga attaatgaat acagcaaaag aaattgcaaa caaaattgtg   600
agcaatgctc cagtagctgt taagttaagc aaacaggcta ttaatagagg aatgcagtgt   660
gatattgata ctgctttagc atttgaatca gaagcatttg gagaatgctt ttcaacagag   720
gatcaaaagg atgcaatgac agctttcata gagaaaagaa aaattgaagg cttcaaaaat   780
agatag                                                              786
```

<210> SEQ ID NO 8
<211> LENGTH: 261
<212> TYPE: PRT
<213> ORGANISM: Clostridium acetobutylicum

<400> SEQUENCE: 8

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
```

```
                210                 215                 220
Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc    60
agaagggaag tactaaatca aatagattat tgtaagaagg ctattgggtt taggggacca   120
aagaaggttt taattgttgg agcctcatct gggtttggtc ttgctactag aatttcagtt   180
gcatttggag gtccagaagc tcacacaatt ggagtatcct atgaaacagg agctacagat   240
agaagaatag gaacagcggg atggtataat aacatatttt ttaaagaatt tgctaaaaaa   300
aaaggattag ttgcaaaaaa cttcattgag gatgcctttt ctaatgaaac caaagataaa   360
gttattaagt atataaagga tgaatttggt aaaatagatt tatttgttta tagttttagct  420 gcgcctagga gaaaggacta taaaactgga atgttttata cttcaagaat aaaaacaatt   480
ttaggagatt ttgagggacc gactattgat gttgaaagag acgagattac tttaaaaaag   540
gttagtagtg ctagcattga agaaattgaa gaaactagaa aggtaatggg tggagaggat   600
tggcaagagt ggtgtgaaga gctgctttat gaagattgtt ttcggataaa gcaactacc    660 atagcatact cgtatatagg atccccaaga acctacaaga tatatagaga aggtactata   720
ggaatagcta aaaaggatct tgaagataag gctaagctta taaatgaaaa acttaacaga   780
gttataggtg gtagagcctt tgtgtctgtg aataaagcat tagttacaaa agcaagtgca   840
tatattccaa cttttcctct ttatgcagct attttatata aggtcatgaa agaaaaaaat   900
attcatgaaa attgtattat gcaaattgag agaatgtttt ctgaaaaaat atattcaaat   960
gaaaaaatac aatttgatga caagggaaga ttaaggatgg acgatttaga gcttagaaaa  1020
gacgttcaag acgaagttga tagaatatgg agtaatatta ctcctgaaaa ttttaaggaa  1080
ttatctgatt ataagggata caaaaaagaa ttcatgaact aaacggtttt tgatctagat  1140
ggggttgatt atagtaaaga cctggatata gaattattaa gaaaattaga accttaa     1197

<210> SEQ ID NO 10
<211> LENGTH: 398
<212> TYPE: PRT
<213> ORGANISM: Clostridium acetobutylicum

<400> SEQUENCE: 10

Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
```

-continued

```
65                  70                  75                  80
Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110
Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160
Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240
Gly Ile Ala Lys Lys Asp Leu Glu Asp Lys Ala Lys Leu Ile Asn Glu
                245                 250                 255
Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335
Glu Leu Arg Lys Asp Val Gln Asp Glu Val Asp Arg Ile Trp Ser Asn
            340                 345                 350
Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395
```

<210> SEQ ID NO 11
<211> LENGTH: 1407
<212> TYPE: DNA
<213> ORGANISM: Clostridium beijerinckii

<400> SEQUENCE: 11

```
atgaataaag acacactaat acctacaact aaagatttaa aagtaaaaac aaatggtgaa      60
aacattaatt taaagaacta caaggataat tcttcatgtt tcggagtatt cgaaaatgtt     120
gaaaatgcta taagcagcgc tgtacacgca caaaagatat tatcccttca ttatacaaaa     180
gagcaaagag aaaaaatcat aactgagata agaaaggccg cattacaaaa taaagaggtc     240
ttggctacaa tgattctaga agaaacacat atgggaagat atgaggataa aatattaaaa     300
```

```
catgaattgg tagctaaata tactcctggt acagaagatt taactactac tgcttggtca    360
ggtgataatg tcttacagt  tgtagaaatg tctccatatg gtgttatagg tgcaataact    420
ccttctacga atccaactga aactgtaata tgtaatagca taggcatgat agctgctgga    480
aatgctgtag tatttaacgg acacccatgc gctaaaaaat gtgttgcctt tgctgttgaa    540
atgataaata aggcaattat ttcatgtggc ggtcctgaaa atctagtaac aactataaaa    600
aatccaacta tggagtctct agatgcaatt attaagcatc cttcaataaa acttctttgc    660
ggaactgggg gtccaggaat ggtaaaaacc ctcttaaatt ctggtaagaa agctataggt    720
gctggtgctg aaatccacc  agttattgta gatgatactg ctgatataga aaaggctggt    780
aggagcatca ttgaaggctg ttcttttgat aataatttac cttgtattgc agaaaaagaa    840
gtatttgttt ttgagaatgt tgcagatgat ttaatatcta acatgctaaa aaataatgct    900
gtaattataa atgaagatca agtatcaaaa ttaatagatt tagtattaca aaaaaataat    960
gaaactcaag aatactttat aaacaaaaaa tgggtaggaa agatgcaaa  attattctta   1020
gatgaaatag atgttgagtc tccttcaaat gttaaatgca taatctgcga agtaaatgca   1080
aatcatccat ttgttatgac agaactcatg atgccaatat tgccaattgt aagagttaaa   1140
gatatagatg aagctattaa atatgcaaag atagcagaac aaaatagaaa acatagtgcc   1200
tatatttatt ctaaaaatat agacaaccta aatagatttg aaagagaaat agatactact   1260
attttttgtaa agaatgctaa atcttttgct ggtgttggtt atgaagcaga aggatttaca   1320
actttcacta ttgctggatc tactggtgag ggaataaccct ctgcaaggaa ttttacaaga   1380
caaagaagat gtgtacttgc cggctaa                                        1407
```

<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro

|     |     |     |     |     | 180 |     |     |     | 185 |     |     |     |     | 190 |
| --- | --- | --- | --- | --- | --- | --- | --- | --- | --- | --- | --- | --- | --- | --- |
| Glu | Asn | Leu | Val | Thr | Thr | Ile | Lys | Asn | Pro | Thr | Met | Glu | Ser | Leu | Asp |

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 13
<211> LENGTH: 1215
<212> TYPE: DNA
<213> ORGANISM: Clostridium acetobutylicum
<400> SEQUENCE: 13

| atggttgatt | tcgaatattc | aataccaact | agaattttt  | tcggtaaaga | taagataaat |  60 |
| gtacttggaa | gagagcttaa | aaaatatggt | tctaaagtgc | ttatagttta | tggtggagga | 120 |
| agtataaaga | gaaatggaat | atatgataaa | gctgtaagta | tacttgaaaa | aaacagtatt | 180 |
| aaattttatg | aacttgcagg | agtagagcca | atccaagag  | taactacagt | tgaaaaagga | 240 |
| gttaaaatat | gtagagaaaa | tggagttgaa | gtagtactag | ctataggtgg | aggaagtgca | 300 |
| atagattgcg | caaaggttat | agcagcagca | tgtgaatatg | atggaaatcc | atgggatatt | 360 |
| gtgttagatg | gctcaaaaat | aaaaagggtg | cttcctatag | ctagtatatt | aaccattgct | 420 |
| gcaacaggat | cagaaatgga | tacgtgggca | gtaataaata | atatggatac | aaacgaaaaa | 480 |

-continued

```
ctaattgcgg cacatccaga tatggctcct aagttttcta tattagatcc aacgtatacg      540
tataccgtac ctaccaatca aacagcagca ggaacagctg atattatgag tcatatattt      600
gaggtgtatt ttagtaatac aaaaacagca tatttgcagg atagaatggc agaagcgtta      660
ttaagaactt gtattaaata tggaggaata gctcttgaga agccggatga ttatgaggca      720
agagccaatc taatgtgggc ttcaagtctt gcgataaatg gacttttaac atatggtaaa      780
gacactaatt ggagtgtaca cttaatggaa catgaattaa gtgcttatta cgacataaca      840
cacggcgtag ggcttgcaat tttaacacct aattggatgg agtatatttt aaataatgat      900
acagtgtaca gtttgttga atatggtgta atgtttggg gaatagacaa agaaaaaaat      960
cactatgaca tagcacatca agcaatacaa aaacaagag attactttgt aaatgtacta     1020
ggtttaccat ctagactgag agatgttgga attgaagaag aaaaattgga cataatggca     1080
aaggaatcag taaagcttac aggaggaacc ataggaaacc taagaccagt aaacgcctcc     1140
gaagtcctac aaatattcaa aaatctgtg taaaacgcct ccgaagtcct acaaatattc     1200
aaaaaatctg tgtaa                                                      1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
```

```
                        245             250             255
Thr Tyr Gly Lys Asp Thr Asn Trp Ser Val His Leu Met Glu His Glu
                260             265             270

Leu Ser Ala Tyr Tyr Asp Ile Thr His Gly Val Gly Leu Ala Ile Leu
            275             280             285

Thr Pro Asn Trp Met Glu Tyr Ile Leu Asn Asn Asp Thr Val Tyr Lys
        290             295             300

Phe Val Glu Tyr Gly Val Asn Val Trp Gly Ile Asp Lys Glu Lys Asn
305             310             315             320

His Tyr Asp Ile Ala His Gln Ala Ile Gln Lys Thr Arg Asp Tyr Phe
                325             330             335

Val Asn Val Leu Gly Leu Pro Ser Arg Leu Arg Asp Val Gly Ile Glu
            340             345             350

Glu Glu Lys Leu Asp Ile Met Ala Lys Glu Ser Val Lys Leu Thr Gly
        355             360             365

Gly Thr Ile Gly Asn Leu Arg Pro Val Asn Ala Ser Glu Val Leu Gln
    370             375             380

Ile Phe Lys Lys Ser Val
385             390

<210> SEQ ID NO 15
<211> LENGTH: 1170
<212> TYPE: DNA
<213> ORGANISM: Clostridium acetobutylicum

<400> SEQUENCE: 15
atgctaagtt ttgattattc aataccaact aaagttttt  ttggaaaagg aaaaatagac      60
gtaattggag aagaaattaa gaaatatggc tcaagagtgc ttatagttta tggcggagga     120
agtataaaaa ggaacggtat atatgataga gcaacagcta tattaaaaga aaacaatata     180
gctttctatg aactttcagg agtagagcca atcctagga taacaacagt aaaaaaaggc     240
atagaaatat gtagagaaaa taatgtggat ttagtattag caataggggg aggaagtgca     300
atagactgtt ctaaggtaat tgcagctgga gtttattatg atggcgatac atgggacatg     360
gttaaagatc catctaaaat aactaaagtt cttccaattg caagtatact tactctttca     420
gcaacagggt ctgaaatgga tcaaattgca gtaatttcaa atatggagac taatgaaaag     480
cttggagtag acatgatga tatgagacct aaattttcag tgttagatcc tacatatact     540
tttacagtac ctaaaaatca acagcagcg ggaacagctg acattatgag tcacaccttt     600
gaatcttact ttagtggtgt tgaaggtgct tatgtgcagg acggtatagc agaagcaatc     660
ttaagaacat gtataaagta tggaaaaata gcaatggaga agactgatga ttacgaggct     720
agagctaatt tgatgtgggc ttcaagttta gctataaatg gtctattatc acttggtaag     780
gatagaaaat ggagttgtca tcctatggaa cacgagttaa gtgcatatta tgatataaca     840
catggtgtag gacttgcaat tttaacacct aattggatgg aatatattct aaatgacgat     900
acacttcata aatttgtttc ttatggaata atgtttggg gaatagacaa gaacaaagat     960
aactatgaaa tagcacgaga ggctattaaa atacgagaa atactttaa ttcattgggt    1020 attccttcaa agcttagaga agttggaata ggaaaagata actagaact aatggcaaag    1080 caagctgtta gaaattctgg aggaacaata ggaagtttaa gaccaataaa tgcagaggat    1140
gttcttgaga tatttaaaaa atcttattaa                                    1170

<210> SEQ ID NO 16
<211> LENGTH: 389
```

```
<212> TYPE: PRT
<213> ORGANISM: Clostridium acetobutylicum

<400> SEQUENCE: 16

Met Leu Ser Phe Asp Tyr Ser Ile Pro Thr Lys Val Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
                35                  40                  45

Asp Arg Ala Thr Ala Ile Leu Lys Glu Asn Asn Ile Ala Phe Tyr Glu
        50                  55                  60

Leu Ser Gly Val Glu Pro Asn Pro Arg Ile Thr Thr Val Lys Lys Gly
65              70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385
```

<210> SEQ ID NO 17
<211> LENGTH: 780
<212> TYPE: DNA
<213> ORGANISM: Klebsiella pneumoniae

<400> SEQUENCE: 17

```
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc      180
ggcacctta atgagctgga cggggagctg atcgccttca gcagtcaggt ctatcagctg      240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa     780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
 1               5                  10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205
```

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 19
<211> LENGTH: 1680
<212> TYPE: DNA
<213> ORGANISM: Klebsiella pneumoniae

<400> SEQUENCE: 19
atggacaaac agtatccggt acgccagtgg gcgcacggcg ccgatctcgt cgtcagtcag      60
ctggaagctc agggagtacg ccaggtgttc ggcatccccg cgccaaaat tgacaaggtc     120
ttcgactcac tgctggattc ctcgattcgc attattccgg tacgccacga agccaacgcc     180
gcgtttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata agcgaagca ggtccaccag     360
agtatggata cggtggcgat gttcagcccg gtcaccaaat acgccgtcga ggtgacggcg     420
ccggatgcgc tggcggaagt ggtctccaac gccttccgcg ccgccgagca gggccggccg     480
ggcagcgcgt tcgttagcct gccgcaggat gtggtcgatg gccggtcag cggcaaagtg     540
ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct cgccgtttg ctggagacca gccatattcc agtcaccagc     720
acctatcagg ccgccggagc ggtgaatcag ataacttct ctcgcttcgc cggccgggtt     780
gggctgttta caaccaggc cggggaccgt ctgctgcagc tcgccgacct ggtgatctgc     840
atcggctaca gcccggtgga atacgaaccg gcgatgtgga acagcggcaa cgcgacgctg     900
gtgcacatcg acgtgctgcc cgcctatgaa gagcgcaact acaccccgga tgtcgagctg     960
gtgggcgata tcgccggcac tctcaacaag ctggcgcaaa atatcgatca tcggctggtg    1020
ctctccccgc aggcggcgga tcctccgc gaccgccagc accagcgcga gctgctggac    1080
cgccgcggcg cgcagctgaa ccagtttgcc ctgcatccgc tgcgcatcgt tcgcgccatg    1140
caggacatcg tcaacagcga cgtcacgttg accgtggaca tgggcagctt ccatatctgg    1200
attgcccgct acctgtacag cttccgcgcc cgtcaggtga tgatctccaa cggccagcag    1260
accatgggcg tcgccctgcc ctgggctatc ggcgcctggc tggtcaatcc tgagcgaaaa    1320
gtggtctccg tctccggcga cggcggcttc ctgcagtcga gcatggagct ggagaccgcc    1380
gtccgcctga agccaacgt actgcacctg atctgggtcg ataacggcta acatatggtg    1440
gccattcagg aagagaaaaa ataccagcgc ctgtccggcg tcgagttcgg ccgatggat    1500
tttaaagcct atgccgaatc cttcggcgcg aaagggtttg ccgtggaaag cgccgaggcg    1560
ctggagccga ccctgcacgc ggcgatggac gtcgacggcc cggcggtggt ggccattccg    1620
gtggattatc gcgataaccc gctgctgatg gccagctgc atctgagtca gattctgtaa    1680

<210> SEQ ID NO 20
<211> LENGTH: 559
<212> TYPE: PRT

-continued

<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
```

```
                            405                 410                 415
Asn Gly Gln Gln Thr Met Gly Val Ala Leu Pro Trp Ala Ile Gly Ala
                420                 425                 430

Trp Leu Val Asn Pro Glu Arg Lys Val Ser Val Ser Gly Asp Gly
        435                 440                 445

Gly Phe Leu Gln Ser Ser Met Glu Leu Glu Thr Ala Val Arg Leu Lys
        450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
                500                 505                 510

Phe Ala Val Glu Ser Ala Glu Ala Leu Glu Pro Thr Leu His Ala Ala
            515                 520                 525

Met Asp Val Asp Gly Pro Ala Val Val Ala Ile Pro Val Asp Tyr Arg
        530                 535                 540

Asp Asn Pro Leu Leu Met Gly Gln Leu His Leu Ser Gln Ile Leu
545                 550                 555

<210> SEQ ID NO 21
<211> LENGTH: 771
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc tgttcccag      420 gccggccacg tcggcaaccc ggagctggcg gtgtatagct ccagtaaatt cgcggtacgc     480
ggcttaaccc agaccgccgc tcgcgacctc gcgccgctgg gcatcaccgt caacggctac     540
tgcccgggga ttgtcaaaac gccaatgtgg gccgaaattg accgccaggt gtccgaagcc     600
gccggtaaac cgctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg tcagtcgtt gctgatcgac ggcgggatgg tatttaacta a               771

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
                20                  25                  30

Asp Tyr Asn Asp Ala Thr Ala Lys Ala Val Ala Ser Glu Ile Asn Gln
        35                  40                  45
```

```
Ala Gly Gly His Ala Val Ala Val Lys Val Asp Val Ser Asp Arg Asp
        50                  55                  60

Gln Val Phe Ala Ala Val Glu Gln Ala Arg Lys Thr Leu Gly Gly Phe
 65                  70                  75                  80

Asp Val Ile Val Asn Asn Ala Gly Val Ala Pro Ser Thr Pro Ile Glu
                 85                  90                  95

Ser Ile Thr Pro Glu Ile Val Asp Lys Val Tyr Asn Ile Asn Val Lys
             100                 105                 110

Gly Val Ile Trp Gly Ile Gln Ala Ala Val Glu Ala Phe Lys Lys Glu
         115                 120                 125

Gly His Gly Gly Lys Ile Ile Asn Ala Cys Ser Gln Ala Gly His Val
     130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 23
<211> LENGTH: 1665
<212> TYPE: DNA
<213> ORGANISM: Klebsiella oxytoca

<400> SEQUENCE: 23
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga aaccggtaag cgattttgac     180
ctgatcgacc actttatcgc cgctacggt atcaacctga accgcgccga agaagtgatg      240
gcgatggatt cggtcaagct ggccaacatg ctgtgcgatc cgaacgttaa acgcagcgaa     300
atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct cctcgcctc gtcctacgcc tctcgcgggc tgaaaatgcg ctttacctcc     780
ggctccggct cggaagtgca gatgggctac gccgaaggca atccatgct ttatctggaa      840 gcgcgctgca tctacatcac caaagccgcg gcgtacagg tctgcaaaa cggttccgta      900 agctgcatcg gcgtgccgtc tgcggtgcct ccggcattc gcgcggtgct ggcggaaaac     960
ctgatctgtt cgtcgctgga tctggagtgc gcctccagca acgaccagac cttcacccac    1020
```

```
tccgatatgc gtcgtaccgc gcgcctgctg atgcagttcc tgccgggcac cgactttatc    1080
tcctccggtt attccgcggt gccgaactac gacaacatgt tcgccggctc caacgaagat    1140
gccgaagact ttgacgacta caacgtcatc cagcgcgacc tgaaggtgga cggcggtttg    1200
cgtccggttc gcgaagagga cgtcatcgcc atccgtaaca aagccgcccg cgcgctgcag    1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                   1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
```

```
                    260                 265                 270
Gly Lys Ser Met Leu Tyr Leu Glu Ala Arg Cys Ile Tyr Ile Thr Lys
        275                 280                 285
Ala Ala Gly Val Gln Gly Leu Gln Asn Gly Ser Val Ser Cys Ile Gly
        290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ala Ser Ser Asn Asp Gln
                325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
        355                 360                 365
Asn Tyr Asp Asn Met Phe Ala Gly Ser Asn Glu Asp Ala Glu Asp Phe
        370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
                405                 410                 415
Arg Ala Leu Gln Ala Val Phe Ala Gly Met Gly Leu Pro Pro Ile Thr
            420                 425                 430
Asp Glu Glu Val Glu Ala Ala Thr Tyr Ala His Gly Ser Lys Asp Met
            435                 440                 445
Pro Glu Arg Asn Ile Val Glu Asp Ile Lys Phe Ala Gln Glu Ile Ile
        450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
Leu Thr Gly Asp Tyr Leu His Thr Ser Ala Ile Ile Val Gly Asp Gly
            500                 505                 510
Gln Val Leu Ser Ala Val Asn Asp Val Asn Asp Tyr Ala Gly Pro Ala
            515                 520                 525
Thr Gly Tyr Arg Leu Gln Gly Glu Arg Trp Glu Glu Ile Lys Asn Ile
        530                 535                 540
Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg cgacggcttc cctgacggaa gtgggcgaag cgtcagggaa acccagcag     180 gacgaagtga ttatcgccgt cggcccggct tccggcctgg cgcagaccgt caatatcgtc     240
ggcatcccgc ataagagcat tttgcgcgaa gtcattgccg gtattgaaga agaaggcatt     300
aaggcgcgcg tgattcgctg ctttaaatcc tccgacgtgg ccttcgtcgc cgttgaaggt     360
aatcgcctga cggctccggg catctctatc ggcatccagt cgaaaggcac acggtgatc     420 caccagcagg ggctgccgcc gctctctaac ctggagctgt tccgcaggc gccgctgctg     480
```

```
acctctggaaa cctatcgcca gatcggcaaa aacgccgccc gctatgcgaa acgcgaatcg      540
ccgcagccgg tcccgacgct gaatgaccag atggcgcggc cgaagtacca ggcgaaatcg      600
gccattttgc acattaaaga gaccaagtac gtggtgacgg caaaaaccc gcaggaactg      660 cgcgtggcgc tttga                                                        675
```

```
<210> SEQ ID NO 26
<211> LENGTH: 224
<212> TYPE: PRT
<213> ORGANISM: Klebsiella oxytoca

<400> SEQUENCE: 26
```

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220

```
<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc gctggcgaa caagcacccg gaatgggtga aaaccgccac caataaaacg     180
ctggacgact ttacgctgga aaacgtgctg agcaataaag tcaccgccca ggatatgcgt     240
attcccccgg aaaccctgcg cttacaggct tctattgcca agacgcggg ccgcgaccgg     300 ctggcgatga acttcgagcg cgccgccgag ctgaccgcgg taccggacga tcgcattctt     360
gaaatctaca cgcccctccg ccccctatcgc tcgacgaaag aggagctgct ggcgatcgcc     420
```

```
gacgatctcg aaagccgcta tcaggcgaag atttgcgccg ctttcgttcg cgaagcggcc    480
acgctgtacg tcgagcgtaa aaaactcaaa ggcgacgatt aa                       522
```

<210> SEQ ID NO 28
<211> LENGTH: 173
<212> TYPE: PRT
<213> ORGANISM: Klebsiella oxytoca

<400> SEQUENCE: 28

```
Met Asn Thr Asp Ala Ile Glu Ser Met Val Arg Asp Val Leu Ser Arg
1               5                   10                  15

Met Asn Ser Leu Gln Gly Glu Ala Pro Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170
```

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc     60
ccggcgcccg gccgggtga gatcctgctg aaggtcaccg cggccggctt gtgccactcg    120
gacatcttcg tgatggacat gccggcagag cagtacatct acggtcttcc cctcacccct    180
ggccacgagg gcgtcggcac cgtcgccgaa ctcggcgccg cgtcaccgg attcgagacg    240 ggggacgccg tcgccgtgta cgggccgtgg ggtgcggtg cgtgccacgc gtgcgcgcgc    300
ggccgggaga actactgcac ccgcgccgcc gagctgggca tcaccccgcc cggtctcggc    360
tcgcccgggt cgatggccga gtacatgatc gtcgactcgg cgcgccacct cgtcccgatc    420
ggggacctcg accccgtcgc ggcggttccg ctcaccgacg cgggcctgac gccgtaccac    480
gcgatctcgc gggtcctgcc cctgctggga cccggctcga ccgcggtcgt catcgggtc    540 ggcggactcg gcacgtcgg catccagatc ctgcgcgccg tcagcgcggc ccgcgtgatc    600
gccgtcgatc tcgacgacga ccgactcgcg ctcgcccgca ggtcggcgc cgacgcggcg    660 gtgaagtcgg cgccggggc ggcggacgcg atccgggagc tgaccggcgg tgagggcgcg    720
acggcggtgt cgacttcgt cggcgcccag tcgacgatcg acacggcgca gcaggtggtc    780
gcgatcgacg ggcacatctc ggtggtcggc atccatgccg gcgcccacgc caaggtcggc    840
```

```
ttcttcatga tcccgttcgg cgcgtccgtc gtgacgccgt actggggcac gcggtccgag    900
ctgatggacg tcgtggacct ggcccgtgcc ggccggctcg acatccacac cgagacgttc    960
accctcgacg agggacccac ggcctaccgg cggctacgcg agggcagcat ccgcggccgc   1020
ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val
1               5                   10                  15

Asp Val Pro Thr Pro Ala Pro Gly Pro Gly Glu Ile Leu Leu Lys Val
                20                  25                  30

Thr Ala Ala Gly Leu Cys His Ser Asp Ile Phe Val Met Asp Met Pro
            35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Val Lys Ser Gly
210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335
```

Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31

| | |
|---|---|
| atggctaact acttcaatac actgaatctg cgccagcagc tggcacagct gggcaaatgt | 60 |
| cgctttatgg gccgcgatga attcgccgat ggcgcgagct accttcaggg taaaaaagta | 120 |
| gtcatcgtcg gctgtggcgc acagggtctg aaccagggcc tgaacatgcg tgattctggt | 180 |
| ctcgatatct cctacgctct gcgtaaagaa gcgattgccg agaagcgcgc gtcctggcgt | 240 |
| aaagcgaccg aaaatggttt taagtgggt acttacgaag aactgatccc acaggcggat | 300 |
| ctggtgatta acctgacgcc ggacaagcag cactctgatg tagtgcgcac cgtacagcca | 360 |
| ctgatgaaag acggcgcggc gctgggctac tcgcacggtt tcaacatcgt cgaagtgggc | 420 |
| gagcagatcc gtaaagatat caccgtagtg atggttgcgc gaaatgcccc aggcaccgaa | 480 |
| gtgcgtgaag agtacaaacg tgggttcggc gtaccgacgc tgattgccgt tcacccggaa | 540 |
| aacgatccga aggcgaagg catggcgatt gccaaagcct gggcggctgc aaccggtggt | 600 |
| caccgtgcgg gtgtgctgga atcgtccttc gttgcggaag tgaaatctga cctgatgggc | 660 |
| gagcaaacca tcctgtgcgg tatgttgcag gctggctctc tgctgtgctt cgacaagctg | 720 |
| gtggaagaag gtaccgatcc agcatacgca gaaaaactga ttcagttcgg ttgggaaacc | 780 |
| atcaccgaag cactgaaaca gggcggcatc accctgatga tggaccgtct ctctaacccg | 840 |
| gcgaaactgc gtgcttatgc gctttctgaa cagctgaaag atcatggc accccctgttc | 900 |
| cagaaacata tggacgacat catctccggc gaattctctt ccggtatgat ggcggactgg | 960 |
| gccaacgatg ataagaaact gctgacctgg cgtgaagaga ccggcaaaac cgcgtttgaa | 1020 |
| accgcgccgc agtatgaagg caaaatcggc gagcaggagt acttcgataa aggcgtactg | 1080 |
| atgattgcga tggtgaaagc gggcgttgaa ctggcgttcg aaaccatggt cgattccggc | 1140 |
| atcattgaag agtctgcata ttatgaatca ctgcacgagc tgccgctgat tgccaacacc | 1200 |
| atcgcccgta agcgtctgta cgaaatgaac gtggttatct ctgataccgc tgagtacggt | 1260 |
| aactatctgt tctcttacgc ttgtgtgccg ttgctgaaac cgtttatggc agagctgcaa | 1320 |
| ccgggcgacc tgggtaaagc tattccggaa ggcgcggtag ataacgggca actgcgtgat | 1380 |
| gtgaacgaag cgattcgcag ccatgcgatt gagcaggtag gtaagaaact gcgcggctat | 1440 |
| atgacagata tgaaacgtat tgctgttgcg ggttaa | 1476 |

<210> SEQ ID NO 32
<211> LENGTH: 491
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Gly Cys Gly Ala Gln
        35                  40                  45

Gly Leu Asn Gln Gly Leu Asn Met Arg Asp Ser Gly Leu Asp Ile Ser
    50                  55                  60

```
Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Gly Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
```

<210> SEQ ID NO 33
<211> LENGTH: 1851
<212> TYPE: DNA
<213> ORGANISM: Escherichia coli

<400> SEQUENCE: 33

| | | | | | |
|---|---|---|---|---|---|
| atgcctaagt | accgttccgc | caccaccact | catggtcgta | atatggcggg | tgctcgtgcg | 60 |
| ctgtggcgcg | ccaccggaat | gaccgacgcc | gatttcggta | agccgattat | cgcggttgtg | 120 |
| aactcgttca | cccaatttgt | accgggtcac | gtccatctgc | gcgatctcgg | taaactggtc | 180 |
| gccgaacaaa | ttgaagcggc | tggcggcgtt | gccaaagagt | caacaccat | tgcggtggat | 240 |
| gatgggattg | ccatgggcca | cggggggatg | ctttattcac | tgccatctcg | cgaactgatc | 300 |
| gctgattccg | ttgagtatat | ggtcaacgcc | cactgcgccg | acgccatggt | ctgcatctct | 360 |
| aactgcgaca | aaatcacccc | gggtgatgctg | atggcttccc | tgcgcctgaa | tattccggtg | 420 |
| atctttgttt | ccggcggccc | gatggaggcc | gggaaaacca | actttccga | tcagatcatc | 480 |
| aagctcgatc | tggttgatgc | gatgatccag | ggcgcagacc | cgaaagtatc | tgactcccag | 540 |
| agcgatcagg | ttgaacgttc | cgcgtgtccg | acctgcggtt | cctgctccgg | atgtttacc | 600 |
| gctaactcaa | tgaactgcct | gaccgaagcg | ctgggcctgt | cgcagccggg | caacggctcg | 660 |
| ctgctggcaa | cccacgccga | ccgtaagcag | ctgttcctta | tgctggtaa | acgcattgtt | 720 |
| gaattgacca | acgttatta | cgagcaaaac | gacgaaagtg | cactgccgcg | taatatcgcc | 780 |
| agtaaggcgg | cgtttgaaaa | cgccatgacg | ctggatatcg | cgatgggtgg | atcgactaac | 840 |
| accgtacttc | acctgctggc | ggcggcgcag | gaagcggaaa | tcgacttcac | catgagtgat | 900 |
| atcgataagc | tttcccgcaa | ggttccacag | ctgtgtaaag | ttgcgccgag | cacccagaaa | 960 |
| taccatatgg | aagatgttca | ccgtgctggt | ggtgttatcg | gtattctcgg | cgaactggat | 1020 |
| cgcgcggggt | tactgaaccg | tgatgtgaaa | aacgtacttg | gcctgacgtt | gccgcaaacg | 1080 |
| ctggaacaat | acgacgttat | gctgacccag | gatgacgcgg | taaaaaatat | gttccgcgca | 1140 |
| ggtcctgcag | gcattcgtac | cacacaggca | ttctcgcaag | attgccgttg | ggatacgctg | 1200 |
| gacgacgatc | gcgccaatgg | ctgtatccgc | tcgctggaac | acgcctacag | caaagacggc | 1260 |
| ggcctggcgg | tgctctacgg | taactttgcg | gaaaacggct | gcatcgtgaa | aacggcaggc | 1320 |
| gtcgatgaca | gcatcctcaa | attcaccggc | ccggcgaaag | tgtacgaaag | ccaggacgat | 1380 |
| gcggtagaag | cgattctcgg | cggtaaagtt | gtcgccggag | atgtggtagt | aattcgctat | 1440 |
| gaaggcccga | aggcggtcc | ggggatgcag | gaaatgctct | acccaaccag | cttcctgaaa | 1500 |
| tcaatgggtc | tcgcaaagc | ctgtgcgctg | atcaccgacg | tcgtttctc | tggtggcacc | 1560 |
| tctggtcttt | ccatcggcca | cgtctcaccg | gaagcggcaa | gcggcggcag | cattggcctg | 1620 |
| attgaagatg | gtgacctgat | cgctatcgac | atcccgaacc | gtggcattca | gttacaggta | 1680 |
| agcgatgccg | aactggcggc | gcgtcgtgaa | gcgcaggacg | ctcgaggtga | caaagcctgg | 1740 |
| acgccgaaaa | atcgtgaacg | tcaggtctcc | tttgccctgc | gtgcttatgc | cagcctggca | 1800 |
| accagcgccg | acaaaggcgc | ggtgcgcgat | aaatcgaaac | tgggggggtta | a | 1851 |

<210> SEQ ID NO 34
<211> LENGTH: 616
<212> TYPE: PRT
<213> ORGANISM: Escherichia coli

<400> SEQUENCE: 34

-continued

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430
```

```
Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Ala Gly Asp Val Val Ile Arg Tyr
465                 470                 475                 480

Glu Gly Pro Lys Gly Pro Gly Met Gln Glu Met Leu Tyr Pro Thr
            485                 490                 495

Ser Phe Leu Lys Ser Met Gly Leu Gly Lys Ala Cys Ala Leu Ile Thr
        500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
        530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
        565                 570                 575

Asp Lys Ala Trp Thr Pro Lys Asn Arg Glu Arg Gln Val Ser Phe Ala
        580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615

<210> SEQ ID NO 35
<211> LENGTH: 1662
<212> TYPE: DNA
<213> ORGANISM: Lactococcus lactis

<400> SEQUENCE: 35
tctagacata tgtatactgt gggggattac ctgctggatc gcctgcacga actggggatt      60
gaagaaattt tcggtgtgcc aggcgattat aacctgcagt tcctggacca gattatctcg     120
cacaaagata tgaagtgggt cggtaacgcc aacgaactga cgcgagcta tatggcagat     180 ggttatgccc gtaccaaaaa agctgctgcg tttctgacga cctttggcgt tggcgaactg     240
agcgccgtca acggactggc aggaagctac gccgagaacc tgccagttgt cgaaattgtt     300
gggtcgccta cttctaaggt tcagaatgaa ggcaaatttg tgcaccatac tctggctgat     360 ggggattta aacattttat gaaatgcat gaaccggtta ctgcggcccg cacgctgctg     420
acagcagaga tgctacggt tgagatcgac gcgtcctgt ctgcgctgct gaaagagcgc     480
aagccggtat atatcaatct gcctgtcgat gttgccgcag cgaaagccga aagccgtcg     540 ctgccactga aaaagaaaa cagcacctcc aatacatcgg accaggaaat tctgaataaa     600
atccaggaat cactgaagaa tgcgaagaaa ccgatcgtca tcaccggaca tgagatcatc     660
tcttttggcc tggaaaaaac ggtcacgcag ttcatttcta agaccaaact gcctatcacc     720
accctgaact tcggcaaatc tagcgtcgat gaagcgctgc cgagttttct gggtatctat     780
aatggtaccc tgtccgaacc gaacctgaaa gaattcgtcg aaagcgcgga ctttatcctg     840
atgctgggcg tgaaactgac ggatagctcc acaggcgcat ttacccacca tctgaacgag     900
aataaaatga tttccctgaa tatcgacgaa ggcaaaatct ttaacgagcg catccagaac     960
ttcgattttg aatctctgat tagttcgctg ctggatctgt ccgaaattga gtataaaggt    1020
aaatatattg ataaaaaaca ggaggatttt gtgccgtcta atgcgctgct gagtcaggat    1080
```

```
cgtctgtggc aagccgtaga aaacctgaca cagtctaatg aaacgattgt tgcggaacag    1140
ggaacttcat ttttcggcgc ctcatccatt tttctgaaat ccaaaagcca tttcattggc    1200
caaccgctgt gggggagtat tggttatacc tttccggcgg cgctgggttc acagattgca    1260
gataaggaat cacgccatct gctgtttatt ggtgacggca gcctgcagct gactgtccag    1320
gaactggggc tggcgatccg tgaaaaaatc aatccgattt gctttatcat caataacgac    1380
ggctacaccg tcgaacgcga aattcatgga ccgaatcaaa gttacaatga catcccgatg    1440
tggaactata gcaaactgcc ggaatccttt ggcgcgacag aggatcgcgt ggtgagtaaa    1500
attgtgcgta cggaaaacga atttgtgtcg gttatgaaag aagcgcaggc tgacccgaat    1560
cgcatgtatt ggattgaact gatcctggca aagaaggcg caccgaaagt tctgaaaaag    1620
atggggaaac tgtttgcgga gcaaaataaa agctaaggat cc                       1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270
```

```
Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 37
<211> LENGTH: 1164
<212> TYPE: DNA
<213> ORGANISM: Escherichia coli

<400> SEQUENCE: 37
atgaacaact ttaatctgca cacccccaacc cgcattctgt ttggtaaagg cgcaatcgct      60
ggtttacgcg aacaaattcc tcacgatgct cgcgtattga ttacctacgg cggcggcagc     120
gtgaaaaaaa ccggcgttct cgatcaagtt ctggatgccc tgaaaggcat ggacgtgctg     180
gaatttggcg gtattgagcc aaacccggct tatgaaacgc tgatgaacgc cgtgaaactg     240
gttcgcgaac agaaagtgac tttcctgctg gcggttggcg gcggttctgt actggacggc     300
accaaattta tcgccgcagc ggctaactat ccggaaaata tcgatccgtg cacattctg     360 caaacgggcg gtaaagagat taaaagcgcc atcccgatgg gctgtgtgct gacgctgcca     420
gcaaccggtt cagaatccaa cgcaggcgcg gtgatctccc gtaaaaccac aggcgacaag     480
caggcgttcc attctgccca tgttcagccg gtatttgccg tgctcgatcc ggtttatacc     540
```

```
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg    1020
acccacctct ccgactacgg tctggacggc agctccatcc cggctttgct gaaaaaactg    1080
gaagagcacg gcatgaccca actgggcgaa atcatgaca ttacgttgga tgtcagccgc    1140
cgtatatacg aagccgcccg ctaa                                            1164
```

<210> SEQ ID NO 38
<211> LENGTH: 387
<212> TYPE: PRT
<213> ORGANISM: Escherichia coli

<400> SEQUENCE: 38

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270
```

```
Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
            290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
            370                 375                 380

Ala Ala Arg
385

<210> SEQ ID NO 39
<211> LENGTH: 1224
<212> TYPE: DNA
<213> ORGANISM: Artificial Sequence
<220> FEATURE:
<223> OTHER INFORMATION: Condon optimized EgTER
<220> FEATURE:
<221> NAME/KEY: CDS
<222> LOCATION: (1)..(1224)

<400> SEQUENCE: 39 atg gcg atg ttt acg acc acc gca aaa gtt att cag ccg aaa att cgt      48
Met Ala Met Phe Thr Thr Thr Ala Lys Val Ile Gln Pro Lys Ile Arg
1               5                   10                  15 ggt ttt att tgc acc acc acc cac ccg att ggt tgc gaa aaa cgt gtt      96
Gly Phe Ile Cys Thr Thr Thr His Pro Ile Gly Cys Glu Lys Arg Val
                20                  25                  30 cag gaa gaa atc gca tac gca cgc gcg cac ccg ccg acc agc ccg ggt     144
Gln Glu Glu Ile Ala Tyr Ala Arg Ala His Pro Pro Thr Ser Pro Gly
            35                  40                  45 ccg aaa cgt gtg ctg gtt att ggc tgc agt acg ggc tat ggc ctg agc     192
Pro Lys Arg Val Leu Val Ile Gly Cys Ser Thr Gly Tyr Gly Leu Ser
        50                  55                  60 acc cgt atc acc gcg gcc ttt ggt tat cag gcc gca acc ctg ggc gtg     240
Thr Arg Ile Thr Ala Ala Phe Gly Tyr Gln Ala Ala Thr Leu Gly Val
65                  70                  75                  80 ttt ctg gca ggc ccg ccg acc aaa ggc cgt ccg gcc gcg gcg ggt tgg     288
Phe Leu Ala Gly Pro Pro Thr Lys Gly Arg Pro Ala Ala Ala Gly Trp
                85                  90                  95 tat aat acg gtt gcg ttc gaa aaa gcc gcc ctg gaa gca ggt ctg tat     336
Tyr Asn Thr Val Ala Phe Glu Lys Ala Ala Leu Glu Ala Gly Leu Tyr
            100                 105                 110 gca cgt tct ctg aat ggt gat gcg ttc gat tct acc acg aaa gcc cgc     384
Ala Arg Ser Leu Asn Gly Asp Ala Phe Asp Ser Thr Thr Lys Ala Arg
        115                 120                 125 acc gtg gaa gca att aaa cgt gat ctg ggt acc gtt gat ctg gtg gtg     432
Thr Val Glu Ala Ile Lys Arg Asp Leu Gly Thr Val Asp Leu Val Val
130                 135                 140 tat agc att gca gcg ccg aaa cgt acc gat ccg gcc acc ggc gtg ctg     480
Tyr Ser Ile Ala Ala Pro Lys Arg Thr Asp Pro Ala Thr Gly Val Leu
145                 150                 155                 160 cat aaa gcg tgc ctg aaa ccg att ggt gca acc tac acc aat cgt acg     528
His Lys Ala Cys Leu Lys Pro Ile Gly Ala Thr Tyr Thr Asn Arg Thr
```

```
                165                 170                 175
gtg aac acc gat aaa gca gaa gtt acc gat gtg agt att gaa ccg gcc      576
Val Asn Thr Asp Lys Ala Glu Val Thr Asp Val Ser Ile Glu Pro Ala
        180                 185                 190 agt ccg gaa gaa atc gca gat acc gtg aaa gtt atg ggt ggc gaa gat      624
Ser Pro Glu Glu Ile Ala Asp Thr Val Lys Val Met Gly Gly Glu Asp
            195                 200                 205 tgg gaa ctg tgg att cag gca ctg agc gaa gcc ggt gtg ctg gcc gaa      672
Trp Glu Leu Trp Ile Gln Ala Leu Ser Glu Ala Gly Val Leu Ala Glu
    210                 215                 220 ggc gca aaa acc gtt gcg tat tct tat att ggc ccg gaa atg acg tgg      720
Gly Ala Lys Thr Val Ala Tyr Ser Tyr Ile Gly Pro Glu Met Thr Trp
225                 230                 235                 240 ccg gtg tat tgg agt ggc acc att ggc gaa gcc aaa aaa gat gtt gaa      768
Pro Val Tyr Trp Ser Gly Thr Ile Gly Glu Ala Lys Lys Asp Val Glu
                245                 250                 255 aaa gcg gcg aaa cgc atc acc cag cag tac ggc tgt ccg gcg tat ccg      816
Lys Ala Ala Lys Arg Ile Thr Gln Gln Tyr Gly Cys Pro Ala Tyr Pro
            260                 265                 270 gtt gtt gcc aaa gcg ctg gtg acc cag gcc agt agc gcc att ccg gtg      864
Val Val Ala Lys Ala Leu Val Thr Gln Ala Ser Ser Ala Ile Pro Val
        275                 280                 285 gtg ccg ctg tat att tgc ctg ctg tat cgt gtt atg aaa gaa aaa ggc      912
Val Pro Leu Tyr Ile Cys Leu Leu Tyr Arg Val Met Lys Glu Lys Gly
    290                 295                 300 acc cat gaa ggc tgc att gaa cag atg gtg cgt ctg ctg acg acg aaa      960
Thr His Glu Gly Cys Ile Glu Gln Met Val Arg Leu Leu Thr Thr Lys
305                 310                 315                 320 ctg tat ccg gaa aat ggt gcg ccg atc gtg gat gaa gcg ggc cgt gtg      1008
Leu Tyr Pro Glu Asn Gly Ala Pro Ile Val Asp Glu Ala Gly Arg Val
                325                 330                 335 cgt gtt gat gat tgg gaa atg gca gaa gat gtt cag cag gca gtt aaa      1056
Arg Val Asp Asp Trp Glu Met Ala Glu Asp Val Gln Gln Ala Val Lys
            340                 345                 350 gat ctg tgg agc cag gtg agt acg gcc aat ctg aaa gat att agc gat      1104
Asp Leu Trp Ser Gln Val Ser Thr Ala Asn Leu Lys Asp Ile Ser Asp
        355                 360                 365 ttt gca ggt tat cag acc gaa ttt ctg cgt ctg ttt ggc ttt ggt att      1152
Phe Ala Gly Tyr Gln Thr Glu Phe Leu Arg Leu Phe Gly Phe Gly Ile
    370                 375                 380 gat ggt gtg gat tac gat cag ccg gtt gat gtt gaa gcg gat ctg ccg      1200
Asp Gly Val Asp Tyr Asp Gln Pro Val Asp Val Glu Ala Asp Leu Pro
385                 390                 395                 400 agc gcc gcc cag cag taa gtc gac                                      1224
Ser Ala Ala Gln Gln     Val Asp
                405

<210> SEQ ID NO 40
<211> LENGTH: 405
<212> TYPE: PRT
<213> ORGANISM: Artificial Sequence
<220> FEATURE:
<223> OTHER INFORMATION: Synthetic Construct

<400> SEQUENCE: 40

Met Ala Met Phe Thr Thr Thr Ala Lys Val Ile Gln Pro Lys Ile Arg
1               5                   10                  15

Gly Phe Ile Cys Thr Thr Thr His Pro Ile Gly Cys Glu Lys Arg Val
            20                  25                  30

Gln Glu Glu Ile Ala Tyr Ala Arg Ala His Pro Pro Thr Pro Ser Pro Gly
        35                  40                  45
```

Pro Lys Arg Val Leu Val Ile Gly Cys Ser Thr Gly Tyr Gly Leu Ser
    50                  55                  60

Thr Arg Ile Thr Ala Ala Phe Gly Tyr Gln Ala Ala Thr Leu Gly Val
65                  70                  75                  80

Phe Leu Ala Gly Pro Pro Thr Lys Gly Arg Pro Ala Ala Ala Gly Trp
                85                  90                  95

Tyr Asn Thr Val Ala Phe Glu Lys Ala Ala Leu Glu Ala Gly Leu Tyr
                100                 105                 110

Ala Arg Ser Leu Asn Gly Asp Ala Phe Asp Ser Thr Thr Lys Ala Arg
            115                 120                 125

Thr Val Glu Ala Ile Lys Arg Asp Leu Gly Thr Val Asp Leu Val Val
130                 135                 140

Tyr Ser Ile Ala Ala Pro Lys Arg Thr Asp Pro Ala Thr Gly Val Leu
145                 150                 155                 160

His Lys Ala Cys Leu Lys Pro Ile Gly Ala Thr Tyr Thr Asn Arg Thr
                165                 170                 175

Val Asn Thr Asp Lys Ala Glu Val Thr Asp Val Ser Ile Glu Pro Ala
                180                 185                 190

Ser Pro Glu Glu Ile Ala Asp Thr Val Lys Val Met Gly Gly Glu Asp
            195                 200                 205

Trp Glu Leu Trp Ile Gln Ala Leu Ser Glu Ala Gly Val Leu Ala Glu
210                 215                 220

Gly Ala Lys Thr Val Ala Tyr Ser Tyr Ile Gly Pro Glu Met Thr Trp
225                 230                 235                 240

Pro Val Tyr Trp Ser Gly Thr Ile Gly Glu Ala Lys Lys Asp Val Glu
                245                 250                 255

Lys Ala Ala Lys Arg Ile Thr Gln Gln Tyr Gly Cys Pro Ala Tyr Pro
            260                 265                 270

Val Val Ala Lys Ala Leu Val Thr Gln Ala Ser Ser Ala Ile Pro Val
                275                 280                 285

Val Pro Leu Tyr Ile Cys Leu Leu Tyr Arg Val Met Lys Glu Lys Gly
            290                 295                 300

Thr His Glu Gly Cys Ile Glu Gln Met Val Arg Leu Leu Thr Thr Lys
305                 310                 315                 320

Leu Tyr Pro Glu Asn Gly Ala Pro Ile Val Asp Glu Ala Gly Arg Val
                325                 330                 335

Arg Val Asp Asp Trp Glu Met Ala Glu Asp Val Gln Gln Ala Val Lys
            340                 345                 350

Asp Leu Trp Ser Gln Val Ser Thr Ala Asn Leu Lys Asp Ile Ser Asp
            355                 360                 365

Phe Ala Gly Tyr Gln Thr Glu Phe Leu Arg Leu Phe Gly Phe Gly Ile
370                 375                 380

Asp Gly Val Asp Tyr Asp Gln Pro Val Asp Val Glu Ala Asp Leu Pro
385                 390                 395                 400

Ser Ala Ala Gln Gln
            405

<210> SEQ ID NO 41
<211> LENGTH: 1476
<212> TYPE: DNA
<213> ORGANISM: Bacillus subtilis

<400> SEQUENCE: 41
atggctaact acttcaatac actgaatctg cgccagcagc tggcacagct gggcaaatgt      60

```
cgctttatgg gccgcgatga attcgccgat ggcgcgagct accttcaggg taaaaaagta    120
gtcatcgtcg gctgtggcgc acagggtctg aaccagggcc tgaacatgcg tgattctggt    180
ctcgatatct cctacgctct gcgtaaagaa gcgattgccg agaagcgcgc gtcctggcgt    240
aaagcgaccg aaaatggttt taaagtgggt acttacgaag aactgatccc acaggcggat    300
ctggtgatta acctgacgcc ggacaagcag cactctgatg tagtgcgcac cgtacagcca    360
ctgatgaaag acggcgcggc gctgggctac tcgcacggtt tcaacatcgt cgaagtgggc    420
gagcagatcc gtaaagatat caccgtagtg atggttgcgc cgaaatgccc aggcaccgaa    480
gtgcgtgaag agtacaaacg tgggttcggc gtaccgacgc tgattgccgt tcacccggaa    540
aacgatccga aggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag agatcatggc accccctgttc    900 cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta gcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                             1476
```

<210> SEQ ID NO 42
<211> LENGTH: 342
<212> TYPE: PRT
<213> ORGANISM: Bacillus subtilis

<400> SEQUENCE: 42

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125
```

```
Pro Lys Gly Pro Gly His Leu Val Arg Arg Thr Tyr Glu Gln Gly Ala
        130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Thr Glu Thr Asp Leu Phe
                180                 185                 190

Gly Glu Gln Ala Val Leu Cys Gly Gly Leu Ser Ala Leu Val Lys Ala
                195                 200                 205

Gly Phe Glu Thr Leu Thr Glu Ala Gly Tyr Gln Pro Glu Leu Ala Tyr
        210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
                260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Glu Ala Val
                325                 330                 335

Val Ser Val Ala Gln Asn
                340

<210> SEQ ID NO 43
<211> LENGTH: 2394
<212> TYPE: DNA
<213> ORGANISM: Shewanella sp.

<400> SEQUENCE: 43
atgaatccga taaacgcaat ctggaaacgt tggctcttag ccatagtatt agcggcctcg      60
ggttgtgcta gcgttgccca ggtggatttc gacagtcttt atggtaaaag ctcgccgcag     120
acgcgggccg acaatcggcc aatccagagt gaactcactt cacaaacaaa ggcttatcac     180
tcgactgttg aacctatcat caacagtcgc tgcgtggttt gccatgcctg ttacgatgcg     240
ccctgccagc ttaaaatgac ttccagtgag gcattgaac ggggcgcgaa caatgaaaaa     300
gtctatcagg gcacccgttt gatggcggca acgccgaatc ggttatttgt cgatgcccac     360
acacctgaag catggcgcga acgcgggttt tatcccgtgc tcaatgagcg cgcccagacc     420
ccgctggcca tacccaggc ctcagtgctg gcgcggatgt taacgctaaa acaggcccat     480
cccctgccgg acactaaaca cctcgataaa agcttcgact ttagcctcga tcgggttcag     540
caatgcgcca gcattgagga aatggacaaa tacgaacaat accaaccgct tgcgggtatg     600
ccctacggct tacctgcgct caatcagcag gaacataagg tattgatgca atggctcgaa     660
cagggcgcag tgttgtcgac gccacccgcg cttagcgccg agttcaatca agaaatcgct     720
cgttgggagc agttcttaaa tgccgacagc ctcaaggcgc aactgagcgc ccgttatatt     780
tacgagcact attttgcctt ccacctgtat tttgagtcat taaccgcggc cgatgctcct     840
gcggcttact tcgagttagt gcgctcacgc acaccgccgg gcaaaccgat tgatctgatt     900
```

-continued

```
gccagccgcc gtcccttcga cgatccgcaa gtgtcgcggg tgtattaccg ctttcagccc    960
tatcacgcca cgatcgtcga taagacccat attccctacg ccttgaataa cactgtgctg   1020
caaaactggc agcagtggtt tatcgacgcc caataccaag tcagctcgct gcccagctat   1080
gcgccgagcg tatcggccaa ccctttcgag gcctttattc aactgcccgc aggctcgcgc   1140
tatcgcttta tgcttacccg cgcccaagac actattatgg gctttatcaa ggggccggtt   1200
tgccgtggtc aggtcgccct caatgtgatc aacgatagat tttgggttta ctttgtcacc   1260
ccagaatata tggacgatag cgactttacc gacttctacc acggccaaat cgagaaccta   1320
cgcatgcctg ctgaggaaga aagcaccgcc cttgccgtga cctgggtgaa atatgccgcc   1380
aaacagggcg agtatatgcg ggcacgaaat cagttttttaa atcataagtt taaaaatggt   1440
cgccacctca ctatcgacgg cctatgggat ggcgacggca acaatgataa tgccagcctg   1500
acggtatttta ggcatttcga taatgccact gtggtgaaag ggttagtggg agaatcccct   1560
aagacggctt gggtgatcga ctatgccctg ctagagcgta ttcactacct tttggtcgcg   1620
ggtttcgatg tgtatggcaa ctatggccac cagctactca cccgcctgta tatggatttt   1680
ttacggatgg agggcgagtc taacttcttg accttattac cccaagagga gcgccgtaag   1740
cagtttaagg attggtatca ggatgcgggc acccagttga ccgcctttat cgcgggggat   1800
attaatacct tcaatcagcc cacgggcgtg ctctactaca cggacgatct aaaagccgaa   1860
ctctaccaaa agttggccgc taaggtcggc gaggttcagc cccaacgcta tcaaatcgca   1920
ctcagtcagt tgcaacctaa cagcaaggca ttgttgcagg cgctaggcag agtcaaaggc   1980
acgcaagcga cccttttgcc cgagctgacg atgatcatga ttgagcctga aaaaacgggc   2040
aaagcggaaa tctttacctt agtacgtaac agtgcccatc gaaatatttc gagcctattc   2100
agtgaggaaa gcaaccgcga tcccgccaag gatgatgtca cgctagtgcg cgggctattg   2160
ggtagttatc ccgaagcctt ctggcatatt aaggagcaag acttagccaa agttgtggct   2220
aaagtcgaag gcatgcaaac cgaaaaagac tacgaggcgt tattggatt  ggcggcagtg   2280
cgccgcaccg atccgcgttt ctgggccttt agtgacaaac ttaaccaagc cttttttcgac   2340
agtcacccga ttgagagcgg ttggctggac tacaatcggc tgcaaaatcg ctaa          2394
```

<210> SEQ ID NO 44
<211> LENGTH: 797
<212> TYPE: PRT
<213> ORGANISM: Shewanella sp.

<400> SEQUENCE: 44

```
Met Asn Pro Ile Asn Ala Ile Trp Lys Arg Trp Leu Leu Ala Ile Val
 1               5                  10                  15
Leu Ala Ala Ser Gly Cys Ala Ser Val Ala Gln Val Asp Phe Asp Ser
             20                  25                  30
Leu Tyr Gly Lys Ser Ser Pro Gln Thr Arg Ala Asp Asn Arg Pro Ile
         35                  40                  45
Gln Ser Glu Leu Thr Ser Gln Thr Lys Ala Tyr His Ser Thr Val Glu
     50                  55                  60
Pro Ile Ile Asn Ser Arg Cys Val Val Cys His Ala Cys Tyr Asp Ala
 65                  70                  75                  80
Pro Cys Gln Leu Lys Met Thr Ser Ser Glu Gly Ile Glu Arg Gly Ala
                 85                  90                  95
Asn Asn Glu Lys Val Tyr Gln Gly Thr Arg Leu Met Ala Ala Thr Pro
            100                 105                 110
Asn Arg Leu Phe Val Asp Ala His Thr Pro Glu Ala Trp Arg Glu Arg
```

-continued

```
            115                 120                 125
Gly Phe Tyr Pro Val Leu Asn Glu Arg Ala Gln Thr Pro Leu Ala Asn
            130                 135                 140
Thr Gln Ala Ser Val Leu Ala Arg Met Leu Thr Leu Lys Gln Ala His
145                 150                 155                 160
Pro Leu Pro Asp Thr Lys His Leu Asp Lys Ser Phe Asp Phe Ser Leu
                165                 170                 175
Asp Arg Val Gln Gln Cys Ala Ser Ile Glu Glu Met Asp Lys Tyr Glu
            180                 185                 190
Gln Tyr Gln Pro Leu Ala Gly Met Pro Tyr Gly Leu Pro Ala Leu Asn
            195                 200                 205
Gln Gln Glu His Lys Val Leu Met Gln Trp Leu Glu Gln Gly Ala Val
            210                 215                 220
Leu Ser Thr Pro Pro Ala Leu Ser Ala Glu Phe Asn Gln Glu Ile Ala
225                 230                 235                 240
Arg Trp Glu Gln Phe Leu Asn Ala Asp Ser Leu Lys Ala Gln Leu Ser
                245                 250                 255
Ala Arg Tyr Ile Tyr Glu His Leu Phe Ala Phe His Leu Tyr Phe Glu
            260                 265                 270
Ser Leu Thr Ala Ala Asp Ala Pro Ala Ala Tyr Phe Glu Leu Val Arg
            275                 280                 285
Ser Arg Thr Pro Pro Gly Lys Pro Ile Asp Leu Ile Ala Ser Arg Arg
            290                 295                 300
Pro Phe Asp Asp Pro Gln Val Ser Arg Val Tyr Tyr Arg Phe Gln Pro
305                 310                 315                 320
Tyr His Ala Thr Ile Val Asp Lys Thr His Ile Pro Tyr Ala Leu Asn
                325                 330                 335
Asn Thr Val Leu Gln Asn Trp Gln Gln Trp Phe Ile Asp Ala Gln Tyr
            340                 345                 350
Gln Val Ser Ser Leu Pro Ser Tyr Ala Pro Ser Val Ser Ala Asn Pro
            355                 360                 365
Phe Glu Ala Phe Ile Gln Leu Pro Ala Gly Ser Arg Tyr Arg Phe Met
            370                 375                 380
Leu Thr Arg Ala Gln Asp Thr Ile Met Gly Phe Ile Lys Gly Pro Val
385                 390                 395                 400
Cys Arg Gly Gln Val Ala Leu Asn Val Ile Asn Asp Arg Phe Trp Val
                405                 410                 415
Tyr Phe Val Thr Pro Glu Tyr Met Asp Asp Ser Asp Phe Thr Asp Phe
            420                 425                 430
Tyr His Gly Gln Ile Glu Asn Leu Arg Met Pro Ala Glu Glu Glu Ser
            435                 440                 445
Thr Ala Leu Ala Val Thr Trp Val Lys Tyr Ala Ala Lys Gln Gly Glu
450                 455                 460
Tyr Met Arg Ala Arg Asn Gln Phe Leu Asn His Lys Phe Lys Asn Gly
465                 470                 475                 480
Arg His Leu Thr Ile Asp Gly Leu Trp Asp Gly Asp Gly Asn Asn Asp
                485                 490                 495
Asn Ala Ser Leu Thr Val Phe Arg His Phe Asp Asn Ala Thr Val Val
            500                 505                 510
Lys Gly Leu Val Gly Glu Ser Pro Lys Thr Ala Trp Val Ile Asp Tyr
            515                 520                 525
Ala Leu Leu Glu Arg Ile His Tyr Leu Leu Val Ala Gly Phe Asp Val
            530                 535                 540
```

| | | | | | | | | | | | | | | |
|---|---|---|---|---|---|---|---|---|---|---|---|---|---|---|
| Tyr | Gly | Asn | Tyr | Gly | His | Gln | Leu | Leu | Thr | Arg | Leu | Tyr | Met | Asp | Phe |
| 545 | | | | 550 | | | | | 555 | | | | | 560 |

Tyr Gly Asn Tyr Gly His Gln Leu Leu Thr Arg Leu Tyr Met Asp Phe
545                 550                 555                 560

Leu Arg Met Glu Gly Glu Ser Asn Phe Leu Thr Leu Pro Gln Glu
            565                 570                 575

Glu Arg Arg Lys Gln Phe Lys Asp Trp Tyr Gln Asp Ala Gly Thr Gln
        580                 585                 590

Leu Thr Ala Phe Ile Ala Gly Asp Ile Asn Thr Phe Asn Gln Pro Thr
        595                 600                 605

Gly Val Leu Tyr Tyr Thr Asp Asp Leu Lys Ala Glu Leu Tyr Gln Lys
        610                 615                 620

Leu Ala Ala Lys Val Gly Glu Val Gln Pro Gln Arg Tyr Gln Ile Ala
625                 630                 635                 640

Leu Ser Gln Leu Gln Pro Asn Ser Lys Ala Leu Leu Gln Ala Leu Gly
            645                 650                 655

Arg Val Lys Gly Thr Gln Ala Thr Leu Leu Pro Glu Leu Thr Met Ile
            660                 665                 670

Met Ile Glu Pro Glu Lys Thr Gly Lys Ala Glu Ile Phe Thr Leu Val
        675                 680                 685

Arg Asn Ser Ala His Arg Asn Ile Ser Ser Leu Phe Ser Glu Glu Ser
        690                 695                 700

Asn Arg Asp Pro Ala Lys Asp Asp Val Thr Leu Val Arg Gly Leu Leu
705                 710                 715                 720

Gly Ser Tyr Pro Glu Ala Phe Trp His Ile Lys Glu Gln Asp Leu Ala
            725                 730                 735

Lys Val Val Ala Lys Val Glu Gly Met Gln Thr Glu Lys Asp Tyr Glu
            740                 745                 750

Ala Leu Leu Asp Leu Ala Ala Val Arg Arg Thr Asp Pro Arg Phe Trp
        755                 760                 765

Ala Phe Ser Asp Lys Leu Asn Gln Ala Phe Phe Asp Ser His Pro Ile
        770                 775                 780

Glu Ser Gly Trp Leu Asp Tyr Asn Arg Leu Gln Asn Arg
785                 790                 795

<210> SEQ ID NO 45
<211> LENGTH: 2394
<212> TYPE: DNA
<213> ORGANISM: Shewanella sp.

<400> SEQUENCE: 45

```
atgaatccga taaacgcaat ctggaaacgt tggctcttag ccatagtatt agctgcctcg    60
ggttgtgcta gcgttgccca ggtggatttc gacagtcttt atggtaaaag ctcgccgcag   120
acgcgggccg acaatcggcc aatccagagt gaactcactt cacaaacaaa ggcttatcac   180
tcgactgttg aacctatcat caacagtcgc tgcgtagttt gccatgcctg ttacgatgcg   240
ccctgccagc tcaaaatgac tccagtgaa ggcatcgaac ggggtgctaa taaggaaaaa    300
gtctatcagg gcaccgcctt ggtggcggca acgccaaatc ggttatttgt cgatgctcac   360
acgcctgcag catggcggga acgcggtttt tatcccgtgc tgaatgagcg cgcccagacc   420
ccacaggcta atacccaggc ctcagtgctg gcgcggatgc taacgctaaa acaggcccat   480
cccctgccgg acactaaact gctcgataag agttttgact ttagcctcga tcgggttcag   540
caatgcgcca gcattgagga aatggacaaa tacgaacaat accaaccgct tgcgggcatg   600
ccctacggct tgcctgcgct caatcagcag gaacataaag tattgatgca atggctcgaa   660
cagggtgcag tgttgccgac gccacctgcg ctcagcgccg agtttaatca agaaatcgcc   720
```

```
cgctgggagc agttcttaaa tgccgacagc ctcaaggcgc aactgagcgc ccgttatatt    780
tacgagcact tatttgcctt ccacctgtat tttgagtcat taaccgcggc cgatgctcct    840
gcggcttact ttgagttagt gcgctcacgc acaccgccgg gcaaaccgat tgatcagatt    900
gccagccgcc gccccttcga cgatccgcaa gtgtcgcggg tgtattaccg ctttcagccc    960
tatcacgcca cgatcgtcga taagacccat attccctacg ccttgaataa cgctgtgctg   1020
caaaactggc agcagtggtt tattgatgcc aagtaccaag tcagctcgct gccaagctat   1080
gcgccgagcg tatcggccaa ccccttcgag gcctttattc aactgcccgc tggctcgcgt   1140
tatcgcttta tgcttacccg cgcccaagac actattatgg gctttatcaa ggggccggtt   1200
tgccgtggtc aggtcgccct caatgtgatc aacgatagat tttgggttta ctttgtcacc   1260
ccagaatata tggacgacag cgactttact gacttctatc agggccaaat cgagaaccta   1320
cgtatgcccg ccgaggaaga aagcaccgcc cttgccgtga cctgggtgaa atacgccgcc   1380
aaacagggcg agtatatgcg ggcgcgaaat cagttttaa atcataagtt taaaaatggt   1440
cgccacctta ctatcgatgg cctatgggat ggcgacggca acaatgataa tgccagcctg   1500
acagtattta ggcatttcga taatgccact gtggtcaaag ggttagtggg agaatctccc   1560
aagacggctt gggtgatcga ctatgccctg ctggagcgca ttcactacct cctagtcgcg   1620
ggtttcgatg tgtatggcaa ctacggccac cagctactca cccgcctgta tatggatttt   1680
ttacggatgg agggcgagtc taacttcttg accttgttgc cccaagagga gcgccgtaag   1740
cagtttaaag actggtatca ggatgcgggc acccagctaa ccgcctttat tgcgggggac   1800
attaatacct tcaatcaacc cacgggcgta ctctactaca cggacgatct taaggccgaa   1860
ctctatcaaa aattggccgc taaggtcggc gaggttcagc cccaacgcta tcaaatcgca   1920
ctcagtcagt tgcaacctaa cagcaaggca ttgttgcagg cgctaggcag agtcaaaggc   1980
acgcaagcga ccccttttgcc cgagctgacg atgatcatga ttgagcctga aaaaacgggc   2040
aaagcggaaa tctttacctt agtacgtaac agtgcccatc gaaatatttc gagcctattc   2100
aatgaggaaa gcaaccgcga tcccaccaag gatgatgtca cgctagtgcg cggacttttg   2160
ggcagttatc ccgaagcctt ctggcatatt aaggaacaag acttagccaa agtcgtggct   2220
aaggtcgaag gcatgcaaac cgaaaaagac tacgaggcgt tattggattt agcggcagtg   2280
cgccgtaccg atccgcgttt ctgggccttt agtgacaaac taaccaagc cttttcgac    2340 agtcacccga ttgagagcgg ttggctggac tacaatcgac tgcaaaatcg ctaa         2394
```

<210> SEQ ID NO 46
<211> LENGTH: 797
<212> TYPE: PRT
<213> ORGANISM: Shewanella sp.

<400> SEQUENCE: 46

```
Met Asn Pro Ile Asn Ala Ile Trp Lys Arg Trp Leu Leu Ala Ile Val
1               5                   10                  15

Leu Ala Ala Ser Gly Cys Ala Ser Val Ala Gln Val Asp Phe Asp Ser
                20                  25                  30

Leu Tyr Gly Lys Ser Ser Pro Gln Thr Arg Ala Asp Asn Arg Pro Ile
            35                  40                  45

Gln Ser Glu Leu Thr Ser Gln Thr Lys Ala Tyr His Ser Thr Val Glu
        50                  55                  60

Pro Ile Ile Asn Ser Arg Cys Val Val Cys His Ala Cys Tyr Asp Ala
65                  70                  75                  80

Pro Cys Gln Leu Lys Met Thr Ser Ser Glu Gly Ile Glu Arg Gly Ala
```

-continued

```
                85                  90                  95
Asn Lys Glu Lys Val Tyr Gln Gly Thr Arg Leu Val Ala Ala Thr Pro
                100                 105                 110

Asn Arg Leu Phe Val Asp Ala His Thr Pro Ala Ala Trp Arg Glu Arg
            115                 120                 125

Gly Phe Tyr Pro Val Leu Asn Glu Arg Ala Gln Thr Pro Gln Ala Asn
        130                 135                 140

Thr Gln Ala Ser Val Leu Ala Arg Met Leu Thr Leu Lys Gln Ala His
145                 150                 155                 160

Pro Leu Pro Asp Thr Lys Leu Leu Asp Lys Ser Phe Asp Phe Ser Leu
                165                 170                 175

Asp Arg Val Gln Gln Cys Ala Ser Ile Glu Glu Met Asp Lys Tyr Glu
                180                 185                 190

Gln Tyr Gln Pro Leu Ala Gly Met Pro Tyr Gly Leu Pro Ala Leu Asn
        195                 200                 205

Gln Gln Glu His Lys Val Leu Met Gln Trp Leu Glu Gln Gly Ala Val
        210                 215                 220

Leu Pro Thr Pro Pro Ala Leu Ser Ala Glu Phe Asn Gln Glu Ile Ala
225                 230                 235                 240

Arg Trp Glu Gln Phe Leu Asn Ala Asp Ser Leu Lys Ala Gln Leu Ser
                245                 250                 255

Ala Arg Tyr Ile Tyr Glu His Leu Phe Ala Phe His Leu Tyr Phe Glu
                260                 265                 270

Ser Leu Thr Ala Ala Asp Ala Pro Ala Ala Tyr Phe Glu Leu Val Arg
        275                 280                 285

Ser Arg Thr Pro Pro Gly Lys Pro Ile Asp Gln Ile Ala Ser Arg Arg
        290                 295                 300

Pro Phe Asp Asp Pro Gln Val Ser Arg Val Tyr Tyr Arg Phe Gln Pro
305                 310                 315                 320

Tyr His Ala Thr Ile Val Asp Lys Thr His Ile Pro Tyr Ala Leu Asn
                325                 330                 335

Asn Ala Val Leu Gln Asn Trp Gln Gln Trp Phe Ile Asp Ala Lys Tyr
                340                 345                 350

Gln Val Ser Ser Leu Pro Ser Tyr Ala Pro Ser Val Ser Ala Asn Pro
        355                 360                 365

Phe Glu Ala Phe Ile Gln Leu Pro Ala Gly Ser Arg Tyr Arg Phe Met
        370                 375                 380

Leu Thr Arg Ala Gln Asp Thr Ile Met Gly Phe Ile Lys Gly Pro Val
385                 390                 395                 400

Cys Arg Gly Gln Val Ala Leu Asn Val Ile Asn Asp Arg Phe Trp Val
                405                 410                 415

Tyr Phe Val Thr Pro Glu Tyr Met Asp Asp Ser Asp Phe Thr Asp Phe
                420                 425                 430

Tyr Gln Gly Gln Ile Glu Asn Leu Arg Met Pro Ala Glu Glu Ser
        435                 440                 445

Thr Ala Leu Ala Val Thr Trp Val Lys Tyr Ala Ala Lys Gln Gly Glu
        450                 455                 460

Tyr Met Arg Ala Arg Asn Gln Phe Leu Asn His Lys Phe Lys Asn Gly
465                 470                 475                 480

Arg His Leu Thr Ile Asp Gly Leu Trp Asp Gly Asp Gly Asn Asn Asp
                485                 490                 495

Asn Ala Ser Leu Thr Val Phe Arg His Phe Asp Asn Ala Thr Val Val
                500                 505                 510
```

```
Lys Gly Leu Val Gly Glu Ser Pro Lys Thr Ala Trp Val Ile Asp Tyr
            515                 520                 525

Ala Leu Leu Glu Arg Ile His Tyr Leu Leu Val Ala Gly Phe Asp Val
        530                 535                 540

Tyr Gly Asn Tyr Gly His Gln Leu Leu Thr Arg Leu Tyr Met Asp Phe
545                 550                 555                 560

Leu Arg Met Glu Gly Glu Ser Asn Phe Leu Thr Leu Leu Pro Gln Glu
            565                 570                 575

Glu Arg Arg Lys Gln Phe Lys Asp Trp Tyr Gln Asp Ala Gly Thr Gln
        580                 585                 590

Leu Thr Ala Phe Ile Ala Gly Asp Ile Asn Thr Phe Asn Gln Pro Thr
            595                 600                 605

Gly Val Leu Tyr Tyr Thr Asp Asp Leu Lys Ala Glu Leu Tyr Gln Lys
610                 615                 620

Leu Ala Ala Lys Val Gly Glu Val Gln Pro Gln Arg Tyr Gln Ile Ala
625                 630                 635                 640

Leu Ser Gln Leu Gln Pro Asn Ser Lys Ala Leu Leu Gln Ala Leu Gly
            645                 650                 655

Arg Val Lys Gly Thr Gln Ala Thr Leu Leu Pro Glu Leu Thr Met Ile
        660                 665                 670

Met Ile Glu Pro Glu Lys Thr Gly Lys Ala Glu Ile Phe Thr Leu Val
            675                 680                 685

Arg Asn Ser Ala His Arg Asn Ile Ser Ser Leu Phe Asn Glu Glu Ser
        690                 695                 700

Asn Arg Asp Pro Thr Lys Asp Asp Val Thr Leu Val Arg Gly Leu Leu
705                 710                 715                 720

Gly Ser Tyr Pro Glu Ala Phe Trp His Ile Lys Glu Gln Asp Leu Ala
            725                 730                 735

Lys Val Val Ala Lys Val Glu Gly Met Gln Thr Glu Lys Asp Tyr Glu
        740                 745                 750

Ala Leu Leu Asp Leu Ala Ala Val Arg Arg Thr Asp Pro Arg Phe Trp
            755                 760                 765

Ala Phe Ser Asp Lys Leu Asn Gln Ala Phe Phe Asp Ser His Pro Ile
        770                 775                 780

Glu Ser Gly Trp Leu Asp Tyr Asn Arg Leu Gln Asn Arg
785                 790                 795

<210> SEQ ID NO 47
<211> LENGTH: 2355
<212> TYPE: DNA
<213> ORGANISM: Vibrio vulnificus

<400> SEQUENCE: 47
atgaaattta gaacatttct aatactagca gtagtcacac ttttttgcagg ttgtgccacc       60 tatgctgggc tcaactatga tcagctgttt ggcgaggccg aagtccgcga ccgaaccgag      120
cacattcaat cggctcaaag tgcgtttttt atgcacgatg tcaagcccat catcgaaaac      180
cgatgtgtgg tttgtcacgc ttgctacgac gcgccatgtc aactcaagct ctcttccgta      240
gaaggtattg accgtggcgc aagcaagacg cttgtttatc aagggactcg tctcacagcc      300
acagcaccca cacgcttatt tgaagatgca caaccaccc aagagtggcg tgatgcgggc      360
tttcaccctg tgctcaacga gcgtgcccaa accggtgttg ccaacattga tgccggcttg      420
attgcgagat gctgcaaca gaaggagcgt catcctcttc ctcaacagga ccaacttgaa      480
ggatttgatt tttcgattga tcgcgaacaa acctgtccga cgattgaaga atttgatcag      540
```

```
tacgagcgta ccaatccaag ctggggaatg cccttggta tgccaaatct ttcggccaaa      600
gaacaccaaa cactcatggc ttggttagag aatggcgcga tcatgaacga tcacctcccg      660
ctcactcgtg agcaggcagc agagatcacg cgatacgaac aaatgttcaa taagagttca      720
cgcaaaaacc agcttgctgc acgttatatc tacgagcatc ttttttatc gcatctctat      780 ttctctgagt tagaggggga acctcgcttc tttactatgg ttcgttcgtc cacccccacca      840 ggcgaacccg tacagcgcat tgttactcgt cgcccctacg atgatcccggg tgtagaacgt      900 gtttactatc gaatccttcc cgagcaaggc actatagttg ataagacaca catgccttt      960 gctctcaata gccagcgaat gaaggattgg aaagcgtggt ttattgacgc agattacgtc     1020
gtcgaacagt tgccaagtta cgatcctgag attgccgcca acccaatgag cgcttttatt     1080
gacctcccag tgaaagcacg ctttaaattc atgctagata cgcacaaaa caccattatg     1140 gcttacataa agggaccagt gtgccgcggc cagttggcgc tgaatgtgat taacgatcgt     1200
ttctgggttt tcttcctcga tcctgacaaa gcggatattc ctgaagttaa tgagttttat     1260
cgctcacaag ccgataatct aaaactaccg ggcgaactcg aaagtaacac cctaccagtc     1320
accaattggg tcaaatattc cgcccaacaa gctcgctatt tagaagcgaa atcggagttc     1380
attaaccatt ggttaaaaa tggtacgcat ctcaccaccg agatcatatg ggatggcaat     1440
ggcactaacc ccaatgccgc gttaaccgtg ttccgtcact tgatagtgc ctcggttgta     1500 cagggattgg tgggtgagaa gcccaaaacg gcctgggttc tcgattacgc cttgctagag     1560
cgcatccact acttgttagt ggcaggtttt gatgtgtatg caactttgg ccatcagttg     1620 atcactcgca tgtttatgga tttcttcgt ttagaaggtg aaagtaactt catcgccttg     1680
ttacccgcgg atatgcgcca ccaagagcaa tccagctggt atcaacagca aaaccgccaa     1740
ctgagcgatt tcttgcagcg caatgtggtg ccctttagcc aaccgactag cgttgtatat     1800
aaaaccgatg atcccaagtc tgagctgttt gacatattac gccgtcaagt gagcccaatc     1860
ctgaattcgc gctatgagat tgtcgatact ggcatgagcc tgaaaaacga agcattgctg     1920
aagtcattga atttggtaaa aggtgaaaag ctgttgccta tcccgcaaat tactatgttg     1980
atggtcaaag cagactctgg aaaagagcag ctttatacac tgctgcataa caatgcacat     2040
ttgaacatct caagtttgtt taacgaagag aaaaatcgtg acccagcgaa tgacgacctc     2100
accatagtgc gcggcgttgt cggaagctac cctgcgcgt tcttctcgtt gaacgaaaac     2160
caagtagccg aattcgttca aatcattact tcaatggaat ctgagcaaga ctacgttaag     2220
ttattggata agtttgcgat tcgtcgtagc tcaaccaatt tctggtcgtt tagcgacaaa     2280
gttcatactt ggtatcgcaa cgatcaacct atcgaatttg gattgcttga ctataatcgt     2340
tttgagaacc gatag                                                    2355
```

<210> SEQ ID NO 48
<211> LENGTH: 784
<212> TYPE: PRT
<213> ORGANISM: Vibrio vulnificus

<400> SEQUENCE: 48

Met Lys Phe Arg Thr Phe Leu Ile Leu Ala Val Val Thr Leu Phe Ala
1               5                   10                  15

Gly Cys Ala Thr Tyr Ala Gly Leu Asn Tyr Asp Gln Leu Phe Gly Glu
            20                  25                  30

Ala Glu Val Arg Asp Arg Thr Glu His Ile Gln Ser Ala Gln Ser Ala
        35                  40                  45

Phe Phe Met His Asp Val Lys Pro Ile Ile Glu Asn Arg Cys Val Val

```
             50                  55                  60
Cys His Ala Cys Tyr Asp Ala Pro Cys Gln Leu Lys Leu Ser Ser Val
 65                  70                  75                  80

Glu Gly Ile Asp Arg Gly Ala Ser Lys Thr Leu Val Tyr Gln Gly Thr
                 85                  90                  95

Arg Leu Thr Ala Thr Ala Pro Thr Arg Leu Phe Glu Asp Ala Gln Thr
                100                 105                 110

Thr Gln Glu Trp Arg Asp Ala Gly Phe His Pro Val Leu Asn Glu Arg
            115                 120                 125

Ala Gln Thr Gly Val Ala Asn Ile Asp Ala Gly Leu Ile Ala Arg Leu
        130                 135                 140

Leu Gln Gln Lys Glu Arg His Pro Leu Pro Gln Gln Asp Gln Leu Glu
145                 150                 155                 160

Gly Phe Asp Phe Ser Ile Asp Arg Glu Gln Thr Cys Pro Thr Ile Glu
                165                 170                 175

Glu Phe Asp Gln Tyr Glu Arg Thr Asn Pro Ser Trp Gly Met Pro Phe
            180                 185                 190

Gly Met Pro Asn Leu Ser Ala Lys Glu His Gln Thr Leu Met Ala Trp
        195                 200                 205

Leu Glu Asn Gly Ala Ile Met Asn Asp His Leu Pro Leu Thr Arg Glu
210                 215                 220

Gln Ala Ala Glu Ile Thr Arg Tyr Glu Gln Met Phe Asn Lys Ser Ser
225                 230                 235                 240

Arg Lys Asn Gln Leu Ala Ala Arg Tyr Ile Tyr Glu His Leu Phe Leu
                245                 250                 255

Ser His Leu Tyr Phe Ser Glu Leu Glu Gly Glu Pro Arg Phe Phe Thr
            260                 265                 270

Met Val Arg Ser Ser Thr Pro Pro Gly Glu Pro Val Gln Arg Ile Val
        275                 280                 285

Thr Arg Arg Pro Tyr Asp Asp Pro Gly Val Glu Arg Val Tyr Tyr Arg
    290                 295                 300

Ile Leu Pro Glu Gln Gly Thr Ile Val Asp Lys Thr His Met Pro Phe
305                 310                 315                 320

Ala Leu Asn Ser Gln Arg Met Lys Asp Trp Lys Ala Trp Phe Ile Asp
                325                 330                 335

Ala Asp Tyr Val Val Glu Gln Leu Pro Ser Tyr Asp Pro Glu Ile Ala
            340                 345                 350

Ala Asn Pro Met Ser Ala Phe Ile Asp Leu Pro Val Lys Ala Arg Phe
        355                 360                 365

Lys Phe Met Leu Asp Asn Ala Gln Asn Thr Ile Met Ala Tyr Ile Lys
    370                 375                 380

Gly Pro Val Cys Arg Gly Gln Leu Ala Leu Asn Val Ile Asn Asp Arg
385                 390                 395                 400

Phe Trp Val Phe Phe Leu Asp Pro Asp Lys Ala Asp Ile Pro Glu Val
                405                 410                 415

Asn Glu Phe Tyr Arg Ser Gln Ala Asp Asn Leu Lys Leu Pro Gly Glu
            420                 425                 430

Leu Glu Ser Asn Thr Leu Pro Val Thr Asn Trp Val Lys Tyr Ser Ala
        435                 440                 445

Gln Gln Ala Arg Tyr Leu Glu Ala Lys Ser Glu Phe Ile Asn His Trp
    450                 455                 460

Phe Lys Asn Gly Thr His Leu Thr Thr Glu Ile Ile Trp Asp Gly Asn
465                 470                 475                 480
```

-continued

```
Gly Thr Asn Pro Asn Ala Ala Leu Thr Val Phe Arg His Phe Asp Ser
            485                 490                 495

Ala Ser Val Val Gln Gly Leu Val Gly Glu Lys Pro Lys Thr Ala Trp
        500                 505                 510

Val Leu Asp Tyr Ala Leu Leu Glu Arg Ile His Tyr Leu Leu Val Ala
    515                 520                 525

Gly Phe Asp Val Tyr Gly Asn Phe Gly His Gln Leu Ile Thr Arg Met
530                 535                 540

Phe Met Asp Phe Leu Arg Leu Glu Gly Glu Ser Asn Phe Ile Ala Leu
545                 550                 555                 560

Leu Pro Ala Asp Met Arg His Gln Glu Gln Ser Ser Trp Tyr Gln Gln
                565                 570                 575

Gln Asn Arg Gln Leu Ser Asp Phe Leu Gln Arg Asn Val Val Pro Phe
            580                 585                 590

Ser Gln Pro Thr Ser Val Val Tyr Lys Thr Asp Pro Lys Ser Glu
        595                 600                 605

Leu Phe Asp Ile Leu Arg Arg Gln Val Ser Pro Ile Leu Asn Ser Arg
    610                 615                 620

Tyr Glu Ile Val Asp Thr Gly Met Ser Leu Lys Asn Glu Ala Leu Leu
625                 630                 635                 640

Lys Ser Leu Asn Leu Val Lys Gly Glu Lys Leu Leu Pro Ile Pro Gln
                645                 650                 655

Ile Thr Met Leu Met Val Lys Ala Asp Ser Gly Lys Glu Gln Leu Tyr
            660                 665                 670

Thr Leu Leu His Asn Asn Ala His Leu Asn Ile Ser Ser Leu Phe Asn
        675                 680                 685

Glu Glu Lys Asn Arg Asp Pro Ala Asn Asp Asp Leu Thr Ile Val Arg
    690                 695                 700

Gly Val Val Gly Ser Tyr Pro Ala Ala Phe Phe Ser Leu Asn Glu Asn
705                 710                 715                 720

Gln Val Ala Glu Phe Val Gln Ile Ile Thr Ser Met Glu Ser Glu Gln
                725                 730                 735

Asp Tyr Val Lys Leu Leu Asp Lys Phe Ala Ile Arg Arg Ser Ser Thr
            740                 745                 750

Asn Phe Trp Ser Phe Ser Asp Lys Val His Thr Trp Tyr Arg Asn Asp
        755                 760                 765

Gln Pro Ile Glu Phe Gly Leu Leu Asp Tyr Asn Arg Phe Glu Asn Arg
    770                 775                 780
```

<210> SEQ ID NO 49
<211> LENGTH: 2325
<212> TYPE: DNA
<213> ORGANISM: Colwellia psychrerythraea

<400> SEQUENCE: 49

```
atggaattcg acaagcttta tggtccaagc aatgttgaaa atagattagt tcaagttaaa      60
gcgactacag cagaagccat tcattttaat agacagatac aaccaattat tgaaaaccgc     120
tgtgttgttt gtcacggctg ttacgatgcc ccttgccagt tgaaaatgga agtcgcgca      180 ggtattgagc gtggtgctaa taaagcaatg gtttataatg gtgagcgctt acttactgca     240
aatattagtg caagccttac aaaattaact gaactgaaac gagataactt agagccactt     300
cgccaacaag gctatttccc agtacttaat gagcgccagc aaacagagca agccaatact     360
caatccagct gtttctatca aatgttacaa ctcaaaaagc aacatccttt acccagtgag     420
ccaatactta tgagagtttt gatgtcgca ctcgatagaa gtcaacaatg cccaacaata     480
```

```
gaagagtttg agcaatataa ggataagtac cctcttggtg gtatgcctta tgcgctaccg    540
gcactctcaa caactgagca tgatcaatta actgattgga tagcccgtgg tgccataatg    600
ccagattcgg tgcctcccaa tgctaaagaa caacaaatga tcaatcgctg ggaaaagtta    660
cttaatggca gctctgctaa agaacagttg attgcccgtt atttatttga acacttatat    720
ttagccaatt tatacttcga taaagcacaa tctagttact ttaaacttgt tcgttcaagc    780
agccctagtg gtgaaaaagt agcggtgatt actactcgtc gtcccttga ttcccttat     840
gctgatggca gcactgatgc cattgtcgat aaacctcaag tgtactatcg attaattaag   900
cacaacgaca ccattattgc caagcgccat atgccctacc cgtttggtga agtaaattg    960
gcgcgtattt cagaactttt ctatcaacct gattacccag taactacttt gcctgattac  1020
caattagcaa acgcctctaa tcccttaag  acctttcagg cgatccccga taaagcacgc   1080
tatcagtttt tattagacca agcgcaattc tctattatga actttatcaa aggccctgtt  1140
tgtcgtggtc aaatcgcgct gaatgtgatt gaagacaatt tttgggtgtt tttcctcagc  1200
cctaataatt ttgatcatta ccctagcgaa caattcatta aagccaatac agagttatta  1260
caattaccgg ctggcaccag tgataaatcc ctatcattac tttactggcg acaatatgct  1320
aaaagccagc aagaatacgt taaaaataaa ttagcttatg tggaagggct taacttgcag  1380
cctaatcagc taaaccttga tttgatttgg tcaggcaaag gaaacccaaa cgccagccta  1440
accgtcttca gacactttga cagtgcttct gtattacagg gttttgtcgg tcctacgcct  1500
aaaacagctt ggctaattag ctacccttta ttagagcgga ttcattattt attagtggct  1560
ggttttgatg tttatggcag tgttagtcat caattaaaaa cacgtctata tatggatttt  1620
ttacgaatgg aagcagaaag taatttcatt agttttttac ctaaagatga acgtaaggca  1680
atacatgagt attggtaccg tgagaccggt gacgacatta aagattatat ttctcagac   1740
ggttttatc  agttaccaga aacaggtatg aactatcaaa gcaataagca tcaagaagag   1800
ctatttcaat tggttggaca gcacaccaaa ataccaatg  ttagccagtt taaccttct    1860
tcattagcac aaagcagtgc cgacaaaatc atagctaact taagtcagtt acctaatgag  1920
agcgttgctc tgttaccaca agtgagttat gtgatggtat caaatggcga tgacaaccaa  1980
gtctatagtt taatcaataa ttccgcacac agtaatgttg cccatttgtt ttctgaagag  2040
aatcgtcgcc tacctagaga agataattta gccattctac gtggtgtcgt aggcactat   2100
cccaatgcct ttttaaagt  agaacaagcg cagctcagtg agtttgttag taacttaaac  2160
gcgataaaaa ccgaacaaga ttaccgtaaa cttaaagacc aatttgccat cgccgcaca   2220
aatcctaagt tctggatttt tgccgatgaa ttacacgctt ggtataaaac caatcaacct  2280
aaatcggcgg gtttacttga ttttaatcgc ttggaaaatc gttaa                  2325
```

<210> SEQ ID NO 50
<211> LENGTH: 774
<212> TYPE: PRT
<213> ORGANISM: Colwellia psychrerythraea

<400> SEQUENCE: 50

Met Glu Phe Asp Lys Leu Tyr Gly Pro Ser Asn Val Glu Asn Arg Leu
1               5                   10                  15

Val Gln Val Lys Ala Thr Thr Ala Glu Ala Ile His Phe Asn Arg Gln
            20                  25                  30

Ile Gln Pro Ile Ile Glu Asn Arg Cys Val Val Cys His Gly Cys Tyr
        35                  40                  45

```
Asp Ala Pro Cys Gln Leu Lys Met Glu Ser Arg Ala Gly Ile Glu Arg
    50                  55                  60
Gly Ala Asn Lys Ala Met Val Tyr Asn Gly Glu Arg Leu Leu Thr Ala
65                  70                  75                  80
Asn Ile Ser Ala Ser Leu Thr Lys Leu Thr Glu Leu Lys Arg Asp Asn
                85                  90                  95
Leu Glu Pro Leu Arg Gln Gln Gly Tyr Phe Pro Val Leu Asn Glu Arg
            100                 105                 110
Gln Gln Thr Glu Gln Ala Asn Thr Gln Ser Ser Leu Phe Tyr Gln Met
        115                 120                 125
Leu Gln Leu Lys Lys Gln His Pro Leu Pro Ser Glu Pro Ile Leu Asn
    130                 135                 140
Glu Ser Phe Asp Val Ala Leu Asp Arg Ser Gln Gln Cys Pro Thr Ile
145                 150                 155                 160
Glu Glu Phe Glu Gln Tyr Lys Asp Lys Tyr Pro Leu Gly Gly Met Pro
                165                 170                 175
Tyr Ala Leu Pro Ala Leu Ser Thr Thr Glu His Asp Gln Leu Thr Asp
            180                 185                 190
Trp Ile Ala Arg Gly Ala Ile Met Pro Asp Ser Val Pro Pro Asn Ala
        195                 200                 205
Lys Glu Gln Gln Met Ile Asn Arg Trp Glu Lys Leu Leu Asn Gly Ser
    210                 215                 220
Ser Ala Lys Glu Gln Leu Ile Ala Arg Tyr Leu Phe Glu His Leu Tyr
225                 230                 235                 240
Leu Ala Asn Leu Tyr Phe Asp Lys Ala Gln Ser Ser Tyr Phe Lys Leu
                245                 250                 255
Val Arg Ser Ser Pro Ser Gly Glu Lys Val Ala Val Ile Thr Thr
            260                 265                 270
Arg Arg Pro Phe Asp Ser Pro Tyr Ala Asp Gly Ser Thr Asp Ala Ile
        275                 280                 285
Val Asp Lys Pro Gln Val Tyr Tyr Arg Leu Ile Lys His Asn Asp Thr
    290                 295                 300
Ile Ile Ala Lys Arg His Met Pro Tyr Pro Phe Gly Glu Ser Lys Leu
305                 310                 315                 320
Ala Arg Ile Ser Glu Leu Phe Tyr Gln Pro Asp Tyr Pro Val Thr Thr
                325                 330                 335
Leu Pro Asp Tyr Gln Leu Ala Asn Ala Ser Asn Pro Phe Lys Thr Phe
            340                 345                 350
Gln Ala Ile Pro Asp Lys Ala Arg Tyr Gln Phe Leu Leu Asp Gln Ala
        355                 360                 365
Gln Phe Ser Ile Met Asn Phe Ile Lys Gly Pro Val Cys Arg Gly Gln
    370                 375                 380
Ile Ala Leu Asn Val Ile Glu Asp Asn Phe Trp Val Phe Phe Leu Ser
385                 390                 395                 400
Pro Asn Asn Phe Asp His Tyr Pro Ser Glu Gln Phe Ile Lys Ala Asn
                405                 410                 415
Thr Glu Leu Leu Gln Leu Pro Ala Gly Thr Ser Asp Lys Ser Leu Ser
            420                 425                 430
Leu Leu Tyr Trp Arg Gln Tyr Ala Lys Ser Gln Gln Glu Tyr Val Lys
        435                 440                 445
Asn Lys Leu Ala Tyr Val Glu Gly Leu Asn Leu Gln Pro Asn Gln Leu
    450                 455                 460
Asn Leu Asp Leu Ile Trp Ser Gly Lys Gly Asn Pro Asn Ala Ser Leu
465                 470                 475                 480
```

```
Thr Val Phe Arg His Phe Asp Ser Ala Ser Val Leu Gln Gly Phe Val
            485                 490                 495

Gly Pro Thr Pro Lys Thr Ala Trp Leu Ile Ser Tyr Pro Leu Leu Glu
            500                 505                 510

Arg Ile His Tyr Leu Leu Val Ala Gly Phe Asp Val Tyr Gly Ser Val
            515                 520                 525

Ser His Gln Leu Lys Thr Arg Leu Tyr Met Asp Phe Leu Arg Met Glu
            530                 535                 540

Ala Glu Ser Asn Phe Ile Ser Phe Leu Pro Lys Asp Glu Arg Lys Ala
545                 550                 555                 560

Ile His Glu Tyr Trp Tyr Arg Glu Thr Gly Asp Asp Ile Lys Asp Tyr
            565                 570                 575

Ile Phe Ser Asp Gly Phe Tyr Gln Leu Pro Glu Thr Gly Met Asn Tyr
            580                 585                 590

Gln Ser Asn Lys His Gln Glu Glu Leu Phe Gln Leu Val Gly Gln His
            595                 600                 605

Thr Lys Asn Thr Asn Val Ser Gln Phe Asn Leu Ser Ser Leu Ala Gln
            610                 615                 620

Ser Ser Ala Asp Lys Ile Ile Ala Asn Leu Ser Gln Leu Pro Asn Glu
625                 630                 635                 640

Ser Val Ala Leu Leu Pro Gln Val Ser Tyr Val Met Val Ser Asn Gly
            645                 650                 655

Asp Asp Asn Gln Val Tyr Ser Leu Ile Asn Asn Ser Ala His Ser Asn
            660                 665                 670

Val Ala His Leu Phe Ser Glu Glu Asn Arg Arg Leu Pro Arg Glu Asp
            675                 680                 685

Asn Leu Ala Ile Leu Arg Gly Val Val Gly Thr Tyr Pro Asn Ala Phe
            690                 695                 700

Phe Lys Val Glu Gln Ala Gln Leu Ser Glu Phe Val Ser Asn Leu Asn
705                 710                 715                 720

Ala Ile Lys Thr Glu Gln Asp Tyr Arg Lys Leu Lys Asp Gln Phe Ala
            725                 730                 735

Ile Arg Arg Thr Asn Pro Lys Phe Trp Ile Phe Ala Asp Glu Leu His
            740                 745                 750

Ala Trp Tyr Lys Thr Asn Gln Pro Lys Ser Ala Gly Leu Leu Asp Phe
            755                 760                 765

Asn Arg Leu Glu Asn Arg
    770

<210> SEQ ID NO 51
<211> LENGTH: 2484
<212> TYPE: DNA
<213> ORGANISM: Saccharophagus degradans

<400> SEQUENCE: 51
atgcttagaa ataaaactag cgtcttattt atcgcacttg ccttaactgc aatggtagca      60
gggctaagct attactatat tcaagaacaa agggaagaac ccgcgtttac tgtactacct     120
cacaacactg tgcacgaaga agttaattat tacagcgaca ttcaaccaat attggataaa     180
aagtgcgtgg cgtgccatag ctgctttgat gcgccatgcc aactaaaact tgtaaatgcg     240
aaagggttac tgcgcggcgc tactgccaag caggtatata acggcggccg caccgaacca     300
caacaaccca cccgccttaa tttgatggt aataccgaag ccgagtggcg caacctcggt     360
tttcactcgg tactagaaac aaacaaccaa agcccactac taaaatcgtt tattgcttgg     420
```

```
ggcttcgcta cacaaaatag tgagaacgca aacactctta acgaagccat taaaaaaaac    480
aatattgaac tgggaacaac cagagaaaac caatgcagcg ctacaatcga agagtttaat    540
aggttcaccc acagccaccc tcataacggt atgccactgg ccacccaagg gctatctcag    600
tcggaatacg atttagttat gacctggttt gaacaaggcg cgaccatccc tgacgcgcct    660
tggacaatca ataagcaaga caaagaagtg atacaaaaat gggaagactg gttaaacgaa    720
acatcgaatg aaagaaagct attagcacgc tatatttacg agcatctttt tctcgcgcac    780
ttgcacttac agccagatga taatctttca gagagaattc tcgatagcga attacaatac    840
cccgtcaatt tctatcgttt agtacggtca agtacgccat caggaacggc tatcattcca    900
atcaacacag ctttaccaaa tcaacctact caatcggatt tttactatcg cttgcaacct    960
gtggaagaaa ccattgtata taatctcac ataccctatc ggtttgataa aaatagatta    1020
acggaaattg aatctttgtt cgcaagcgaa agctggcaag taaaaaactt acctagctat    1080
gagtacgaat ttagatctaa tccatttaaa acttacagcg cgataccagc caagcttcgc    1140
tataagtttt tattgcagga tgcagaatat tttgttcgta catttattcg aggcccggtg    1200
tgccacggcc ctatcgcaac cgatgttatt cgagaccact tttgggtaat gtttgaaaac    1260
cctgaaacag agctattcgt taacaacaaa aattatcgcc aatccgttga aagcttactt    1320
gggctaccgg gagaaaatag ccagctttct gagttcggtg acgaatggac aatctatcaa    1380
aacaaccgca ataaatatgc agaagaccgc aatacagctt atcgcgaaag ttacaatact    1440
ggcagaccac taaatacaat ttggacagaa aaaggcgaaa accccaatgc ctttcttacc    1500
gtatttaggc accacaacaa tgctacggta ctgcagggct ggcaaggcag taaaccacgc    1560
accgcatggg tattagacta ccccttattc gaacgtacct actatgaact tgttgcaggt    1620
tttgatgttt tcggcaacgt gtcacatcag ttacaaacac gtttgtattt tgatttaatt    1680
cgccatggcg gtgaaactaa ctttctagcc tatatgccca aagactccag agaagcaata    1740
tttaaccatt ggtaccaagg gctagcccag ttaaaaacaa gtatctctta ccctaaacta    1800
gacaccttag cactgggtgc tccagagcta aatgagagcg ctcctaaaga cgccttttt    1860 aactacttct ttgacaaatt cccaagctcc accaatgcgc acgacccgat aaatcgtgca    1920
gaatctagta caacaaatac agacgatgga aaagagcaag cgcatacgca aaacttggta    1980
gcaacccagc tagcctctat agctagcaaa cccgctaaag aactcgcatt tataaaagat    2040
ttacccgatc ttagcttact ttttattacg tccaacaatg ccacgtccag caatgccatt    2100
tccaacaata gtacttcaag caatgaaaat caaagcattg tttattcact agtgcgcaac    2160
agaatgcata gcaatgttgc atttcttacc ggcgaggaac ttaggtacca accagaacaa    2220
gattatttat caattcgaaa aggccttgtg ggtagctacc ccaaccttat atttaaggtc    2280
gatgaaagtg atataaatcg cttcataggc gcgttgaata cgccagataa cgataccgaa    2340
tttagagaac gcatggatga attttatttta aaacgtttag acgacaattt ttggcaaact    2400
gtacatgcga taagtaattc cgaaaaaaac agaaacccaa tttctagcgg actactagac    2460
ttgaatcgtt atgaatgctg gtaa                                          2484
```

<210> SEQ ID NO 52
<211> LENGTH: 827
<212> TYPE: PRT
<213> ORGANISM: Saccharophagus degradans

<400> SEQUENCE: 52

Met Leu Arg Asn Lys Thr Ser Val Leu Phe Ile Ala Leu Ala Leu Thr
1               5                   10                  15

```
Ala Met Val Ala Gly Leu Ser Tyr Tyr Tyr Ile Gln Glu Gln Arg Glu
            20                  25                  30

Glu Pro Ala Phe Thr Val Leu Pro His Asn Thr Val His Glu Glu Val
            35                  40                  45

Asn Tyr Tyr Ser Asp Ile Gln Pro Ile Leu Asp Lys Lys Cys Val Ala
 50                  55                  60

Cys His Ser Cys Phe Asp Ala Pro Cys Gln Leu Lys Leu Val Asn Ala
 65                  70                  75                  80

Lys Gly Leu Leu Arg Gly Ala Thr Ala Lys Gln Val Tyr Asn Gly Gly
                85                  90                  95

Arg Thr Glu Pro Gln Gln Pro Thr Arg Leu Asn Leu Asp Gly Asn Thr
            100                 105                 110

Glu Ala Glu Trp Arg Asn Leu Gly Phe His Ser Val Leu Glu Thr Asn
            115                 120                 125

Asn Gln Ser Pro Leu Leu Lys Ser Phe Ile Ala Trp Gly Phe Ala Thr
130                 135                 140

Gln Asn Ser Glu Asn Ala Asn Thr Leu Asn Glu Ala Ile Lys Lys Asn
145                 150                 155                 160

Asn Ile Glu Leu Gly Thr Thr Arg Glu Asn Gln Cys Ser Ala Thr Ile
                165                 170                 175

Glu Glu Phe Asn Arg Phe Thr His Ser His Pro His Asn Gly Met Pro
            180                 185                 190

Leu Ala Thr Gln Gly Leu Ser Gln Ser Glu Tyr Asp Leu Val Met Thr
            195                 200                 205

Trp Phe Glu Gln Gly Ala Thr Ile Pro Asp Ala Pro Trp Thr Ile Asn
            210                 215                 220

Lys Gln Asp Lys Glu Val Ile Gln Lys Trp Asp Trp Leu Asn Glu
225                 230                 235                 240

Thr Ser Asn Glu Arg Lys Leu Leu Ala Arg Tyr Ile Tyr Glu His Leu
                245                 250                 255

Phe Leu Ala His Leu His Leu Gln Pro Asp Asp Asn Leu Ser Glu Arg
            260                 265                 270

Ile Leu Asp Ser Glu Leu Gln Tyr Pro Val Asn Phe Tyr Arg Leu Val
            275                 280                 285

Arg Ser Ser Thr Pro Ser Gly Thr Ala Ile Ile Pro Ile Asn Thr Ala
            290                 295                 300

Leu Pro Asn Gln Pro Thr Gln Ser Asp Phe Tyr Tyr Arg Leu Gln Pro
305                 310                 315                 320

Val Glu Glu Thr Ile Val Tyr Lys Ser His Ile Pro Tyr Arg Phe Asp
                325                 330                 335

Lys Asn Arg Leu Thr Glu Ile Glu Ser Leu Phe Ala Ser Glu Ser Trp
            340                 345                 350

Gln Val Lys Asn Leu Pro Ser Tyr Glu Tyr Glu Phe Arg Ser Asn Pro
            355                 360                 365

Phe Lys Thr Tyr Ser Ala Ile Pro Ala Lys Leu Arg Tyr Lys Phe Leu
            370                 375                 380

Leu Gln Asp Ala Glu Tyr Phe Val Arg Thr Phe Ile Arg Gly Pro Val
385                 390                 395                 400

Cys His Gly Pro Ile Ala Thr Asp Val Ile Arg Asp His Phe Trp Val
                405                 410                 415

Met Phe Glu Asn Pro Glu Thr Glu Leu Phe Val Asn Asn Lys Asn Tyr
            420                 425                 430

Arg Gln Ser Val Glu Ser Leu Leu Gly Leu Pro Gly Glu Asn Ser Gln
```

```
                435                 440                 445
Leu Ser Glu Phe Gly Asp Glu Trp Thr Ile Tyr Gln Asn Asn Arg Asn
450                 455                 460

Lys Tyr Ala Glu Asp Arg Asn Thr Ala Tyr Arg Glu Ser Tyr Asn Thr
465                 470                 475                 480

Gly Arg Pro Leu Asn Thr Ile Trp Thr Glu Lys Gly Glu Asn Pro Asn
                485                 490                 495

Ala Phe Leu Thr Val Phe Arg His His Asn Asn Ala Thr Val Leu Gln
                500                 505                 510

Gly Trp Gln Gly Ser Lys Pro Arg Thr Ala Trp Val Leu Asp Tyr Pro
                515                 520                 525

Leu Phe Glu Arg Thr Tyr Tyr Glu Leu Val Ala Gly Phe Asp Val Phe
                530                 535                 540

Gly Asn Val Ser His Gln Leu Gln Thr Arg Leu Tyr Phe Asp Leu Ile
545                 550                 555                 560

Arg His Gly Gly Glu Thr Asn Phe Leu Ala Tyr Met Pro Lys Asp Ser
                565                 570                 575

Arg Glu Ala Ile Phe Asn His Trp Tyr Gln Gly Leu Ala Gln Leu Lys
                580                 585                 590

Thr Ser Ile Ser Tyr Pro Lys Leu Asp Thr Leu Ala Leu Gly Ala Pro
                595                 600                 605

Glu Leu Asn Glu Ser Ala Pro Lys Asp Ala Phe Phe Asn Tyr Phe Phe
610                 615                 620

Asp Lys Phe Pro Ser Ser Thr Asn Ala His Asp Pro Ile Asn Arg Ala
625                 630                 635                 640

Glu Ser Ser Thr Thr Asn Thr Asp Asp Gly Lys Glu Gln Ala His Thr
                645                 650                 655

Gln Asn Leu Val Ala Thr Gln Leu Ala Ser Ile Ala Ser Lys Pro Ala
                660                 665                 670

Lys Glu Leu Ala Phe Ile Lys Asp Leu Pro Asp Leu Ser Leu Leu Phe
                675                 680                 685

Ile Thr Ser Asn Asn Ala Thr Ser Asn Ala Ile Ser Asn Asn Ser
690                 695                 700

Thr Ser Ser Asn Glu Asn Gln Ser Ile Val Tyr Ser Leu Val Arg Asn
705                 710                 715                 720

Arg Met His Ser Asn Val Ala Phe Leu Thr Gly Glu Glu Leu Arg Tyr
                725                 730                 735

Gln Pro Glu Gln Asp Tyr Leu Ser Ile Arg Lys Gly Leu Val Gly Ser
                740                 745                 750

Tyr Pro Asn Leu Ile Phe Lys Val Asp Glu Ser Asp Ile Asn Arg Phe
                755                 760                 765

Ile Gly Ala Leu Asn Thr Pro Asp Asn Asp Thr Glu Phe Arg Glu Arg
                770                 775                 780

Met Asp Glu Phe Ile Leu Lys Arg Leu Asp Asp Asn Phe Trp Gln Thr
785                 790                 795                 800

Val His Ala Ile Ser Asn Ser Glu Lys Asn Arg Asn Pro Ile Ser Ser
                805                 810                 815

Gly Leu Leu Asp Leu Asn Arg Tyr Glu Cys Trp
                820                 825

<210> SEQ ID NO 53
<211> LENGTH: 2394
<212> TYPE: DNA
<213> ORGANISM: Pseudomonas fluorescens
```

<400> SEQUENCE: 53

```
atggttttgc ggcatgcgtg gtttttgcat gaatatcgct catgttggtc gaggagtgag      60
accggtagaa tcgcggcgtt tttttctttc gggaccaggg acatgccgtt tcgttttatc     120
gtcagcagcg cgctgctgct tctgagttca gtgtgcctgg cacaaggtcc ggcgccggtg     180
atttcctata cccgcgacat ccagccgatc tttaccgaga aatgcgtggc ctgtcatgcc     240
tgttacgact ccgcctgtca gctcaacctg ggcagtggcg aggggggccag ccgcggtgct    300
tcgaagattc cggtgtacga cggcgagcgc agcaaggccc aagcgcctac gcggctgttc     360
tatgacgcca ctggccagcg tgcctggcag cagaagggtc tctattcggt gcttgacgcc     420
cagggcagcc aggcggcgct gatggcgcgc atgctggaac tgggccatcg caccccgctg     480
caacccaacg ccaagttgcc caacgagatc gccctgggcc tgagccgcga aacatgtgc     540
ccgcagccgg cggagttcga cgcctatgcc ggggctcacc ccaaggaagg catgcccctg     600
gcggtcaccg gcctgaccga tcagcaatac ctgaccctgc aacgctggct ggcctcgggc     660
gcgcccatcg acgagcaagg cctggccccc agtgcccggg aaagcctgca agtggctcag     720
tgggaaaacc tgctcaacgc ccctggcgcc cgggagagcc tggtggcgcg ctggctctac     780
gaacacttgt tcctcgccca tctctatttt gaaggcggcg agccggggca tttcttccag     840
tgggtgcgtt cccgtacccc cagtggccag cccatcgacc tgatcaacac ccgtcgcccc     900
aacgacgacc cgggcaccca ggtgtactac cgcctgtggc cggtgcaagg ggtgatcgtg     960
cacaagaccc atatcaccta cccgctgagc gcggcgaaga tggcccgggt caagaccctg    1020
ttctacagcg gcgactggca ggtcacggcc ctgccgggct acgggccggc gcgccgggcc    1080
aacccgttcg agaccttcga ggcgattccg gccaaggccc gctaccagtt catgctggat    1140
aacgccgaat acttcgtgcg caccttatc cgtggcccgg tgtgccgcgg gcagatcgcc    1200
accgacgtga tccgcgacaa cttctgggcg ctgttccagg cccccgaaca tgacctgtac    1260
atcaccgacc cggcctatcg cggccaggcc acgccgttgc tggccatgcc cgggcagaac    1320
gacgacgtcg gcagcgtgct cagcctgtgg ctggcctatc gcgacaagcg caacgagtac    1380
gaggccctgc gccgcgattc ctatgccgat tcgccggcgc ccagctggtc gaccctgtgg    1440
gccggcaacg acaacgcgct gctgagcatc ttccgccact tcgacagcgc ctcggtgacc    1500
aagggcctga tcggcgaagt gccacagacg atgtggctgt cgactaccc gctgctggag    1560
cgcacctact atcaattggc ggtgaacttc gacgtgttcg gcaacgtctc ccaccaggcc    1620
cagaccggt tgtacttcga cctgatccgc aatggcgcgg agcagaactt cctgcgcctg    1680
atgcccgccg gcacccgcga ggatttcctc gacgattggt accagaacag cggcaagttc    1740
aagatgtggc tggattacga gtccatcgac gacgacaagc gcagcgcgct gaagctcgac    1800
ctcaaggacc cgaaaaagga cttcgccaac cagttgctgg cccgctatgg cgacctcaac    1860
gccaagccgg atccgatcaa ccgctgtgac agcgcctact gctcacgccc gaacatcgac    1920
ccggcgctgc aggatgccga acaggccctg agccgcctgg catcgcgccc ggcggcgggc    1980
ctcaaggtca tcgaacagtt gccggaagcg accctgctgc gtgtccagac cgccagcggc    2040
aagcgcgagt tctacagcat gctgcgcaac cgcgcccaca gtaacgtggc cttcatgctc    2100
ggcgagtcgc tgcgctacca gccggggctg gacaccctga ccatattccc ggggattctc    2160
agcagctatc cgaacttcat gttcaacgta ccggccgggc aagtgccgga gttcgtcgac    2220
gccatgcagg cggccgggga caccgccagc ttcgagaaga tcgtcgagcg ctggggcatc    2280
cgccgcagcc atccgcagtt ctggctgtac ttccatgacc agacccgcta cctgcaggaa    2340
```

```
accgacccgg tggaagccgg ggtcctggac atgaaccgtt acgaaaacct ctga          2394
```

<210> SEQ ID NO 54
<211> LENGTH: 797
<212> TYPE: PRT
<213> ORGANISM: Pseudomonas fluorescens

<400> SEQUENCE: 54

| | | | | | | | | | | | | | | | |
|---|---|---|---|---|---|---|---|---|---|---|---|---|---|---|---|
| Met | Val | Leu | Arg | His | Ala | Trp | Phe | Leu | His | Glu | Tyr | Arg | Ser | Cys | Trp |
| 1 | | | | 5 | | | | | 10 | | | | | 15 | |
| Ser | Arg | Ser | Glu | Thr | Gly | Arg | Ile | Ala | Ala | Phe | Phe | Ser | Phe | Gly | Thr |
| | | | 20 | | | | | 25 | | | | | 30 | | |
| Arg | Asp | Met | Pro | Phe | Arg | Phe | Ile | Val | Ser | Ser | Ala | Leu | Leu | Leu | Leu |
| | | 35 | | | | | 40 | | | | | 45 | | | |
| Ser | Ser | Val | Cys | Leu | Ala | Gln | Gly | Pro | Ala | Pro | Val | Ile | Ser | Tyr | Thr |
| 50 | | | | | 55 | | | | | 60 | | | | | |
| Arg | Asp | Ile | Gln | Pro | Ile | Phe | Thr | Glu | Lys | Cys | Val | Ala | Cys | His | Ala |
| 65 | | | | | 70 | | | | | 75 | | | | | 80 |
| Cys | Tyr | Asp | Ser | Ala | Cys | Gln | Leu | Asn | Leu | Gly | Ser | Gly | Glu | Gly | Ala |
| | | | | 85 | | | | | 90 | | | | | 95 | |
| Ser | Arg | Gly | Ala | Ser | Lys | Ile | Pro | Val | Tyr | Asp | Gly | Glu | Arg | Ser | Lys |
| | | | 100 | | | | | 105 | | | | | 110 | | |
| Ala | Gln | Ala | Pro | Thr | Arg | Leu | Phe | Tyr | Asp | Ala | Thr | Gly | Gln | Arg | Ala |
| | | 115 | | | | | 120 | | | | | 125 | | | |
| Trp | Gln | Gln | Lys | Gly | Phe | Tyr | Ser | Val | Leu | Asp | Ala | Gln | Gly | Ser | Gln |
| 130 | | | | | 135 | | | | | 140 | | | | | |
| Ala | Ala | Leu | Met | Ala | Arg | Met | Leu | Glu | Leu | Gly | His | Arg | Thr | Pro | Leu |
| 145 | | | | | 150 | | | | | 155 | | | | | 160 |
| Gln | Pro | Asn | Ala | Lys | Leu | Pro | Asn | Glu | Ile | Ala | Leu | Gly | Leu | Ser | Arg |
| | | | | 165 | | | | | 170 | | | | | 175 | |
| Glu | Asn | Met | Cys | Pro | Gln | Pro | Ala | Glu | Phe | Asp | Ala | Tyr | Ala | Gly | Ala |
| | | | 180 | | | | | 185 | | | | | 190 | | |
| His | Pro | Lys | Glu | Gly | Met | Pro | Leu | Ala | Val | Thr | Gly | Leu | Thr | Asp | Gln |
| | | 195 | | | | | 200 | | | | | 205 | | | |
| Gln | Tyr | Leu | Thr | Leu | Gln | Arg | Trp | Leu | Ala | Ser | Gly | Ala | Pro | Ile | Asp |
| 210 | | | | | 215 | | | | | 220 | | | | | |
| Glu | Gln | Gly | Leu | Ala | Pro | Ser | Ala | Arg | Glu | Ser | Leu | Gln | Val | Ala | Gln |
| 225 | | | | | 230 | | | | | 235 | | | | | 240 |
| Trp | Glu | Asn | Leu | Leu | Asn | Ala | Pro | Gly | Ala | Arg | Glu | Ser | Leu | Val | Ala |
| | | | | 245 | | | | | 250 | | | | | 255 | |
| Arg | Trp | Leu | Tyr | Glu | His | Leu | Phe | Leu | Ala | His | Leu | Tyr | Phe | Glu | Gly |
| | | | 260 | | | | | 265 | | | | | 270 | | |
| Gly | Glu | Pro | Gly | His | Phe | Phe | Gln | Trp | Val | Arg | Ser | Arg | Thr | Pro | Ser |
| | | 275 | | | | | 280 | | | | | 285 | | | |
| Gly | Gln | Pro | Ile | Asp | Leu | Ile | Asn | Thr | Arg | Arg | Pro | Asn | Asp | Asp | Pro |
| 290 | | | | | 295 | | | | | 300 | | | | | |
| Gly | Thr | Gln | Val | Tyr | Tyr | Arg | Leu | Trp | Pro | Val | Gln | Gly | Val | Ile | Val |
| 305 | | | | | 310 | | | | | 315 | | | | | 320 |
| His | Lys | Thr | His | Ile | Thr | Tyr | Pro | Leu | Ser | Ala | Ala | Lys | Met | Ala | Arg |
| | | | | 325 | | | | | 330 | | | | | 335 | |
| Val | Lys | Thr | Leu | Phe | Tyr | Ser | Gly | Asp | Trp | Gln | Val | Thr | Ala | Leu | Pro |
| | | | 340 | | | | | 345 | | | | | 350 | | |
| Gly | Tyr | Gly | Pro | Ala | Arg | Arg | Ala | Asn | Pro | Phe | Glu | Thr | Phe | Glu | Ala |
| | | 355 | | | | | 360 | | | | | 365 | | | |
| Ile | Pro | Ala | Lys | Ala | Arg | Tyr | Gln | Phe | Met | Leu | Asp | Asn | Ala | Glu | Tyr |

```
              370                 375                 380
Phe Val Arg Thr Phe Ile Arg Gly Pro Val Cys Arg Gly Gln Ile Ala
385                 390                 395                 400

Thr Asp Val Ile Arg Asp Asn Phe Trp Ala Leu Phe Gln Ala Pro Glu
                405                 410                 415

His Asp Leu Tyr Ile Thr Asp Pro Ala Tyr Arg Gly Gln Ala Thr Pro
                420                 425                 430

Leu Leu Ala Met Pro Gly Gln Asn Asp Val Gly Ser Val Leu Ser
                435                 440                 445

Leu Trp Leu Ala Tyr Arg Asp Lys Arg Asn Glu Tyr Glu Ala Leu Arg
450                 455                 460

Arg Asp Ser Tyr Ala Asp Ser Pro Ala Pro Ser Trp Ser Thr Leu Trp
465                 470                 475                 480

Ala Gly Asn Asp Asn Ala Leu Leu Ser Ile Phe Arg His Phe Asp Ser
                485                 490                 495

Ala Ser Val Thr Lys Gly Leu Ile Gly Glu Val Pro Gln Thr Met Trp
                500                 505                 510

Leu Phe Asp Tyr Pro Leu Leu Glu Arg Thr Tyr Tyr Gln Leu Ala Val
                515                 520                 525

Asn Phe Asp Val Phe Gly Asn Val Ser His Gln Ala Gln Thr Arg Leu
530                 535                 540

Tyr Phe Asp Leu Ile Arg Asn Gly Ala Glu Gln Asn Phe Leu Arg Leu
545                 550                 555                 560

Met Pro Ala Gly Thr Arg Glu Asp Phe Leu Asp Asp Trp Tyr Gln Asn
                565                 570                 575

Ser Gly Lys Phe Lys Met Trp Leu Asp Tyr Glu Ser Ile Asp Asp Asp
                580                 585                 590

Lys Arg Ser Ala Leu Lys Leu Asp Leu Lys Asp Pro Lys Lys Asp Phe
                595                 600                 605

Ala Asn Gln Leu Leu Ala Arg Tyr Gly Asp Leu Asn Ala Lys Pro Asp
                610                 615                 620

Pro Ile Asn Arg Cys Asp Ser Ala Tyr Cys Ser Arg Pro Asn Ile Asp
625                 630                 635                 640

Pro Ala Leu Gln Asp Ala Glu Gln Ala Leu Ser Arg Leu Ala Ser Arg
                645                 650                 655

Pro Ala Ala Gly Leu Lys Val Ile Glu Gln Leu Pro Glu Ala Thr Leu
                660                 665                 670

Leu Arg Val Gln Thr Ala Ser Gly Lys Arg Glu Phe Tyr Ser Met Leu
                675                 680                 685

Arg Asn Arg Ala His Ser Asn Val Ala Phe Met Leu Gly Glu Ser Leu
690                 695                 700

Arg Tyr Gln Pro Gly Leu Asp Thr Leu Thr Ile Phe Pro Gly Ile Leu
705                 710                 715                 720

Ser Ser Tyr Pro Asn Phe Met Phe Asn Val Pro Ala Gly Gln Val Pro
                725                 730                 735

Glu Phe Val Asp Ala Met Gln Ala Ala Arg Asp Thr Ala Ser Phe Glu
                740                 745                 750

Lys Ile Val Glu Arg Trp Gly Ile Arg Arg Ser His Pro Gln Phe Trp
                755                 760                 765

Leu Tyr Phe His Asp Gln Thr Arg Tyr Leu Gln Glu Thr Asp Pro Val
                770                 775                 780

Glu Ala Gly Val Leu Asp Met Asn Arg Tyr Glu Asn Leu
785                 790                 795
```

<210> SEQ ID NO 55
<211> LENGTH: 2289
<212> TYPE: DNA
<213> ORGANISM: Pseudomonas aeruginosa

<400> SEQUENCE: 55

| | | | | | |
|---|---|---|---|---|---|
| atgttgccaa | gaccgttggt | tgggttggcc | ttcgttttgt | cgtcttttat | ccagtctgtt | 60 |
| tccgctgctg | aaatttccta | tagccgtgac | gtccagccga | tctttaccgc | caagtgcgtc | 120 |
| gcctgccacg | cctgctacga | ttcgccctgc | cagctcaacc | tgagcagcgc | cgagggcgcg | 180 |
| cagcgcggcg | ccaaccaact | gccggtctac | gacggcacgc | ggaccaaggc | gcaggaaacc | 240 |
| acccgcctgt | acctcgatgc | gcacggtgcc | gacgcctggc | ggcgcaagga | cttctggtcg | 300 |
| gtgctcgaac | gcaggacgg | ccaggccgca | ctgatggcgc | ggatgctcga | gcttggccac | 360 |
| agccagccgt | tgcagccgaa | tgcgaagatc | cccgaaggcc | tggacatttc | gatcaaccgc | 420 |
| gccaaccagt | gcccgacgcc | ggccagcatc | gatgcgttca | tccgcaagaa | cccaggttcc | 480 |
| ggcatgcctt | tcgcggtggc | cgggctgagc | gacgacgaat | acgccacttt | gcagaagtgg | 540 |
| ctggccgcgg | gcgccccggt | cgaccagcag | ccgttgcggc | cgaccgccgc | cgaggcgcgc | 600 |
| caggtggcca | gctgggagcg | tttcctcaac | cagcctgggg | ccaagcagag | cctggtctcg | 660 |
| cgctggctct | acgagcacct | gttcctggcg | cacctgtatt | tcccggaaca | gggcgcgccc | 720 |
| ggccacttct | tccagctggt | gcgttcacgc | acgcccagcg | gccagccgat | cgacccgatc | 780 |
| ccgaccggc | gtcccaacga | cgatccgggc | aacagcttct | attaccgcct | ctggccgatc | 840 |
| cagggcgtga | tcgtacacaa | gacgcacatc | acctatccgc | tgacggcgaa | gaagctggaa | 900 |
| cgcgtccagg | agctgttctt | cggcacccag | tggaacaccg | acaaggttcc | cggctacggc | 960 |
| gtgcagagcc | gtgccaaccc | gttcgccacc | ttcgccgcga | tcccgccacg | ggcgcgctac | 1020 |
| cagttcatgc | tggacaacgc | cgaatacttc | acccgtacct | tcatccgcgg | gccggtgtgc | 1080 |
| cgtggacaga | tcgccaccga | cgtgatccgc | gacaacttct | gggtggtatt | ccaggacccc | 1140 |
| gagcaggacc | tgttcgtcac | cgacgccaac | ttccgcgcgc | agagcgagcc | gctgctggcc | 1200 |
| ttgccggggc | agatcgacga | gctgaagaac | ctgctcggcc | tgtggagcgc | ctaccgggac | 1260 |
| aagcgcaacg | agtacgaaga | cctgcgccag | gacgtctacg | ccgacgcgcc | gccgccgacc | 1320 |
| tggaacacga | tctggcacgg | caacgacaac | gccctgctga | gcatcttccg | ccagttcgac | 1380 |
| agcgcctcgg | tgcgcaaggg | actgcttggc | gaggtaccgc | agaccctgtg | gctgatggac | 1440 |
| tacccgctgt | tcgagcgaac | ctactacggg | ctggtggtga | acttcgatgt | cttcggcaac | 1500 |
| gtctcgcacc | aggcgcagac | gcggctgtac | ttcgacctga | tccgcaacgg | cgccgagcag | 1560 |
| aacttcctcc | gcctgatgcc | ggtcgacgcg | cgccagccgt | tgctcgacga | ctggtaccag | 1620 |
| aacagcggca | agctgaagat | gtggatggac | taccaggcct | tcgacgacga | cacgccgagc | 1680 |
| gcgctgggat | tgccggagaa | gcagccgaag | aaggccttcg | ccgaagaact | gctgcgtcgc | 1740 |
| tacggcgacc | tcaatgcgcg | tcccgacccg | atcaaccgct | gcctggacgg | caactgctat | 1800 |
| cgaccgggca | tcgaccgcga | actgcaggac | gccgagcagg | ccttcagtcg | cctggtgagc | 1860 |
| cggccggcgg | ccggcctcaa | ggtcatcgag | cgcttccccg | aggcgtccat | gctgcggata | 1920 |
| cgtacgtcca | gcggcaagcg | cgaggtctat | accgtgctgc | gcaaccgcgc | gcacagcaat | 1980 |
| gtcgccttca | tgctcggcga | gtcgctgcgc | taccagccgg | gcctggacac | cctgacgatc | 2040 |
| tacccgggcg | tgctgtccag | ctacccgaac | ttcatgttcg | atctgccggc | gacggatgcc | 2100 |
| gaggccttcg | tcggcgccct | ggaggcggcg | aagagcggcg | aggacttcga | caaggtggtc | 2160 |

```
gaacgctggg gcgtgcgccg cagcaatccg cagttctgga gctacttcca cgatctcgag    2220
gcgtacatcc gcgaaaccga gccggtcgag gcgggcgcac tggacatgaa ccgctacgag    2280
aacctctga                                                            2289
```

<210> SEQ ID NO 56
<211> LENGTH: 762
<212> TYPE: PRT
<213> ORGANISM: Pseudomonas aeruginosa

<400> SEQUENCE: 56

```
Met Leu Pro Arg Pro Leu Val Gly Leu Ala Phe Val Leu Ser Ser Phe
1               5                   10                  15

Ile Gln Ser Val Ser Ala Ala Glu Ile Ser Tyr Ser Arg Asp Val Gln
            20                  25                  30

Pro Ile Phe Thr Ala Lys Cys Val Ala Cys His Ala Cys Tyr Asp Ser
        35                  40                  45

Pro Cys Gln Leu Asn Leu Ser Ser Ala Glu Gly Ala Gln Arg Gly Ala
    50                  55                  60

Asn Gln Leu Pro Val Tyr Asp Gly Thr Arg Thr Lys Ala Gln Glu Thr
65                  70                  75                  80

Thr Arg Leu Tyr Leu Asp Ala His Gly Ala Asp Ala Trp Arg Arg Lys
                85                  90                  95

Asp Phe Trp Ser Val Leu Glu Pro Gln Asp Gly Gln Ala Ala Leu Met
            100                 105                 110

Ala Arg Met Leu Glu Leu Gly His Ser Gln Pro Leu Gln Pro Asn Ala
        115                 120                 125

Lys Ile Pro Glu Gly Leu Asp Ile Ser Ile Asn Arg Ala Asn Gln Cys
    130                 135                 140

Pro Thr Pro Ala Ser Ile Asp Ala Phe Ile Arg Lys Asn Pro Gly Ser
145                 150                 155                 160

Gly Met Pro Phe Ala Val Ala Gly Leu Ser Asp Asp Glu Tyr Ala Thr
                165                 170                 175

Leu Gln Lys Trp Leu Ala Ala Gly Ala Pro Val Asp Gln Gln Pro Leu
            180                 185                 190

Arg Pro Thr Ala Ala Glu Ala Arg Gln Val Ala Ser Trp Glu Arg Phe
        195                 200                 205

Leu Asn Gln Pro Gly Ala Lys Gln Ser Leu Val Ser Arg Trp Leu Tyr
    210                 215                 220

Glu His Leu Phe Leu Ala His Leu Tyr Phe Pro Glu Gln Gly Ala Pro
225                 230                 235                 240

Gly His Phe Phe Gln Leu Val Arg Ser Arg Thr Pro Ser Gly Gln Pro
                245                 250                 255

Ile Asp Pro Ile Pro Thr Arg Arg Pro Asn Asp Asp Pro Gly Asn Ser
            260                 265                 270

Phe Tyr Tyr Arg Leu Trp Pro Ile Gln Gly Val Ile Val His Lys Thr
        275                 280                 285

His Ile Thr Tyr Pro Leu Thr Ala Lys Lys Leu Glu Arg Val Gln Glu
    290                 295                 300

Leu Phe Phe Gly Thr Gln Trp Asn Thr Asp Lys Val Pro Gly Tyr Gly
305                 310                 315                 320

Val Gln Ser Arg Ala Asn Pro Phe Ala Thr Phe Ala Ala Ile Pro Pro
                325                 330                 335

Arg Ala Arg Tyr Gln Phe Met Leu Asp Asn Ala Glu Tyr Phe Thr Arg
            340                 345                 350
```

Thr Phe Ile Arg Gly Pro Val Cys Arg Gly Gln Ile Ala Thr Asp Val
            355                 360                 365

Ile Arg Asp Asn Phe Trp Val Phe Gln Asp Pro Glu Gln Asp Leu
    370                 375                 380

Phe Val Thr Asp Ala Asn Phe Arg Ala Gln Ser Glu Pro Leu Leu Ala
385                 390                 395                 400

Leu Pro Gly Gln Ile Asp Glu Leu Lys Asn Leu Leu Gly Leu Trp Ser
                405                 410                 415

Ala Tyr Arg Asp Lys Arg Asn Glu Tyr Glu Asp Leu Arg Gln Asp Val
            420                 425                 430

Tyr Ala Asp Ala Pro Pro Thr Trp Asn Thr Ile Trp His Gly Asn
            435                 440                 445

Asp Asn Ala Leu Leu Ser Ile Phe Arg Gln Phe Asp Ser Ala Ser Val
    450                 455                 460

Arg Lys Gly Leu Leu Gly Glu Val Pro Gln Thr Leu Trp Leu Met Asp
465                 470                 475                 480

Tyr Pro Leu Phe Glu Arg Thr Tyr Tyr Gly Leu Val Val Asn Phe Asp
                485                 490                 495

Val Phe Gly Asn Val Ser His Gln Ala Gln Thr Arg Leu Tyr Phe Asp
            500                 505                 510

Leu Ile Arg Asn Gly Ala Glu Gln Asn Phe Leu Arg Leu Met Pro Val
    515                 520                 525

Asp Ala Arg Gln Pro Leu Leu Asp Asp Trp Tyr Gln Asn Ser Gly Lys
530                 535                 540

Leu Lys Met Trp Met Asp Tyr Gln Ala Phe Asp Asp Thr Pro Ser
545                 550                 555                 560

Ala Leu Gly Leu Pro Glu Lys Gln Pro Lys Lys Ala Phe Ala Glu Glu
                565                 570                 575

Leu Leu Arg Arg Tyr Gly Asp Leu Asn Ala Arg Pro Asp Pro Ile Asn
            580                 585                 590

Arg Cys Leu Asp Gly Asn Cys Tyr Arg Pro Gly Ile Asp Arg Glu Leu
    595                 600                 605

Gln Asp Ala Glu Gln Ala Phe Ser Arg Leu Val Ser Arg Pro Ala Ala
610                 615                 620

Gly Leu Lys Val Ile Glu Arg Phe Pro Glu Ala Ser Met Leu Arg Ile
625                 630                 635                 640

Arg Thr Ser Ser Gly Lys Arg Glu Val Tyr Thr Val Leu Arg Asn Arg
                645                 650                 655

Ala His Ser Asn Val Ala Phe Met Leu Gly Ser Leu Arg Tyr Gln
            660                 665                 670

Pro Gly Leu Asp Thr Leu Thr Ile Tyr Pro Gly Val Leu Ser Ser Tyr
            675                 680                 685

Pro Asn Phe Met Phe Asp Leu Pro Ala Thr Asp Ala Glu Ala Phe Val
    690                 695                 700

Gly Ala Leu Glu Ala Ala Lys Ser Gly Glu Asp Phe Asp Lys Val Val
705                 710                 715                 720

Glu Arg Trp Gly Val Arg Arg Ser Asn Pro Gln Phe Trp Ser Tyr Phe
                725                 730                 735

His Asp Leu Glu Ala Tyr Ile Arg Glu Thr Glu Pro Val Glu Ala Gly
            740                 745                 750

Ala Leu Asp Met Asn Arg Tyr Glu Asn Leu
            755                 760

<210> SEQ ID NO 57

<211> LENGTH: 1986
<212> TYPE: DNA
<213> ORGANISM: Vibrio vulnificus

<400> SEQUENCE: 57
gtgctcaacg agcgtgccca aaccggtgtt gccaacattg atgccggctt gattgcgaga 60
ttgctgcaac agaaggagcg tcatcccctt cctcaacagg accaacttga aggatttgat 120
ttttcgattg atcgcgaaca aacctgtccg acgattgaag aatttgatca gtacgagcgt 180
accaatccaa gctggggaat gccctttggt atgccaaatc tttcggccaa agaacaccaa 240
acactcatgg cttggttaga aaatggcgcg atcatgaacg atcacctccc gctcactcgt 300
gagcaggcag cagagatcac gcgatacgaa caaatgttca ataagagttc acgcaaaaac 360
cagcttgctg cacgttatat ctacgagcat ctttttttat cgcatctcta tttctctgag 420
ttagaggggg aacctcgctt ctttactatg gttcgttcgt ccaccccacc aggcgaaccc 480
gtacagcgca ttgttactcg tcgcccctac gatgatccgg gtgtagaacg tgtttactat 540
cgaatcattc ccgagcaagg cacgattgtt gataagacac acatgccttt tgctctcaat 600
agccagcgaa tgaaggattg gaaagcgtgg tttattgacg cagattacgt cgtcgagcag 660
ttgccaagtt acgatcctga gattgccgcc aacccaatga gcgcttttat tgacctccca 720
gtgaaagcac gctttaaatt catgctagat aacgcacaaa acaccattat ggcttacata 780
aagggaccag tgtgccgcgg ccagttggcg ctgaatgtga ttaacgatcg tttctgggtt 840
ttcttcctcg atcctgacaa agcggatctt cctgcagtta atgagtttta tcgctcacaa 900
gccgataatc taaaactacc gggcgaactc gaaagtaaca ccctaccagt caccaattgg 960
gtcaaatatt ccgcccaaca agctcgctat ttagaagcga aatcggagtt cattaaccat 1020
tggtttaaaa atggtacgca tctcaccacc gacatcatat gggatggcaa tggcactaac 1080
cccaatgccg cgttaaccgt gttccgtcac tttgatagtg cctcagtggt acagggattg 1140
gtgggtgaga agcccaaaac ggcctgggtt ctcgactacg ccttgctaga acgcatccac 1200
tacttgttag tggcgggttt tgatgtgtat ggcaactttg gccatcagtt gatcactcgc 1260
atgtttatgg attttcttcg tttagaaggt gaaagtaact tcatcgcctt gttgcccgca 1320
gatatgcgcc accaagagca atccagctgg tatcaacagc aaaaccgcca actgagcgat 1380
ttcttgcagc gcaatgtggt gccctttagc caaccgacta gcgttgtata taaaaccgat 1440
gatcccaagt ctgagctgtt tgacatatta cgccgtcaag taagcccaat cctgaattcg 1500
cgctatgaga ttgtcgatac tggcatgagc ctgaaaaacg aagcattgct gaagtcattg 1560
aatttggtaa aaggtgaaaa gctgttgcct atcccgcaaa ttactatgtt gatggtcaaa 1620
gcagactctg gaaaagagca gctttataca ctgctgcaca acaatgcaca tttgaacatc 1680
tcaagtttgt ttaacgaaga gaaaaatcgt gacccagcga atgacgacct caccatagtg 1740
cgcggcgttg tcggaagcta ccctgcggcg ttcttctcgt tgaacgaaaa ccaagtagcc 1800
gaattcgttc aaatcattac ttcaatggaa tctgagcaag actacgttaa gttattggat 1860
aagtttgcga ttcgtcgtag ctcaaccaat ttctggtcgt ttagcgacaa agttcatact 1920
tggtatcgca acgatcaacc tatcgaattt ggattgcttg actataatcg ttttgagaac 1980
cgatag 1986

<210> SEQ ID NO 58
<211> LENGTH: 661
<212> TYPE: PRT
<213> ORGANISM: Vibrio vulnificus -continued

```
<400> SEQUENCE: 58

Met Leu Asn Glu Arg Ala Gln Thr Gly Val Ala Asn Ile Asp Ala Gly
1               5                   10                  15

Leu Ile Ala Arg Leu Leu Gln Gln Lys Glu Arg His Pro Leu Pro Gln
            20                  25                  30

Gln Asp Gln Leu Glu Gly Phe Asp Phe Ser Ile Asp Arg Glu Gln Thr
        35                  40                  45

Cys Pro Thr Ile Glu Glu Phe Asp Gln Tyr Glu Arg Thr Asn Pro Ser
    50                  55                  60

Trp Gly Met Pro Phe Gly Met Pro Asn Leu Ser Ala Lys Glu His Gln
65                  70                  75                  80

Thr Leu Met Ala Trp Leu Glu Asn Gly Ala Ile Met Asn Asp His Leu
                85                  90                  95

Pro Leu Thr Arg Glu Gln Ala Ala Glu Ile Thr Arg Tyr Glu Gln Met
            100                 105                 110

Phe Asn Lys Ser Ser Arg Lys Asn Gln Leu Ala Ala Arg Tyr Ile Tyr
        115                 120                 125

Glu His Leu Phe Leu Ser His Leu Tyr Phe Ser Glu Leu Glu Gly Glu
    130                 135                 140

Pro Arg Phe Phe Thr Met Val Arg Ser Ser Thr Pro Pro Gly Glu Pro
145                 150                 155                 160

Val Gln Arg Ile Val Thr Arg Arg Pro Tyr Asp Asp Pro Gly Val Glu
                165                 170                 175

Arg Val Tyr Tyr Arg Ile Ile Pro Glu Gln Gly Thr Ile Val Asp Lys
            180                 185                 190

Thr His Met Pro Phe Ala Leu Asn Ser Gln Arg Met Lys Asp Trp Lys
        195                 200                 205

Ala Trp Phe Ile Asp Ala Asp Tyr Val Val Glu Gln Leu Pro Ser Tyr
    210                 215                 220

Asp Pro Glu Ile Ala Ala Asn Pro Met Ser Ala Phe Ile Asp Leu Pro
225                 230                 235                 240

Val Lys Ala Arg Phe Lys Phe Met Leu Asp Asn Ala Gln Asn Thr Ile
                245                 250                 255

Met Ala Tyr Ile Lys Gly Pro Val Cys Arg Gly Gln Leu Ala Leu Asn
            260                 265                 270

Val Ile Asn Asp Arg Phe Trp Val Phe Phe Leu Asp Pro Asp Lys Ala
        275                 280                 285

Asp Leu Pro Ala Val Asn Glu Phe Tyr Arg Ser Gln Ala Asp Asn Leu
    290                 295                 300

Lys Leu Pro Gly Glu Leu Glu Ser Asn Thr Leu Pro Val Thr Asn Trp
305                 310                 315                 320

Val Lys Tyr Ser Ala Gln Gln Ala Arg Tyr Leu Glu Ala Lys Ser Glu
                325                 330                 335

Phe Ile Asn His Trp Phe Lys Asn Gly Thr His Leu Thr Thr Asp Ile
            340                 345                 350

Ile Trp Asp Gly Asn Gly Thr Asn Pro Asn Ala Ala Leu Thr Val Phe
        355                 360                 365

Arg His Phe Asp Ser Ala Ser Val Val Gln Gly Leu Val Gly Glu Lys
    370                 375                 380

Pro Lys Thr Ala Trp Val Leu Asp Tyr Ala Leu Leu Glu Arg Ile His
385                 390                 395                 400

Tyr Leu Leu Val Ala Gly Phe Asp Val Tyr Gly Asn Phe Gly His Gln
                405                 410                 415
```

```
Leu Ile Thr Arg Met Phe Met Asp Phe Leu Arg Leu Glu Gly Glu Ser
            420                 425                 430

Asn Phe Ile Ala Leu Leu Pro Ala Asp Met Arg His Gln Glu Gln Ser
            435                 440                 445

Ser Trp Tyr Gln Gln Gln Asn Arg Gln Leu Ser Asp Phe Leu Gln Arg
            450                 455                 460

Asn Val Val Pro Phe Ser Gln Pro Thr Ser Val Val Tyr Lys Thr Asp
465                 470                 475                 480

Asp Pro Lys Ser Glu Leu Phe Asp Ile Leu Arg Arg Gln Val Ser Pro
                485                 490                 495

Ile Leu Asn Ser Arg Tyr Glu Ile Val Asp Thr Gly Met Ser Leu Lys
            500                 505                 510

Asn Glu Ala Leu Leu Lys Ser Leu Asn Leu Val Lys Gly Glu Lys Leu
            515                 520                 525

Leu Pro Ile Pro Gln Ile Thr Met Leu Met Val Lys Ala Asp Ser Gly
            530                 535                 540

Lys Glu Gln Leu Tyr Thr Leu Leu His Asn Asn Ala His Leu Asn Ile
545                 550                 555                 560

Ser Ser Leu Phe Asn Glu Glu Lys Asn Arg Asp Pro Ala Asn Asp Asp
                565                 570                 575

Leu Thr Ile Val Arg Gly Val Val Gly Ser Tyr Pro Ala Ala Phe Phe
            580                 585                 590

Ser Leu Asn Glu Asn Gln Val Ala Glu Phe Val Gln Ile Ile Thr Ser
            595                 600                 605

Met Glu Ser Glu Gln Asp Tyr Val Lys Leu Leu Asp Lys Phe Ala Ile
            610                 615                 620

Arg Arg Ser Ser Thr Asn Phe Trp Ser Phe Ser Asp Lys Val His Thr
625                 630                 635                 640

Trp Tyr Arg Asn Asp Gln Pro Ile Glu Phe Gly Leu Leu Asp Tyr Asn
                645                 650                 655

Arg Phe Glu Asn Arg
            660

<210> SEQ ID NO 59
<211> LENGTH: 2289
<212> TYPE: DNA
<213> ORGANISM: Pseudomonas aeruginosa

<400> SEQUENCE: 59
atgttgccaa gaccgttggt tgggttggcc ttcgttttgt cgtctttat  ccagtctgtt       60 tccgctgctg aaatttccta tagccgtgac gtccagccga tctttaccgc caaatgcgtc      120
gcctgccacg cctgctacga ttcgccctgc agctcaacc tgagcagcgc cgagggcgcg       180
cagcgcggcg ccaaccaact gccggtctac gacggcacgc ggaccaaggc gcaggaaacc      240
acccgcctgt acctcgatgc gcacggtgcc gacgcctggc ggcgcaagga cttctggtcg      300
gtgctcgaat cgcaggatgg ccaggccgca ctgatggcgc ggatgctcga gcttggccac      360
agccagccgt tgcagccgaa tgcgaagatc cccgaaggcc tggacatttc gatcaaccgc      420
gccaaccagt gcccgacgcc ggccagcatc gatgcgttca tccgcaagaa cccgggttcc      480
ggcatgcctt tcgcggtggc cgggctgagc gacgacgaat acgccacctt gcagaagtgg      540
ctggccgcgg gcgccccggt cgaccagcag ccgttgcggc cgaccgccgc cgaggcgcgc      600
caggtggcca gctgggagcg tttcctcaac cagcctgggg ccaagcagag cctggtctcg      660
cgctggctct acgagcacct gttcctggcg cacctgtatt tcccggaaca gggcgcgccc      720
```

```
ggccacttct tccagctggt gcgttcacgc acgcccagcg gccagccgat cgacccgatc    780
ccgacccggc gtcccaacga cgatccgggc aacagcttct attaccgcct ctggccgatc    840
cagggcgtga tcgtccacaa gacgcacatc acctatccgc tgacggcgaa gaagctggaa    900
cgcgtccagg agctgttctt cggcacccag tggaacaccg acaaggttcc cggctacggc    960
gtgcagagcc gcgccaaccc gttcgtcacc ttcgccgcga tcccgccacg ggcgcgctac   1020
cagttcatgc tggacaacgc cgagtacttc acccgtacct tcatccgcgg gccggtgtgc   1080
cgtggacaga tcgccaccga cgtgatccgc gacaacttct gggtggtatt ccaggacccc   1140
gagcaggacc tgttcgtcac cgacgccaac ttccgcgcgc agagcgagcc gctgctggcc   1200
ttgccggggc agatcgacga gctgaagaac ctgctcggcc tgtggagcgc ctaccgggac   1260
aagcgcaacg agtacgaaga cctgcgccag gacgtctacg ccgacgcgcc gccgccgacc   1320
tggaacacga tctggcacgg caacgacaac gccctgctga gcatcttccg ccagttcgac   1380
agcgcctcgg tgcgcaaggg cctgcttggc gaggtaccgc agaccctgtg gctgatggac   1440
tacccgctgt cgagcgaacc tactacgggc tggtggtga acttcgatgt cttcggcaac    1500
gtctcgcacc aggcgcagac gcgcctgtac ttcgacctga tccgcaacgg cgccgagcag   1560
aacttcctcc gcttgatgcc ggtcgacgcg cgccagccgt tgcttgacga ctggtaccag   1620
aacagcggca agctgaagat gtggatggac taccaggcct tcgacgatga cacgccgagc   1680
gcgctgggat tgccggagaa gcagccgaag aaggccttcg ccgaagaact gctgcgtcgc   1740
tacggcgacc tcaatgcgcg ccccgacccg atcaaccgct gcctggacgg caactgctat   1800
cgaccgggca tcgaccgcga actgcaggac gccgagcagg ccttcagtcg cctggtcagc   1860
cggccggcgg ccggcctcaa ggtcatagag cgcttcccg aggcgaccat gctgcggata   1920
cgtacgtcca gcggcaagcg cgagatctat accgtgctgc gcaaccgcgc gcacagcaat   1980
gtcgccttca tgctcggcga gtcgctgcgc taccagccgg gcctggacac cctgacgatc   2040
taccccggcg tgctgtccag ctatccgaac ttcatgttcg atctgccggc gacggatgcc   2100
gaggccttcg tcggcgccct ggaggcggcg aagagtagcg aggacttcga caaggtggtc   2160
gaacgctggg gcgtgcgccg cagcaatccg cagttctgga gctacttcca cgatctggag   2220
gcgtacatcc gcgaaaccga accggtcgag gcgggcgcgc tggacatgaa tcgctacgag   2280
aacctctga                                                            2289

<210> SEQ ID NO 60
<211> LENGTH: 762
<212> TYPE: PRT
<213> ORGANISM: Pseudomonas aeruginosa

<400> SEQUENCE: 60

Met Leu Pro Arg Pro Leu Val Gly Leu Ala Phe Val Leu Ser Ser Phe
1               5                   10                  15

Ile Gln Ser Val Ser Ala Ala Glu Ile Ser Tyr Ser Arg Asp Val Gln
            20                  25                  30

Pro Ile Phe Thr Ala Lys Cys Val Ala Cys His Ala Cys Tyr Asp Ser
        35                  40                  45

Pro Cys Gln Leu Asn Leu Ser Ser Ala Glu Gly Ala Gln Arg Gly Ala
    50                  55                  60

Asn Gln Leu Pro Val Tyr Asp Gly Thr Arg Thr Lys Ala Gln Glu Thr
65                  70                  75                  80

Thr Arg Leu Tyr Leu Asp Ala His Gly Ala Asp Ala Trp Arg Arg Lys
                85                  90                  95
```

-continued

```
Asp Phe Trp Ser Val Leu Glu Ser Gln Asp Gly Gln Ala Ala Leu Met
                100                 105                 110

Ala Arg Met Leu Glu Leu Gly His Ser Gln Pro Leu Gln Pro Asn Ala
            115                 120                 125

Lys Ile Pro Glu Gly Leu Asp Ile Ser Ile Asn Arg Ala Asn Gln Cys
130                 135                 140

Pro Thr Pro Ala Ser Ile Asp Ala Phe Ile Arg Lys Asn Pro Gly Ser
145                 150                 155                 160

Gly Met Pro Phe Ala Val Ala Gly Leu Ser Asp Asp Glu Tyr Ala Thr
                165                 170                 175

Leu Gln Lys Trp Leu Ala Ala Gly Ala Pro Val Asp Gln Pro Leu
            180                 185                 190

Arg Pro Thr Ala Ala Glu Ala Arg Gln Val Ala Ser Trp Glu Arg Phe
            195                 200                 205

Leu Asn Gln Pro Gly Ala Lys Gln Ser Leu Val Ser Arg Trp Leu Tyr
        210                 215                 220

Glu His Leu Phe Leu Ala His Leu Tyr Phe Pro Glu Gln Gly Ala Pro
225                 230                 235                 240

Gly His Phe Phe Gln Leu Val Arg Ser Arg Thr Pro Ser Gly Gln Pro
                245                 250                 255

Ile Asp Pro Ile Pro Thr Arg Arg Pro Asn Asp Asp Pro Gly Asn Ser
                260                 265                 270

Phe Tyr Tyr Arg Leu Trp Pro Ile Gln Gly Val Ile Val His Lys Thr
        275                 280                 285

His Ile Thr Tyr Pro Leu Thr Ala Lys Lys Leu Glu Arg Val Gln Glu
        290                 295                 300

Leu Phe Phe Gly Thr Gln Trp Asn Thr Asp Lys Val Pro Gly Tyr Gly
305                 310                 315                 320

Val Gln Ser Arg Ala Asn Pro Phe Val Thr Phe Ala Ala Ile Pro Pro
                325                 330                 335

Arg Ala Arg Tyr Gln Phe Met Leu Asp Asn Ala Glu Tyr Phe Thr Arg
            340                 345                 350

Thr Phe Ile Arg Gly Pro Val Cys Arg Gly Gln Ile Ala Thr Asp Val
            355                 360                 365

Ile Arg Asp Asn Phe Trp Val Val Phe Gln Asp Pro Glu Gln Asp Leu
370                 375                 380

Phe Val Thr Asp Ala Asn Phe Arg Ala Gln Ser Glu Pro Leu Leu Ala
385                 390                 395                 400

Leu Pro Gly Gln Ile Asp Glu Leu Lys Asn Leu Leu Gly Leu Trp Ser
                405                 410                 415

Ala Tyr Arg Asp Lys Arg Asn Glu Tyr Glu Asp Leu Arg Gln Asp Val
            420                 425                 430

Tyr Ala Asp Ala Pro Pro Thr Trp Asn Thr Ile Trp His Gly Asn
            435                 440                 445

Asp Asn Ala Leu Leu Ser Ile Phe Arg Gln Phe Asp Ser Ala Ser Val
        450                 455                 460

Arg Lys Gly Leu Leu Gly Glu Val Pro Gln Thr Leu Trp Leu Met Asp
465                 470                 475                 480

Tyr Pro Leu Phe Glu Arg Thr Tyr Tyr Gly Leu Val Val Asn Phe Asp
                485                 490                 495

Val Phe Gly Asn Val Ser His Gln Ala Gln Thr Arg Leu Tyr Phe Asp
                500                 505                 510

Leu Ile Arg Asn Gly Ala Glu Gln Asn Phe Leu Arg Leu Met Pro Val
        515                 520                 525
```

```
Asp Ala Arg Gln Pro Leu Leu Asp Asp Trp Tyr Gln Asn Ser Gly Lys
    530                 535                 540

Leu Lys Met Trp Met Asp Tyr Gln Ala Phe Asp Asp Thr Pro Ser
545                 550                 555                 560

Ala Leu Gly Leu Pro Glu Lys Gln Pro Lys Lys Ala Phe Ala Glu Glu
                565                 570                 575

Leu Leu Arg Arg Tyr Gly Asp Leu Asn Ala Arg Pro Asp Pro Ile Asn
            580                 585                 590

Arg Cys Leu Asp Gly Asn Cys Tyr Arg Pro Gly Ile Asp Arg Glu Leu
        595                 600                 605

Gln Asp Ala Glu Gln Ala Phe Ser Arg Leu Val Ser Arg Pro Ala Ala
    610                 615                 620

Gly Leu Lys Val Ile Glu Arg Phe Pro Glu Ala Thr Met Leu Arg Ile
625                 630                 635                 640

Arg Thr Ser Ser Gly Lys Arg Glu Ile Tyr Thr Val Leu Arg Asn Arg
                645                 650                 655

Ala His Ser Asn Val Ala Phe Met Leu Gly Glu Ser Leu Arg Tyr Gln
            660                 665                 670

Pro Gly Leu Asp Thr Leu Thr Ile Tyr Pro Gly Val Leu Ser Ser Tyr
        675                 680                 685

Pro Asn Phe Met Phe Asp Leu Pro Ala Thr Ala Glu Ala Phe Val
    690                 695                 700

Gly Ala Leu Glu Ala Ala Lys Ser Ser Glu Asp Phe Asp Lys Val Val
705                 710                 715                 720

Glu Arg Trp Gly Val Arg Arg Ser Asn Pro Gln Phe Trp Ser Tyr Phe
                725                 730                 735

His Asp Leu Glu Ala Tyr Ile Arg Glu Thr Glu Pro Val Glu Ala Gly
            740                 745                 750

Ala Leu Asp Met Asn Arg Tyr Glu Asn Leu
        755                 760

<210> SEQ ID NO 61
<211> LENGTH: 2295
<212> TYPE: DNA
<213> ORGANISM: Pseudomonas fluorescens

<400> SEQUENCE: 61
atgtcgtacc gcgtcatcag cattgcattg ctgtttttaa gctttggcgc ggcggcgcag    60
agtcccgctg tttcttcttc tatttcctac acccgggaca tccagccgat cttcaccgaa   120
aagtgtgtgg cctgccatgc gtgctacgac tctgcttgcc agcttaatct gggcagcggc   180
gaaggtgcgg cccgtggcgc gagcaagatg cccgtctacg atggcgaacg cacccaggcg   240
gcgccgacca cgcggctgtt ctatgacgcc ttcggcaaac gggcctggca gcagaaagat   300
ttctactcgg tgctcgacgc ccagggcagt caggcggcgc tgatggcgcg catgctggag   360
ctggggcaca aaacgccact gacccccaac gccaaattgc cggaagacat cgtgctgggc   420
ctcaatcgcg agaacctgtg cgcgatgccc gccgagttcg acggctatgc cggcgcccat   480
ccgaaagagg gcatgccgct ggcggtgacc ggtctgaccg atcagcaata tcagacgctg   540
caacgctggc tcgcttccgg tgcgccgatc gacgagcaag gcctggcgcc aagcgctaag   600
gaggcgatgc agatcgtcca gtgggaaaac ctgctcaacc agcctggcgc gcgggaaagt   660
ctggtcgggc gctggttgtt cgaacactgg ttttggcgc acatctattt caaggacggc   720
gagccggggc attacttcca gtgggtgcgt tcgcgcacac cgaccggcca gccgatcgat   780
```

```
ctgatcgcca cgcgtcgccc gaacgacgat ccgggcaccc aggtttacta tcgcttgtgg    840
ccggtgcagg gcgtgatcgt gcacaagacc cacatcacct atccgctgag cgcggcgaag    900
atggcgcggg tcaaaagcct gttctacaac ggcaactggc aggtcaacgc tttgccgggc    960
tacgggccgc agagtcgagc caacccgttc gcgaccttcg aggcgatccc ggcgcaggcg   1020
cgttaccagt tcatgctcga taacgccgaa tacttcgtgc gcaccttcat tcgcggccca   1080
gtgtgccgtg gcagatcgc gaccgacgtg atccgcgaca acttctgggc gctgttccag    1140
gcgccggaac acgacctgta catcaccgac ccgaactatc gcggccaggc cacgccgttg   1200
ctggccatgc cggggcagaa cgacgatgtc ggcagtgtcc tgagcctgtg cacaactac    1260 cgcaacaagc gaaaccaata cgaagccctg cgccgtgaca gctacgccga cctgccggca   1320
ccgagctggt cgaccctgtg ggccggcaac gacaacgcct tgctcagcat cttccgtcac   1380
ttcgacagcg cttcggtgac caagggcctg atcggcgagg tgccgcagac gatgtggctg   1440
ttcgactatc cgctgctgga gcgcacctat taccagctgg cggtgaattt cgatgtgttc   1500
ggcaacgtct ctcatcaggc gcaaacacgc ctgtatttcg acctgatccg caacggcgcc   1560
gagcagaact cctgcgcct gatgcctgcc gattcccgcg agggttacct tgacgattgg    1620
taccagagca gcggccagtt caagatgtgg ctcgattacg aagccatcga cgacgacaag   1680
ccgaccgcac tgaaactcga cgagaaagac ccgaaacacg atttcgccat gcaattgctg   1740
gcgcgctacg gcgatctcaa cgcgcgtccg gatccgatca accgttgcga agacgcctat   1800
tgctcgcgcc cgaacatcga cccggcgctg caaaatgccg agcaggcgct gagtcgcctg   1860
acttcgcgcc cggcggcggg gctgaaagtg atcgatcaat tgccggaagc caccatgctg   1920
cgggttgaaa cccgtagcgg caaacgtgag gtctacagcc tgctgcgcaa tcgtgcccac   1980
agcaacgtgg cgttcctgct cggtgaatcg ctgcgttatc agccgggcct ggacacgctg   2040
acgatctatc caggcgtgct cagcagctac ccgaatttca tgttcaacgt cccggcggat   2100
caggtgcctg cgtttgtcga tgccatggaa aacgcgaagg atgcgccgca attcgagaag   2160
atcgtcgaac gttggggcat ccgccgcagt catccgcagt tctggttcta tttccacgac   2220
ctgagccagt acatccacga gaccgagccg gtggaagagg gcgtgctgga tatgaaccgg   2280
tacgagaatc tttga                                                    2295
```

<210> SEQ ID NO 62
<211> LENGTH: 764
<212> TYPE: PRT
<213> ORGANISM: Pseudomonas fluorescens

<400> SEQUENCE: 62

Met Ser Tyr Arg Val Ile Ser Ile Ala Leu Leu Phe Leu Ser Phe Gly
1               5                   10                  15

Ala Ala Ala Gln Ser Pro Ala Val Ser Ser Ser Ile Ser Tyr Thr Arg
            20                  25                  30

Asp Ile Gln Pro Ile Phe Thr Glu Lys Cys Val Ala Cys His Ala Cys
        35                  40                  45

Tyr Asp Ser Ala Cys Gln Leu Asn Leu Gly Ser Gly Glu Gly Ala Ala
    50                  55                  60

Arg Gly Ala Ser Lys Met Pro Val Tyr Asp Gly Glu Arg Thr Gln Ala
65                  70                  75                  80

Ala Pro Thr Thr Arg Leu Phe Tyr Asp Ala Phe Gly Lys Arg Ala Trp
                85                  90                  95

Gln Gln Lys Asp Phe Tyr Ser Val Leu Asp Ala Gln Gly Ser Gln Ala
            100                 105                 110

Ala Leu Met Ala Arg Met Leu Glu Leu Gly His Lys Thr Pro Leu Thr
            115                 120                 125

Pro Asn Ala Lys Leu Pro Glu Asp Ile Val Leu Gly Leu Asn Arg Glu
130                 135                 140

Asn Leu Cys Ala Met Pro Ala Glu Phe Asp Gly Tyr Ala Gly Ala His
145                 150                 155                 160

Pro Lys Glu Gly Met Pro Leu Ala Val Thr Gly Leu Thr Asp Gln Gln
                165                 170                 175

Tyr Gln Thr Leu Gln Arg Trp Leu Ala Ser Gly Ala Pro Ile Asp Glu
            180                 185                 190

Gln Gly Leu Ala Pro Ser Ala Lys Glu Ala Met Gln Ile Val Gln Trp
        195                 200                 205

Glu Asn Leu Leu Asn Gln Pro Gly Ala Arg Glu Ser Leu Val Gly Arg
    210                 215                 220

Trp Leu Phe Glu His Trp Phe Leu Ala His Ile Tyr Phe Lys Asp Gly
225                 230                 235                 240

Glu Pro Gly His Tyr Phe Gln Trp Val Arg Ser Arg Thr Pro Thr Gly
                245                 250                 255

Gln Pro Ile Asp Leu Ile Ala Thr Arg Arg Pro Asn Asp Pro Gly
            260                 265                 270

Thr Gln Val Tyr Tyr Arg Leu Trp Pro Val Gln Gly Val Ile Val His
        275                 280                 285

Lys Thr His Ile Thr Tyr Pro Leu Ser Ala Ala Lys Met Ala Arg Val
    290                 295                 300

Lys Ser Leu Phe Tyr Asn Gly Asn Trp Gln Val Asn Ala Leu Pro Gly
305                 310                 315                 320

Tyr Gly Pro Gln Ser Arg Ala Asn Pro Phe Ala Thr Phe Glu Ala Ile
                325                 330                 335

Pro Ala Gln Ala Arg Tyr Gln Phe Met Leu Asp Asn Ala Glu Tyr Phe
            340                 345                 350

Val Arg Thr Phe Ile Arg Gly Pro Val Cys Arg Gly Gln Ile Ala Thr
        355                 360                 365

Asp Val Ile Arg Asp Asn Phe Trp Ala Leu Phe Gln Ala Pro Glu His
    370                 375                 380

Asp Leu Tyr Ile Thr Asp Pro Asn Tyr Arg Gly Gln Ala Thr Pro Leu
385                 390                 395                 400

Leu Ala Met Pro Gly Gln Asn Asp Asp Val Gly Ser Val Leu Ser Leu
                405                 410                 415

Trp His Asn Tyr Arg Asn Lys Arg Asn Gln Tyr Glu Ala Leu Arg Arg
            420                 425                 430

Asp Ser Tyr Ala Asp Leu Pro Ala Pro Ser Trp Ser Thr Leu Trp Ala
        435                 440                 445

Gly Asn Asp Asn Ala Leu Leu Ser Ile Phe Arg His Phe Asp Ser Ala
    450                 455                 460

Ser Val Thr Lys Gly Leu Ile Gly Glu Val Pro Gln Thr Met Trp Leu
465                 470                 475                 480

Phe Asp Tyr Pro Leu Leu Glu Arg Thr Tyr Tyr Gln Leu Ala Val Asn
                485                 490                 495

Phe Asp Val Phe Gly Asn Val Ser His Gln Ala Gln Thr Arg Leu Tyr
            500                 505                 510

Phe Asp Leu Ile Arg Asn Gly Ala Glu Gln Asn Phe Leu Arg Leu Met
        515                 520                 525

Pro Ala Asp Ser Arg Glu Gly Tyr Leu Asp Asp Trp Tyr Gln Ser Ser

```
                530             535             540
Gly Gln Phe Lys Met Trp Leu Asp Tyr Glu Ala Ile Asp Asp Lys
545                 550                 555                 560

Pro Thr Ala Leu Lys Leu Asp Glu Lys Asp Pro Lys His Asp Phe Ala
                565                 570                 575

Met Gln Leu Leu Ala Arg Tyr Gly Asp Leu Asn Ala Arg Pro Asp Pro
                580                 585                 590

Ile Asn Arg Cys Glu Asp Ala Tyr Cys Ser Arg Pro Asn Ile Asp Pro
                595                 600                 605

Ala Leu Gln Asn Ala Glu Gln Ala Leu Ser Arg Leu Thr Ser Arg Pro
                610                 615                 620

Ala Ala Gly Leu Lys Val Ile Asp Gln Leu Pro Glu Ala Thr Met Leu
625                 630                 635                 640

Arg Val Glu Thr Arg Ser Gly Lys Arg Glu Val Tyr Ser Leu Leu Arg
                645                 650                 655

Asn Arg Ala His Ser Asn Val Ala Phe Leu Leu Gly Glu Ser Leu Arg
                660                 665                 670

Tyr Gln Pro Gly Leu Asp Thr Leu Thr Ile Tyr Pro Gly Val Leu Ser
                675                 680                 685

Ser Tyr Pro Asn Phe Met Phe Asn Val Pro Ala Asp Gln Val Pro Ala
                690                 695                 700

Phe Val Asp Ala Met Glu Asn Ala Lys Asp Ala Pro Gln Phe Glu Lys
705                 710                 715                 720

Ile Val Glu Arg Trp Gly Ile Arg Arg Ser His Pro Gln Phe Trp Phe
                725                 730                 735

Tyr Phe His Asp Leu Ser Gln Tyr Ile His Glu Thr Glu Pro Val Glu
                740                 745                 750

Glu Gly Val Leu Asp Met Asn Arg Tyr Glu Asn Leu
                755                 760

<210> SEQ ID NO 63
<211> LENGTH: 2397
<212> TYPE: DNA
<213> ORGANISM: Methylococcus capsulatus

<400> SEQUENCE: 63
gtgctggcga tcgccggctg catcgaggct taccgcaccg gtcacgatgc acgtcatggt      60
ccacgggtgc cgtgggagcg gcgcctgagc gaggaggact atctggcccg cctcgccgcc     120
ggcagcgtgt cttacagccg cgatgtccag cctatcctcg attcgcgctg tgtcgtctgt     180
catggctgtt atgacgcgcc ttgccagctg aagctggagt ccttcgacgg cctggagcgc     240
ggcgccagca agactcccgt ctatgacacc acccgtctcc aggccactcc gccaacgcgt     300 tgttcatcg atgcagaaaa tgttcaaggc tggcgttcca aggggttctt cccggtactg     360
aacgaacggg gcgattcgcc cgaggcgaat ctgcgggatt ccttactgtt ccggatgctc     420
gaactgaaga aagcgcatcc cttgcccgtt ccggcgcgt tgccggacac tttcgacttc     480
cgtctggacc gcaccctgaa ctgtcccacc gtcaagagt tcgacgattt cgaggacgat     540
caccccgagt gggggatgcc ttacggtttc cccggtctga gcgagcgcga gcacgatatc     600
gtggtgaagt ggctgcgcga gggcgggttc gcgccgcctc ccgcgcccgt gtcggccgag     660
gccgcatcgg ccgtggcgca atgggaggcg ttcctcaacg gctccagtcc aaaggaacgg     720
ctgtttgccc gctatgtcta cgaacatctc ttcctcggcc atctgcattt ccgtggtctg     780
gcgccccgcg agttcttccg gctggtgcgc tcccgcacgc cgcccgggga gccgatccgg     840
```

-continued

```
gaaatcgcga cgacccgacc ctacgacagt ccgggaccgg gggaattcta ttaccgcttg    900
cgaccggtgc agcaaagcat cgtcgctaag acccacatgg tctacgaact cgacgacgcc    960
cggatgcggc gctaccggga gctgtttctg gatcccgagt acgcggtcga ccggctgccg   1020
gggtatgccg ccgccgatgc cgccaacccc ttcaagacgt cgttgccat tcctcccagg   1080
tcgcgctacc ggtttctgct cgacgacgcc catttctttt tctccggttt tatgaagggg   1140
tcggtgtgcc gcggccaggc cgcactcaat gtgatccagg atcggttttg ggtggctttc   1200
actcatccgg acgccgatcc cgtcagcaac gacgcccaat tcctggccga tcaggcggag   1260
cgtctgcggc tgccggccga aaggaaaac tcgcccggga tcggggacat ctggtacacc   1320
taccgggcac tggaagagga ttatcaggcg gccaaggcgg cgtggcttcg ggcacacggt   1380
gagcgcggcg gcaccacgct ggctgacctg tgggatggcg acggcgacaa tcgcgatgcc   1440
ttgctgacgg tgttccggca tttcgacagc gcttcggttg agcgagggct ggtcggcgac   1500
acgccgctga ccggctgggt cgtcgattat cccttgctgg aacggattca ttatctgttg   1560
gtggccgggt tcgatgtgtt cggcaacgtc ggccaccagt tggcaacccg tttgtacatg   1620
gacttcatgc gtatggaggc ggaaaacaat tttctgcggt tcctgccgtc gagcatacgg   1680
caggccgaac gcgcccggtg gtacaaaggc attggtgcga gaatcaacga tctttggcag   1740
agtccgcgct gggggatggg gggggagacg ctcatcgatt atcggaccgg caatcccaag   1800
caggagttct tcgatcgggt ccgggccggt ttcggcaagg cggcgggccg tcccgatccg   1860
ttcaccggct gcggtgtgga agtggaagga tgcggggagg gcggcgagcc agcgttgccg   1920
ccggtgcagg cgtccgtcga gcgcgaactg cgacgcctgg cattcgccag gggcggtgga   1980
gtcgcctttc ttccggaact gtcgtacctg cgcatccgga ccgggagcgg tggggcggaa   2040
gacggctgga tctacagctt ggtcaagaat acggcgctcg aaaacgtgtc gatgctgttt   2100
ctcgaagaga taaggcggac gccggcggac gatacagtga ccctggttcg cggtatcgtc   2160
ggaagttatc cgaatttctt tttcgatctg gatgcagccg aggtcggcga attcgtggac   2220
gccatcctga gtgtggacgg ttccaaggcg tttgggcgga ggctggtcga gcgcttcggt   2280
gtccgccgaa gcaatccggc attctggaga atatcggatt ggttcaaccg gcggtacctc   2340
gaagccagcc ccgtcacggc gggctggctg gatctgagcc gttacgacaa tccatga      2397
```

<210> SEQ ID NO 64
<211> LENGTH: 798
<212> TYPE: PRT
<213> ORGANISM: Methylococcus capsulatus

<400> SEQUENCE: 64

Met Leu Ala Ile Ala Gly Cys Ile Glu Ala Tyr Arg Thr Gly His Asp
1               5                   10                  15

Ala Arg His Gly Pro Arg Val Pro Trp Glu Arg Arg Leu Ser Glu Glu
            20                  25                  30

Asp Tyr Leu Ala Arg Leu Ala Ala Gly Ser Val Ser Tyr Ser Arg Asp
        35                  40                  45

Val Gln Pro Ile Leu Asp Ser Arg Cys Val Val His Gly Cys Tyr
    50                  55                  60

Asp Ala Pro Cys Gln Leu Lys Leu Glu Ser Phe Asp Gly Leu Glu Arg
65                  70                  75                  80

Gly Ala Ser Lys Thr Pro Val Tyr Asp Thr Thr Arg Leu Gln Ala Thr
                85                  90                  95

Pro Pro Thr Arg Leu Phe Ile Asp Ala Glu Asn Val Gln Gly Trp Arg
            100                 105                 110

Ser Lys Gly Phe Phe Pro Val Leu Asn Glu Arg Gly Asp Ser Pro Glu
115                 120                 125

Ala Asn Leu Arg Asp Ser Leu Leu Phe Arg Met Leu Glu Leu Lys Lys
130                 135                 140

Ala His Pro Leu Pro Val Ser Gly Ala Leu Pro Asp Thr Phe Asp Phe
145                 150                 155                 160

Arg Leu Asp Arg Thr Leu Asn Cys Pro Thr Val Glu Phe Asp Asp
                165                 170                 175

Phe Glu Asp Asp His Pro Glu Trp Gly Met Pro Tyr Gly Phe Pro Gly
                180                 185                 190

Leu Ser Glu Arg Glu His Asp Ile Val Val Lys Trp Leu Arg Glu Gly
                195                 200                 205

Gly Phe Ala Pro Pro Pro Ala Pro Val Ser Ala Glu Ala Ala Ser Ala
        210                 215                 220

Val Ala Gln Trp Glu Ala Phe Leu Asn Gly Ser Ser Pro Lys Glu Arg
225                 230                 235                 240

Leu Phe Ala Arg Tyr Val Tyr Glu His Leu Phe Leu Gly His Leu His
                245                 250                 255

Phe Arg Gly Leu Ala Pro Arg Glu Phe Phe Arg Leu Val Arg Ser Arg
                260                 265                 270

Thr Pro Pro Gly Glu Pro Ile Arg Glu Ile Ala Thr Thr Arg Pro Tyr
                275                 280                 285

Asp Ser Pro Gly Pro Gly Glu Phe Tyr Tyr Arg Leu Arg Pro Val Gln
                290                 295                 300

Gln Ser Ile Val Ala Lys Thr His Met Val Tyr Glu Leu Asp Asp Ala
305                 310                 315                 320

Arg Met Arg Arg Tyr Arg Glu Leu Phe Leu Asp Pro Glu Tyr Ala Val
                325                 330                 335

Asp Arg Leu Pro Gly Tyr Ala Ala Ala Asp Ala Ala Asn Pro Phe Lys
                340                 345                 350

Thr Phe Val Ala Ile Pro Pro Arg Ser Arg Tyr Arg Phe Leu Leu Asp
                355                 360                 365

Asp Ala His Phe Phe Phe Ser Gly Phe Met Lys Gly Ser Val Cys Arg
                370                 375                 380

Gly Gln Ala Ala Leu Asn Val Ile Gln Asp Arg Phe Trp Val Ala Phe
385                 390                 395                 400

Thr His Pro Asp Ala Asp Pro Val Ser Asn Asp Ala Gln Phe Leu Ala
                405                 410                 415

Asp Gln Ala Glu Arg Leu Arg Leu Pro Ala Glu Lys Glu Asn Ser Pro
                420                 425                 430

Gly Ile Gly Asp Ile Trp Tyr Thr Tyr Arg Ala Leu Glu Glu Asp Tyr
                435                 440                 445

Gln Ala Ala Lys Ala Ala Trp Leu Arg Ala His Gly Glu Arg Gly Gly
450                 455                 460

Thr Thr Leu Ala Asp Leu Trp Asp Gly Asp Gly Asp Asn Arg Asp Ala
465                 470                 475                 480

Leu Leu Thr Val Phe Arg His Phe Asp Ser Ala Ser Val Glu Arg Gly
                485                 490                 495

Leu Val Gly Asp Thr Pro Leu Thr Gly Trp Val Val Asp Tyr Pro Leu
                500                 505                 510

Leu Glu Arg Ile His Tyr Leu Leu Val Ala Gly Phe Asp Val Phe Gly
                515                 520                 525

Asn Val Gly His Gln Leu Ala Thr Arg Leu Tyr Met Asp Phe Met Arg

```
                530             535             540
Met Glu Ala Glu Asn Asn Phe Leu Arg Phe Leu Pro Ser Ser Ile Arg
545                 550                 555                 560

Gln Ala Glu Arg Ala Arg Trp Tyr Lys Gly Ile Gly Ala Arg Ile Asn
                565                 570                 575

Asp Leu Trp Gln Ser Pro Arg Trp Gly Met Gly Glu Thr Leu Ile
            580                 585                 590

Asp Tyr Arg Thr Gly Asn Pro Lys Gln Glu Phe Phe Asp Arg Val Arg
                595                 600                 605

Ala Gly Phe Gly Lys Ala Ala Gly Arg Pro Asp Pro Phe Thr Gly Cys
            610                 615                 620

Gly Val Glu Val Glu Gly Cys Gly Glu Gly Gly Glu Pro Ala Leu Pro
625                 630                 635                 640

Pro Val Gln Ala Ser Val Glu Arg Glu Leu Arg Leu Ala Phe Ala
                645                 650                 655

Arg Gly Gly Gly Val Ala Phe Leu Pro Glu Leu Ser Tyr Leu Arg Ile
            660                 665                 670

Arg Thr Gly Ser Gly Gly Ala Glu Asp Gly Trp Ile Tyr Ser Leu Val
            675                 680                 685

Lys Asn Thr Ala Leu Glu Asn Val Ser Met Leu Phe Leu Glu Glu Ile
690                 695                 700

Arg Arg Thr Pro Ala Asp Asp Thr Val Thr Leu Val Arg Gly Ile Val
705                 710                 715                 720

Gly Ser Tyr Pro Asn Phe Phe Asp Leu Asp Ala Ala Glu Val Gly
                725                 730                 735

Glu Phe Val Asp Ala Ile Leu Ser Val Asp Gly Ser Lys Ala Phe Gly
            740                 745                 750

Arg Arg Leu Val Glu Arg Phe Gly Val Arg Arg Ser Asn Pro Ala Phe
            755                 760                 765

Trp Arg Ile Ser Asp Trp Phe Asn Arg Tyr Leu Glu Ala Ser Pro
770                 775                 780

Val Thr Ala Gly Trp Leu Asp Leu Ser Arg Tyr Asp Asn Pro
785                 790                 795

<210> SEQ ID NO 65
<211> LENGTH: 2313
<212> TYPE: DNA
<213> ORGANISM: Pseudomonas syringae

<400> SEQUENCE: 65
atgccgctcc gtttgttggc aagcgtcgcc ttactgttta tctgctgtgc tacccaggcc        60 cagaaccctca catcgcccgc tacatcagcg ccaccggcta tttcctatgt tcaggacatt      120
cagccaatcc ttaccgagaa gtgcgttgcc tgccacgcct gcaatgacgc gccgtgccaa      180
ctgaatctgg gcagcgggga agggctgagc cgtggcgcga gcaagattcc tgtttatcaa      240
ggggagcgta gcgaagcggt tgcgcccacc cggctgtttt acgatgcgcg caacactgat      300
gcatggcgcg gtaaaggctt ctattcggta ctggaagccc aggcggtca ggcggctttg       360 atggcgcgca tgctcgatct ggggcgcagc gcgccgttgc cggccaacag caaaatcccc      420
gatgagatcg cgctgggcct caatcgcgag aacgtctgcc cgatgcccgg cgaattcaat      480
gcctatgctg cggcccacac gcagcaaggc atgccgctgg cagtcgccgg tctgaccgac      540
gctgaatacc agacactgca cgcgctggct gccgctggtg cccggtcga acaacagtcg      600 atcaccccga gcgtcagtga gaccgcgcaa atcaacgcct gggaggcgct gctcaaccag      660
```

```
ccgggtgcca ggcaggcgct ggttggccgc tggctgttcg agcatttgtt tctggcacac    720
atctatttcg agggcggcga gacgcagcac ttttcccaat gggtacgctc gcgaacccca    780
agtggtcagc cggtggacct gatcgccacc cggcgccccg atgacgaccc aggcagcgac    840
ttctattacc gcctggtgcc tgtgcaaggc gtgatcgttc acaagaccca catcaccttt    900
gccatgagcc gcagaaaact cgaccgggtc cgccacttgt tctatggcac cgactggaca    960
gtcaacgcgc tgcccggtta cggtccgggc accgtgccaa tccgtttcct gacctttgaa   1020
gcgattccgg ccgtcgcgcg ttaccagttc atgctcgata cgccgagta ttttgtgcgt   1080
acgtttatcc gcgggccggt ctgtcgcggg cagattgcga ctgatgtgat tcgtgaccag   1140
ttctgggtac tgtttcagga ccccgcgcac gatcattaca tcaccgatgc cgcttatcgg   1200
gggcacgcca tgcctttgct ggccatgccg gggcagaacg acgacgtcgg cagtgtgctc   1260
agcctgtggt tgtcctatcg ggaccggcgt aaccagtacg aggacctgcg ccgcgacagc   1320
tacgcgaaaa tgcctgcgcc gggctggagt acgctatgga ctggtaacga taatgccttg   1380
ctgaccgttt ccgccatttt cgacagtgct tcggtgaata aaggcctgat tggtgatgtg   1440
ccgcattcca tgtggttgtt cgactttccc ctgcttgagc gcacctatta ccagttggcg   1500
gtgaatttcg atgtgtacgg caatgtttcg catcaggcac agacacgtct gtatttcgac   1560
ctgatccgca acggcgcaga gatcaacttc ctgcgcctga tgcctgccga tcagcgcgac   1620
ggcatgctcg gcgacctta tcaggatggc ggcaaattca agatgtggct cgattatcag   1680
agcatcgacg acgatacgcc gaccggcatc aaactcgacg caaaggcccc gcagcgtgac   1740
ttcgcattca agctgatcga gcgctccggc agcctgaacg ccgcgccgga cccgatcaat   1800
cgctgcgcag gtgcttattg ctcgcgggcc agtctggaca gcacgttcgc ccaggcagag   1860
caggcgctga gccgcttgac gtcgcgtccg gcagcgggcc tgaaagtcat cgatcaactg   1920
ccggaagcga gcatgctgcg catccagggc agcgacggca gcggctgat gtacagcatg   1980
ctgcgcaacc gcgcacacag taacgtcgcg tttctgctgg gtgagtcata ccgctatata   2040
ccggggctgg acaccctgac catttatccc ggcgtactga gcagctaccc gaacttcatc   2100
ttcaacattc cggctgcaca agtgcctgcc tttgtcgacg ccatgcagca gagcaaggac   2160
caggcgagtt ttgaacagat cgtccagcgt tggggcattc gtcggaccca cccactgttc   2220
tggacctatt tccacgacct gaatcactat cttcaggaaa ccgaaccgcg tgaagcggcg   2280
gtgcttgaca tgaatcgcta cgagaacctc taa                                2313
```

<210> SEQ ID NO 66
<211> LENGTH: 770
<212> TYPE: PRT
<213> ORGANISM: Pseudomonas syringae

<400> SEQUENCE: 66

Met Pro Leu Arg Leu Leu Ala Ser Val Ala Leu Leu Phe Ile Cys Cys
1               5                   10                  15

Ala Thr Gln Ala Gln Asn Leu Thr Ser Pro Ala Thr Ser Ala Pro Pro
            20                  25                  30

Ala Ile Ser Tyr Val Gln Asp Ile Gln Pro Ile Leu Thr Glu Lys Cys
        35                  40                  45

Val Ala Cys His Ala Cys Asn Asp Ala Pro Cys Gln Leu Asn Leu Gly
    50                  55                  60

Ser Gly Glu Gly Leu Ser Arg Gly Ala Ser Lys Ile Pro Val Tyr Gln
65                  70                  75                  80

Gly Glu Arg Ser Glu Ala Val Ala Pro Thr Arg Leu Phe Tyr Asp Ala

-continued

```
                85                  90                  95
Arg Asn Thr Asp Ala Trp Arg Gly Lys Gly Phe Tyr Ser Val Leu Glu
                100                 105                 110

Ala Gln Gly Gly Gln Ala Ala Leu Met Ala Arg Met Leu Asp Leu Gly
            115                 120                 125

Arg Ser Ala Pro Leu Pro Ala Asn Ser Lys Ile Pro Asp Glu Ile Ala
        130                 135                 140

Leu Gly Leu Asn Arg Glu Asn Val Cys Pro Met Pro Gly Glu Phe Asn
145                 150                 155                 160

Ala Tyr Ala Ala Ala His Thr Gln Gln Gly Met Pro Leu Ala Val Ala
                165                 170                 175

Gly Leu Thr Asp Ala Glu Tyr Gln Thr Leu Gln Arg Trp Leu Ala Ala
            180                 185                 190

Gly Ala Pro Val Glu Gln Gln Ser Ile Thr Pro Ser Val Ser Glu Thr
        195                 200                 205

Ala Gln Ile Asn Ala Trp Glu Ala Leu Leu Asn Gln Pro Gly Ala Arg
    210                 215                 220

Gln Ala Leu Val Gly Arg Trp Leu Phe Glu His Leu Phe Leu Ala His
225                 230                 235                 240

Ile Tyr Phe Glu Gly Gly Glu Thr Gln His Phe Phe Gln Trp Val Arg
                245                 250                 255

Ser Arg Thr Pro Ser Gly Gln Pro Val Asp Leu Ile Ala Thr Arg Arg
            260                 265                 270

Pro Asp Asp Asp Pro Gly Ser Asp Phe Tyr Tyr Arg Leu Val Pro Val
        275                 280                 285

Gln Gly Val Ile Val His Lys Thr His Ile Thr Phe Ala Met Ser Pro
    290                 295                 300

Gln Lys Leu Asp Arg Val Arg His Leu Phe Tyr Gly Thr Asp Trp Thr
305                 310                 315                 320

Val Asn Ala Leu Pro Gly Tyr Gly Pro Gly His Arg Ala Asn Pro Phe
                325                 330                 335

Leu Thr Phe Glu Ala Ile Pro Ala Val Ala Arg Tyr Gln Phe Met Leu
            340                 345                 350

Asp Asn Ala Glu Tyr Phe Val Arg Thr Phe Ile Arg Gly Pro Val Cys
        355                 360                 365

Arg Gly Gln Ile Ala Thr Asp Val Ile Arg Asp Gln Phe Trp Val Leu
    370                 375                 380

Phe Gln Asp Pro Ala His Asp His Tyr Ile Thr Asp Ala Ala Tyr Arg
385                 390                 395                 400

Gly His Ala Met Pro Leu Leu Ala Met Pro Gly Gln Asn Asp Asp Val
                405                 410                 415

Gly Ser Val Leu Ser Leu Trp Leu Ser Tyr Arg Asp Arg Arg Asn Gln
            420                 425                 430

Tyr Glu Asp Leu Arg Arg Asp Ser Tyr Ala Lys Met Pro Ala Pro Gly
        435                 440                 445

Trp Ser Thr Leu Trp Thr Gly Asn Asp Asn Ala Leu Leu Thr Val Phe
    450                 455                 460

Arg His Phe Asp Ser Ala Ser Val Asn Lys Gly Leu Ile Gly Asp Val
465                 470                 475                 480

Pro His Ser Met Trp Leu Phe Asp Phe Pro Leu Leu Glu Arg Thr Tyr
                485                 490                 495

Tyr Gln Leu Ala Val Asn Phe Asp Val Tyr Gly Asn Val Ser His Gln
            500                 505                 510
```

-continued

```
Ala Gln Thr Arg Leu Tyr Phe Asp Leu Ile Arg Asn Gly Ala Glu Ile
            515                 520                 525

Asn Phe Leu Arg Leu Met Pro Ala Asp Gln Arg Asp Gly Met Leu Gly
    530                 535                 540

Asp Leu Tyr Gln Asp Gly Gly Lys Phe Lys Met Trp Leu Asp Tyr Gln
545                 550                 555                 560

Ser Ile Asp Asp Thr Pro Thr Gly Ile Lys Leu Asp Ala Lys Ala
                565                 570                 575

Pro Gln Arg Asp Phe Ala Phe Lys Leu Ile Glu Arg Ser Gly Ser Leu
                580                 585                 590

Asn Ala Ala Pro Asp Pro Ile Asn Arg Cys Ala Gly Ala Tyr Cys Ser
            595                 600                 605

Arg Ala Ser Leu Asp Ser Thr Phe Ala Gln Ala Glu Gln Ala Leu Ser
610                 615                 620

Arg Leu Thr Ser Arg Pro Ala Ala Gly Leu Lys Val Ile Asp Gln Leu
625                 630                 635                 640

Pro Glu Ala Ser Met Leu Arg Ile Gln Gly Ser Asp Gly Lys Arg Leu
                645                 650                 655

Met Tyr Ser Met Leu Arg Asn Arg Ala His Ser Asn Val Ala Phe Leu
            660                 665                 670

Leu Gly Glu Ser Tyr Arg Tyr Ile Pro Gly Leu Asp Thr Leu Thr Ile
            675                 680                 685

Tyr Pro Gly Val Leu Ser Ser Tyr Pro Asn Phe Ile Phe Asn Ile Pro
    690                 695                 700

Ala Ala Gln Val Pro Ala Phe Val Asp Ala Met Gln Gln Ser Lys Asp
705                 710                 715                 720

Gln Ala Ser Phe Glu Gln Ile Val Gln Arg Trp Gly Ile Arg Arg Thr
                725                 730                 735

His Pro Leu Phe Trp Thr Tyr Phe His Asp Leu Asn His Tyr Leu Gln
            740                 745                 750

Glu Thr Glu Pro Arg Glu Ala Ala Val Leu Asp Met Asn Arg Tyr Glu
        755                 760                 765

Asn Leu
    770

<210> SEQ ID NO 67
<211> LENGTH: 2316
<212> TYPE: DNA
<213> ORGANISM: Vibrio parahaemolyticus

<400> SEQUENCE: 67
ctgtttgctg gttgtgctac ttatgctggc ctgaactttg accaattgtt cggccctcag      60
ttggttcgtg agcgtactgc cagcgttgaa acgccacagg cagatttctt ccaacgcgag     120
gtaaaaccta tcgtcgataa ccgctgtgtg gtttgccacg cctgctacga tgcgccatgt     180
cagctaaaac tctcatcggt agaagggatc gaccgcggag catcgaaggc gttggtttat     240
gaaggcactc gcctgactgc ggctgcacct actcgcttgt ttgaagatgc agaaaccacc     300
caagaatggc gcgacgctgg cttccaccct gttttgaatg aacgcgacca agcatggcg      360 gcaaaccttg aagctggcct tatcgctcgt ttattgcaac agaaagagcg ccatcccttg     420
ccagaccaag tgcaattaga aggttttgat ttttcgattg atcgtgagca aacctgcccg     480
acaattgaag agtacgaaca gtacgaaaaa gacaacccaa actggggaat gccatttggt     540
atgccgaatc taaccaacag cgaataccac acgctgatga cttggctaga aaacggcgcg     600
atcatgaata tgcacacgcc aatcagtgac caagagcagg cgaaaatcaa tcaatacgaa     660
```

```
acactgctca accattcaga cctcaaaaac cagttgatgt cgcgttacat ttacgagcac    720
ttgttcctgt cgcacctgta cttctctgag ttgagcgaaa aaccgcgctt ctttacccte    780 gtgcgctccg caacgccacc aggacagcca gtaaaacgca tttccactcg tcgcccttac    840
gacgatccgg gcgttgaacg cgtctactac cgaatcattc cagaacaagg cactattgtt    900
gacaaaacgc acatgccatt tgcgctcaac aaacagcgca tcagtaactg aaaaagtgg     960 tttattgaag cggattactc cgttactcag ctacctagct acgagccaga agttgcagct   1020
aacccgatga cggcattcat tgatatgcca gtgaagtctc gcttcaaatt catgcttgat   1080
aacgcgcaaa acaccataat ggcgtatatc aaaggccctg tttgtcgtgg tcagcttgca   1140
cttaacgtca tcaatgatcg cttctgggta ttcttcttag cccagacaa agctgacatt    1200 cctgaggtta acgagttcta ccgttcacaa gcagataact taaaactgcc agccgaacaa   1260
gaaagtaata cgcttccagt cacaaactgg gttaagtacg cacgccaaca agcgcgttat   1320
cttgaggcga atctgagtt tacgaacaac tggtttaagc atggcgaaaa cctatcgact    1380
gacgtcattt gggatggtaa cggcaccaac ccaaatgcag cattaacagt attccgtcat   1440
tttgacagtg catctgtagt tcaagggttg gttggcgagc agccaaaaac agtctggatc   1500
ttagattacg ctttgctaga gcgtattcac tacctattgg tagcagggtt tgacgtatac   1560
ggtaactttg gtcaccagtt gatgacgcgt atgttcatgg acttcttacg tcttgaaggc   1620
gagagtaact tgttaccctt gttgcctgcg gatatgcgcc accagcttca atcgagctgg   1680
tatcaagatc aaagccctca gcttagtgac ttttgcaac gtaacgtgaa gccttttaat    1740
caaccgacca gcgttgttta caaaacggac gatccaaaaa ccgaactact gaacatgatg   1800
cgcaaacgct tatcgccagt gctgctgccg cgttatgaga ttaccgatac tgcgcttta    1860 gataaaacgg aaaaagagct aaaacgcatc ggtcaagtgc gtggtgaagg gctacaaacc   1920
gtcccacaaa tcacgatgct gatggtgcgt agtaagtcag gtaaggacga actgttcacc   1980
ctacttcaca ataatgcgca caccaatatt tcgagtttgt ttgatgaaga aagcaaccga   2040
gacttcgcca acgacgatat gaccatcgtg cgcggcgttg tcggtagcta cccagcagca   2100 ttttttctcgc ttaaagaaaa ccaagtaaaa gaatttgtcg atcagtttag cgcgattcaa   2160
aacgaagccg attacgttaa gttgttggat agttttgcga ttcgccgtag ctcggaaaaa   2220
ttctggccgt ttagcgatcg tatccacaat tggtaccgta caaatcaacc gatcgaattt   2280
ggattacttg actataatcg ttttgagaat cgatga                             2316
```

<210> SEQ ID NO 68
<211> LENGTH: 771
<212> TYPE: PRT
<213> ORGANISM: Vibrio parahaemolyticus

<400> SEQUENCE: 68

Met Phe Ala Gly Cys Ala Thr Tyr Ala Gly Leu Asn Phe Asp Gln Leu
1               5                   10                  15

Phe Gly Pro Gln Leu Val Arg Glu Arg Thr Ala Ser Val Glu Thr Pro
            20                  25                  30

Gln Ala Asp Phe Phe Gln Arg Glu Val Lys Pro Ile Val Asp Asn Arg
        35                  40                  45

Cys Val Val Cys His Ala Cys Tyr Asp Ala Pro Cys Gln Leu Lys Leu
    50                  55                  60

Ser Ser Val Glu Gly Ile Asp Arg Gly Ala Ser Lys Ala Leu Val Tyr
65                  70                  75                  80

```
Glu Gly Thr Arg Leu Thr Ala Ala Pro Thr Arg Leu Phe Glu Asp
                85                  90                  95

Ala Glu Thr Thr Gln Glu Trp Arg Asp Ala Gly Phe His Pro Val Leu
            100                 105                 110

Asn Glu Arg Asp Gln Ser Met Ala Ala Asn Leu Glu Ala Gly Leu Ile
        115                 120                 125

Ala Arg Leu Leu Gln Gln Lys Glu Arg His Pro Leu Pro Asp Gln Val
    130                 135                 140

Gln Leu Glu Gly Phe Asp Phe Ser Ile Asp Arg Glu Gln Thr Cys Pro
145                 150                 155                 160

Thr Ile Glu Glu Tyr Glu Gln Tyr Glu Lys Asp Asn Pro Asn Trp Gly
                165                 170                 175

Met Pro Phe Gly Met Pro Asn Leu Thr Asn Ser Glu Tyr His Thr Leu
            180                 185                 190

Met Thr Trp Leu Glu Asn Gly Ala Ile Met Asn Met His Thr Pro Ile
        195                 200                 205

Ser Asp Gln Glu Gln Ala Lys Ile Asn Gln Tyr Glu Thr Leu Leu Asn
    210                 215                 220

His Ser Asp Leu Lys Asn Gln Leu Met Ser Arg Tyr Ile Tyr Glu His
225                 230                 235                 240

Leu Phe Leu Ser His Leu Tyr Phe Ser Glu Leu Ser Glu Lys Pro Arg
                245                 250                 255

Phe Phe Thr Leu Val Arg Ser Ala Thr Pro Gly Gln Pro Val Lys
            260                 265                 270

Arg Ile Ser Thr Arg Arg Pro Tyr Asp Asp Pro Gly Val Glu Arg Val
    275                 280                 285

Tyr Tyr Arg Ile Ile Pro Glu Gln Gly Thr Ile Val Asp Lys Thr His
290                 295                 300

Met Pro Phe Ala Leu Asn Lys Gln Arg Ile Ser Asn Trp Lys Lys Trp
305                 310                 315                 320

Phe Ile Glu Ala Asp Tyr Ser Val Thr Gln Leu Pro Ser Tyr Glu Pro
                325                 330                 335

Glu Val Ala Ala Asn Pro Met Thr Ala Phe Ile Asp Met Pro Val Lys
            340                 345                 350

Ser Arg Phe Lys Phe Met Leu Asp Asn Ala Gln Asn Thr Ile Met Ala
    355                 360                 365

Tyr Ile Lys Gly Pro Val Cys Arg Gly Gln Leu Ala Leu Asn Val Ile
370                 375                 380

Asn Asp Arg Phe Trp Val Phe Leu Asp Pro Asp Lys Ala Asp Ile
385                 390                 395                 400

Pro Glu Val Asn Glu Phe Tyr Arg Ser Gln Ala Asp Asn Leu Lys Leu
                405                 410                 415

Pro Ala Glu Gln Glu Ser Asn Thr Leu Pro Val Thr Asn Trp Val Lys
            420                 425                 430

Tyr Ala Arg Gln Gln Ala Arg Tyr Leu Glu Ala Lys Ser Glu Phe Thr
    435                 440                 445

Asn Asn Trp Phe Lys His Gly Glu Asn Leu Ser Thr Asp Val Ile Trp
450                 455                 460

Asp Gly Asn Gly Thr Asn Pro Asn Ala Ala Leu Thr Val Phe Arg His
465                 470                 475                 480

Phe Asp Ser Ala Ser Val Val Gln Gly Leu Val Gly Glu Gln Pro Lys
                485                 490                 495

Thr Val Trp Ile Leu Asp Tyr Ala Leu Leu Glu Arg Ile His Tyr Leu
            500                 505                 510
```

Leu Val Ala Gly Phe Asp Val Tyr Gly Asn Phe Gly His Gln Leu Met
            515                 520                 525

Thr Arg Met Phe Met Asp Phe Leu Arg Leu Glu Gly Glu Ser Asn Phe
            530                 535                 540

Val Thr Leu Leu Pro Ala Asp Met Arg His Gln Leu Gln Ser Ser Trp
545                 550                 555                 560

Tyr Gln Asp Gln Ser Pro Gln Leu Ser Asp Phe Leu Gln Arg Asn Val
                565                 570                 575

Lys Pro Phe Asn Gln Pro Thr Ser Val Val Tyr Lys Thr Asp Asp Pro
                580                 585                 590

Lys Thr Glu Leu Leu Asn Met Met Arg Lys Arg Leu Ser Pro Val Leu
            595                 600                 605

Leu Pro Arg Tyr Glu Ile Thr Asp Thr Ala Leu Ser Asp Lys Thr Glu
            610                 615                 620

Lys Glu Leu Lys Arg Ile Gly Gln Val Arg Gly Glu Gly Leu Gln Thr
625                 630                 635                 640

Val Pro Gln Ile Thr Met Leu Met Val Arg Ser Lys Ser Gly Lys Asp
                645                 650                 655

Glu Leu Phe Thr Leu Leu His Asn Asn Ala His Thr Asn Ile Ser Ser
                660                 665                 670

Leu Phe Asp Glu Glu Ser Asn Arg Asp Phe Ala Asn Asp Met Thr
            675                 680                 685

Ile Val Arg Gly Val Val Gly Ser Tyr Pro Ala Ala Phe Phe Ser Leu
            690                 695                 700

Lys Glu Asn Gln Val Lys Glu Phe Val Asp Gln Phe Ser Ala Ile Gln
705                 710                 715                 720

Asn Glu Ala Asp Tyr Val Lys Leu Leu Asp Ser Phe Ala Ile Arg Arg
                725                 730                 735

Ser Ser Glu Lys Phe Trp Pro Phe Ser Asp Arg Ile His Asn Trp Tyr
            740                 745                 750

Arg Thr Asn Gln Pro Ile Glu Phe Gly Leu Leu Asp Tyr Asn Arg Phe
            755                 760                 765

Glu Asn Arg
    770

<210> SEQ ID NO 69
<211> LENGTH: 2331
<212> TYPE: DNA
<213> ORGANISM: Nitrosomonas europaea

<400> SEQUENCE: 69
atgctgtctg catgtcagga cagcaagcct ctattattcg acaacaaccc tactccgact    60
cctgctgatt tgccggcacc tgccgggcat cagatctctt ttgcaaaaga agtccagccg   120
atcatcgaaa ccaagtgcct ttcctgtcac agctgttttg atgcaccctg tcagctcaaa   180
ctggaaagtg ccgagagtct gctgcgtggt gcttctcagg aaccggtata cagcagtgca   240
cgcaccacag agatgaaacc tacccgcctg ggcatcgacg aactcaccgt cgctggctgg   300
cgcaagcggg ttttttattc tgtgctgcaa tcagacaggg aacacgctca atctctgctg   360
aaaaatatga tcactctggg gaaacagtac ccgtttccgc cgaacagcaa gctgcctgac   420
tcgatcaaaa caggttttgc acgcaaaaac cagtgtgtct cagaagaaga atttcccggc   480
tatgcgcatg atcatccatt tgaaggtatg ccgtttggca ccagcggact gaccgatcgg   540
gaatactcac tcctggccgg atggctgaat cagggagcag cagtgacaga tgaacccgtt   600

-continued

```
acgctgacac gggatgagga acaaacgatc cggacatggg aaacgctgtt caaccgggat    660
gacaagcgtg gccggttggt agcacgctgg ctgtacgaac acctgtttct ggcttatctg    720
tatttcccgg aagcaggcga tgagccccgt tctttgaac tgctgcgttc atccacccca    780
tccggcgaag ccatcatccc tgttgccaca gtcagcccga atagtgatcc gggcgggcca    840
ttcttttacc gcctgcgtcc gatctcgggc acgatcgtgc acaaacggcg tatcagctat    900
ccactcgacc agatgaaact gaggcgcatc agtgaactgt ttttcagtga agactggccc    960
gtgggagatc tgccagggta tgactatacg gaacgttcca atcccttgt cacttttgcc   1020
gccataccgg cgcgtgcacg ttaccagttc atgctggacg aggcagagta ttttgtgcgc   1080
actttcattc acgggccagt ctgccgcggc cagattgcaa ccgatgtcat acgcgatcat   1140
ttctggacat tatttcagtc cccggagtcc gatctcttca ttacagcgga cacctatcga   1200
agacaagcca ttcctttgct gggaatcccc gggcaggatg atgatctgct cgatgccggc   1260
gagaactggt tgcgctatct caaacgccac aatgattatc tggcattgcg ccagcagcat   1320
tatgtcgcgc aacaaccaca gggtgcgtca ctggcccata tctggaatgg tgatggtcac   1380
aacgaaaatg cgctgctgac catttttccgc catcacaata gtgcttctgt cgtaagagga   1440
ctggccggtg ctgttccgca gaccatctgg ctgatggatt atccattact ggagcagacc   1500
tactatcagc tggtcgtcaa tttcaatgta ttcggcaacg ttgcacatca gtcctgacc   1560
cggctttact tcgatctgat ccgtaatggt tcggaacaga ttttgtgcg tctgcttcca   1620
gccgggcagc gtaaaaccat attgaacgac tggtaccagg atctgggtaa actgaagttc   1680
ggtatcgttt acgaggatat tgacgatcga tctccctcag cggagcgctt cgtcacagaa   1740
aacccgaaac tggaactggc atcacacatg cttgaacgtt tccagtccat caacaccctg   1800
tcacatgatc cattgaatcg ctgcgaacaa ggaaactgca gtcgtattga ccagccgcac   1860
tggatacagc aagctgatcg tgcattatca ggtattgcgg cacagcctgc tgccagtctg   1920
ccgggaatca gcctgcttcc ggaagtgaca ttcgtacgcg tccagcatgg acagaatgaa   1980
cgcaccgttt ataccctgct gagagatcgc gctcacagta atgtcgcctt catgctgggt   2040
gaagaactgc gctatcagcc tgaaaaagat cgcgttaccg tttatcccgg cattaccggc   2100
agctatccca atttcatgtt cgatgttcct gctgcacaag ttggggagtt cgtagcgaaa   2160
ttgagtaaag caggaaaaat aaaggacttt gaacagatcg tggaacctg gggaatacgg   2220
cgcacgcacc cgcaattctg ggaaattctg cacgacatca ccgcctggca aaaacagcag   2280
caacctttac aggcgggaat cttcgatatc aaccggtatg agaattttta g            2331
```

<210> SEQ ID NO 70
<211> LENGTH: 776
<212> TYPE: PRT
<213> ORGANISM: Nitrosomonas europaea

<400> SEQUENCE: 70

| Met | Leu | Ser | Ala | Cys | Gln | Asp | Ser | Lys | Pro | Leu | Phe | Asp | Asn | Asn |
|---|---|---|---|---|---|---|---|---|---|---|---|---|---|---|
| 1 | | | | 5 | | | | | 10 | | | | | 15 |

| Pro | Thr | Pro | Thr | Pro | Ala | Asp | Leu | Pro | Ala | Pro | Ala | Gly | His | Gln | Ile |
|---|---|---|---|---|---|---|---|---|---|---|---|---|---|---|---|
| | | 20 | | | | | 25 | | | | | 30 | | | |

| Ser | Phe | Ala | Lys | Glu | Val | Gln | Pro | Ile | Ile | Glu | Thr | Lys | Cys | Leu | Ser |
|---|---|---|---|---|---|---|---|---|---|---|---|---|---|---|---|
| | | | 35 | | | | | 40 | | | | | 45 | | |

| Cys | His | Ser | Cys | Phe | Asp | Ala | Pro | Cys | Gln | Leu | Lys | Leu | Glu | Ser | Ala |
|---|---|---|---|---|---|---|---|---|---|---|---|---|---|---|---|
| | 50 | | | | | 55 | | | | | 60 | | | | |

| Glu | Ser | Leu | Leu | Arg | Gly | Ala | Ser | Gln | Glu | Pro | Val | Tyr | Ser | Ser | Ala |
|---|---|---|---|---|---|---|---|---|---|---|---|---|---|---|---|
| 65 | | | | | 70 | | | | | 75 | | | | | 80 |

```
Arg Thr Thr Glu Met Lys Pro Thr Arg Leu Gly Ile Asp Glu Leu Thr
                85                  90                  95

Val Ala Gly Trp Arg Lys Arg Gly Phe Tyr Ser Val Leu Gln Ser Asp
            100                 105                 110

Arg Glu His Ala Gln Ser Leu Leu Lys Asn Met Ile Thr Leu Gly Lys
        115                 120                 125

Gln Tyr Pro Phe Pro Pro Asn Ser Lys Leu Pro Asp Ser Ile Lys Thr
    130                 135                 140

Gly Phe Ala Arg Lys Asn Gln Cys Val Ser Glu Glu Phe Pro Gly
145                 150                 155                 160

Tyr Ala His Asp His Pro Phe Glu Gly Met Pro Phe Gly Thr Ser Gly
                165                 170                 175

Leu Thr Asp Arg Glu Tyr Ser Leu Leu Ala Gly Trp Leu Asn Gln Gly
            180                 185                 190

Ala Ala Val Thr Asp Glu Pro Val Thr Leu Thr Arg Asp Glu Glu Gln
        195                 200                 205

Thr Ile Arg Thr Trp Glu Thr Leu Phe Asn Arg Asp Asp Lys Arg Gly
    210                 215                 220

Arg Leu Val Ala Arg Trp Leu Tyr Glu His Leu Phe Leu Ala Tyr Leu
225                 230                 235                 240

Tyr Phe Pro Glu Ala Gly Asp Glu Pro Arg Phe Phe Glu Leu Leu Arg
                245                 250                 255

Ser Ser Thr Pro Ser Gly Glu Ala Ile Ile Pro Val Ala Thr Val Ser
            260                 265                 270

Pro Asn Ser Asp Pro Gly Gly Pro Phe Phe Tyr Arg Leu Arg Pro Ile
        275                 280                 285

Ser Gly Thr Ile Val His Lys Arg Arg Ile Ser Tyr Pro Leu Asp Gln
    290                 295                 300

Met Lys Leu Arg Arg Ile Ser Glu Leu Phe Phe Ser Glu Asp Trp Pro
305                 310                 315                 320

Val Gly Asp Leu Pro Gly Tyr Asp Tyr Thr Glu Arg Ser Asn Pro Phe
                325                 330                 335

Val Thr Phe Ala Ala Ile Pro Ala Arg Ala Arg Tyr Gln Phe Met Leu
            340                 345                 350

Asp Glu Ala Glu Tyr Phe Val Arg Thr Phe Ile His Gly Pro Val Cys
        355                 360                 365

Arg Gly Gln Ile Ala Thr Asp Val Ile Arg Asp His Phe Trp Thr Leu
    370                 375                 380

Phe Gln Ser Pro Glu Ser Asp Leu Phe Ile Thr Ala Asp Thr Tyr Arg
385                 390                 395                 400

Arg Gln Ala Ile Pro Leu Leu Gly Ile Pro Gly Gln Asp Asp Leu
                405                 410                 415

Leu Asp Ala Gly Glu Asn Trp Leu Arg Tyr Leu Lys Arg His Asn Asp
            420                 425                 430

Tyr Leu Ala Leu Arg Gln Gln His Tyr Val Ala Gln Pro Gln Gly
        435                 440                 445

Ala Ser Leu Ala His Ile Trp Asn Gly Asp Gly His Asn Glu Asn Ala
    450                 455                 460

Leu Leu Thr Ile Phe Arg His His Asn Ser Ala Ser Val Val Arg Gly
465                 470                 475                 480

Leu Ala Gly Ala Val Pro Gln Thr Ile Trp Leu Met Asp Tyr Pro Leu
                485                 490                 495

Leu Glu Gln Thr Tyr Tyr Gln Leu Val Val Asn Phe Asn Val Phe Gly
```

```
                        500             505             510
Asn Val Ala His Gln Val Leu Thr Arg Leu Tyr Phe Asp Leu Ile Arg
            515                 520                 525

Asn Gly Ser Glu Gln Asn Phe Val Arg Leu Leu Pro Ala Gly Gln Arg
        530                 535                 540

Lys Thr Ile Leu Asn Asp Trp Tyr Gln Asp Leu Gly Lys Leu Lys Phe
545                 550                 555                 560

Gly Ile Val Tyr Glu Asp Ile Asp Asp Arg Ser Pro Ser Ala Glu Arg
                565                 570                 575

Phe Val Thr Glu Asn Pro Lys Leu Glu Leu Ala Ser His Met Leu Glu
            580                 585                 590

Arg Phe Gln Ser Ile Asn Thr Leu Ser His Asp Pro Leu Asn Arg Cys
        595                 600                 605

Glu Gln Gly Asn Cys Ser Arg Ile Asp Gln Pro His Trp Ile Gln Gln
    610                 615                 620

Ala Asp Arg Ala Leu Ser Gly Ile Ala Ala Gln Pro Ala Ala Ser Leu
625                 630                 635                 640

Pro Gly Ile Ser Leu Leu Pro Glu Val Thr Phe Val Arg Val Gln His
                645                 650                 655

Gly Gln Asn Glu Arg Thr Val Tyr Thr Leu Leu Arg Asp Arg Ala His
            660                 665                 670

Ser Asn Val Ala Phe Met Leu Gly Glu Glu Leu Arg Tyr Gln Pro Glu
        675                 680                 685

Lys Asp Arg Val Thr Val Tyr Pro Gly Ile Thr Gly Ser Tyr Pro Asn
    690                 695                 700

Phe Met Phe Asp Val Pro Ala Ala Gln Val Gly Glu Phe Val Ala Lys
705                 710                 715                 720

Leu Ser Lys Ala Gly Lys Ile Lys Asp Phe Glu Gln Ile Val Glu Thr
                725                 730                 735

Trp Gly Ile Arg Arg Thr His Pro Gln Phe Trp Glu Ile Leu His Asp
            740                 745                 750

Ile Thr Ala Trp Gln Lys Gln Gln Pro Leu Gln Ala Gly Ile Phe
        755                 760                 765

Asp Ile Asn Arg Tyr Glu Asn Phe
    770                 775

<210> SEQ ID NO 71
<211> LENGTH: 2301
<212> TYPE: DNA
<213> ORGANISM: Vibrio cholerae

<400> SEQUENCE: 71
atgtacgcag gcatcaacta tgatcagctc tttggcacag agcaggtacg tgagcgacaa      60
ttacctttgc actctagcca agctcagcat tttttaaacg aagtaaaacc catcttagat     120
aaccgctgtg tcgtctgtca cgcctgttac gatgcaccct gtcagctcaa aatgacctcg     180
gctgaaggca ttgatcgcgg ggcgagcaaa gcgttggttt atcagggaac tcggctgacg     240
gccgctactc caactcgtct ctacgaagat gctcagttaa cccaagagtg gcgagctgct     300
ggttttcatc ccgtgctgaa tgagcgaaat caaaccgcgc aagccaatct tgatgctggg     360
gtgatggcac gtttgctgat gcagaaagag cgtcatccac taccacagca agatcagtta     420
caaggatttg attttcaat tgatcgtgag caaacctgcc aacgatcaa cgaaatggat     480 cacttcgaac aagtgaatcc taattgggga atgcccttg gtatgccgaa tttatccccc     540
aaggagtaca ctaccctgct ctcttggcta caagagggag ccgtgatgaa tcaagcgctc     600
```

```
ccgctgagtg cgcaagaaca agctttggtt acggaatacg aagccttgtt gaatcacagc    660
tcgcgtaaaa atcagctcgc agcacgctat atctacgaac atctattcct ctcacatctg    720 tactttttcag agatagcgca ggagcggcct cgtttcttta aactcatccg ctccagtact   780
ccaccgggtg agcctgtaaa gcgaatcgtg acgcgtcgtc cgtacgatga tccgggcgtt    840
gagcgagtct attatcgcct tgtgccagaa caagagacga ttgtcgataa acccacatg     900 cctttcgcac tcaacaagca acggattgcg aactggaaac tctggtttat tgatgcggat   960
tatgaggttg ccgagcttcc aagttatcgt ccggatattg ccgcaaaccc gatgtccgcg   1020
ttcatcgacc ttcccgtgaa agcgcgcttt aagttcttgc tcgataatgc gcaaaatacg   1080
gtgatggcct ttatcaaagg cccagtgtgt cgaggccagt tggcgctgaa tgtgattaac   1140
gatagattct gggtcttctt cctcgatcct gagaaagccg atcttccaga agtcaacgaa   1200
ttctatcgct cacaagtcaa caatttgaag ctaccggctg aacaagagaa tacggcactg   1260
ccgctgagta actgggtacg ttattcgcta caacaaagcc gttatctcga agcaaaatct   1320
gaatttatta atcaatggtt taaaaatggt acgcacctta ccacggacat catttgggat   1380
ggagcgggca taaaccctaa tgccgcatta acgattttcc gccatttcga tagcgcatct   1440
gtcgtgcaag gattggtggg tgagcctccc aaaaccgctt ggataatgga ttatgcgctg   1500
cttgagcgca ttcattatct gcttgttgct ggttttgatg tatatggcaa tttcggacat   1560
cagttgatta ctcgtatgtt catggatttt ctgcgcatgg agggtgagag taattttgtt   1620
gccctgctac cacgcgatat cgccatcag gagttatcta gttggtacca aaatcaaagt    1680
gtacagtttt ccgatttctt gcaacgtaac gtaaaaccct tgatcagcc aaccagcgtt    1740 aactatgtga ctgataaccc gaaacaggag ctgtttgcta aactccgcaa gcaagtacag   1800
tcggtattga gtgatcgata cgtgataact caaacgggat tcaaagccga acatgagttt   1860
gctttgcgcc aaatcgatca tctgcgtggt gaaggtttgc tgcccattcc gcaattgatg   1920
atgttgatga ttgaaagtga acaaggtaaa ccgcaactgt ttacgctcat ccacaacaat   1980
gcccacacca atatctcgag cttgtttgat gaacagaaca accgcgaccc caaaaatgat   2040
aatttgactt tagtgcgcgg agtggtcggc agttatccat cggcgtactt aacactgaaa   2100
gaaaaccaga tcccggagct gtatcaacgc cttgcggcga tgaagtcaga gcaagattat   2160
gtcgccctat tggatcgttt tgcagtacgc cgcagctcac ccgaattttg ggcatttagc   2220
gatcttgtgc atcaatggta tcgccaagat caacccattg agtttggttt gctcgattac   2280
aaccgtttcg aaaaccgttg a                                             2301
```

<210> SEQ ID NO 72
<211> LENGTH: 766
<212> TYPE: PRT
<213> ORGANISM: Vibrio cholerae

<400> SEQUENCE: 72

Met Tyr Ala Gly Ile Asn Tyr Asp Gln Leu Phe Gly Thr Glu Gln Val
1               5                   10                  15

Arg Glu Arg Gln Leu Pro Leu His Ser Ser Gln Ala Gln His Phe Leu
            20                  25                  30

Asn Glu Val Lys Pro Ile Leu Asp Asn Arg Cys Val Val Cys His Ala
        35                  40                  45

Cys Tyr Asp Ala Pro Cys Gln Leu Lys Met Thr Ser Ala Glu Gly Ile
    50                  55                  60

Asp Arg Gly Ala Ser Lys Ala Leu Val Tyr Gln Gly Thr Arg Leu Thr

```
                65                  70                  75                  80
Ala Ala Thr Pro Thr Arg Leu Tyr Glu Asp Ala Gln Leu Thr Gln Glu
                    85                  90                  95
Trp Arg Ala Ala Gly Phe His Pro Val Leu Asn Glu Arg Asn Gln Thr
            100                 105                 110
Ala Gln Ala Asn Leu Asp Ala Gly Val Met Ala Arg Leu Leu Met Gln
        115                 120                 125
Lys Glu Arg His Pro Leu Pro Gln Gln Asp Gln Leu Gln Gly Phe Asp
    130                 135                 140
Phe Ser Ile Asp Arg Glu Gln Thr Cys Pro Thr Ile Asn Glu Met Asp
145                 150                 155                 160
His Phe Glu Gln Val Asn Pro Asn Trp Gly Met Pro Phe Gly Met Pro
                165                 170                 175
Asn Leu Ser Pro Lys Glu Tyr Thr Thr Leu Leu Ser Trp Leu Gln Glu
            180                 185                 190
Gly Ala Val Met Asn Gln Ala Leu Pro Leu Ser Ala Gln Glu Gln Ala
        195                 200                 205
Leu Val Thr Glu Tyr Glu Ala Leu Leu Asn His Ser Ser Arg Lys Asn
    210                 215                 220
Gln Leu Ala Ala Arg Tyr Ile Tyr Glu His Leu Phe Leu Ser His Leu
225                 230                 235                 240
Tyr Phe Ser Glu Ile Ala Gln Glu Arg Pro Arg Phe Lys Leu Ile
                245                 250                 255
Arg Ser Ser Thr Pro Pro Gly Glu Pro Val Lys Arg Ile Val Thr Arg
            260                 265                 270
Arg Pro Tyr Asp Asp Pro Gly Val Glu Arg Val Tyr Arg Leu Val
        275                 280                 285
Pro Glu Gln Glu Thr Ile Val Asp Lys Thr His Met Pro Phe Ala Leu
    290                 295                 300
Asn Lys Gln Arg Ile Ala Asn Trp Lys Leu Trp Phe Ile Asp Ala Asp
305                 310                 315                 320
Tyr Glu Val Ala Glu Leu Pro Ser Tyr Arg Pro Asp Ile Ala Ala Asn
                325                 330                 335
Pro Met Ser Ala Phe Ile Asp Leu Pro Val Lys Ala Arg Phe Lys Phe
            340                 345                 350
Leu Leu Asp Asn Ala Gln Asn Thr Val Met Ala Phe Ile Lys Gly Pro
        355                 360                 365
Val Cys Arg Gly Gln Leu Ala Leu Asn Val Ile Asn Asp Arg Phe Trp
    370                 375                 380
Val Phe Phe Leu Asp Pro Glu Lys Ala Asp Leu Pro Glu Val Asn Glu
385                 390                 395                 400
Phe Tyr Arg Ser Gln Val Asn Asn Leu Lys Leu Pro Ala Glu Gln Glu
                405                 410                 415
Asn Thr Ala Leu Pro Leu Ser Asn Trp Val Arg Tyr Ser Leu Gln Gln
            420                 425                 430
Ser Arg Tyr Leu Glu Ala Lys Ser Glu Phe Ile Asn Gln Trp Phe Lys
        435                 440                 445
Asn Gly Thr His Leu Thr Thr Asp Ile Ile Trp Asp Gly Ala Gly Ile
    450                 455                 460
Asn Pro Asn Ala Ala Leu Thr Ile Phe Arg His Phe Asp Ser Ala Ser
465                 470                 475                 480
Val Val Gln Gly Leu Val Gly Glu Pro Pro Lys Thr Ala Trp Ile Met
                485                 490                 495
```

-continued

```
Asp Tyr Ala Leu Leu Glu Arg Ile His Tyr Leu Leu Val Ala Gly Phe
            500                 505                 510
Asp Val Tyr Gly Asn Phe Gly His Gln Leu Ile Thr Arg Met Phe Met
            515                 520                 525
Asp Phe Leu Arg Met Glu Gly Glu Ser Asn Phe Val Ala Leu Leu Pro
        530                 535                 540
Arg Asp Met Arg His Gln Glu Leu Ser Ser Trp Tyr Gln Asn Gln Ser
545                 550                 555                 560
Val Gln Phe Ser Asp Phe Leu Gln Arg Asn Val Lys Pro Phe Asp Gln
                565                 570                 575
Pro Thr Ser Val Asn Tyr Val Thr Asp Asn Pro Lys Gln Glu Leu Phe
            580                 585                 590
Ala Lys Leu Arg Lys Gln Val Gln Ser Val Leu Ser Asp Arg Tyr Val
        595                 600                 605
Ile Thr Gln Thr Gly Phe Lys Ala Glu His Glu Phe Ala Leu Arg Gln
    610                 615                 620
Ile Asp His Leu Arg Gly Glu Gly Leu Leu Pro Ile Pro Gln Leu Met
625                 630                 635                 640
Met Leu Met Ile Glu Ser Glu Gln Gly Lys Pro Gln Leu Phe Thr Leu
                645                 650                 655
Ile His Asn Asn Ala His Thr Asn Ile Ser Ser Leu Phe Asp Glu Gln
            660                 665                 670
Asn Asn Arg Asp Pro Lys Asn Asp Asn Leu Thr Leu Val Arg Gly Val
        675                 680                 685
Val Gly Ser Tyr Pro Ser Ala Tyr Leu Thr Leu Lys Glu Asn Gln Ile
    690                 695                 700
Pro Glu Leu Tyr Gln Arg Leu Ala Ala Met Lys Ser Glu Gln Asp Tyr
705                 710                 715                 720
Val Ala Leu Leu Asp Arg Phe Ala Val Arg Arg Ser Ser Pro Glu Phe
                725                 730                 735
Trp Ala Phe Ser Asp Leu Val His Gln Trp Tyr Arg Gln Asp Gln Pro
            740                 745                 750
Ile Glu Phe Gly Leu Leu Asp Tyr Asn Arg Phe Glu Asn Arg
        755                 760                 765

<210> SEQ ID NO 73
<211> LENGTH: 2307
<212> TYPE: DNA
<213> ORGANISM: Pseudomonas syringae

<400> SEQUENCE: 73
atgccgcacc gtttgttggc aagcatcgcc ttgcttttta tctgctgtgc tgcacaggcc      60
cagacaccct cagccacacc cgcaagcccg gctatttcct acgtaaagga tattcagccg     120
atccttaccg agaaatgcgt tgcctgccat gcctgcaacg acgctccctg ccagttgaac     180
ctgggcagcg gggaaggcgt gagccgtggt gccagcaaga tcccggttta ccagggcgag     240
cgcagtgagg cggtagcgcc gacccgactg ttttatgatg cgcgtgatac cgaggcgtgg     300
cgcggcaagg gttttttactc tgtgctggag gcccagggca gtcaggcagc cctgatggcg     360
cgcatgctcg atctggggcg cagcgcgccg ttgccagcca acagcaaaat tccggacgag     420
atcgcactgg gcatcaatcg cgaaaatgtc tgcccgctgc ccggcgaatt caacgcctat     480
gccgcagctc atgcgcaaca aggcatgcca ctggcggtgg ctggcctgac cgatgccgaa     540
taccagacac tgcagcgctg gctggctgcc ggttcgccgg tggagcagca gaccattacc     600
ccgagtgtca cggaaacggc gcagatcaat gcctgggagg cgcagctcaa ccagcctggc     660
```

```
gcgaatcagg cgctggtcgg tcgctggctg tttgagcacc tgtttctggc acatatctat    720
ttcgagggcg gcgaagcggg gcacttcttt cagtgggtgc gctcgcgaac cccaagcggc    780
aagcctgtgg acctgatcgc tactcgtcgc cccgacgatg atccgggcag tgacttctat    840
tatcgattga tccctgtgca gggcgtgatc gttcacaaga cccacattac ctatgccatg    900
agcccgcaga aactgacgcg ggtcaggcag ttgttctatg gtaacgactg gaaggtcaac    960
gcactgcctg gctatggccc tggccatcgg gccaatccgt ttctgacctt tgaagccatc   1020
ccggcagcgt cgcgctatca gttcatgctc gacaatgccg agtatttcgt ccgcaccttc   1080
attcgcggac cggtttgtcg cgggcaaatc gcgaccgatg tgattcgcga tcagttctgg   1140
gtgctgtttc aggaccctga gcacgaccac tacatcaccg atgcggctta tcgcgggcag   1200
gccacgcctt tactggccat gccggggcag aacgatgatg tcggcagcgt gctcagcctg   1260
tggctgtcgt accgggaccg gcgtaatcaa tatgaagaca tgcgccgcga cagttacgcg   1320
aaaatgccgg caccggggtg gagcacgctg tgggctggca acgacaatgc cttgctgacc   1380
gttttccgtc atttcgacag cgcttcggtc aataaaggcc tgattggcga cgtgccgcac   1440
tccatgtggt tgttcgactt cccgttgctg gagcgtacct attaccagtt ggcggtgaac   1500
ttcgatgtct atggcaatgt ttcacatcag gcacagaccc ggctgtattt cgatttgatc   1560
cgcaacggtg ccgagatcaa cttcctgcgc ctgatgcccg ccgatcgccg ggaagacata   1620
ctcagcgatc tttatcagga tggcggcaag atcaagatgt ggctggatta ccagaagatc   1680
gatgacgata cgccaaccgg tatcaaactc gatgaaaagg ccccgcagcg tgactttgcg   1740
ttcaagctga tcgagcgttc cggcagcctg aatgccgcgc tgatccaat caaccgctgt   1800
agcggggcgt attgttctcg gccgaacctc gacagcagtt tgcccaggc ggaacaggca   1860
ctgagccgtt tgacctcacg cccggcggcg ggcctgaaag tcatcgatca attgccggaa   1920
gcaagcatgc tgcgcatcga gggcagcgac ggcaaacgca tgatctacag catgctgcgc   1980
aaccgtgcac acagtaacgt cgcgtttctg ctgggcgagt cctatcgcta tacctggg    2040
ctggacacac tgaccgtcta cccgggcgtg ctcagcagtt atccgaattt catcttcaat   2100
attccggtcg cacaggtgcc ggcctttgtc gatgccatgc agcagagcaa ggatcaggcg   2160
agtttcgaac aaatcgtcca gcgttggggc atccgtcgta ctcatccact gttctggagt   2220
tacttccacg atctgaatcg ctacgttcag gaaactgaac cacgcgaagc gggtgtgctg   2280
gacatgaatc gctacgagaa cctctga                                        2307
```

<210> SEQ ID NO 74
<211> LENGTH: 768
<212> TYPE: PRT
<213> ORGANISM: Pseudomonas syringae

<400> SEQUENCE: 74

```
Met Pro His Arg Leu Leu Ala Ser Ile Ala Leu Leu Phe Ile Cys Cys
1               5                   10                  15

Ala Ala Gln Ala Gln Thr Pro Ser Ala Thr Pro Ala Ser Pro Ala Ile
            20                  25                  30

Ser Tyr Val Lys Asp Ile Gln Pro Ile Leu Thr Glu Lys Cys Val Ala
        35                  40                  45

Cys His Ala Cys Asn Asp Ala Pro Cys Gln Leu Asn Leu Gly Ser Gly
    50                  55                  60

Glu Gly Val Ser Arg Gly Ala Ser Lys Ile Pro Val Tyr Gln Gly Glu
65                  70                  75                  80
```

-continued

```
Arg Ser Glu Ala Val Ala Pro Thr Arg Leu Phe Tyr Asp Ala Arg Asp
                85                  90                  95

Thr Glu Ala Trp Arg Gly Lys Gly Phe Tyr Ser Val Leu Glu Ala Gln
            100                 105                 110

Gly Ser Gln Ala Ala Leu Met Ala Arg Met Leu Asp Leu Gly Arg Ser
        115                 120                 125

Ala Pro Leu Pro Ala Asn Ser Lys Ile Pro Asp Glu Ile Ala Leu Gly
    130                 135                 140

Ile Asn Arg Glu Asn Val Cys Pro Leu Pro Gly Glu Phe Asn Ala Tyr
145                 150                 155                 160

Ala Ala Ala His Ala Gln Gln Gly Met Pro Leu Ala Val Ala Gly Leu
                165                 170                 175

Thr Asp Ala Glu Tyr Gln Thr Leu Gln Arg Trp Leu Ala Ala Gly Ser
            180                 185                 190

Pro Val Glu Gln Gln Thr Ile Thr Pro Ser Val Thr Glu Thr Ala Gln
        195                 200                 205

Ile Asn Ala Trp Glu Ala Gln Leu Asn Gln Pro Gly Ala Asn Gln Ala
    210                 215                 220

Leu Val Gly Arg Trp Leu Phe Glu His Leu Phe Leu Ala His Ile Tyr
225                 230                 235                 240

Phe Glu Gly Gly Glu Ala Gly His Phe Phe Gln Trp Val Arg Ser Arg
                245                 250                 255

Thr Pro Ser Gly Lys Pro Val Asp Leu Ile Ala Thr Arg Arg Pro Asp
            260                 265                 270

Asp Asp Pro Gly Ser Asp Phe Tyr Tyr Arg Leu Ile Pro Val Gln Gly
        275                 280                 285

Val Ile Val His Lys Thr His Ile Thr Tyr Ala Met Ser Pro Gln Lys
    290                 295                 300

Leu Thr Arg Val Arg Gln Leu Phe Tyr Gly Asn Asp Trp Lys Val Asn
305                 310                 315                 320

Ala Leu Pro Gly Tyr Gly Pro Gly His Arg Ala Asn Pro Phe Leu Thr
                325                 330                 335

Phe Glu Ala Ile Pro Ala Ala Ser Arg Tyr Gln Phe Met Leu Asp Asn
            340                 345                 350

Ala Glu Tyr Phe Val Arg Thr Phe Ile Arg Gly Pro Val Cys Arg Gly
        355                 360                 365

Gln Ile Ala Thr Asp Val Ile Arg Asp Gln Phe Trp Val Leu Phe Gln
    370                 375                 380

Asp Pro Glu His Asp His Tyr Ile Thr Asp Ala Ala Tyr Arg Gly Gln
385                 390                 395                 400

Ala Thr Pro Leu Leu Ala Met Pro Gly Gln Asn Asp Asp Val Gly Ser
                405                 410                 415

Val Leu Ser Leu Trp Leu Ser Tyr Arg Asp Arg Arg Asn Gln Tyr Glu
            420                 425                 430

Asp Met Arg Arg Asp Ser Tyr Ala Lys Met Pro Ala Pro Gly Trp Ser
        435                 440                 445

Thr Leu Trp Ala Gly Asn Asp Asn Ala Leu Leu Thr Val Phe Arg His
    450                 455                 460

Phe Asp Ser Ala Ser Val Asn Lys Gly Leu Ile Gly Asp Val Pro His
465                 470                 475                 480

Ser Met Trp Leu Phe Asp Phe Pro Leu Leu Glu Arg Thr Tyr Tyr Gln
                485                 490                 495

Leu Ala Val Asn Phe Asp Val Tyr Gly Asn Val Ser His Gln Ala Gln
            500                 505                 510
```

```
Thr Arg Leu Tyr Phe Asp Leu Ile Arg Asn Gly Ala Glu Ile Asn Phe
        515                 520                 525

Leu Arg Leu Met Pro Ala Asp Arg Arg Glu Asp Ile Leu Ser Asp Leu
    530                 535                 540

Tyr Gln Asp Gly Gly Lys Ile Lys Met Trp Leu Asp Tyr Gln Lys Ile
545                 550                 555                 560

Asp Asp Asp Thr Pro Thr Gly Ile Lys Leu Asp Glu Lys Ala Pro Gln
                565                 570                 575

Arg Asp Phe Ala Phe Lys Leu Ile Glu Arg Ser Gly Ser Leu Asn Ala
            580                 585                 590

Ala Pro Asp Pro Ile Asn Arg Cys Ser Gly Ala Tyr Cys Ser Arg Pro
        595                 600                 605

Asn Leu Asp Ser Ser Phe Ala Gln Ala Glu Gln Ala Leu Ser Arg Leu
    610                 615                 620

Thr Ser Arg Pro Ala Ala Gly Leu Lys Val Ile Asp Gln Leu Pro Glu
625                 630                 635                 640

Ala Ser Met Leu Arg Ile Glu Gly Ser Asp Gly Lys Arg Met Ile Tyr
                645                 650                 655

Ser Met Leu Arg Asn Arg Ala His Ser Asn Val Ala Phe Leu Leu Gly
            660                 665                 670

Glu Ser Tyr Arg Tyr Ile Pro Gly Leu Asp Thr Leu Thr Val Tyr Pro
        675                 680                 685

Gly Val Leu Ser Ser Tyr Pro Asn Phe Ile Phe Asn Ile Pro Val Ala
    690                 695                 700

Gln Val Pro Ala Phe Val Asp Ala Met Gln Gln Ser Lys Asp Gln Ala
705                 710                 715                 720

Ser Phe Glu Gln Ile Val Gln Arg Trp Gly Ile Arg Arg Thr His Pro
                725                 730                 735

Leu Phe Trp Ser Tyr Phe His Asp Leu Asn Arg Tyr Val Gln Glu Thr
            740                 745                 750

Glu Pro Arg Glu Ala Gly Val Leu Asp Met Asn Arg Tyr Glu Asn Leu
        755                 760                 765

<210> SEQ ID NO 75
<211> LENGTH: 2400
<212> TYPE: DNA
<213> ORGANISM: Bdellovibrio bacteriovorus

<400> SEQUENCE: 75
atgcaattca ttctgatgct ggtagtttgt ttttcggcgg cagcgggcag tgcctcggcc      60
cccgccggca gtgctggagt gccggcaggc acgcaagctg aagctccggc tctgccgggc     120
agagcgcagg cgccatctgg cgccgtagct gaagcaactc tttattcccg caaaatccaa     180 ccgcttttg acaatcgctg tctggcctgc cacagctgtt ttaatgctcc ctgccagctg     240
aatctgcaga attttgaggg ttttcagagg ggtgcgaaca aattaaacgt ctatgatggc     300
actcgcttaa aaagtgttga gccctcacgt ctttggattg atgcccatgc agacgagtgg     360
cgaaaacgtg gtttctatga ggtcagcacc agtaaagatc ctgaccaaaa cctgttttc     420 cagatcacac agctacgcgc cacagcgaaa gatgccgtga tcaccaagca ggtcgcggat     480
actcacgtct cgcgcagac gatgacggac tatcagcttt ggccaaaaa ctccccggaa      540 ctgggcatgc cctacggatt tccggccctg agccgtcag agctggcaac cctgaaggac     600
tgggtgaaag ccggcagtcc cggtccggat gcagaagagt tcaagcgcca gaatactccc     660
tctgtcgaat tgcagactca ggtgcacgaa tgggaagagt tcctgaacca ggaaagtctt     720
```

```
cgtcaccagt tggtcagccg ctatctttac gagcatcttt tcctggcgca tatttatttc    780
ccggaaaagc cggaagaatt tttccgtctg gtgcgctcaa agcagtcctg cgcccagggt    840
attcaagaga tcgccactcg tcgtcccaat gacaacccgg gaatgaaaaa gttctggtac    900
tgtcttaaga agttccccgg cacggtggtg aaaaagaccc acatcccata ccaatggagt    960
ccggcaaaga tggcccgcta taaagagctt ttcctggccg agggctggaa agtttcagcg   1020
ctgccaagtt atgagtcggg tgtggctgaa atccatttg tggcgttcaa agacattccg    1080
gtgaaggccc gctatcagtt tctgctcgac gatgcccagt accaggtgag cacctttatt   1140
aaaggtccgg tgtgtaacgg gagcatggcg gtgaactcca ttcaggagca gttctatgtg   1200
ttcttcctga atccgtcttc agacaacatg gtgctgtcgc aaaagtacgc cgacaaggcc   1260
gccgggcttt tgatgatgcc gggggtttgg ggcagtgatg ttgatattaa agaaacgccg   1320
ctgttttata aaaaactggt cgatcaccgg gaaaactatc gcaagcttcg catcgaagaa   1380
ctcgcgaagc ttcgtcctga aggttacacc ctgaaagacg tctgggatgg cgggggcttt   1440
aaccccaatg ccactctgac cgtgcttcgc catgatgaca atgccgtggt gatgaaaggc   1500
gctgtggggg atttgtcgaa gaccgtcttc atgctggatt accgctgttt gaacgcctg    1560
gtctacaacc tggtggtgaa ctttgatgtc tttggcaatg tgtctcatca actgctgact   1620
cgggtgtaca tggacatgat ccgcatggag gctgaagagc tgttcctgac cttcctgcca   1680
tcggaagagc gtctgagcta tcgccggtcc tggtatcgtg gtttgttgac ccaggctaaa   1740
atgtcctatg tttaccccac agtgggttcc gcagttccca ccgggattaa attcaacgag   1800
gacaacaaca ccaaaaagca gtttgtgcag aaggtgttgt tcttccatca gaacgaaacc   1860
gtgcgtggtg gctgggacct tatcaactgg aagagtctgg aaatcccgga cagcatgcag   1920
gggcagtgga agtgaaggg actggataaa gaacttcgca agatcgcggc agtgaaagcc    1980
gaagcggcca caccgttttc ccggttcttc ccggacctgg cactgctcaa tatcaaaaca   2040
cccaaggggc tgaagatcta ctcgctcatt cacaataaag agcacgaaaa tatttcctgg   2100
atcctggggg agtcgctgcg catggaccct gaaagcgaca ctctgaccgt gcgtgaaggg   2160
gtgtggggtt cttatccgaa tatgatcttt aatgtgaaag aaaatgagct ggcggcgttt   2220
gtgacccagg tgcgcgcaat gaaatccgcg gcagactatc agaatctggt cactcgctac   2280
ggccttcgcc gcagcaatgc caagttctgg tctttctatg atgacatgca cgtcgcgatg   2340
agaaaatcag acccggtgag tttcggatac ctggatctga cccgttatga attaaaatag   2400
```

<210> SEQ ID NO 76
<211> LENGTH: 799
<212> TYPE: PRT
<213> ORGANISM: Bdellovibrio bacteriovorus

<400> SEQUENCE: 76

```
Met Gln Phe Ile Leu Met Leu Val Val Cys Phe Ser Ala Ala Ala Gly
1               5                   10                  15

Ser Ala Ser Ala Pro Ala Gly Ser Ala Gly Val Pro Ala Gly Thr Gln
            20                  25                  30

Ala Glu Ala Pro Ala Leu Pro Gly Arg Ala Gln Ala Pro Ser Gly Ala
        35                  40                  45

Val Ala Glu Ala Thr Leu Tyr Ser Arg Lys Ile Gln Pro Leu Phe Asp
    50                  55                  60

Asn Arg Cys Leu Ala Cys His Ser Cys Phe Asn Ala Pro Cys Gln Leu
65                  70                  75                  80
```

-continued

```
Asn Leu Gln Asn Phe Glu Gly Phe Gln Arg Gly Ala Asn Lys Leu Asn
                85                  90                  95

Val Tyr Asp Gly Thr Arg Leu Lys Ser Val Glu Pro Ser Arg Leu Trp
            100                 105                 110

Ile Asp Ala His Ala Asp Glu Trp Arg Lys Arg Gly Phe Tyr Glu Val
        115                 120                 125

Ser Thr Ser Lys Asp Pro Asp Gln Asn Leu Phe Phe Gln Ile Thr Gln
    130                 135                 140

Leu Arg Ala Thr Ala Lys Asp Ala Val Ile Thr Lys Gln Val Ala Asp
145                 150                 155                 160

Thr His Val Cys Ala Gln Thr Met Thr Asp Tyr Gln Leu Leu Ala Lys
                165                 170                 175

Asn Ser Pro Glu Leu Gly Met Pro Tyr Gly Phe Pro Ala Leu Ser Pro
            180                 185                 190

Ser Glu Leu Ala Thr Leu Lys Asp Trp Val Lys Ala Gly Ser Pro Gly
        195                 200                 205

Pro Asp Ala Glu Glu Phe Lys Arg Gln Asn Thr Pro Ser Val Glu Leu
    210                 215                 220

Gln Thr Gln Val His Glu Trp Glu Phe Leu Asn Gln Glu Ser Leu
225                 230                 235                 240

Arg His Gln Leu Val Ser Arg Tyr Leu Tyr Glu His Leu Phe Leu Ala
                245                 250                 255

His Ile Tyr Phe Pro Glu Lys Pro Glu Glu Phe Phe Arg Leu Val Arg
            260                 265                 270

Ser Lys Gln Ser Cys Ala Gln Gly Ile Gln Glu Ile Ala Thr Arg Arg
        275                 280                 285

Pro Asn Asp Asn Pro Gly Met Lys Lys Phe Trp Tyr Cys Leu Lys Lys
    290                 295                 300

Phe Pro Gly Thr Val Val Lys Lys Thr His Ile Pro Tyr Gln Trp Ser
305                 310                 315                 320

Pro Ala Lys Met Ala Arg Tyr Lys Glu Leu Phe Leu Ala Glu Gly Trp
                325                 330                 335

Lys Val Ser Ala Leu Pro Ser Tyr Glu Ser Gly Val Ala Glu Asn Pro
            340                 345                 350

Phe Val Ala Phe Lys Asp Ile Pro Val Lys Ala Arg Tyr Gln Phe Leu
        355                 360                 365

Leu Asp Asp Ala Gln Tyr Gln Val Ser Thr Phe Ile Lys Gly Pro Val
    370                 375                 380

Cys Asn Gly Ser Met Ala Val Asn Ser Ile Gln Glu Gln Phe Tyr Val
385                 390                 395                 400

Phe Phe Leu Asn Pro Ser Ser Asp Asn Met Val Leu Ser Gln Lys Tyr
                405                 410                 415

Ala Asp Lys Ala Ala Gly Leu Leu Met Met Pro Gly Val Trp Gly Ser
            420                 425                 430

Asp Val Asp Ile Lys Glu Thr Pro Leu Phe Tyr Lys Lys Leu Val Asp
        435                 440                 445

His Arg Glu Asn Tyr Arg Lys Leu Arg Ile Glu Glu Leu Ala Lys Leu
    450                 455                 460

Arg Pro Glu Gly Tyr Thr Leu Lys Asp Val Trp Asp Gly Gly Phe
465                 470                 475                 480

Asn Pro Asn Ala Thr Leu Thr Val Leu Arg His Asp Asn Ala Val
                485                 490                 495

Val Met Lys Gly Ala Val Gly Asp Leu Ser Lys Thr Val Phe Met Leu
            500                 505                 510
```

```
Asp Tyr Pro Leu Phe Glu Arg Leu Val Tyr Asn Leu Val Val Asn Phe
        515                 520                 525

Asp Val Phe Gly Asn Val Ser His Gln Leu Leu Thr Arg Val Tyr Met
    530                 535                 540

Asp Met Ile Arg Met Glu Ala Glu Leu Phe Leu Thr Phe Leu Pro
545                 550                 555                 560

Ser Glu Glu Arg Leu Ser Tyr Arg Arg Ser Trp Tyr Arg Gly Leu Leu
                565                 570                 575

Thr Gln Ala Lys Met Ser Tyr Val Tyr Pro Thr Val Gly Ser Ala Val
            580                 585                 590

Pro Thr Gly Ile Lys Phe Asn Glu Asp Asn Asn Thr Lys Lys Gln Phe
        595                 600                 605

Val Gln Lys Val Leu Phe His Gln Asn Glu Thr Val Arg Gly Gly
    610                 615                 620

Trp Asp Leu Ile Asn Trp Lys Ser Leu Glu Ile Pro Asp Ser Met Gln
625                 630                 635                 640

Gly Gln Trp Lys Val Lys Gly Leu Asp Lys Glu Leu Arg Lys Ile Ala
                645                 650                 655

Ala Val Lys Ala Glu Ala Ala Thr Pro Phe Ser Arg Phe Pro Asp
            660                 665                 670

Leu Ala Leu Leu Asn Ile Lys Thr Pro Lys Gly Leu Lys Ile Tyr Ser
        675                 680                 685

Leu Ile His Asn Lys Glu His Glu Asn Ile Ser Trp Ile Leu Gly Glu
        690                 695                 700

Ser Leu Arg Met Asp Pro Glu Ser Asp Thr Leu Thr Val Arg Glu Gly
705                 710                 715                 720

Val Trp Gly Ser Tyr Pro Asn Met Ile Phe Asn Val Lys Glu Asn Glu
                725                 730                 735

Leu Ala Ala Phe Val Thr Gln Val Arg Ala Met Lys Ser Ala Ala Asp
            740                 745                 750

Tyr Gln Asn Leu Val Thr Arg Tyr Gly Leu Arg Arg Ser Asn Ala Lys
        755                 760                 765

Phe Trp Ser Phe Tyr Asp Asp Met His Val Ala Met Arg Lys Ser Asp
        770                 775                 780

Pro Val Ser Phe Gly Tyr Leu Asp Leu Thr Arg Tyr Glu Leu Lys
785                 790                 795

<210> SEQ ID NO 77
<211> LENGTH: 2355
<212> TYPE: DNA
<213> ORGANISM: Vibrio fischeri

<400> SEQUENCE: 77
atgttttcta aacgctcatt attaattgct tttgttgtta ttttctccgg ttgtgccacg      60
tacgccacat ataactacga tcaattattt ggagaggagc aagttcaaga acgtattcac     120
gaatataagt caccagagag tattgattac cttgatgatg tgaaacctct tatcgataaa     180
cgctgtgtgg tatgtcacgc ctgctatgat gcgccctgcc aattaaaaat gtcttcagcg     240
gaaggtattg atcgtggtgc gcataaatcg aaaatttatg aaggaacacg tttagttgct     300
gcaaatccta ctcgttttat tgaggatgct caaacgacgc aagaatggcg tgatattggt     360
ttctctcctg tacttaatga acgtgaccag aatgaaattg caaacaccga agctggtgtt     420
atggcacgca tgctgacttt aaaacagaca aatccacttg ctaaagagaa acaattaaca     480
ggttatgatt tctctatcga tcgtgatcaa caatgcccta cgatcgaaga aatgtctgat     540
```

```
tatgagagtc aatatccaag ctggggtatg ccatatggaa tgcctgagtt gtctaattca    600
gaacacgatt tactaatgaa ttggctagag caaggcgctc atatgagtga tattgctccg    660
ctttcggatt ctgatattgc aaatgttgaa aaatgggaaa ccttttttcaa tggtaattca   720 ttaaaagagc aacttaccgc tcgttaccta tacgaacact tattttttaaa tcatttatat  780 tttacaaaag atcctaatac gctacgcttc tttaaagttg tacgttcagc aacgcctcca    840
ggtgaaccgt tatcacttat cgcaacacgt cgcccatatg atgatccggg tgtagagcgt    900
gtttattatc gtgtagttcc tgtcagaagt agtattgttg ataaaacaca tatgccctac    960
ttacttgatc aagaacgttt tgaaaaatgg actaagtggt ttgttactgc agattatcaa   1020
gtaacatcgc taccaagtta ctcaactgaa attgccgcta atcctctagt tacttttgtg   1080
gatctacccg ttcactcgcg ttacagctat ttattggatg aagcacaaga taccattcaa   1140
ggctttatta aggtccggt ttgtcgtggt caacttgctc ttaatgtgat taatgatcat    1200
ttttgggttt tctttgtcga tccagacaaa accgatagtc ccgatgtggt gaagttctat   1260
cgtgaacaaa aagagaatct tgctttacct gcagagttag acagtacaac agtgccaatt   1320
acaagttgga ttcaatattc tcgaaatcaa gcaagatatt tagaagcaaa aaatacgtat   1380
ctaaatagta tcttttctaa tggtcagcac ttaactctcg atctaatttg gaatggtaat   1440
caaactaatg ataatgcggc attaactatc taccgtcatt ttgatagtgc ttcagttatt   1500
aaaggattaa atggacctac tccaaaaaca gcttgggtaa ttgattatgc attattagaa   1560
cgtattcatt acctattggt tgctggtttt gatgtgtatg gtaatttcgg ccatcaattg   1620
atgactcgta tgtacatgga tttcttaaga atggaaggtg aaagtaactt tttagcttta   1680
ttacctaaga aaatgcgtaa ggctgaattt gaaagctggt atcaagatcc atcacctcaa   1740
ctaagtcgtt tcttacagcg tgatgtacag ccatttgagc agccaacaca aataaaatat   1800
atttctaata atccaaaaga tgaactcttt actaaattaa gaaaacgcat gggtagtggt   1860
ttatcaaccc gttacaatgt aactaattct gagttggata atcgtctca cattgcttta   1920 aatagtattg atcgcattca aggcgatgga ctgcaatact tacctcaaat catgacggtt   1980
aaagttgtgt ctaataaagg aaaaagtgaa tttttcaccc tattaaatac aagtgcgcat   2040
aagaacattt cttctttatt taatgaagaa ggaaatcgta ttcctaaact tgaccgcttg   2100
tctatcctat acggtgttgt aggtagttac cctgctgcct ttttagagat tgaagaatct   2160
aaattacctg attttgttaa acaattaagc aaagtcggtt ctgaagaaga ttacgtcgca   2220
ttacttgatg gctatgcaat tagacgcagc tcaaataaat tctgggctta tagtgacgag   2280
ttaacagaat ggtataaaat gaaatatcca atcgaagctg gtcttttaga ttacaatcga   2340
tttgaaaata gataa                                                    2355
```

<210> SEQ ID NO 78
<211> LENGTH: 784
<212> TYPE: PRT
<213> ORGANISM: Vibrio fischeri

<400> SEQUENCE: 78

```
Met Phe Ser Lys Arg Ser Leu Leu Ile Ala Phe Val Val Ile Phe Ser
1               5                   10                  15

Gly Cys Ala Thr Tyr Ala Thr Tyr Asn Tyr Asp Gln Leu Phe Gly Glu
            20                  25                  30

Glu Gln Val Gln Glu Arg Ile His Glu Tyr Lys Ser Pro Glu Ser Ile
        35                  40                  45
```

```
Asp Tyr Leu Asp Asp Val Lys Pro Leu Ile Asp Lys Arg Cys Val Val
 50                  55                  60
Cys His Ala Cys Tyr Asp Ala Pro Cys Gln Leu Lys Met Ser Ser Ala
 65                  70                  75                  80
Glu Gly Ile Asp Arg Gly Ala His Lys Ser Lys Ile Tyr Glu Gly Thr
                 85                  90                  95
Arg Leu Val Ala Ala Asn Pro Thr Arg Leu Phe Glu Asp Ala Gln Thr
            100                 105                 110
Thr Gln Glu Trp Arg Asp Ile Gly Phe Ser Pro Val Leu Asn Glu Arg
        115                 120                 125
Asp Gln Asn Glu Ile Ala Asn Thr Glu Ala Gly Val Met Ala Arg Met
130                 135                 140
Leu Thr Leu Lys Gln Thr Asn Pro Leu Ala Lys Glu Lys Gln Leu Thr
145                 150                 155                 160
Gly Tyr Asp Phe Ser Ile Asp Arg Asp Gln Gln Cys Pro Thr Ile Glu
                165                 170                 175
Glu Met Ser Asp Tyr Glu Ser Gln Tyr Pro Ser Trp Gly Met Pro Tyr
            180                 185                 190
Gly Met Pro Glu Leu Ser Asn Ser Glu His Asp Leu Leu Met Asn Trp
        195                 200                 205
Leu Glu Gln Gly Ala His Met Ser Asp Ile Ala Pro Leu Ser Asp Ser
210                 215                 220
Asp Ile Ala Asn Val Glu Lys Trp Glu Thr Phe Phe Asn Gly Asn Ser
225                 230                 235                 240
Leu Lys Glu Gln Leu Thr Ala Arg Tyr Leu Tyr Glu His Leu Phe Leu
                245                 250                 255
Asn His Leu Tyr Phe Thr Lys Asp Pro Asn Thr Leu Arg Phe Phe Lys
            260                 265                 270
Val Val Arg Ser Ala Thr Pro Pro Gly Glu Pro Leu Ser Leu Ile Ala
        275                 280                 285
Thr Arg Arg Pro Tyr Asp Asp Pro Gly Val Glu Arg Val Tyr Tyr Arg
290                 295                 300
Val Val Pro Val Arg Ser Ser Ile Val Asp Lys Thr His Met Pro Tyr
305                 310                 315                 320
Leu Leu Asp Gln Glu Arg Phe Glu Lys Trp Thr Lys Trp Phe Val Thr
                325                 330                 335
Ala Asp Tyr Gln Val Thr Ser Leu Pro Ser Tyr Ser Thr Glu Ile Ala
            340                 345                 350
Ala Asn Pro Leu Val Thr Phe Val Asp Leu Pro Val His Ser Arg Tyr
        355                 360                 365
Ser Tyr Leu Leu Asp Glu Ala Gln Asp Thr Ile Gln Gly Phe Ile Lys
    370                 375                 380
Gly Pro Val Cys Arg Gly Gln Leu Ala Leu Asn Val Ile Asn Asp His
385                 390                 395                 400
Phe Trp Val Phe Phe Val Asp Pro Asp Lys Thr Asp Ser Pro Asp Val
                405                 410                 415
Val Lys Phe Tyr Arg Glu Gln Lys Glu Asn Leu Ala Leu Pro Ala Glu
            420                 425                 430
Leu Asp Ser Thr Thr Val Pro Ile Thr Ser Trp Ile Gln Tyr Ser Arg
        435                 440                 445
Asn Gln Ala Arg Tyr Leu Glu Ala Lys Asn Thr Tyr Leu Asn Ser Ile
    450                 455                 460
Phe Ser Asn Gly Gln His Leu Thr Leu Asp Leu Ile Trp Asn Gly Asn
465                 470                 475                 480
```

Gln Thr Asn Asp Asn Ala Ala Leu Thr Ile Tyr Arg His Phe Asp Ser
                485                 490                 495

Ala Ser Val Ile Lys Gly Leu Asn Gly Pro Thr Pro Lys Thr Ala Trp
        500                 505                 510

Val Ile Asp Tyr Ala Leu Leu Glu Arg Ile His Tyr Leu Leu Val Ala
            515                 520                 525

Gly Phe Asp Val Tyr Gly Asn Phe Gly His Gln Leu Met Thr Arg Met
530                 535                 540

Tyr Met Asp Phe Leu Arg Met Glu Gly Glu Ser Asn Phe Leu Ala Leu
545                 550                 555                 560

Leu Pro Lys Lys Met Arg Lys Ala Glu Phe Glu Ser Trp Tyr Gln Asp
                565                 570                 575

Pro Ser Pro Gln Leu Ser Arg Phe Leu Gln Arg Asp Val Gln Pro Phe
            580                 585                 590

Glu Gln Pro Thr Gln Ile Lys Tyr Ile Ser Asn Asn Pro Lys Asp Glu
                595                 600                 605

Leu Phe Thr Lys Leu Arg Lys Arg Met Gly Ser Gly Leu Ser Thr Arg
        610                 615                 620

Tyr Asn Val Thr Asn Ser Glu Leu Asp Lys Ser Ser His Ile Ala Leu
625                 630                 635                 640

Asn Ser Ile Asp Arg Ile Gln Gly Asp Gly Leu Gln Tyr Leu Pro Gln
                645                 650                 655

Ile Met Thr Val Lys Val Ser Asn Lys Gly Lys Ser Glu Phe Phe
                660                 665                 670

Thr Leu Leu Asn Thr Ser Ala His Lys Asn Ile Ser Ser Leu Phe Asn
        675                 680                 685

Glu Glu Gly Asn Arg Ile Pro Lys Leu Asp Arg Leu Ser Ile Leu Tyr
    690                 695                 700

Gly Val Val Gly Ser Tyr Pro Ala Ala Phe Leu Glu Ile Glu Ser
705                 710                 715                 720

Lys Leu Pro Asp Phe Val Lys Gln Leu Ser Lys Val Gly Ser Glu Glu
                725                 730                 735

Asp Tyr Val Ala Leu Leu Asp Gly Tyr Ala Ile Arg Arg Ser Ser Asn
            740                 745                 750

Lys Phe Trp Ala Tyr Ser Asp Glu Leu Thr Glu Trp Tyr Lys Met Lys
        755                 760                 765

Tyr Pro Ile Glu Ala Gly Leu Leu Asp Tyr Asn Arg Phe Glu Asn Arg
770                 775                 780

<210> SEQ ID NO 79
<211> LENGTH: 321
<212> TYPE: DNA
<213> ORGANISM: Photobacterium profundum

<400> SEQUENCE: 79
atgaacgctt acaatcacca gatgccaata cacaagctgg tgttccgcca tttcgatagt    60
gcatcgatgg ttaaaggctt aatcggtgtg caacctaaaa cggcatggat catcgactat   120
tcgctattag aacgtattca ttacttactc gtcgctggtt ttgatgtcta tggtgattat   180
gaaaggttat tagataaata cggaattcgt cgaacaaatc cttccttctg gtctttcagt   240
gatgtactga ttaaacagta caagatcaac taccccattg agtccggcat tcttgattac   300
aaccgacttc aaaacaggta a                                              321

<210> SEQ ID NO 80

```
<211> LENGTH: 106
<212> TYPE: PRT
<213> ORGANISM: Photobacterium profundum

<400> SEQUENCE: 80

Met Asn Ala Tyr Asn His Gln Met Pro Ile His Lys Leu Val Phe Arg
1               5                   10                  15

His Phe Asp Ser Ala Ser Met Val Lys Gly Leu Ile Gly Val Gln Pro
            20                  25                  30

Lys Thr Ala Trp Ile Ile Asp Tyr Ser Leu Leu Glu Arg Ile His Tyr
        35                  40                  45

Leu Leu Val Ala Gly Phe Asp Val Tyr Gly Asp Tyr Glu Arg Leu Leu
    50                  55                  60

Asp Lys Tyr Gly Ile Arg Arg Thr Asn Pro Ser Phe Trp Ser Phe Ser
65                  70                  75                  80

Asp Val Leu Ile Lys Gln Tyr Lys Ile Asn Tyr Pro Ile Glu Ser Gly
                85                  90                  95

Ile Leu Asp Tyr Asn Arg Leu Gln Asn Arg
            100                 105

<210> SEQ ID NO 81
<211> LENGTH: 2340
<212> TYPE: DNA
<213> ORGANISM: Pseudoalteromonas haloplanktis

<400> SEQUENCE: 81
```

| | |
|---|---|
| atgatgagaa aagtcgtaat aagtacgcta atactgatta ttttaagtgg ctgtgcgtat | 60 |
| ttaggtaatg ctcattacaa tgatttattt ggccctgagc aaacacaaga tcgtatggtt | 120 |
| ttacatagta caattgaggg ggctgatttt ttacaaaatg taaagccagt gcttgataca | 180 |
| cgctgtgtag tttgccacgg ttgctacgat gcgccatgtc agcttaagct ctcatctccc | 240 |
| gaaggcattg atagaggttt aagtaaagag ctggtctatg atggtacgcg tttattagcc | 300 |
| actacaccga gccgtttgtt gtttgatgca gataataccc agcaatggcg tgataaaggt | 360 |
| ttttcgccgg tgctaaatga gcgcgagcaa agcttagaag caaacttagc aggcagtgtg | 420 |
| ttatttaata gcttagtgct aaagcaaagc tctgatattg ctaacaatga agtacttgat | 480 |
| gatgatgatt tgattttttc gttaagtcgc tctcaaacct gtgccactat gggagagttt | 540 |
| gataggttgg cggatgatca accacatggt ggtatgcctt atggtttgcc aggcgtatcg | 600 |
| cgtgaggaat ttaagcactt acaaaattgg ctgaaaaacg tggtaaaaat ggccaatatt | 660 |
| gcaccgccaa cagcgtttga gctacaacaa attaagcgtt gggaagcatt tttaaatcaa | 720 |
| gatagtttaa agtatcagct ttctgcgcgt tatatttacg agcattggtt tttagcaaat | 780 |
| atctatttca ctccagaaaa cacgcaaacc tttttttaaat tagtgcgctc aagtacacca | 840 |
| cccggtgaag atattaaact cattagcaca cgtcgtcctt atgatgatcc taatgttgaa | 900 |
| cgtgtttact atcgaatgat gcatgaacgc tcaactattt tgtcaaaaac acatttgcca | 960 |
| cttaaattaa atgatgcaaa gctaacgcgt ttatatcagc agtttataga gcctgaatat | 1020 |
| acggtagcga gcatgccaag ctatgagcca aaggctgcct ctaatccttt taaaacctat | 1080 |
| gaagtgattc caatcgactc aaaatatcag tttatgcttg atgaagctga gttaataatt | 1140 |
| atgggcttta ttaaagggcc ggtttgtcgt gggcaaattg cacttaacgt cataaatgat | 1200 |
| catttttggg ttgcatttgc tgatcctaaa aaagtggcta ctcctgctgt aggtgaaatg | 1260 |
| ctgattcagc acgaagatgc gcttgagcta cctgccgctg aagaaagtaa cgcattagcg | 1320 |
| attaaaagct ggattaaata ttcggtgcgc gaaaaacgtt acttaaaagc taaagttgag | 1380 |

```
ctggctaatg agctgtttaa aaatggcgat cacttaacca ctaatttatt gtggaaaggt    1440
gatggtgtta ataaaaatgc tgcgttaact gtatttcgtc actcagacag tgctacggtt    1500
gtgaaaggct taattggaca agagcctaaa actatgtggg tgcttgatta tgctttattt    1560
gagcgcattc actatttatt ggttgctgga tttgatgtat acggcaatgt agggcaccaa    1620
ctcgttacac gtttatatat ggattttta cgtttagagg gagagggtaa ctttcttggc    1680
ctattacctg aagataaacg agagcaaatt aaaagtagtt ggtatcgtaa gtcaccgcct    1740
agcttatcta agttctttaa aagtaaccaa gagtttagcc aacctagcgg aatagtttat    1800
aaaaccgatg atccgcaaca tgagctttat ggcttaatta aaacggcatt atcgcccgta    1860
cttagcgagc attacgatta cactagcgtt tctgggccgt tagcaagtat taatactatg    1920
cctgttaagg caataaactt attgccacct gtatcttatg tattggttaa gcaaacagac    1980
aatagccata aagcgtatac cattattcat cataacgcac attacaatat ctctagctta    2040
cttaacgaag aaggtcagcg agcttttgaa gaagatactg tcactctagt tcctggtttt    2100 attgggatt atccaagtgc tatttggtat ttaaataatc aacagcaagt tgcagcattt    2160
gcagagcagt taccactgat gcaaattgaa gctgattatc gtgcgttaaa atctaagttt    2220
ggcattcgcc gtactcatcc acaattttgg cagtatagcg acattttaca tcgggctgct    2280
aagcagtatc gtggtgttga atacggtatg tttgactata atcgcttaga aaaccgctag    2340
```

<210> SEQ ID NO 82
<211> LENGTH: 779
<212> TYPE: PRT
<213> ORGANISM: Pseudoalteromonas haloplanktis

<400> SEQUENCE: 82

```
Met Met Arg Lys Val Val Ile Ser Thr Leu Ile Leu Ile Ile Leu Ser
1               5                   10                  15

Gly Cys Ala Tyr Leu Gly Asn Ala His Tyr Asn Asp Leu Phe Gly Pro
            20                  25                  30

Glu Gln Thr Gln Asp Arg Met Val Leu His Ser Thr Ile Glu Gly Ala
        35                  40                  45

Asp Phe Leu Gln Asn Val Lys Pro Val Leu Asp Thr Arg Cys Val Val
    50                  55                  60

Cys His Gly Cys Tyr Asp Ala Pro Cys Gln Leu Lys Leu Ser Ser Pro
65                  70                  75                  80

Glu Gly Ile Asp Arg Gly Leu Ser Lys Glu Leu Val Tyr Asp Gly Thr
                85                  90                  95

Arg Leu Leu Ala Thr Thr Pro Ser Arg Leu Leu Phe Asp Ala Asp Asn
            100                 105                 110

Thr Gln Gln Trp Arg Asp Lys Gly Phe Ser Pro Val Leu Asn Glu Arg
        115                 120                 125

Glu Gln Ser Leu Glu Ala Asn Leu Ala Gly Ser Val Leu Phe Asn Ser
    130                 135                 140

Leu Val Leu Lys Gln Ser Ser Asp Ile Ala Asn Asn Glu Val Leu Asp
145                 150                 155                 160

Asp Asp Asp Phe Asp Phe Ser Leu Ser Arg Ser Gln Thr Cys Ala Thr
                165                 170                 175

Met Gly Glu Phe Asp Arg Leu Ala Asp Asp Gln Pro His Gly Gly Met
            180                 185                 190

Pro Tyr Gly Leu Pro Gly Val Ser Arg Glu Glu Phe Lys His Leu Gln
        195                 200                 205
```

-continued

Asn Trp Leu Lys Asn Gly Gly Lys Met Ala Asn Ile Ala Pro Pro Thr
210                 215                 220

Ala Phe Glu Leu Gln Gln Ile Lys Arg Trp Glu Ala Phe Leu Asn Gln
225                 230                 235                 240

Asp Ser Leu Lys Tyr Gln Leu Ser Ala Arg Tyr Ile Tyr Glu His Trp
            245                 250                 255

Phe Leu Ala Asn Ile Tyr Phe Thr Pro Glu Asn Thr Gln Thr Phe Phe
            260                 265                 270

Lys Leu Val Arg Ser Ser Thr Pro Pro Gly Glu Asp Ile Lys Leu Ile
            275                 280                 285

Ser Thr Arg Arg Pro Tyr Asp Asp Pro Asn Val Glu Arg Val Tyr Tyr
290                 295                 300

Arg Met Met His Glu Arg Ser Thr Ile Leu Ser Lys Thr His Leu Pro
305                 310                 315                 320

Leu Lys Leu Asn Asp Ala Lys Leu Thr Arg Leu Tyr Gln Gln Phe Ile
            325                 330                 335

Glu Pro Glu Tyr Thr Val Ala Ser Met Pro Ser Tyr Glu Pro Lys Ala
            340                 345                 350

Ala Ser Asn Pro Phe Lys Thr Tyr Glu Val Ile Pro Ile Asp Ser Lys
            355                 360                 365

Tyr Gln Phe Met Leu Asp Glu Ala Glu Leu Ile Met Gly Phe Ile
370                 375                 380

Lys Gly Pro Val Cys Arg Gly Gln Ile Ala Leu Asn Val Ile Asn Asp
385                 390                 395                 400

His Phe Trp Val Ala Phe Ala Asp Pro Lys Lys Val Ala Thr Pro Ala
            405                 410                 415

Val Gly Glu Met Leu Ile Gln His Glu Asp Ala Leu Glu Leu Pro Ala
            420                 425                 430

Ala Glu Glu Ser Asn Ala Leu Ala Ile Lys Ser Trp Ile Lys Tyr Ser
            435                 440                 445

Val Arg Glu Lys Arg Tyr Leu Lys Ala Lys Val Glu Leu Ala Asn Glu
450                 455                 460

Leu Phe Lys Asn Gly Asp His Leu Thr Thr Asn Leu Leu Trp Lys Gly
465                 470                 475                 480

Asp Gly Val Asn Lys Asn Ala Ala Leu Thr Val Phe Arg His Ser Asp
            485                 490                 495

Ser Ala Thr Val Val Lys Gly Leu Ile Gly Gln Glu Pro Lys Thr Met
            500                 505                 510

Trp Val Leu Asp Tyr Ala Leu Phe Glu Arg Ile His Tyr Leu Leu Val
            515                 520                 525

Ala Gly Phe Asp Val Tyr Gly Asn Val Gly His Gln Leu Val Thr Arg
530                 535                 540

Leu Tyr Met Asp Phe Leu Arg Leu Glu Gly Gly Asn Phe Leu Gly
545                 550                 555                 560

Leu Leu Pro Glu Asp Lys Arg Glu Gln Ile Lys Ser Trp Tyr Arg
            565                 570                 575

Lys Ser Pro Pro Ser Leu Ser Lys Phe Phe Lys Ser Asn Gln Glu Phe
            580                 585                 590

Ser Gln Pro Ser Gly Ile Val Tyr Lys Thr Asp Asp Pro Gln His Glu
            595                 600                 605

Leu Tyr Gly Leu Ile Lys Thr Ala Leu Ser Pro Val Leu Ser Glu His
            610                 615                 620

Tyr Asp Tyr Thr Ser Val Ser Gly Pro Leu Ala Ser Ile Asn Thr Met
625                 630                 635                 640

Pro Val Lys Ala Ile Asn Leu Leu Pro Pro Val Ser Tyr Val Leu Val
            645                 650                 655

Lys Gln Thr Asp Asn Ser His Lys Ala Tyr Thr Ile Ile His His Asn
        660                 665                 670

Ala His Tyr Asn Ile Ser Ser Leu Leu Asn Glu Glu Gly Gln Arg Ala
            675                 680                 685

Phe Glu Glu Asp Thr Val Thr Leu Val Pro Gly Phe Ile Gly Asp Tyr
    690                 695                 700

Pro Ser Ala Ile Trp Tyr Leu Asn Asn Gln Gln Val Ala Ala Phe
705                 710                 715                 720

Ala Glu Gln Leu Pro Leu Met Gln Ile Glu Ala Asp Tyr Arg Ala Leu
                725                 730                 735

Lys Ser Lys Phe Gly Ile Arg Arg Thr His Pro Gln Phe Trp Gln Tyr
            740                 745                 750

Ser Asp Ile Leu His Arg Ala Ala Lys Gln Tyr Arg Gly Val Glu Tyr
        755                 760                 765

Gly Met Phe Asp Tyr Asn Arg Leu Glu Asn Arg
    770                 775

<210> SEQ ID NO 83
<211> LENGTH: 2397
<212> TYPE: DNA
<213> ORGANISM: Pseudoalteromonas atlantica

<400> SEQUENCE: 83
atgcaaaata cacattccag atggattaaa atattcatcg ccgtcattct tgtctgttcg      60
ggttgcgcga ccattgccaa tcttgatttc aacaagcttt atggccacga agccccagtg    120
aaccgcgcac cagccagtgt cacgcaagcg ttattagaaa gccctgccac cgcattctac    180
caaaccaaag tagcacccgt aattgaaggg cgttgtgttg tgtgccatgc ctgctacgac    240
gccccttgcc agcttaagat gagctcgcca gaaggaatag atcgcggcgc gagtaaagaa    300
gttgtctacc atggctcgcg tatacttgcc gccacgccaa tcgattgtt tttagacgca    360 ttagattctc ccgactggcg caagcgtggc ttttatcctg tgctaaatga gcagaacaa    420 accccctattg ccaacacgca ggcgtcagtt ttagcaaaaa tgctgaagct taaacagcaa    480
caccctttac ctgacgacaa attattagac gaacgcttcg atgtctctat cgatcgcagc    540
caacaatgtc ctaccatttc ggaatttgat ggctatgcca caagccaagc atttggtgga    600
atgccctacg ctctcccaga attaaccggt gaggagcaca atatactcat gagttggatg    660
gagagcggcg cttatatgcc tgctcgcgca ccactgtctg aagcccaaga gacagcgata    720
aactcgttag aagacttttt aaatgctgac gatttgaaaa tgcagttaag tgctcgctac    780
atttatgaac acttgtttag ctctcatttg tactttagtg agataaccgc gcctaatacc    840
cagccacagt tttttaatct tgtgcgttca agaacgccat cagggcaagc tattgatgtc    900
attccgagtc gccgccctt tgatgagcca ggggtaaagc gcgtttatta ccgcttgcag    960
cctgttatgt cgaccatagt caacaaaaca caccagcctt atgctattca caaagcactc    1020
accgacaaat ggcagaagtg gtttgtagac gctgactaca cagtgaccga gttacctagc    1080
tatcagccaa aagtagcggc aaaccccgcta acgctttca ctcaattacc ggaaaacgcg    1140
cgctaccgct ttatgctcga gcgtgcacag aacaccatta tgggttacat caagggccc    1200 gtttgtcgtg gtcaggtggc gttgaatgtc atcaatgatc gtttctgggt ttactttgta    1260
aaaccagaag tggcagattc acccaagata cacgccttct acgaatcaca aaaagacaac    1320

-continued

```
cttcgcctcc ctgcggaaca cgagagcacc gcatttgcgg taacttggct tgaatatgcc    1380
tcacgacaag gtgattacat gcgtgcacgg catgatttca tggcaaccgc cttggaagat    1440
ggccagcatt tcactgctaa cgatatatgg gatggtgacg gtgaaaatga caacgccacg    1500
ctgacggtgt ttcgtcactt tgacaatgcc accgtcatta aaggcttagt gggtaagcct    1560
cccaaaaccg cttgggttat cgactacgca ttactagagc gtattcacta cctgttagtc    1620
gctgggtttg atgtgtatgg caattatggc catcaattga tgacgcgcct gtacatggac    1680
tttctgcgca tggaaggtga atcaaacttt ttggcctttt taccgcctaa aacgcgtcac    1740
gaagagttgg cctcttggta tcaaaaagct gggccagagc taaccgaatt tgttgagggt    1800
aaaatcaacc cgttcgatca acctagtggt atgcagttta aaacccagca ccacaagaaa    1860
gaattatatg atatttttgc tgaacatgtg aaagacgtgc aacccagccg ttaccgatta    1920
caagacagcg aattaggtca aaatagcaaa gccctgctcg acaattagc caacatcaaa     1980
ggccaaagcg cctcaatatt gcccgagctg agcatgatca tggtcgagcc cacagacagt    2040
gataaaccag agattttcac cttggtgaga acagtgcgc atttcaatgt gaacagcttg      2100
ttttctgaag atgctaatcg cgaccacgcc aatgatgacg tgacgttagt acatgggtta    2160
ctcggtagtt atcccgatgt attctggcgg gtaaaagaag cagatctggc caaattagtg    2220
gcgaaagctc agcaaattga aaacgagcaa aattatgaag ccttcttgga tctatttgcg    2280
gtaaggcgca caaccaaaga ttttgggca ttcagcgaca aactcaatca aaccttcatg      2340
gagcacaatc cgatcgaagg tggactgctg gattacaatc gattagaaaa ccgttag       2397
```

<210> SEQ ID NO 84
<211> LENGTH: 798
<212> TYPE: PRT
<213> ORGANISM: Pseudoalteromonas atlantica

<400> SEQUENCE: 84

```
Met Gln Asn Thr His Ser Arg Trp Ile Lys Ile Phe Ile Ala Val Ile
 1               5                  10                  15

Leu Val Cys Ser Gly Cys Ala Thr Ile Ala Asn Leu Asp Phe Asn Lys
             20                  25                  30

Leu Tyr Gly His Glu Ala Pro Val Asn Arg Ala Pro Ala Ser Val Thr
         35                  40                  45

Gln Ala Leu Leu Glu Ser Pro Ala Thr Ala Phe Tyr Gln Thr Lys Val
     50                  55                  60

Ala Pro Val Ile Glu Gly Arg Cys Val Cys His Ala Cys Tyr Asp
 65                  70                  75                  80

Ala Pro Cys Gln Leu Lys Met Ser Ser Pro Glu Gly Ile Asp Arg Gly
                 85                  90                  95

Ala Ser Lys Glu Val Val Tyr His Gly Ser Arg Ile Leu Ala Ala Thr
            100                 105                 110

Pro Asn Arg Leu Phe Leu Asp Ala Leu Asp Ser Pro Asp Trp Arg Lys
        115                 120                 125

Arg Gly Phe Tyr Pro Val Leu Asn Glu Arg Glu Gln Thr Pro Ile Ala
    130                 135                 140

Asn Thr Gln Ala Ser Val Leu Ala Lys Met Leu Lys Leu Lys Gln Gln
145                 150                 155                 160

His Pro Leu Pro Asp Lys Leu Leu Asp Glu Arg Phe Asp Val Ser
                165                 170                 175

Ile Asp Arg Ser Gln Gln Cys Pro Thr Ile Ser Glu Phe Asp Gly Tyr
            180                 185                 190
```

-continued

```
Ala Thr Ser Gln Ala Phe Gly Gly Met Pro Tyr Ala Leu Pro Glu Leu
        195                 200                 205
Thr Gly Glu Glu His Asn Ile Leu Met Ser Trp Met Glu Ser Gly Ala
210                 215                 220
Tyr Met Pro Ala Arg Ala Pro Leu Ser Glu Ala Gln Glu Thr Ala Ile
225                 230                 235                 240
Asn Ser Leu Glu Asp Phe Leu Asn Ala Asp Asp Leu Lys Met Gln Leu
            245                 250                 255
Ser Ala Arg Tyr Ile Tyr Glu His Leu Phe Ser Ser His Leu Tyr Phe
                260                 265                 270
Ser Glu Ile Thr Ala Pro Asn Thr Gln Pro Gln Phe Phe Asn Leu Val
        275                 280                 285
Arg Ser Arg Thr Pro Ser Gly Gln Ala Ile Asp Val Ile Pro Ser Arg
290                 295                 300
Arg Pro Phe Asp Glu Pro Gly Val Lys Arg Val Tyr Arg Leu Gln
305                 310                 315                 320
Pro Val Met Ser Thr Ile Val Asn Lys Thr His Gln Pro Tyr Ala Ile
            325                 330                 335
His Lys Ala Leu Thr Asp Lys Trp Gln Lys Trp Phe Val Asp Ala Asp
                340                 345                 350
Tyr Thr Val Thr Glu Leu Pro Ser Tyr Gln Pro Lys Val Ala Ala Asn
        355                 360                 365
Pro Leu Thr Ala Phe Thr Gln Leu Pro Glu Asn Ala Arg Tyr Arg Phe
370                 375                 380
Met Leu Glu Arg Ala Gln Asn Thr Ile Met Gly Tyr Ile Lys Gly Pro
385                 390                 395                 400
Val Cys Arg Gly Gln Val Ala Leu Asn Val Ile Asn Asp Arg Phe Trp
            405                 410                 415
Val Tyr Phe Val Lys Pro Glu Val Ala Asp Ser Pro Lys Ile His Ala
                420                 425                 430
Phe Tyr Glu Ser Gln Lys Asp Asn Leu Arg Leu Pro Ala Glu His Glu
        435                 440                 445
Ser Thr Ala Phe Ala Val Thr Trp Leu Glu Tyr Ala Ser Arg Gln Gly
450                 455                 460
Asp Tyr Met Arg Ala Arg His Asp Phe Met Ala Thr Ala Leu Glu Asp
465                 470                 475                 480
Gly Gln His Phe Thr Ala Asn Asp Ile Trp Asp Gly Asp Gly Glu Asn
            485                 490                 495
Asp Asn Ala Thr Leu Thr Val Phe Arg His Phe Asp Asn Ala Thr Val
                500                 505                 510
Ile Lys Gly Leu Val Gly Lys Pro Pro Lys Thr Ala Trp Val Ile Asp
        515                 520                 525
Tyr Ala Leu Leu Glu Arg Ile His Tyr Leu Leu Val Ala Gly Phe Asp
530                 535                 540
Val Tyr Gly Asn Tyr Gly His Gln Leu Met Thr Arg Leu Tyr Met Asp
545                 550                 555                 560
Phe Leu Arg Met Glu Gly Glu Ser Asn Phe Leu Ala Phe Leu Pro Pro
            565                 570                 575
Lys Thr Arg His Glu Glu Leu Ala Ser Trp Tyr Gln Lys Ala Gly Pro
                580                 585                 590
Glu Leu Thr Glu Phe Val Glu Gly Lys Ile Asn Pro Phe Asp Gln Pro
        595                 600                 605
Ser Gly Met Gln Phe Lys Thr Gln His His Lys Lys Glu Leu Tyr Asp
610                 615                 620
```

```
Ile Phe Ala Glu His Val Lys Asp Val Gln Pro Ser Arg Tyr Arg Leu
625                 630                 635                 640

Gln Asp Ser Glu Leu Gly Gln Asn Ser Lys Ala Leu Leu Gly Gln Leu
            645                 650                 655

Ala Asn Ile Lys Gly Gln Ser Ala Ser Ile Leu Pro Glu Leu Ser Met
            660                 665                 670

Ile Met Val Glu Pro Thr Asp Ser Asp Lys Pro Glu Ile Phe Thr Leu
            675                 680                 685

Val Arg Asn Ser Ala His Phe Asn Val Asn Ser Leu Phe Ser Glu Asp
        690                 695                 700

Ala Asn Arg Asp His Ala Asn Asp Asp Val Thr Leu Val His Gly Leu
705                 710                 715                 720

Leu Gly Ser Tyr Pro Asp Val Phe Trp Arg Val Lys Glu Ala Asp Leu
                725                 730                 735

Ala Lys Leu Val Ala Lys Ala Gln Gln Ile Glu Asn Glu Gln Asn Tyr
            740                 745                 750

Glu Ala Phe Leu Asp Leu Phe Ala Val Arg Arg Thr Thr Lys Asp Phe
            755                 760                 765

Trp Ala Phe Ser Asp Lys Leu Asn Gln Thr Phe Met Glu His Asn Pro
            770                 775                 780

Ile Glu Gly Gly Leu Leu Asp Tyr Asn Arg Leu Glu Asn Arg
785                 790                 795

<210> SEQ ID NO 85
<211> LENGTH: 2271
<212> TYPE: DNA
<213> ORGANISM: Azotobacter vinelandii

<400> SEQUENCE: 85
atgccgcttc gccttttcct cctcgtgctg ctggcgctcg gcgtcgtggc gcgggccgaa      60
gaattgtcgt accgccgcga catccagccg atcttcaccg ccaaatgcgt ggcttgccat     120
gcctgctacg actcgccctg ccagctcaac ctgggcagcg cgaaggggc acagcgcggc     180
gcccacaagt tgccggtgta cgacgggctg cgcaccgagg cccaggaaac cacccggctg     240
ttcctcgatg ccgaaggtga ggcggcctgg cggcgcaagg gctttcattc ggtgctcgac     300
ggcggcggcc aggcggcgct gatggcgcgc atgctggagc tcggtcgcgg ccgtccgctg     360
gtgcacaacg cccctttgcc gaaggatctg gagatcggca tcgaacggcg caacagttgt     420
ccgctgcccg cgaattcga ggccttcgcc cgcgccaatc tctggccgg catgcctttc     480
gccgtcaccg gcctgaccga cggcgagtac gcgaccctga ggaaatggct ggaacagggg     540
gctccgatcg acgcggcgcc gctcgaaccg tcgccggccg aggtggcgca gatcgccgcc     600
tgggaacggc tgctgaacgc gcgtgatccg cgttcccggc tggtcgcccg ctggctgtac     660
gagcacctgt tcctcgccca cctgcatttc gagggtggcg cgccggggca cttcttccaa     720
ctggtgcgtt cgcgcacgcc ttccggccag ccggtcgagc cgatcgccac gcggcgcccc     780
aacgacgacc ccggcggcga tttccattac cggctgcgac cggttgccga cgtgatcgtg     840
cacaagacgc acatcaccta tccgctcggc ccgcgcaagc tcgcccgggt gcgcgagctg     900
ttcttctccg cgactggca ggtggcgaa ctgcccggcc acggtgccca gcaccgcgcc     960
aatccgttcg agaccttcgc ggcgattccg gcgcaggcgc gctaccgctt catgctggac    1020
aatgccgaat acttcgtgcg taccttcatc cgtggcccgg tatgccgcgg gcagatcgcc    1080
acggacgtga tccgcgacca cttctggacg ttgttccagg ctcccgagcg ggatctctat    1140
```

```
ctcaccgacg cgcagtatcg cgaggcgacg acgccgctgc tcgtgctgcc cggccagatc    1200
gacgatatcg ccggcctttg gggcctctgg agcgcctaca cggatcgcct caagcgctac    1260
gagaacctgc gccgccaggc ttacgccgag catccggccg catggtcgga tttgtggagc    1320
ggcaacgaca acgccttgct gaccatcttc cgccagcacg acagcgcctc ggtacgcaag    1380
ggactggtcg gagccgtgcc gcagaccctg tggctgctgg atttcccgct gttcgagcgc    1440
acctactacc agttggtggt gaatttcgac gtattcggca acgtttccca tcaattgcag    1500
acgcgcctgt acttcgacct gatccgcaac ggcgccgagc agaacttcct gcgcctgctg    1560
ccgtccggca cgcgccaggc gatcctcgac agttggtacg agaacagtgg ccagctcaag    1620
ctctggctcg cctataccga ggtcgacagc gagacgccct cggtgctgga tctgccgcaa    1680
cgcgaaccgg tccgcgcttt cgccggacgc ctgctggaac ggcacgtagc gatcaatgcc    1740
cgtcccgatc cgttcaaccg ctgccgctcg gcgcattgcc accggctgg cgtggcgcgg    1800 gagttgcagt atgccgaaca ggtcctcagc cgtctggtca gccggcccgc ggccggcctg    1860
ccggtggtgc tcgccctgcc ggaggccagc ctgctgcgca tcgaatacgg cgaaggaaaa    1920
cgggaggtct acagcctgct gcgcaaccga gcgcacagca acgtggcatt cattttcggc    1980
gagcgtctgc gctaccagcc gacgctggat acactgacgc tctatccggg cgtgctgagc    2040
agctacccca acttcctctt caatgtccgt gccgaggaag tgccggattt cgtcgcggcg    2100
ctggagcagg cgagggcagg agcgagcttc gtggccgtcg tcgagcgctg gggcgtgcgc    2160
cgcagccatc cggagttctg cgcctatttc aacgatcttt cggcctggat gcgggaaacc    2220
gaaccgctgg aggccggggt gctggacatg aaccgctacc agaacctgtg a              2271

<210> SEQ ID NO 86
<211> LENGTH: 756
<212> TYPE: PRT
<213> ORGANISM: Azotobacter vinelandii

<400> SEQUENCE: 86

Met Pro Leu Arg Leu Phe Leu Val Leu Leu Ala Leu Gly Val Val
1               5                   10                  15

Ala Arg Ala Glu Glu Leu Ser Tyr Arg Arg Asp Ile Gln Pro Ile Phe
            20                  25                  30

Thr Ala Lys Cys Val Ala Cys His Ala Cys Tyr Asp Ser Pro Cys Gln
        35                  40                  45

Leu Asn Leu Gly Ser Gly Glu Gly Ala Gln Arg Gly Ala His Lys Leu
    50                  55                  60

Pro Val Tyr Asp Gly Leu Arg Thr Glu Ala Gln Glu Thr Thr Arg Leu
65                  70                  75                  80

Phe Leu Asp Ala Glu Gly Glu Ala Ala Trp Arg Arg Lys Gly Phe His
                85                  90                  95

Ser Val Leu Asp Gly Gly Gly Gln Ala Ala Leu Met Ala Arg Met Leu
            100                 105                 110

Glu Leu Gly Arg Gly Arg Pro Leu Val His Asn Ala Pro Leu Pro Lys
        115                 120                 125

Asp Leu Glu Ile Gly Ile Glu Arg Arg Asn Ser Cys Pro Leu Pro Gly
    130                 135                 140

Glu Phe Glu Ala Phe Ala Arg Ala Asn Pro Leu Ala Gly Met Pro Phe
145                 150                 155                 160

Ala Val Thr Gly Leu Thr Asp Gly Glu Tyr Ala Thr Leu Arg Lys Trp
                165                 170                 175

Leu Glu Gln Gly Ala Pro Ile Asp Ala Ala Pro Leu Glu Pro Ser Pro
```

```
                180                 185                 190
Ala Glu Val Ala Gln Ile Ala Ala Trp Glu Arg Leu Leu Asn Ala Arg
            195                 200                 205
Asp Pro Arg Ser Arg Leu Val Ala Arg Trp Leu Tyr Glu His Leu Phe
210                 215                 220
Leu Ala His Leu His Phe Glu Gly Gly Ala Pro Gly His Phe Phe Gln
225                 230                 235                 240
Leu Val Arg Ser Arg Thr Pro Ser Gly Gln Pro Val Glu Pro Ile Ala
            245                 250                 255
Thr Arg Arg Pro Asn Asp Asp Pro Gly Gly Asp Phe His Tyr Arg Leu
            260                 265                 270
Arg Pro Val Ala Asp Val Ile Val His Lys Thr His Ile Thr Tyr Pro
            275                 280                 285
Leu Gly Pro Arg Lys Leu Ala Arg Val Arg Glu Leu Phe Phe Ser Gly
            290                 295                 300
Asp Trp Gln Val Ala Glu Leu Pro Gly His Gly Ala Gln His Arg Ala
305                 310                 315                 320
Asn Pro Phe Glu Thr Phe Ala Ala Ile Pro Ala Gln Ala Arg Tyr Arg
            325                 330                 335
Phe Met Leu Asp Asn Ala Glu Tyr Phe Val Arg Thr Phe Ile Arg Gly
            340                 345                 350
Pro Val Cys Arg Gly Gln Ile Ala Thr Asp Val Ile Arg Asp His Phe
            355                 360                 365
Trp Thr Leu Phe Gln Ala Pro Glu Arg Asp Leu Tyr Leu Thr Asp Ala
            370                 375                 380
Gln Tyr Arg Glu Ala Thr Thr Pro Leu Leu Val Leu Pro Gly Gln Ile
385                 390                 395                 400
Asp Asp Ile Ala Gly Leu Trp Gly Leu Trp Ser Ala Tyr Thr Asp Arg
            405                 410                 415
Leu Lys Arg Tyr Glu Asn Leu Arg Arg Gln Ala Tyr Ala Glu His Pro
            420                 425                 430
Ala Ala Trp Ser Asp Leu Trp Ser Gly Asn Asp Asn Ala Leu Leu Thr
            435                 440                 445
Ile Phe Arg Gln His Asp Ser Ala Ser Val Arg Lys Gly Leu Val Gly
            450                 455                 460
Ala Val Pro Gln Thr Leu Trp Leu Leu Asp Phe Pro Leu Phe Glu Arg
465                 470                 475                 480
Thr Tyr Tyr Gln Leu Val Val Asn Phe Asp Val Phe Gly Asn Val Ser
            485                 490                 495
His Gln Leu Gln Thr Arg Leu Tyr Phe Asp Leu Ile Arg Asn Gly Ala
            500                 505                 510
Glu Gln Asn Phe Leu Arg Leu Leu Pro Ser Gly Thr Arg Gln Ala Ile
            515                 520                 525
Leu Asp Ser Trp Tyr Glu Asn Ser Gly Gln Leu Lys Leu Trp Leu Ala
            530                 535                 540
Tyr Thr Glu Val Asp Ser Glu Thr Pro Ser Val Leu Asp Leu Pro Gln
545                 550                 555                 560
Arg Glu Pro Val Arg Ala Phe Ala Gly Arg Leu Leu Glu Arg His Val
            565                 570                 575
Ala Ile Asn Ala Arg Pro Asp Pro Phe Asn Arg Cys Arg Ser Ala His
            580                 585                 590
Cys His Arg Pro Gly Val Ala Arg Glu Leu Gln Tyr Ala Glu Gln Val
            595                 600                 605
```

-continued

```
Leu Ser Arg Leu Val Ser Arg Pro Ala Ala Gly Leu Pro Val Val Leu
        610                 615                 620

Ala Leu Pro Glu Ala Ser Leu Leu Arg Ile Glu Tyr Gly Glu Gly Lys
625                 630                 635                 640

Arg Glu Val Tyr Ser Leu Leu Arg Asn Arg Ala His Ser Asn Val Ala
                645                 650                 655

Phe Ile Phe Gly Glu Arg Leu Arg Tyr Gln Pro Thr Leu Asp Thr Leu
            660                 665                 670

Thr Leu Tyr Pro Gly Val Leu Ser Ser Tyr Pro Asn Phe Leu Phe Asn
        675                 680                 685

Val Arg Ala Glu Glu Val Pro Asp Phe Val Ala Leu Glu Gln Ala
    690                 695                 700

Arg Ala Gly Ala Ser Phe Val Ala Val Val Glu Arg Trp Gly Val Arg
705                 710                 715                 720

Arg Ser His Pro Glu Phe Trp Arg Tyr Phe Asn Asp Leu Ser Ala Trp
                725                 730                 735

Met Arg Glu Thr Glu Pro Leu Glu Ala Gly Val Leu Asp Met Asn Arg
            740                 745                 750

Tyr Gln Asn Leu
        755
```

```
<210> SEQ ID NO 87
<211> LENGTH: 2301
<212> TYPE: DNA
<213> ORGANISM: Pseudomonas entomophila

<400> SEQUENCE: 87
atgttgcttc gcatacttgc cagcgtcttc gccctgctga tcagtggcgt ggcgttcgcg      60 caggccccc aatcgagccc ggcgatttcg tacacccggg acatccaacc gatcttcacc     120
gagaagtgcg tggcctgcca cgcctgcaac gatgccgcct gccagctcaa cctgggcagc     180
gccgagggcg ccgagcgtgg cgcctcgaag gtgccggtgt accagggcga gcgcagccag     240
gcggtgccca ccacgcggct gttctacgac gcccacgacg aggccggctg cgcaaggcc      300 gggttctact cggtgctgga caagcagggc agccaggccg cgctgatggc gcgcatgctc     360
gagctgggcc acaagacacc gctcacgccc aacgccaagc tgccggacga gatcgtgctg     420
gggctcaacc gcaacaacat gtgccccatg ccccacgagt cgacgcccta tgccggtgcc     480
catccgaagg agggcatgcc gctggcggtc accggcctga ccgaccagga gtaccagacg     540
ctgcaacgct ggttggcggc tggcgcgccg gtggagaaga cccagttcgt gcccaacgcg     600
gcggaagccc ggcagatctt cgaatgggaa gagttgctca accgcccggg ctcgaccgag     660
gcactggttg cccgttggct gtacgagcat tgttcctgg cccacatcta tttcgtcggc     720
ggtgagcagg gccacttctt ccagtggtg cgttcgcgca cccgagcgg ccggccggtc      780 gacctgatcg ccacccgccg ccccaatgat ccaccgggca ccgacttcta ttaccgcttg     840
gtgccggtgc agggcgtgat cgtccacaag acccacatca cctacccgat gggcccgcag     900
aagctcaagc gggtcaagca gctgttctac agcggcgact ggcatgccag cgcgctgccc     960
ggctacggcc gcggcaccg cgccaacccg ttcgagacct tcgaggcgat cccggcggtg    1020
gcccgctacc agttcatgct ggacaacgcc gagtacttcg tgcgcacctt catccgtggc    1080
ccggtgtgcc gcgggcagat cgccaccgac gtgatccgcg acaacttctg ggcgctgttc    1140
caggagccgg cccacgacct gtacatcacc gacgccaagt accggggcga ggccacgccg    1200
ttgctggcca tgcccggcca gatcgacgac gtcggcagcg tgctgggcct ttggcatgcc    1260
```

-continued

```
taccgcgaca agcgcaacga gtacgaggcg ctgcgccgcg aggcctacgc cgagcagccg    1320
gcgccgagct ggtcgacgct gtgggcgggc aacgacaacg ccttgctcag catcttccgc    1380
cacttcgaca gcgcctcggt gaccaagggc ctgatcggtg acgtgccact gaccatgtgg    1440
ctgttcgact acccgctgtt cgagcgcacc tactatcagt tggcggtgaa cttcgatgtg    1500
ttcggcaacg tctcgcatca gttgcagacg cgcctgtact tcgacctgat ccgcaatggc    1560
gctgaggtca atttcctgcg cctgatgccg gccggcaagc gcagtgagat cctgggcaac    1620
tggtaccaga acagcggcaa ggtgaagatg tggatggact acgaggacat cgacaccagc    1680
accccgagcg cgttgaagct ggacaagcac gaccccaagc gtgatttcgg cctgaaaacta   1740 ttgcagcgca ccggcagcct gaatgccgcg ccagatccga tcaaccgctg cctgagcgct    1800
tattgctcgc gaccgcagat gagcgaagag ttccgcgacg tcgagcagtc gctcagccgc    1860
ctggtgtcgc gcccggccgc gggcctgaaa gtgatcgacc agttgcccga ggcgacgatg    1920
ctgcgcatcg aagggcaggg cggccagcgc caggtgtaca gcctgctgcg caaccgtgcc    1980
cacagcaacg tggcgttcct gctgggcgag gcctaccgct accagccggg gctggacacc    2040
ctgaccctgg tgccgggcgt gctcagcagc tacccgaact tcatcttcaa cgtgcctgcg    2100
aaggaggtgc cggagttcgt cgaggacctg gaagcggccc gcgacgacac ggccaagttc    2160
gagcgcatcg tcatgcgctg gggcgtacgc cgcagccacc cggagttctg cgctacttc     2220 catgacctga accgctatat ccaggagacc gatccggtgg aggcgggggt gctggacatg    2280
aaccgctacg agaacctctg a                                              2301
```

<210> SEQ ID NO 88
<211> LENGTH: 766
<212> TYPE: PRT
<213> ORGANISM: Pseudomonas entomophila

<400> SEQUENCE: 88

```
Met Leu Leu Arg Ile Leu Ala Ser Val Phe Ala Leu Leu Ile Ser Gly
1               5                   10                  15

Val Ala Phe Ala Gln Ala Pro Gln Ser Ser Pro Ala Ile Ser Tyr Thr
            20                  25                  30

Arg Asp Ile Gln Pro Ile Phe Thr Glu Lys Cys Val Ala Cys His Ala
        35                  40                  45

Cys Asn Asp Ala Ala Cys Gln Leu Asn Leu Gly Ser Ala Glu Gly Ala
    50                  55                  60

Glu Arg Gly Ala Ser Lys Val Pro Val Tyr Gln Gly Glu Arg Ser Gln
65                  70                  75                  80

Ala Val Pro Thr Thr Arg Leu Phe Tyr Asp Ala His Asp Glu Ala Gly
                85                  90                  95

Trp Arg Lys Ala Gly Phe Tyr Ser Val Leu Asp Lys Gln Gly Ser Gln
            100                 105                 110

Ala Ala Leu Met Ala Arg Met Leu Glu Leu Gly His Lys Thr Pro Leu
        115                 120                 125

Thr Pro Asn Ala Lys Leu Pro Asp Glu Ile Val Leu Gly Leu Asn Arg
    130                 135                 140

Asn Asn Met Cys Pro Met Pro His Glu Phe Asp Ala Tyr Ala Gly Ala
145                 150                 155                 160

His Pro Lys Glu Gly Met Pro Leu Ala Val Thr Gly Leu Thr Asp Gln
                165                 170                 175

Glu Tyr Gln Thr Leu Gln Arg Trp Leu Ala Ala Gly Ala Pro Val Glu
            180                 185                 190
```

```
Lys Thr Gln Phe Val Pro Asn Ala Ala Glu Ala Arg Gln Ile Phe Glu
            195                 200                 205

Trp Glu Glu Leu Leu Asn Arg Pro Gly Ser Thr Glu Ala Leu Val Ala
    210                 215                 220

Arg Trp Leu Tyr Glu His Leu Phe Leu Ala His Ile Tyr Phe Val Gly
225                 230                 235                 240

Gly Glu Gln Gly His Phe Phe Gln Trp Val Arg Ser Arg Thr Pro Ser
                245                 250                 255

Gly Arg Pro Val Asp Leu Ile Ala Thr Arg Arg Pro Asn Asp Pro Pro
                260                 265                 270

Gly Thr Asp Phe Tyr Tyr Arg Leu Val Pro Val Gln Gly Val Ile Val
                275                 280                 285

His Lys Thr His Ile Thr Tyr Pro Met Gly Pro Gln Lys Leu Lys Arg
    290                 295                 300

Val Lys Gln Leu Phe Tyr Ser Gly Asp Trp His Ala Ser Ala Leu Pro
305                 310                 315                 320

Gly Tyr Gly Pro Arg His Arg Ala Asn Pro Phe Glu Thr Phe Glu Ala
                325                 330                 335

Ile Pro Ala Val Ala Arg Tyr Gln Phe Met Leu Asp Asn Ala Glu Tyr
                340                 345                 350

Phe Val Arg Thr Phe Ile Arg Gly Pro Val Cys Arg Gly Gln Ile Ala
                355                 360                 365

Thr Asp Val Ile Arg Asp Asn Phe Trp Ala Leu Phe Gln Glu Pro Ala
    370                 375                 380

His Asp Leu Tyr Ile Thr Asp Ala Lys Tyr Arg Gly Glu Ala Thr Pro
385                 390                 395                 400

Leu Leu Ala Met Pro Gly Gln Ile Asp Asp Val Gly Ser Val Leu Gly
                405                 410                 415

Leu Trp His Ala Tyr Arg Asp Lys Arg Asn Glu Tyr Glu Ala Leu Arg
                420                 425                 430

Arg Glu Ala Tyr Ala Glu Gln Pro Ala Pro Ser Trp Ser Thr Leu Trp
    435                 440                 445

Ala Gly Asn Asp Asn Ala Leu Leu Ser Ile Phe Arg His Phe Asp Ser
    450                 455                 460

Ala Ser Val Thr Lys Gly Leu Ile Gly Asp Val Pro Leu Thr Met Trp
465                 470                 475                 480

Leu Phe Asp Tyr Pro Leu Phe Glu Arg Thr Tyr Tyr Gln Leu Ala Val
                485                 490                 495

Asn Phe Asp Val Phe Gly Asn Val Ser His Gln Leu Gln Thr Arg Leu
                500                 505                 510

Tyr Phe Asp Leu Ile Arg Asn Gly Ala Glu Val Asn Phe Leu Arg Leu
                515                 520                 525

Met Pro Ala Gly Lys Arg Ser Glu Ile Leu Gly Asn Trp Tyr Gln Asn
    530                 535                 540

Ser Gly Lys Val Lys Met Trp Met Asp Tyr Glu Asp Ile Asp Thr Ser
545                 550                 555                 560

Thr Pro Ser Ala Leu Lys Leu Asp Lys His Asp Pro Lys Arg Asp Phe
                565                 570                 575

Gly Leu Lys Leu Leu Gln Arg Thr Gly Ser Leu Asn Ala Ala Pro Asp
                580                 585                 590

Pro Ile Asn Arg Cys Leu Ser Ala Tyr Cys Ser Arg Pro Gln Met Ser
                595                 600                 605

Glu Glu Phe Arg Asp Val Glu Gln Ser Leu Ser Arg Leu Val Ser Arg
610                 615                 620
```

| | | | | | | | | | | | | | | | |
|---|---|---|---|---|---|---|---|---|---|---|---|---|---|---|---|
|Pro|Ala|Ala|Gly|Leu|Lys|Val|Ile|Asp|Gln|Leu|Pro|Glu|Ala|Thr|Met|
|625| | | | |630| | | | |635| | | | |640|

| | | | | | | | | | | | | | | | |
|---|---|---|---|---|---|---|---|---|---|---|---|---|---|---|---|
|Leu|Arg|Ile|Glu|Gly|Gln|Gly|Gln|Arg|Gln|Val|Tyr|Ser|Leu|Leu| |
| | | | | |645| | | | |650| | | | |655|

| | | | | | | | | | | | | | |
|---|---|---|---|---|---|---|---|---|---|---|---|---|---|---|
|Arg|Asn|Arg|Ala|His|Ser|Asn|Val|Ala|Phe|Leu|Leu|Gly|Glu|Ala|Tyr|
| | | | |660| | | | |665| | | | |670| |

| | | | | | | | | | | | | | | | |
|---|---|---|---|---|---|---|---|---|---|---|---|---|---|---|---|
|Arg|Tyr|Gln|Pro|Gly|Leu|Asp|Thr|Leu|Thr|Leu|Val|Pro|Gly|Val|Leu|
| | | |675| | | | |680| | | | |685| | |

| | | | | | | | | | | | | | | | |
|---|---|---|---|---|---|---|---|---|---|---|---|---|---|---|---|
|Ser|Ser|Tyr|Pro|Asn|Phe|Ile|Phe|Asn|Val|Pro|Ala|Lys|Glu|Val|Pro|
| | |690| | | | |695| | | | |700| | | |

| | | | | | | | | | | | | | | | |
|---|---|---|---|---|---|---|---|---|---|---|---|---|---|---|---|
|Glu|Phe|Val|Glu|Asp|Leu|Glu|Ala|Ala|Arg|Asp|Asp|Thr|Ala|Lys|Phe|
|705| | | | |710| | | | |715| | | | |720|

| | | | | | | | | | | | | | | | |
|---|---|---|---|---|---|---|---|---|---|---|---|---|---|---|---|
|Glu|Arg|Ile|Val|Met|Arg|Trp|Gly|Val|Arg|Arg|Ser|His|Pro|Glu|Phe|
| | | | |725| | | | |730| | | | |735| |

| | | | | | | | | | | | | | | | |
|---|---|---|---|---|---|---|---|---|---|---|---|---|---|---|---|
|Trp|Arg|Tyr|Phe|His|Asp|Leu|Asn|Arg|Tyr|Ile|Gln|Glu|Thr|Asp|Pro|
| | | |740| | | | |745| | | | |750| | |

| | | | | | | | | | | |
|---|---|---|---|---|---|---|---|---|---|---|
|Val|Glu|Ala|Gly|Val|Leu|Asp|Met|Asn|Arg|Tyr|Glu|Asn|Leu|
| | |755| | | | |760| | | | |765| |

<210> SEQ ID NO 89
<211> LENGTH: 2364
<212> TYPE: DNA
<213> ORGANISM: Alcanivorax borkumensis

<400> SEQUENCE: 89

```
atgaaaaacc attgggattc acatggcccc ttttcactag ggatattgtt cttttttgctt      60
tgcgctctgt ctgcaccggt taccagcgcc ccgctccctc ccaagtacct caccaatacc     120
tcacccaatt accatgacga cattcatcct attttcgaaa gaaatgtttt agcctgtcat     180
ggctgctatg acgcccccctg ccaattgaaa cttgaagcgg tagaaggcct agaccggggg     240
gccagcaaga aaaacgttta cgatggggct cgtactcaaa ccatctcccc aacgcgcttg     300
ttcaaggatg cacaaaccac ggcacaatgg cgtgacaagg cttctattc tgtcatcgac     360
agcacctctg gcctgcagga ttctttgctt tatcaaatgc tggcgttagg aaaaaaacac     420
agttttaaac cgaaccagaa acttccagac gatattgtct gggcctagc tcggcagaac     480
gaatgccccg caccagatga attcgatgac tatgccgaaa gtcacccat ggaaggcatg     540
ccattggcgg tcgcagggct gaccgacagc gaatttacga ccatccgtca atggttggag     600
caagggggcc ctttggagcc taaaataatt actcccacca acgaagagca gcaactgatt     660
gccgactggg aagcttttct caaccaaaga gacctaaaac accagctggt ggcccgctgg     720
ctatacgaac ccttttttct tgcccaccctg tacctggaca aggtcaaga cagcaagccg     780
gcacatttt taaacttca tcgctctagc accccctccg gggagccgat taagccagta     840
gccaccgatc gccccaatgg catgccaccg gaaaatttct ggtaccgtat tgcacctgtg     900
cccggcacct tagtgcacaa acacacatt accttggcc tagccaagga caaactggct     960
aggaccaaag agcacttctt cagcactgac tggagcgtgg aaacgttacc aggctatggc    1020
tacgaacaac gtgccaatcc ctttgttacc ttttcccgcta tcccagcccg ggcccgctac    1080
cagtttatgc tggatgaagc cgaatacttt gttcgtacct tcattcgcgg tccggtttgt    1140
cgcgggcaag tagccaccga tgtaattcgc gatcatttct gggccgtgtt tcaggccccg    1200
gaacaggacc tttacatcac cgataacaat taccgcgcgc aagtcagtga tctgttgggc    1260
ttacccggtc aagacgatga cctattggct ttagggccac agtggctcaa gtacagtgaa    1320
```

-continued

```
aaacgtaacg actacctgaa agctcgcaaa caggcctatg gcaccaataa acccaaaggc    1380
ccagattggg attcattgtg ggatggcgat ggggataatc gcaatgcact actaaccatc    1440
ttccgtcacc acgataactc ctcggtacgc aaaggcctga tcggcgactt gcctttaacg    1500
acctgggtga tggattaccc gttattcgaa cgcagctatt acaacctagt ggttaacttt    1560
aatgttttcg gatccgtgtc ccatcaggcg cagactcgcc tctactttga tctgatccgt    1620
aatggcgcag aacagaacac gctccgctac ctcccagcaa actgcgcca actcgtgttg     1680 gccaactggt atcaaaacac cgggaaactg cggttggcga tcagttatga atccgtagat    1740
acggatctgc ccacgagtat ccagttcgat accagcaccc caatgaacga gttcaacaat    1800
aatctgctga ttaaatttgc caaactaaac gcccgcccag acccgataaa ccgttgtgac    1860
ggtgaaaact gccaacggcc caatgtctct gcctggaaac aggacgcaga ccacatcctc    1920
agcagtatct cttcacggcg cgcggccaac ctgcaagccg tcaatttcat gccggaagtc    1980
agcatgatcc acgtaagggg caacaagggt gaacaggaaa tctattcctt attccgaaac    2040
cgggcacaca ccaatgtcgc gttcatgatg ggtgaatctc tgcgctacca accgccactg    2100
gacaccttaa ccctgtatcc cggcgtcttg gcgagctatc ccaacttcat gttcctggtg    2160
caggaagatc agctgcaagc tttcgttact caaatggaag cggtgaaaac ggagaaagat    2220
tttaccgaac tagtggatgc ctatggtatt cgccgcactc accctgagtt ttggcaatac    2280
ttccatgcgc tgaaccagta tctggaaaag cacgagccaa cccaggctgg cattctcgat    2340
atgaaccggt acgaaaacct ttga                                           2364
```

<210> SEQ ID NO 90
<211> LENGTH: 787
<212> TYPE: PRT
<213> ORGANISM: Alcanivorax borkumensis

<400> SEQUENCE: 90

```
Met Lys Asn His Trp Asp Ser His Gly Pro Phe Ser Leu Gly Ile Leu
1               5                   10                  15

Phe Phe Leu Leu Cys Ala Leu Ser Ala Pro Val Thr Ser Ala Pro Leu
            20                  25                  30

Pro Pro Lys Tyr Leu Thr Asn Thr Ser Pro Asn Tyr His Asp Asp Ile
        35                  40                  45

His Pro Ile Phe Glu Lys Lys Cys Leu Ala Cys His Gly Cys Tyr Asp
    50                  55                  60

Ala Pro Cys Gln Leu Lys Leu Glu Ala Val Glu Gly Leu Asp Arg Gly
65                  70                  75                  80

Ala Ser Lys Lys Asn Val Tyr Asp Gly Ala Arg Thr Gln Thr Ile Ser
                85                  90                  95

Pro Thr Arg Leu Phe Lys Asp Ala Gln Thr Thr Ala Gln Trp Arg Asp
            100                 105                 110

Lys Gly Phe Tyr Ser Val Ile Asp Ser Thr Ser Gly Leu Gln Asp Ser
        115                 120                 125

Leu Leu Tyr Gln Met Leu Ala Leu Gly Lys Lys His Ser Phe Lys Pro
    130                 135                 140

Asn Gln Lys Leu Pro Asp Asp Ile Val Leu Gly Leu Ala Arg Gln Asn
145                 150                 155                 160

Glu Cys Pro Ala Pro Asp Glu Phe Asp Tyr Ala Glu Ser His Pro
                165                 170                 175

Met Glu Gly Met Pro Leu Ala Val Ala Gly Leu Thr Ser Ser Glu Phe
            180                 185                 190
```

```
                    -continued

Thr Thr Ile Arg Gln Trp Leu Glu Gln Gly Ala Pro Leu Glu Pro Lys
        195                 200                 205

Ile Ile Thr Pro Thr Asn Glu Glu Gln Leu Ile Ala Asp Trp Glu
210                 215                 220

Ala Phe Leu Asn Gln Arg Asp Leu Lys His Gln Leu Val Ala Arg Trp
225                 230                 235                 240

Leu Tyr Glu His Leu Phe Leu Ala His Leu Tyr Leu Asp Lys Gly Gln
                    245                 250                 255

Asp Ser Lys Pro Ala His Phe Phe Lys Leu His Arg Ser Ser Thr Pro
                260                 265                 270

Pro Gly Glu Pro Ile Lys Pro Val Ala Thr Asp Arg Pro Asn Gly Met
            275                 280                 285

Pro Pro Glu Asn Phe Trp Tyr Arg Ile Ala Pro Val Pro Gly Thr Leu
        290                 295                 300

Val His Lys Thr His Ile Thr Phe Gly Leu Ala Lys Asp Lys Leu Ala
305                 310                 315                 320

Arg Thr Lys Glu His Phe Ser Thr Asp Trp Ser Val Glu Thr Leu
                    325                 330                 335

Pro Gly Tyr Gly Tyr Glu Gln Arg Ala Asn Pro Phe Val Thr Phe Ser
                340                 345                 350

Ala Ile Pro Ala Arg Ala Arg Tyr Gln Phe Met Leu Asp Glu Ala Glu
            355                 360                 365

Tyr Phe Val Arg Thr Phe Ile Arg Gly Pro Val Cys Arg Gly Gln Val
        370                 375                 380

Ala Thr Asp Val Ile Arg Asp His Phe Trp Ala Val Phe Gln Ala Pro
385                 390                 395                 400

Glu Gln Asp Leu Tyr Ile Thr Asp Asn Asn Tyr Arg Ala Gln Val Ser
                    405                 410                 415

Asp Leu Leu Gly Leu Pro Gly Gln Asp Asp Leu Leu Ala Leu Gly
                420                 425                 430

Pro Gln Trp Leu Lys Tyr Ser Glu Lys Arg Asn Asp Tyr Leu Lys Ala
            435                 440                 445

Arg Lys Gln Ala Tyr Gly Thr Asn Lys Pro Lys Gly Pro Asp Trp Asp
450                 455                 460

Ser Leu Trp Asp Gly Asp Gly Asp Asn Arg Asn Ala Leu Leu Thr Ile
465                 470                 475                 480

Phe Arg His His Asp Asn Ser Ser Val Arg Lys Gly Leu Ile Gly Asp
                    485                 490                 495

Leu Pro Leu Thr Thr Trp Val Met Asp Tyr Pro Leu Phe Glu Arg Ser
                500                 505                 510

Tyr Tyr Asn Leu Val Val Asn Phe Asn Val Phe Gly Ser Val Ser His
            515                 520                 525

Gln Ala Gln Thr Arg Leu Tyr Phe Asp Leu Ile Arg Asn Gly Ala Glu
        530                 535                 540

Gln Asn Thr Leu Arg Tyr Leu Pro Ala Lys Leu Arg Gln Leu Val Leu
545                 550                 555                 560

Ala Asn Trp Tyr Gln Asn Thr Gly Lys Leu Arg Leu Ala Ile Ser Tyr
                    565                 570                 575

Glu Ser Val Asp Thr Asp Leu Pro Thr Ser Ile Gln Phe Asp Thr Ser
                580                 585                 590

Thr Pro Met Asn Glu Phe Asn Asn Leu Leu Ile Lys Phe Ala Lys
            595                 600                 605

Leu Asn Ala Arg Pro Asp Pro Ile Asn Arg Cys Asp Gly Glu Asn Cys
        610                 615                 620
```

| | | | | | | | | | | |
|---|---|---|---|---|---|---|---|---|---|---|
| Gln | Arg | Pro | Asn | Val | Ser | Ala | Trp | Lys | Gln | Asp | Ala | Asp | His | Ile | Leu |
| 625 | | | | 630 | | | | 635 | | | | 640 | | | |

Ser Ser Ile Ser Ser Arg Arg Ala Ala Asn Leu Gln Ala Val Asn Phe
            645                 650                 655

Met Pro Glu Val Ser Met Ile His Val Arg Gly Asn Lys Gly Glu Gln
        660                 665                 670

Glu Ile Tyr Ser Leu Phe Arg Asn Arg Ala His Thr Asn Val Ala Phe
    675                 680                 685

Met Met Gly Glu Ser Leu Arg Tyr Gln Pro Pro Leu Asp Thr Leu Thr
690                 695                 700

Leu Tyr Pro Gly Val Leu Ala Ser Tyr Pro Asn Phe Met Phe Leu Val
705                 710                 715                 720

Gln Glu Asp Gln Leu Gln Ala Phe Val Thr Gln Met Glu Ala Val Lys
                725                 730                 735

Thr Glu Lys Asp Phe Thr Glu Leu Val Asp Ala Tyr Gly Ile Arg Arg
            740                 745                 750

Thr His Pro Glu Phe Trp Gln Tyr Phe His Ala Leu Asn Gln Tyr Leu
        755                 760                 765

Glu Lys His Glu Pro Thr Gln Ala Gly Ile Leu Asp Met Asn Arg Tyr
    770                 775                 780

Glu Asn Leu
785

<210> SEQ ID NO 91
<211> LENGTH: 1020
<212> TYPE: DNA
<213> ORGANISM: Vibrio cholerae

<400> SEQUENCE: 91

```
atgaatttca atcttcgat  tctgttgctg ctggccacga ttttctccgg ttgcgctatg     60
tacgcaggca tcaactatga tcagctcttt ggcacagagc aggtacgtga gcgacaattg    120
cctttgcact ctagccaagc tcagcatttt ttaaacgaag taaaacccat cttagataac    180
cgctgtgtcg tctgtcacgc ctgttacgat gccccctgtc agctcaaaat gacctcgggct   240
gaaggcattg atcgcggggc gagcaaagcg ttggtttatc agggaactcg gctgacggcc    300
gctactccaa ctcgtctcta cgaagatgct cagttaaccc aagagtggcg agctgctggt    360
tttcatcccg tgctgaatga gcgagatcaa accgcgcaag ccaatcttga tgctggggtg    420
atggcacgtt tgctgatgca gaaagagcgt catccactac acagcaaga tcagttacaa     480
ggatttgatt ttcaattga tcgtgagcaa acctgcccaa cgatcaacga aatggatcac     540
ttcgaacaag tgaatcctaa ttggggaatg ccctttggta tgccgaattt atccccaag    600
gagtacgcta ccctgctctc ttggctacaa gagggagcag tgatgaatca agcgctcccg    660
ctgagtgcgc aagaacaagc tttggttacg gaatacgaag ccgtgttgaa tcacagctcg    720
cgtaaaaatc agctcgcagc acgctatatc tacgaacatc tattcctctc acatctgtac    780
tttttcagaga tagcgcagga gcggcctcgt ttctttaaac tcatccgatc cagtactcca    840
ccgggtgagc ctgtaaagcg aatcgtgacg cgtcgtccgt acgatgatcc gggcgttgag    900
cgagtctatt atcgccttgt gccagaacaa gagacgattg tcgataaaac ccacatgcct    960
ttcgcactca acaagcaacg gattgccaac tggaaactct ggtttattga tgcggattat   1020
```

<210> SEQ ID NO 92
<211> LENGTH: 340
<212> TYPE: PRT

<213> ORGANISM: Vibrio cholerae

<400> SEQUENCE: 92

| | | | | | | | | | | | | | | |
|---|---|---|---|---|---|---|---|---|---|---

```
tacgcaggca tcaactatga tcagctcttt ggcacagagc aggtacgtga gcgacaatta      120
cctttgcact ctagccaagc tcagcatttt ttaaacgaag taaaacccat cttagataac      180
cgctgtgtcg tctgtcacgc ctgttacgat gcaccctgtc agctcaaaat gacctcggct      240
gaaggcattg atcgcgggc gagcaaagcg ttggtttatc agggaactcg gctgacggcc       300
gctactccaa ctcgtctcta cgaagatgct cagttaaccc aagagtggcg agctgctggt      360
tttcatcccg tgctgaatga gcgaaatcaa accgcgcaag ccaatcttga tgctggggtg      420
atggcacgtt tgctgatgca gaaagagcgt catccactac cacagcaaga tcagttacaa      480
ggatttgatt tttcaattga tcgtgagcaa acctgcccaa cgatcaacga aatggatcac      540
ttcgaacaag tgaatcctaa ttggggaatg cccctttggta tgccgaattt atcccccaag     600
gagtacacta ccctgctctc ttggctacaa gagggagccg tgatgaatca agcgctcccg      660
ctgagtgcgc aagaacaagc tttggttacg aatacgaag ccttgttgaa tcacagctcg       720
cgtaaaaatc agctcgcagc acgctatatc tacgaacatc tattcctctc acatctgtac      780
ttttcagaga tagcgcagga gcggcctcgt ttctttaaac tcatccgctc cagtactcca      840
ccgggtgagc ctgtaaagcg aatcgtgacg cgtcgtccgt acgatgatcc gggcgttgag      900
cgagtctatt atcgccttgt gccagaacaa gagacgattg tcgataaaac ccacatgcct      960
ttcgcactca acaagcaacg gattgcgaac tggaaactct ggtttattga tgcggattat     1020
gaggttgccg agcttccaag ttatcgtccg gatattgccg caaacccgat gtccgcgttc     1080
atcgaccttc ccgtgaaagc gcgctttaag ttcttgctcg ataatgcgca aaatacggtg     1140
atggccttta tcaaaggccc agtgtgtcga ggccagttgg cgctgaatgt gattaacgat     1200
agattctggg tcttcttcct cgatcctgag aaagccgatc ttccagaagt caacgaattc     1260
tatcgctcac aagtcaacaa tttgaagcta ccggctgaac aagagaatac ggcactgccg     1320
ctgagtaact gggtacgtta ttcgctacaa caaagccgtt atctcgaagc aaaatctgaa     1380
tttattaatc aatggtttaa aaatggtacg caccttacca cggacatcat ttgggatgga     1440
gcgggcataa accctaatgc cgcattaacg atttttcgcc atttcgatag cgcatctgtc     1500
gtgcaaggat tggtgggtga gcctcccaaa accgcttgga taatgggatta tgcgctgctt     1560 gagcgcattc attatctgct tgttgctggt tttgatgtat atggcaattt cggacatcag     1620
ttgattactc gtatgttcat ggattttctg cgcatggagg gtgagagtaa ttttgttgcc     1680
ctgctaccac gcgatatgcg ccatcaggag ttatctagtt ggtaccaaaa tcaaagtgta     1740
cagttttccg atttcttgca acgtaacgta aaaccctttg atcagccaac cagcgttaac     1800
tatgtgactg ataacccgaa acaggagctg tttgctaaac tccgcaagca agtacagtcg     1860
gtattgagtg atcgatacgt gataactcaa acgggattca aagccgaaca tgagtttgct     1920
ttgcgccaaa tcgatcatct gcgtggtgaa ggtttgctgc ccattccgca attgatgatg     1980
ttgatgattg aaagtgaaca aggtaaaccg caactgtttta cgctcatcca caacaatgcc     2040
cacaccaata tctcgagctt gtttgatgaa cagaacaacc gcgacccaa aaatgataat      2100 ttgactttag tgcgcggagt ggtcggcagt tatccatcgg cgtacttaac actgaaagaa     2160
aaccagatcc cggagctgta tcaacgcctt gcggcgatga agtcagagca agattatgtc     2220
gccctattgg atcgttttgc agtacgccgc agctcacccg aattttgggc atttagcgat     2280
cttgtgcatc aatggtatcg ccaagatcaa cccattgagt ttggtttgct cgattacaac     2340
cgtttcgaaa accgttga                                                   2358
```

<210> SEQ ID NO 94

<211> LENGTH: 785
<212> TYPE: PRT
<213> ORGANISM: Vibrio cholerae

<400> SEQUENCE: 94

```
Met Asn Phe Lys Ser Ser Ile Leu Leu Leu Ala Thr Val Phe Ser
1               5                   10                  15

Gly Cys Ala Met Tyr Ala Gly Ile Asn Tyr Asp Gln Leu Phe Gly Thr
            20                  25                  30

Glu Gln Val Arg Glu Arg Gln Leu Pro Leu His Ser Ser Gln Ala Gln
        35                  40                  45

His Phe Leu Asn Glu Val Lys Pro Ile Leu Asp Asn Arg Cys Val Val
    50                  55                  60

Cys His Ala Cys Tyr Asp Ala Pro Cys Gln Leu Lys Met Thr Ser Ala
65                  70                  75                  80

Glu Gly Ile Asp Arg Gly Ala Ser Lys Ala Leu Val Tyr Gln Gly Thr
                85                  90                  95

Arg Leu Thr Ala Ala Thr Pro Thr Arg Leu Tyr Glu Asp Ala Gln Leu
            100                 105                 110

Thr Gln Glu Trp Arg Ala Ala Gly Phe His Pro Val Leu Asn Glu Arg
        115                 120                 125

Asn Gln Thr Ala Gln Ala Asn Leu Asp Ala Gly Val Met Ala Arg Leu
    130                 135                 140

Leu Met Gln Lys Glu Arg His Pro Leu Pro Gln Gln Asp Gln Leu Gln
145                 150                 155                 160

Gly Phe Asp Phe Ser Ile Asp Arg Glu Gln Thr Cys Pro Thr Ile Asn
                165                 170                 175

Glu Met Asp His Phe Glu Gln Val Asn Pro Asn Trp Gly Met Pro Phe
            180                 185                 190

Gly Met Pro Asn Leu Ser Pro Lys Glu Tyr Thr Thr Leu Leu Ser Trp
        195                 200                 205

Leu Gln Glu Gly Ala Val Met Asn Gln Ala Leu Pro Leu Ser Ala Gln
    210                 215                 220

Glu Gln Ala Leu Val Thr Glu Tyr Glu Ala Leu Leu Asn His Ser Ser
225                 230                 235                 240

Arg Lys Asn Gln Leu Ala Ala Arg Tyr Ile Tyr Glu His Leu Phe Leu
                245                 250                 255

Ser His Leu Tyr Phe Ser Glu Ile Ala Gln Glu Arg Pro Arg Phe Phe
            260                 265                 270

Lys Leu Ile Arg Ser Ser Thr Pro Pro Gly Glu Pro Val Lys Arg Ile
        275                 280                 285

Val Thr Arg Arg Pro Tyr Asp Asp Pro Gly Val Glu Arg Val Tyr Tyr
    290                 295                 300

Arg Leu Val Pro Glu Gln Glu Thr Ile Val Asp Lys Thr His Met Pro
305                 310                 315                 320

Phe Ala Leu Asn Lys Gln Arg Ile Ala Asn Trp Lys Leu Trp Phe Ile
                325                 330                 335

Asp Ala Asp Tyr Glu Val Ala Glu Leu Pro Ser Tyr Arg Pro Asp Ile
            340                 345                 350

Ala Ala Asn Pro Met Ser Ala Phe Ile Asp Leu Pro Val Lys Ala Arg
        355                 360                 365

Phe Lys Phe Leu Leu Asp Asn Ala Gln Asn Thr Val Met Ala Phe Ile
    370                 375                 380

Lys Gly Pro Val Cys Arg Gly Gln Leu Ala Leu Asn Val Ile Asn Asp
385                 390                 395                 400
```

```
Arg Phe Trp Val Phe Leu Asp Pro Glu Lys Ala Asp Leu Pro Glu
            405                 410                 415

Val Asn Glu Phe Tyr Arg Ser Gln Val Asn Asn Leu Lys Leu Pro Ala
            420                 425                 430

Glu Gln Glu Asn Thr Ala Leu Pro Leu Ser Asn Trp Val Arg Tyr Ser
            435                 440                 445

Leu Gln Gln Ser Arg Tyr Leu Glu Ala Lys Ser Glu Phe Ile Asn Gln
            450                 455                 460

Trp Phe Lys Asn Gly Thr His Leu Thr Thr Asp Ile Ile Trp Asp Gly
465                 470                 475                 480

Ala Gly Ile Asn Pro Asn Ala Ala Leu Thr Ile Phe Arg His Phe Asp
                    485                 490                 495

Ser Ala Ser Val Val Gln Gly Leu Val Gly Glu Pro Lys Thr Ala
            500                 505                 510

Trp Ile Met Asp Tyr Ala Leu Leu Glu Arg Ile His Tyr Leu Leu Val
            515                 520                 525

Ala Gly Phe Asp Val Tyr Gly Asn Phe Gly His Gln Leu Ile Thr Arg
            530                 535                 540

Met Phe Met Asp Phe Leu Arg Met Glu Gly Glu Ser Asn Phe Val Ala
545                 550                 555                 560

Leu Leu Pro Arg Asp Met Arg His Gln Glu Leu Ser Ser Trp Tyr Gln
                    565                 570                 575

Asn Gln Ser Val Gln Phe Ser Asp Phe Leu Gln Arg Asn Val Lys Pro
            580                 585                 590

Phe Asp Gln Pro Thr Ser Val Asn Tyr Val Thr Asp Asn Pro Lys Gln
            595                 600                 605

Glu Leu Phe Ala Lys Leu Arg Lys Gln Val Gln Ser Val Leu Ser Asp
            610                 615                 620

Arg Tyr Val Ile Thr Gln Thr Gly Phe Lys Ala Glu His Glu Phe Ala
625                 630                 635                 640

Leu Arg Gln Ile Asp His Leu Arg Gly Glu Gly Leu Leu Pro Ile Pro
                    645                 650                 655

Gln Leu Met Met Leu Met Ile Glu Ser Glu Gln Gly Lys Pro Gln Leu
            660                 665                 670

Phe Thr Leu Ile His Asn Asn Ala His Thr Asn Ile Ser Ser Leu Phe
            675                 680                 685

Asp Glu Gln Asn Asn Arg Asp Pro Lys Asn Asp Leu Thr Leu Val
            690                 695                 700

Arg Gly Val Val Gly Ser Tyr Pro Ser Ala Tyr Leu Thr Leu Lys Glu
705                 710                 715                 720

Asn Gln Ile Pro Glu Leu Tyr Gln Arg Leu Ala Ala Met Lys Ser Glu
                    725                 730                 735

Gln Asp Tyr Val Ala Leu Leu Asp Arg Phe Ala Val Arg Arg Ser Ser
            740                 745                 750

Pro Glu Phe Trp Ala Phe Ser Asp Leu Val His Gln Trp Tyr Arg Gln
            755                 760                 765

Asp Gln Pro Ile Glu Phe Gly Leu Leu Asp Tyr Asn Arg Phe Glu Asn
            770                 775                 780

Arg
785

<210> SEQ ID NO 95
<211> LENGTH: 2358
<212> TYPE: DNA
```

<213> ORGANISM: Vibrio cholerae

<400> SEQUENCE: 95

```
atgaatttca aatcttcgat tctgttgctg ctggccacga ttttctccgg ttgcgctatg     60
tacgcaggca tcaactatga tcagctcttt ggcacagagc aggtacgtga gcgacaattg    120
cctttgcact ctagccaagc tcagcatttt ttaaacgaag taaaacccat cttagataac    180
cgatgtgtcg tctgtcacgc ctgttacgat gccccctgtc agctcaaaat gacctcggct    240
gaaggcattg atcgcggggc gagcaaagcg ttggtttatc agggaactcg gctgacggcc    300
gctactccaa ctcgtctcta cgaagatgct cagttaaccc aagaatggcg agctgctggt    360
tttcatcccg tgctgaatga gcgagatcaa accgcgcaag ccaatcttga tgctggggtg    420
atggcacgtt tgctgatgca gaaagagcgt catccactac cacagcaaga tcagttacaa    480
ggatttgatt tttcaattga tcgtgagcaa acctgcccaa cgatcaacga aatggatcac    540
ttcgaacaag tgaatcctaa ttggggaatg ccctttggta tgccgaattt atcccccaag    600
gagtacgcta ccctgctctc ttggctacaa gagggagcag tgatgaatca agcgctcccg    660
ctgagtgcgc aagaacaagc tttggttacg gaatacgaag ccttgttgaa tcacagctcg    720
cgtaaaaatc agctcgcagc acgctatatc tacgagcatc tattcctctc acatctgtac    780
ttttcagaaa tagcgcagga gcggcctcgt ttctttaaac tcatccgctc cagtactcca    840
ccgggtgagc ctgtaaagcg aatcgtgacg cgtcgtccgt acgatgattc gggcgttgag    900
cgagtctatt atcgccttgt gccagaacaa gagacgattg tcgataaaac ccacatgcct    960
ttcgcactcc acaaacaacg gattgcgaac tggaaactct ggtttattga tgcggattat   1020
gaggttgccg agcttccaag ttatcgtccg gatattgccg caaacccgat gtccgcgttc   1080
atcgaccttc ccgttaaagc gcgctttaag tttttgctcg ataatgcgca aaatacggtg   1140
atggccttta tcaaaggccc agtgtgtcga ggccagttgg cgctgaatgt gattaacgat   1200
agattctggg tcttcttcct cgatcctgag aaagccgatc ttccagaagt caacgaattc   1260
tatcgctcac aagtcgacaa tttgaagcta ccggctgaac aagagaatac ggcactgccg   1320
ctgagtaact gggtacgtta ttcgctacaa caaagccgtt atctcgaagc aaaatctgaa   1380
tttattaatc aatggtttaa aaatggtacg caccttacca cggacattat ttgggatgga   1440
gcgggcacaa accctaatgc cgcattaacg attttccgcc atttcgatag cgcatctgtc   1500
gtgcaaggat tggtgggtga gcctcccaaa accgcttgga taatggatta tgcgctgctt   1560
gagcgcattc attatctgct tgttgctggt tttgatgtat atggcaattt cggacatcag   1620
ttgattactc gtatgttcat ggattttctg cgcatggagg gtgagagtaa ttttgttgcc   1680
ctgctaccac gcgatatgcg ccatcaggag ttatctagtt ggtaccaaaa tcaaagtgta   1740
cagttttccg atttcttgca acgtaacgta aaaccctttg atcagccaac cagcgttaac   1800
tatgtgactg ataacccgaa acaggagctg tttgctaaac tccgcaagca agtacagtcg   1860
gtattgagtg atcgatacgt gataactcaa acgggattca aagccgaaca tgagtttgct   1920
ttgcgccaga tagatcatct gcgtggtgaa ggtttgctgc ccattccaca attgatgatg   1980
ttgatgattg aaagtgaaca aggtaaaccg caactgttta ctctcattca caacaatgcc   2040
cacaccaata tctcgagctt gtttgatgaa cagaacaacc gcgaccccaa aaatgataat   2100
ttgactttag tgcgcggagt ggtcggcagt tatccatcgg cgtacttaac actgaaagaa   2160
aaccagatcc cggagctgta tcaacgccta gtggcgatga agtcagagca agattatgtc   2220
gccctattgg atcgttttgc agtacgccgc agctcacccg aattttgggc atttagcgat   2280
```

```
cttgtgcatc aatggtatcg ccaagatcaa cccattgagt ttggtttgct cgattacaac    2340
cgtttcgaaa accgttga                                                  2358
```

<210> SEQ ID NO 96
<211> LENGTH: 785
<212> TYPE: PRT
<213> ORGANISM: Vibrio cholerae

<400> SEQUENCE: 96

```
Met Asn Phe Lys Ser Ser Ile Leu Leu Leu Ala Thr Ile Phe Ser
1               5                   10                  15

Gly Cys Ala Met Tyr Ala Gly Ile Asn Tyr Asp Gln Leu Phe Gly Thr
            20                  25                  30

Glu Gln Val Arg Glu Arg Gln Leu Pro Leu His Ser Ser Gln Ala Gln
        35                  40                  45

His Phe Leu Asn Glu Val Lys Pro Ile Leu Asp Asn Arg Cys Val Val
        50                  55                  60

Cys His Ala Cys Tyr Asp Ala Pro Cys Gln Leu Lys Met Thr Ser Ala
65                  70                  75                  80

Glu Gly Ile Asp Arg Gly Ala Ser Lys Ala Leu Val Tyr Gln Gly Thr
                85                  90                  95

Arg Leu Thr Ala Ala Thr Pro Thr Arg Leu Tyr Glu Asp Ala Gln Leu
            100                 105                 110

Thr Gln Glu Trp Arg Ala Ala Gly Phe His Pro Val Leu Asn Glu Arg
        115                 120                 125

Asp Gln Thr Ala Gln Ala Asn Leu Asp Ala Gly Val Met Ala Arg Leu
    130                 135                 140

Leu Met Gln Lys Glu Arg His Pro Leu Pro Gln Gln Asp Gln Leu Gln
145                 150                 155                 160

Gly Phe Asp Phe Ser Ile Asp Arg Glu Gln Thr Cys Pro Thr Ile Asn
                165                 170                 175

Glu Met Asp His Phe Glu Gln Val Asn Pro Asn Trp Gly Met Pro Phe
            180                 185                 190

Gly Met Pro Asn Leu Ser Pro Lys Glu Tyr Ala Thr Leu Leu Ser Trp
        195                 200                 205

Leu Gln Glu Gly Ala Val Met Asn Gln Ala Leu Pro Leu Ser Ala Gln
    210                 215                 220

Glu Gln Ala Leu Val Thr Glu Tyr Glu Ala Leu Leu Asn His Ser Ser
225                 230                 235                 240

Arg Lys Asn Gln Leu Ala Ala Arg Tyr Ile Tyr Glu His Leu Phe Leu
                245                 250                 255

Ser His Leu Tyr Phe Ser Glu Ile Ala Gln Glu Arg Pro Arg Phe Phe
            260                 265                 270

Lys Leu Ile Arg Ser Ser Thr Pro Pro Gly Glu Pro Val Lys Arg Ile
        275                 280                 285

Val Thr Arg Arg Pro Tyr Asp Asp Ser Gly Val Glu Arg Val Tyr Tyr
    290                 295                 300

Arg Leu Val Pro Glu Gln Glu Thr Ile Val Asp Lys Thr His Met Pro
305                 310                 315                 320

Phe Ala Leu His Lys Gln Arg Ile Ala Asn Trp Lys Leu Trp Phe Ile
                325                 330                 335

Asp Ala Asp Tyr Glu Val Ala Glu Leu Pro Ser Tyr Arg Pro Asp Ile
            340                 345                 350

Ala Ala Asn Pro Met Ser Ala Phe Ile Asp Leu Pro Val Lys Ala Arg
        355                 360                 365
```

```
Phe Lys Phe Leu Leu Asp Asn Ala Gln Asn Thr Val Met Ala Phe Ile
    370                 375                 380
Lys Gly Pro Val Cys Arg Gly Gln Leu Ala Leu Asn Val Ile Asn Asp
385                 390                 395                 400
Arg Phe Trp Val Phe Phe Leu Asp Pro Glu Lys Ala Asp Leu Pro Glu
                    405                 410                 415
Val Asn Glu Phe Tyr Arg Ser Gln Val Asp Asn Leu Lys Leu Pro Ala
                420                 425                 430
Glu Gln Glu Asn Thr Ala Leu Pro Leu Ser Asn Trp Val Arg Tyr Ser
            435                 440                 445
Leu Gln Gln Ser Arg Tyr Leu Glu Ala Lys Ser Glu Phe Ile Asn Gln
        450                 455                 460
Trp Phe Lys Asn Gly Thr His Leu Thr Thr Asp Ile Ile Trp Asp Gly
465                 470                 475                 480
Ala Gly Thr Asn Pro Asn Ala Ala Leu Thr Ile Phe Arg His Phe Asp
                    485                 490                 495
Ser Ala Ser Val Val Gln Gly Leu Val Gly Glu Pro Pro Lys Thr Ala
                500                 505                 510
Trp Ile Met Asp Tyr Ala Leu Leu Glu Arg Ile His Tyr Leu Leu Val
            515                 520                 525
Ala Gly Phe Asp Val Tyr Gly Asn Phe Gly His Gln Leu Ile Thr Arg
        530                 535                 540
Met Phe Met Asp Phe Leu Arg Met Glu Gly Glu Ser Asn Phe Val Ala
545                 550                 555                 560
Leu Leu Pro Arg Asp Met Arg His Gln Glu Leu Ser Ser Trp Tyr Gln
                    565                 570                 575
Asn Gln Ser Val Gln Phe Ser Asp Phe Leu Gln Arg Asn Val Lys Pro
                580                 585                 590
Phe Asp Gln Pro Thr Ser Val Asn Tyr Val Thr Asp Asn Pro Lys Gln
            595                 600                 605
Glu Leu Phe Ala Lys Leu Arg Lys Gln Val Gly Ser Val Leu Ser Asp
        610                 615                 620
Arg Tyr Val Ile Thr Gln Thr Gly Phe Lys Ala Glu His Glu Phe Ala
625                 630                 635                 640
Leu Arg Gln Ile Asp His Leu Arg Gly Glu Gly Leu Leu Pro Ile Pro
                    645                 650                 655
Gln Leu Met Met Leu Met Ile Glu Ser Glu Gln Gly Lys Pro Gln Leu
                660                 665                 670
Phe Thr Leu Ile His Asn Asn Ala His Thr Asn Ile Ser Ser Leu Phe
            675                 680                 685
Asp Glu Gln Asn Asn Arg Asp Pro Lys Asn Asp Asn Leu Thr Leu Val
        690                 695                 700
Arg Gly Val Val Gly Ser Tyr Pro Ser Ala Tyr Leu Thr Leu Lys Glu
705                 710                 715                 720
Asn Gln Ile Pro Glu Leu Tyr Gln Arg Leu Val Ala Met Lys Ser Glu
                    725                 730                 735
Gln Asp Tyr Val Ala Leu Leu Asp Arg Phe Ala Val Arg Arg Ser Ser
                740                 745                 750
Pro Glu Phe Trp Ala Phe Ser Asp Leu Val His Gln Trp Tyr Arg Gln
            755                 760                 765
Asp Gln Pro Ile Glu Phe Gly Leu Leu Asp Tyr Asn Arg Phe Glu Asn
        770                 775                 780
Arg
```

<210> SEQ ID NO 97
<211> LENGTH: 2394
<212> TYPE: DNA
<213> ORGANISM: Shewanella baltica

<400> SEQUENCE: 97

| | | | | | |
|---|---|---|---|---|---|
| atggacgcga | taaaaagaat | atggaaaagg | ttgttattgg | ccacagtgct | gttggcgacg | 60 |
| ggttgtgcca | gtgtagcgca | aatcgatttc | aatgctctgt | ttggcactag | ctcaccgcaa | 120 |
| aagcgcgtcg | agaatgcaca | gcttaacaac | caatttgttc | aacaggccga | atttgtgcac | 180 |
| aaagaagttg | aaccgatcct | caatagccgc | tgcgtggtgt | gccatgcctg | ctacgatgct | 240 |
| ccctgccagc | tcaaaatgac | ctcaagcgaa | ggcatagaac | gcggagcgag | taaggaaaaa | 300 |
| gtctatcaag | gcacacgttt | agtcgccgcc | acgcccaatc | gcttatttgt | cgatgccttt | 360 |
| accccagaag | cttggcgtca | acgcgggttt | taccccatgt | aaacgagcg | caatcaaacc | 420 |
| ccagaagcca | atacccaagc | ctcggtattg | gccagaatgc | tcacgcttaa | gcaaatgcat | 480 |
| cccctgcccg | aagacaaaat | tttagataag | cgttttgatt | tcagcctaga | cagggttcag | 540 |
| caatgcgcca | gcctagagga | aatggacaaa | tacgagcaaa | gccaaccgtt | tgcgggtatg | 600 |
| ccctatggct | tgccagcatt | gaatgcgaat | gaacatcaag | tgttgatgca | ctggctcgaa | 660 |
| caaggtgcgc | cattgccatt | cgcgccatcg | ctagctcctg | aatttataac | ggaaatcacc | 720 |
| cattgggagc | aatttttaaa | cggcgacagt | ttaaaaagcc | aattaagcgc | acgctacatc | 780 |
| tacgagcatt | tgtttgcctt | tcacttatat | tttgaatctt | taaatcagcc | aaacgcccag | 840 |
| cctctgtttt | tcgagttagt | tcgttcgagg | acgccgccgg | ggcaagcgct | ggatattatc | 900 |
| gcctcccgtc | gtcccttcga | cgatcctaag | gtggaacgtg | tctattaccg | ttttcgacct | 960 |
| tatcgggcga | ccatagtcga | taaaactcac | atccccctatg | ccttaaatac | cagcttgctg | 1020 |
| cacgactggc | tgcaatggtt | tatcgatgcg | gattactcag | tgactcagct | gccgagctac | 1080 |
| cagccgagca | ttgcggccaa | tcccttcgaa | gcctttattc | aaattcctgc | cggtgcgcgc | 1140 |
| tatcgcttta | tgctgaaccg | cgcccaagac | accattatgg | gctttatcaa | aggcccagtg | 1200 |
| tgccgtggtc | aggtggcgct | caatgtgatt | aacgacagat | tctgggtgta | ctttgttacc | 1260 |
| ccagattata | tggacgacac | ggattttagg | accttctacc | attcccagat | tgaaaaccta | 1320 |
| cgaatgcctg | cggaggaaga | aagcactgca | ctcgccgtaa | cttgggtgaa | atatgccgcc | 1380 |
| aagcaaggta | agtatatgcg | ggcgcgtaat | cagttcttaa | cgagaagtt | taaaaacggc | 1440 |
| caacacctca | ccatcgacgg | gctctgggat | ggcgacgaca | gcaatgataa | tgctagcctg | 1500 |
| actgtgtttc | gccacttcga | taatgccact | gtagtcaaag | gtttagttgg | cgagccgccc | 1560 |
| aaaaccgctt | ggattatcga | ttacgcctta | ttggagcgta | tccactattt | gctggtcgca | 1620 |
| ggtttcgatg | tgtatggtaa | ctacggccac | cagctattaa | ctcgcttata | catggatttt | 1680 |
| ttacgcatgg | agggggaatc | aaatttccta | actttgttac | cgcaggagga | aaggcgcaaa | 1740 |
| cagtttagtg | attggtatca | aggggctggc | actcaactca | cggcgtttat | cgcggggat | 1800 |
| atcaacacct | ttaatcagcc | cacgggcgtg | ctctactata | gcgattacct | caagggcgaa | 1860 |
| ctgtatcaaa | aactcgggca | gaaggtcgct | aaggttcagc | aaatagata | tcaaatagaa | 1920 |
| aacagtcact | tgcaagccaa | cagcaaggca | ctgttgcagg | ctttaggtcg | attaaaaggc | 1980 |
| acccaagcga | ccctgttacc | tgagctaacc | atgatcatgg | tcgagcctga | aaagcgggt | 2040 |
| aaagccgagg | tctttacctt | agttcgcaat | agcgcccatc | gtaatatttc | gagcctgttt | 2100 |

-continued

```
aatgaggcca gcaaccgcga acccgcaaaa gatgatgtca ccttagtaca tggtttattg     2160
ggcagttacc cagaagcttt ctggctggtg aaagaacaag atttacctaa atcgtggcg      2220 gcggtagagc aaatgcaaac cgagaaagac tatgaggcac tgctcgatat tgcggctgta     2280
cgccgtagcg atcccacctt tgggccttt agtgacaaac tcaatcagat cttttcgac      2340 aatcacccga tagaaagtgg ttggctggat tataaccgcc tgcaaaatcg ttaa           2394
```

<210> SEQ ID NO 98
<211> LENGTH: 797
<212> TYPE: PRT
<213> ORGANISM: Shewanella baltica

<400> SEQUENCE: 98

```
Met Asp Ala Ile Lys Arg Ile Trp Lys Arg Leu Leu Leu Ala Thr Val
1               5                   10                  15

Leu Leu Ala Thr Gly Cys Ala Ser Val Ala Gln Ile Asp Phe Asn Ala
            20                  25                  30

Leu Phe Gly Thr Ser Ser Pro Gln Lys Arg Val Glu Asn Ala Gln Leu
        35                  40                  45

Asn Asn Gln Phe Val Gln Ala Glu Phe Val His Lys Glu Val Glu
    50                  55                  60

Pro Ile Leu Asn Ser Arg Cys Val Val Cys His Ala Cys Tyr Asp Ala
65                  70                  75                  80

Pro Cys Gln Leu Lys Met Thr Ser Ser Glu Gly Ile Glu Arg Gly Ala
                85                  90                  95

Ser Lys Glu Lys Val Tyr Gln Gly Thr Arg Leu Val Ala Ala Thr Pro
            100                 105                 110

Asn Arg Leu Phe Val Asp Ala Phe Thr Pro Glu Ala Trp Arg Gln Arg
        115                 120                 125

Gly Phe Tyr Pro Met Leu Asn Glu Arg Asn Gln Thr Pro Glu Ala Asn
    130                 135                 140

Thr Gln Ala Ser Val Leu Ala Arg Met Leu Thr Leu Lys Gln Met His
145                 150                 155                 160

Pro Leu Pro Glu Asp Lys Ile Leu Asp Lys Arg Phe Asp Phe Ser Leu
                165                 170                 175

Asp Arg Val Gln Gln Cys Ala Ser Leu Glu Glu Met Asp Lys Tyr Glu
            180                 185                 190

Gln Ser Gln Pro Phe Ala Gly Met Pro Tyr Gly Leu Pro Ala Leu Asn
        195                 200                 205

Ala Asn Glu His Gln Val Leu Met His Trp Leu Glu Gln Gly Ala Pro
    210                 215                 220

Leu Pro Phe Ala Pro Ser Leu Ala Pro Glu Phe Ile Thr Glu Ile Thr
225                 230                 235                 240

His Trp Glu Gln Phe Leu Asn Gly Asp Ser Leu Lys Ser Gln Leu Ser
                245                 250                 255

Ala Arg Tyr Ile Tyr Glu His Leu Phe Ala Phe His Leu Tyr Phe Glu
            260                 265                 270

Ser Leu Asn Gln Pro Asn Ala Gln Pro Leu Phe Glu Leu Val Arg
        275                 280                 285

Ser Arg Thr Pro Pro Gly Gln Ala Leu Asp Ile Ile Ala Ser Arg Arg
    290                 295                 300

Pro Phe Asp Asp Pro Lys Val Glu Arg Val Tyr Tyr Arg Phe Arg Pro
305                 310                 315                 320

Tyr Arg Ala Thr Ile Val Asp Lys Thr His Ile Pro Tyr Ala Leu Asn
                325                 330                 335
```

```
Thr Ser Leu Leu His Asp Trp Leu Gln Trp Phe Ile Asp Ala Asp Tyr
            340                 345                 350

Ser Val Thr Gln Leu Pro Ser Tyr Gln Pro Ser Ile Ala Ala Asn Pro
            355                 360                 365

Phe Glu Ala Phe Ile Gln Ile Pro Ala Gly Ala Arg Tyr Arg Phe Met
370                 375                 380

Leu Asn Arg Ala Gln Asp Thr Ile Met Gly Phe Ile Lys Gly Pro Val
385                 390                 395                 400

Cys Arg Gly Gln Val Ala Leu Asn Val Ile Asn Asp Arg Phe Trp Val
                405                 410                 415

Tyr Phe Val Thr Pro Asp Tyr Met Asp Thr Asp Phe Arg Thr Phe
                420                 425                 430

Tyr His Ser Gln Ile Glu Asn Leu Arg Met Pro Ala Glu Glu Ser
            435                 440                 445

Thr Ala Leu Ala Val Thr Trp Val Lys Tyr Ala Ala Lys Gln Gly Lys
            450                 455                 460

Tyr Met Arg Ala Arg Asn Gln Phe Leu Asn Glu Lys Phe Lys Asn Gly
465                 470                 475                 480

Gln His Leu Thr Ile Asp Gly Leu Trp Asp Gly Asp Ser Asn Asp
                485                 490                 495

Asn Ala Ser Leu Thr Val Phe Arg His Phe Asp Asn Ala Thr Val Val
            500                 505                 510

Lys Gly Leu Val Gly Glu Pro Pro Lys Thr Ala Trp Ile Ile Asp Tyr
            515                 520                 525

Ala Leu Leu Glu Arg Ile His Tyr Leu Leu Val Ala Gly Phe Asp Val
530                 535                 540

Tyr Gly Asn Tyr Gly His Gln Leu Leu Thr Arg Leu Tyr Met Asp Phe
545                 550                 555                 560

Leu Arg Met Glu Gly Glu Ser Asn Phe Leu Thr Leu Pro Gln Glu
                565                 570                 575

Glu Arg Arg Lys Gln Phe Ser Asp Trp Tyr Gln Gly Ala Gly Thr Gln
                580                 585                 590

Leu Thr Ala Phe Ile Ala Gly Asp Ile Asn Thr Phe Asn Gln Pro Thr
            595                 600                 605

Gly Val Leu Tyr Tyr Ser Asp Tyr Leu Lys Gly Glu Leu Tyr Gln Lys
            610                 615                 620

Leu Gly Gln Lys Val Ala Lys Val Gln Pro Asn Arg Tyr Gln Ile Glu
625                 630                 635                 640

Asn Ser His Leu Gln Ala Asn Ser Lys Ala Leu Leu Gln Ala Leu Gly
                645                 650                 655

Arg Leu Lys Gly Thr Gln Ala Thr Leu Leu Pro Glu Leu Thr Met Ile
                660                 665                 670

Met Val Glu Pro Glu Lys Ala Gly Lys Ala Glu Val Phe Thr Leu Val
            675                 680                 685

Arg Asn Ser Ala His Arg Asn Ile Ser Ser Leu Phe Asn Glu Ala Ser
690                 695                 700

Asn Arg Glu Pro Ala Lys Asp Asp Val Thr Leu Val His Gly Leu Leu
705                 710                 715                 720

Gly Ser Tyr Pro Glu Ala Phe Trp Leu Val Lys Glu Gln Asp Leu Pro
                725                 730                 735

Lys Ile Val Ala Ala Val Glu Gln Met Gln Thr Glu Lys Asp Tyr Glu
                740                 745                 750

Ala Leu Leu Asp Ile Ala Ala Val Arg Arg Ser Asp Pro Thr Phe Trp
```

```
                755               760               765
Ala Phe Ser Asp Lys Leu Asn Gln Ile Phe Phe Asp Asn His Pro Ile
        770               775               780

Glu Ser Gly Trp Leu Asp Tyr Asn Arg Leu Gln Asn Arg
785                 790               795

<210> SEQ ID NO 99
<211> LENGTH: 2007
<212> TYPE: DNA
<213> ORGANISM: Vibrio cholerae

<400> SEQUENCE: 99
gctgctggtt tcatcccgt gctgaatgag cgagctcaaa ccgcgcaagc caatcttgat      60
gctggggtga tggcacgttt gctgatgcag aaagagcgtc atccactacc acagcaagat    120
cagttacaag gatttgattt tcaattgat cgtgagcaaa cctgcccaac gatcaacgaa     180
atggatcact tcgaacaagt gaatcctaat tggggaatgc cctttggtat gccgaattta    240
tcccccaagg agtacgctac cctgctctct ggctacaag agggagcagt gatgaatcaa     300
gcgctcccgc tgagtgcgca agaacaagct ttggttacgg aatacgaagc cttgttgaat    360
cacagctcgc gtaaaaatca gctcgcagca cgctatatct acgaacatct attcctctca    420
catctgtact tttcagagat agcgcaggag cggcctcgtt tctttaaact catccgctcc    480
agtactccac cgggtgagcc tgtaaaacga atcgtgacac gtcgtccgta cgatgatccg    540
ggcgttgagc gagtctatta tcgccttgtg ccagaacaag agacgattgt cgataaaacc    600
cacatgcctt tcgcactcca caagcaacgg attgccaact ggaaactctg gtttattgat    660
gcggattatg aggttgccga gcttccaagt tatcgtccgg atattgccgc aaacccgatg    720
tccgcgttca tcgaccttcc cgttaaagcg cgctttaagt tcttgctcga taatgcgcaa    780
aatacggtga tggcctttat caaaggccca gtgtgtcgag acagttggc gctgaatgtg    840 attaacgata gattctgggt cttcttcctc gatcctgaga aagccgatct tccagaagtc    900
aacgaattct atcgctcaca agtcgacaac ttgaagctac ctgctgaaca agagaatacg    960
gcactgccgc tgagtaactg ggtacgttat tcgctacaac aaagccgtta tctcgaagca   1020
aaatctgaat ttattaatca atggtttaaa aatggtacgc accttaccac ggacatcatt   1080
tgggatggag cgggcacaaa ccctaatgcc gcattaacga ttttccgcca tttcgatagc   1140
gcatctgtcg tgcaaggatt ggtgggtgag cctcccaaaa ccgcttggat aatggattat   1200
gcgctgcttg agcgcattca ttatctgctt gttgctggtt tgatgtgta tggcaatttc    1260 gggcatcagt tgattactcg tatgttcatg gattttctgc gcatggaggg tgagagtaat   1320
tttgttgccc tgctaccacg cgatatgcgc catcaggagt tatctagttg gtatcaaaat   1380
caaagtgtac agttttccga tttcttgcaa cgtaacgtaa acccttttga tcagccaacc   1440
agcgttaact atgtgactga taacccgaaa caggagctgt tgctaaaact ccgcaagcaa   1500
gtacagtcgg tattgagtga tcgatacgta ataactcaaa cggaattcaa agccgaacat   1560
gagtttgctt tgcgccagat agatcatctg cgtggtgaag gttgctgcc cattccgcaa    1620 ttgatgatgt tgatgattga aagtgaacaa ggtaaaccgc aactctttac gctcatccat   1680
aacaatgccc acaccaatat ctcgagcttg tttgatgaac agaacaaccg cgaccccaaa   1740
aatgataatt tgactttagt gcgcggagtg gtcggcagtt atccatctgc gtacttaaca   1800
ctgaaagaaa accagatccc ggagctgtat caacgcctag tggcgatgaa gtcagagcaa   1860
gattatgtcg ccctattgga tcgttttgca gtacgccgca gctcacccga attttgggca   1920
```

```
tttagcgatc ttgtgcatca atggtatcgc caagatcaac ccattgagtt tggtttgctc    1980
gattacaacc gtttcgaaaa ccgctag                                        2007
```

<210> SEQ ID NO 100
<211> LENGTH: 668
<212> TYPE: PRT
<213> ORGANISM: Vibrio cholerae

<400> SEQUENCE: 100

| | | | | | | | | | | | | | | | |
|---|---|---|---|---|---|---|---|---|---|---|---|---|---|---|---|
| Ala | Ala | Gly | Phe | His | Pro | Val | Leu | Asn | Glu | Arg | Ala | Gln | Thr | Ala | Gln |
| 1 | | | | 5 | | | | | 10 | | | | | 15 | |
| Ala | Asn | Leu | Asp | Ala | Gly | Val | Met | Ala | Arg | Leu | Leu | Met | Gln | Lys | Glu |
| | | | 20 | | | | 25 | | | | | 30 | | | |
| Arg | His | Pro | Leu | Pro | Gln | Gln | Asp | Gln | Leu | Gln | Gly | Phe | Asp | Phe | Ser |
| | | 35 | | | | | 40 | | | | | 45 | | | |
| Ile | Asp | Arg | Glu | Gln | Thr | Cys | Pro | Thr | Ile | Asn | Glu | Met | Asp | His | Phe |
| | 50 | | | | | 55 | | | | | 60 | | | | |
| Glu | Gln | Val | Asn | Pro | Asn | Trp | Gly | Met | Pro | Phe | Gly | Met | Pro | Asn | Leu |
| 65 | | | | | 70 | | | | | 75 | | | | | 80 |
| Ser | Pro | Lys | Glu | Tyr | Ala | Thr | Leu | Leu | Ser | Trp | Leu | Gln | Glu | Gly | Ala |
| | | | | 85 | | | | | 90 | | | | | 95 | |
| Val | Met | Asn | Gln | Ala | Leu | Pro | Leu | Ser | Ala | Gln | Glu | Gln | Ala | Leu | Val |
| | | | 100 | | | | | 105 | | | | | 110 | | |
| Thr | Glu | Tyr | Glu | Ala | Leu | Leu | Asn | His | Ser | Ser | Arg | Lys | Asn | Gln | Leu |
| | | | 115 | | | | | 120 | | | | | 125 | | |
| Ala | Ala | Arg | Tyr | Ile | Tyr | Glu | His | Leu | Phe | Leu | Ser | His | Leu | Tyr | Phe |
| | | 130 | | | | | 135 | | | | | 140 | | | |
| Ser | Glu | Ile | Ala | Gln | Glu | Arg | Pro | Arg | Phe | Phe | Lys | Leu | Ile | Arg | Ser |
| 145 | | | | | 150 | | | | | 155 | | | | | 160 |
| Ser | Thr | Pro | Pro | Gly | Glu | Pro | Val | Lys | Arg | Ile | Val | Thr | Arg | Arg | Pro |
| | | | | 165 | | | | | 170 | | | | | 175 | |
| Tyr | Asp | Asp | Pro | Gly | Val | Glu | Arg | Val | Tyr | Tyr | Arg | Leu | Val | Pro | Glu |
| | | | 180 | | | | | 185 | | | | | 190 | | |
| Gln | Glu | Thr | Ile | Val | Asp | Lys | Thr | His | Met | Pro | Phe | Ala | Leu | His | Lys |
| | | | 195 | | | | | 200 | | | | | 205 | | |
| Gln | Arg | Ile | Ala | Asn | Trp | Lys | Leu | Trp | Phe | Ile | Asp | Ala | Asp | Tyr | Glu |
| | | 210 | | | | | 215 | | | | | 220 | | | |
| Val | Ala | Glu | Leu | Pro | Ser | Tyr | Arg | Pro | Asp | Ile | Ala | Ala | Asn | Pro | Met |
| 225 | | | | | 230 | | | | | 235 | | | | | 240 |
| Ser | Ala | Phe | Ile | Asp | Leu | Pro | Val | Lys | Ala | Arg | Phe | Lys | Phe | Leu | Leu |
| | | | | 245 | | | | | 250 | | | | | 255 | |
| Asp | Asn | Ala | Gln | Asn | Thr | Val | Met | Ala | Phe | Ile | Lys | Gly | Pro | Val | Cys |
| | | | 260 | | | | | 265 | | | | | 270 | | |
| Arg | Gly | Gln | Leu | Ala | Leu | Asn | Val | Ile | Asn | Asp | Arg | Phe | Trp | Val | Phe |
| | | 275 | | | | | 280 | | | | | 285 | | | |
| Phe | Leu | Asp | Pro | Glu | Lys | Ala | Asp | Leu | Pro | Glu | Val | Asn | Glu | Phe | Tyr |
| | 290 | | | | | 295 | | | | | 300 | | | | |
| Arg | Ser | Gln | Val | Asp | Asn | Leu | Lys | Leu | Pro | Ala | Glu | Gln | Glu | Asn | Thr |
| 305 | | | | | 310 | | | | | 315 | | | | | 320 |
| Ala | Leu | Pro | Leu | Ser | Asn | Trp | Val | Arg | Tyr | Ser | Leu | Gln | Gln | Ser | Arg |
| | | | | 325 | | | | | 330 | | | | | 335 | |
| Tyr | Leu | Glu | Ala | Lys | Ser | Glu | Phe | Ile | Asn | Gln | Trp | Phe | Lys | Asn | Gly |
| | | | 340 | | | | | 345 | | | | | 350 | | |
| Thr | His | Leu | Thr | Thr | Asp | Ile | Ile | Trp | Asp | Gly | Ala | Gly | Thr | Asn | Pro |
| | | 355 | | | | | 360 | | | | | 365 | | | |

Asn Ala Ala Leu Thr Ile Phe Arg His Phe Asp Ser Ala Ser Val Val
    370                 375                 380

Gln Gly Leu Val Gly Glu Pro Pro Lys Thr Ala Trp Ile Met Asp Tyr
385                 390                 395                 400

Ala Leu Leu Glu Arg Ile His Tyr Leu Leu Val Ala Gly Phe Asp Val
                405                 410                 415

Tyr Gly Asn Phe Gly His Gln Leu Ile Thr Arg Met Phe Met Asp Phe
                420                 425                 430

Leu Arg Met Glu Gly Glu Ser Asn Phe Val Ala Leu Leu Pro Arg Asp
            435                 440                 445

Met Arg His Gln Glu Leu Ser Ser Trp Tyr Gln Asn Gln Ser Val Gln
            450                 455                 460

Phe Ser Asp Phe Leu Gln Arg Asn Val Lys Pro Phe Asp Gln Pro Thr
465                 470                 475                 480

Ser Val Asn Tyr Val Thr Asp Asn Pro Lys Gln Glu Leu Phe Ala Lys
                485                 490                 495

Leu Arg Lys Gln Val Gln Ser Val Leu Ser Asp Arg Tyr Val Ile Thr
            500                 505                 510

Gln Thr Glu Phe Lys Ala Glu His Glu Phe Ala Leu Arg Gln Ile Asp
            515                 520                 525

His Leu Arg Gly Glu Gly Leu Leu Pro Ile Pro Gln Leu Met Met Leu
            530                 535                 540

Met Ile Glu Ser Glu Gln Gly Lys Pro Gln Leu Phe Thr Leu Ile His
545                 550                 555                 560

Asn Asn Ala His Thr Asn Ile Ser Ser Leu Phe Asp Glu Gln Asn Asn
                565                 570                 575

Arg Asp Pro Lys Asn Asp Asn Leu Thr Leu Val Arg Gly Val Val Gly
            580                 585                 590

Ser Tyr Pro Ser Ala Tyr Leu Thr Leu Lys Glu Asn Gln Ile Pro Glu
            595                 600                 605

Leu Tyr Gln Arg Leu Val Ala Met Lys Ser Glu Gln Asp Tyr Val Ala
            610                 615                 620

Leu Leu Asp Arg Phe Ala Val Arg Arg Ser Ser Pro Glu Phe Trp Ala
625                 630                 635                 640

Phe Ser Asp Leu Val His Gln Trp Tyr Arg Gln Asp Gln Pro Ile Glu
                645                 650                 655

Phe Gly Leu Leu Asp Tyr Asn Arg Phe Glu Asn Arg
            660                 665

<210> SEQ ID NO 101
<211> LENGTH: 2355
<212> TYPE: DNA
<213> ORGANISM: Pelobacter propionicus

<400> SEQUENCE: 101
ttgagactcg tcaccatttc atgcctgatc atggccagca tcgccgctgg ctgcgccctg     60
aagacgctac cagcggtcac cgtcaaaata ccaaccagaa cgatagagta ctcaagcgaa    120
gtcaaaccga tactggacaa cgcctgcacg tctgccact cctgctacaa ttcccctgc      180 cagctgaagc tggactcctt cgagggagct gaccggggcg ccagcaagcg ggccatctac    240
aacgccgcgc gcctcaccac catggatccc acccgcctgt tcatcgacgc ccgtacaacc    300
gaggagtggc gcaaaaaaca gttcttcagc atcaccgaca gcagcgtggg aaatggtctc    360
aatgattcga tcatgatcca gctgctctcc cacaagatga agaaccccgc aagcagtggc    420

-continued

```
gagtaccatg ccgaggccga tgacctgacc tgctcggaaa accggaacga gctggcaggc    480
tatctggata acaccccaa caacggcatg cccttcggct ttccccccct gaaacaggac    540
gagttcgaca tcatagccgg ttggctggtg cagggagcca ggggacccac ccctgaccag    600
caagcgcaac tggtcacccc caaaccagag gatgcccggg ccatcctgcg ctgggaatcg    660
ttcctcaacc agaccgaccc aaagcacgcc atgaccgccc gctacctgta cgagcatctg    720
ttcctggccc acatcaactt cgccaccggc agcaacgaat tcttcgaact ggtccgctcc    780
cgaaccgctc ccggacagcc ggtggaggtg atacccacgg tgcgccccta tgacgacccc    840
ggcccggaac ctttctttta ccgcttccgc aaaattcact ccaccatcgt ccacaagacc    900
cacatggtct tcgatctgga cgatgcccag tttcagcgga tcaacgagct gttcatccag    960
ccagagtggt tgcagacgcc ccacaccatg ggctatgagc cggtcatgag cgccaacccc   1020
ttcacggcct tcgagcagat tccccccga tcgcgctacc agttcctgct ggacaacgcc   1080
cactacatca tcatgacctt catccacggc ccggtctgca gggtcagat cgccctgaac   1140 gttatcgacg accacttctg ggtcatgttc atggacccgg accacgacct gagtgtcgcc   1200
tatcccggtt cctcaggct gcacgccggc aagctgcgca tgccgatcga aaaggggagc   1260
aaccagcaca tcttctcggc gctgaccgac gagcaccgca aagcggtgat tgaattctac   1320 cggggccaggc aggactacta cgccgcccac tactatgccg ggttggacta cgatttcatc   1380 tggaaggga atcggcctgc cgatgcgccg cttctgaccg tgtaccggca tttcaacagc   1440
gcctcggtgc accggggcat actgggcagc ctgcccaaga ccatgtgggt catcgattac   1500
cccctgctgg agcgcatcta ctacgccctg gtggccggct cgacgtgta cggcaccgcc   1560 ggacatcagc ttgccatccg gctctatatg gacgcgctgc gcgtggaagg ggagagcaac   1620
ttcctggatt tcctgccccc cgccaagcgc aaggcgatca tgaaatcctg gtacaagggg   1680
gtcgagctga agaaggtgaa ctactacccc tcgctcctgc cggccgggat agtgtttacc   1740
agcgacgacc ccaaacggga gttcatcgag cagctggtga accggcacct gctccccgcc   1800
agcgggattg ccttcgaccc gatcaactat ctccccgccg gacagcctac tccgcaactg   1860
ccgcacaact acgaaaagcg ggaggactat ttgcgggcct tcaccgccct ctcccgcccc   1920
ggaaccccct tcttctccct gatcaaggag accgacgcca acctggccta cgtgagaata   1980
cggctcaaaa acggcaggga tatcgccgga tccatcgtca tcaaccgctg gcacgacaac   2040
gtggccttca tgctggggga agacgacagg ctcgatgcgt caaggacag cgccgacttc   2100 ataccgggggc tgatcggttc ctatcccaac tatttcgtgg atgtgcgcga ggaggagctg   2160
cccgacttct tcgacctgct ggccaatttc agcggaagcc gacgggacct ggagcgggtg   2220
gcacgctacg gcgtaaaccg ggccgacgac cgtctctggg aagcatacga ctggttccag   2280
atgcgcttca tgaaggatga accggtcaag gggggactgt tcgacctgaa ccgctacttc   2340
caccgggcgc gctga                                                    2355
```

<210> SEQ ID NO 102
<211> LENGTH: 784
<212> TYPE: PRT
<213> ORGANISM: Pelobacter propionicus

<400> SEQUENCE: 102

```
Met Arg Leu Val Thr Ile Ser Cys Leu Ile Met Ala Ser Ile Ala Ala
1               5                   10                  15

Gly Cys Ala Leu Lys Thr Leu Pro Ala Val Thr Val Lys Ile Pro Thr
            20                  25                  30
```

```
Arg Thr Ile Glu Tyr Ser Ser Glu Val Lys Pro Ile Leu Asp Lys Arg
         35                  40                  45

Cys Thr Val Cys His Ser Cys Tyr Asn Ser Pro Cys Gln Leu Lys Leu
 50                  55                  60

Asp Ser Phe Glu Gly Ala Asp Arg Gly Ala Ser Lys Arg Ala Ile Tyr
 65                  70                  75                  80

Asn Ala Ala Arg Leu Thr Thr Met Asp Pro Thr Arg Leu Phe Ile Asp
                 85                  90                  95

Ala Arg Thr Thr Glu Glu Trp Arg Lys Lys Gln Phe Phe Ser Ile Thr
             100                 105                 110

Asp Ser Ser Val Gly Asn Gly Leu Asn Asp Ser Ile Met Ile Gln Leu
         115                 120                 125

Leu Ser His Lys Met Lys Asn Pro Ala Ser Ser Gly Glu Tyr His Ala
130                 135                 140

Glu Ala Asp Asp Leu Thr Cys Ser Glu Asn Arg Asn Glu Leu Ala Gly
145                 150                 155                 160

Tyr Leu Asp Lys His Pro Asn Asn Gly Met Pro Phe Gly Phe Pro Pro
                 165                 170                 175

Leu Lys Gln Asp Glu Phe Asp Ile Ile Ala Gly Trp Leu Val Gln Gly
             180                 185                 190

Ala Arg Gly Pro Thr Pro Asp Gln Gln Ala Gln Leu Val Thr Pro Lys
         195                 200                 205

Pro Glu Asp Ala Arg Ala Ile Leu Arg Trp Glu Ser Phe Leu Asn Gln
210                 215                 220

Thr Asp Pro Lys His Ala Met Thr Ala Arg Tyr Leu Tyr Glu His Leu
225                 230                 235                 240

Phe Leu Ala His Ile Asn Phe Ala Thr Gly Ser Asn Glu Phe Phe Glu
                 245                 250                 255

Leu Val Arg Ser Arg Thr Ala Pro Gly Gln Pro Val Glu Val Ile Pro
             260                 265                 270

Thr Val Arg Pro Tyr Asp Asp Pro Gly Pro Glu Pro Phe Phe Tyr Arg
         275                 280                 285

Phe Arg Lys Ile His Ser Thr Ile Val His Lys Thr His Met Val Phe
290                 295                 300

Asp Leu Asp Asp Ala Gln Phe Gln Arg Ile Asn Glu Leu Phe Ile Gln
305                 310                 315                 320

Pro Glu Trp Leu Gln Thr Pro His Thr Met Gly Tyr Glu Pro Val Met
                 325                 330                 335

Ser Ala Asn Pro Phe Thr Ala Phe Glu Gln Ile Pro Pro Arg Ser Arg
             340                 345                 350

Tyr Gln Phe Leu Leu Asp Asn Ala His Tyr Ile Ile Met Thr Phe Ile
         355                 360                 365

His Gly Pro Val Cys Lys Gly Gln Ile Ala Leu Asn Val Ile Asp Asp
370                 375                 380

His Phe Trp Val Met Phe Met Asp Pro Asp His Asp Leu Ser Val Ala
385                 390                 395                 400

Tyr Pro Gly Phe Leu Arg Leu His Ala Gly Lys Leu Arg Met Pro Ile
                 405                 410                 415

Glu Lys Gly Ser Asn Gln His Ile Phe Ser Ala Leu Thr Asp Glu His
             420                 425                 430

Arg Lys Ala Val Ile Glu Phe Tyr Arg Ala Arg Gln Asp Tyr Tyr Ala
         435                 440                 445

Ala His Tyr Tyr Ala Gly Leu Asp Tyr Asp Phe Ile Trp Lys Gly Asn
450                 455                 460
```

Arg Pro Ala Asp Ala Pro Leu Leu Thr Val Tyr Arg His Phe Asn Ser
465                 470                 475                 480

Ala Ser Val His Arg Gly Ile Leu Gly Ser Leu Pro Lys Thr Met Trp
            485                 490                 495

Val Ile Asp Tyr Pro Leu Leu Glu Arg Ile Tyr Tyr Ala Leu Val Ala
        500                 505                 510

Gly Phe Asp Val Tyr Gly Thr Ala Gly His Gln Leu Ala Ile Arg Leu
        515                 520                 525

Tyr Met Asp Ala Leu Arg Val Glu Gly Glu Ser Asn Phe Leu Asp Phe
530                 535                 540

Leu Pro Pro Ala Lys Arg Lys Ala Ile Met Lys Ser Trp Tyr Lys Gly
545                 550                 555                 560

Val Glu Leu Lys Lys Val Asn Tyr Tyr Pro Ser Leu Leu Pro Ala Gly
            565                 570                 575

Ile Val Phe Thr Ser Asp Asp Pro Lys Arg Glu Phe Ile Glu Gln Leu
        580                 585                 590

Val Asn Arg His Leu Leu Pro Ala Ser Gly Ile Ala Phe Asp Pro Ile
        595                 600                 605

Asn Tyr Leu Pro Ala Gly Thr Ala Tyr Pro Gln Leu Pro His Asn Tyr
610                 615                 620

Glu Lys Arg Glu Asp Tyr Leu Arg Ala Phe Thr Ala Leu Ser Arg Pro
625                 630                 635                 640

Gly Thr Pro Phe Phe Ser Leu Ile Lys Glu Thr Asp Ala Asn Leu Ala
            645                 650                 655

Tyr Val Arg Ile Arg Leu Lys Asn Gly Arg Asp Ile Ala Gly Ser Ile
        660                 665                 670

Val Ile Asn Arg Trp His Asp Asn Val Ala Phe Met Leu Gly Glu Asp
        675                 680                 685

Asp Arg Leu Asp Ala Ser Lys Asp Ser Ala Asp Phe Ile Pro Gly Leu
690                 695                 700

Ile Gly Ser Tyr Pro Asn Tyr Phe Val Asp Val Arg Glu Glu Glu Leu
705                 710                 715                 720

Pro Asp Phe Phe Asp Leu Leu Ala Asn Phe Ser Gly Ser Arg Arg Asp
            725                 730                 735

Leu Glu Arg Val Ala Arg Tyr Gly Val Asn Arg Ala Asp Arg Leu
        740                 745                 750

Trp Glu Ala Tyr Asp Trp Phe Gln Met Arg Phe Met Lys Asp Glu Pro
        755                 760                 765

Val Lys Gly Gly Leu Phe Asp Leu Asn Arg Tyr Phe His Arg Ala Arg
770                 775                 780

<210> SEQ ID NO 103
<211> LENGTH: 2253
<212> TYPE: DNA
<213> ORGANISM: Pseudomonas aeruginosa

<400> SEQUENCE: 103
ttgtcgtctt ttatccagtc tgtttccgct gctgaaattt cctatagccg tgacgtccag     60
ccgatcttta ccgccaagtg cgtcgcctgc acgcctgct acgattcgcc ctgccagctc     120
aacctgagca gcgccgaggg cgcgcagcgc ggcgccaacc aactgccggt ctacgacggc     180
acgcggacca aggcgcagga aaccacccgc ctgtacctcg atgcgcacgg tgccgacgcc     240
tggcggcgca aggacttctg gtcggtgctc gaaccgcagg acggccaggc cgcactgatg     300
gcgcggatgc tcgagcttgg ccacagccag ccgttgcagc cgaatgcgaa gatccccgaa     360

```
ggcctggaca tttcgatcaa ccgcgccaac cagtgcccga cgccggccag catcgatgcg    420
ttcatccgca agaacccagg ttccggcatg cctttcgcgg tggccgggct gagcgacgac    480
gaatacgcca ccttgcagaa gtggctggcc gcgggcgccc cggtcgacca gcagccgttg    540
cggccgaccg ccgccgaggc gcgccaggtg gccagctggg agcgtttcct caaccagcct    600
ggggccaagc agagcctggt ctcgcgctgg ctctacgagc acctgttcct ggcgcacctg    660
tatttcccgg agcagggcgc gcccggccac ttcttccagc tggtgcgttc acgcacgccc    720
agcggccagc cgatcgaccc gatcccgacc cggcgtccca cgacgatccc gggcaacagc    780
ttctattacc gcctctggcc gatccagggc gtgatcgtcc acaagacgca catcacctat    840
ccgctgacgg cgaagaagct ggaacgcgtc caggagctgt tcttcggcac ccagtggaac    900
accgacaagg ttcccggcta cggcgtgcag agccgcgcca cccgttcgt caccttcgcc    960 gcgatcccgc cacgggcgcg ctaccagttc atgctggaca cgccgagta cttcacccgt   1020 accttcatcc gcgggccggt gtgccgtgga cagatcgcca ccgacgtgat ccgcgacaac   1080
ttctgggtgg tattccagga ccccgagcag gacctgttcg tcaccgacgc caacttccgc   1140
gcgcagagcg agccgctgct ggccttgccg gggcagatcg acgagctgaa gaacctgctc   1200
ggcctgtgga gcgcctaccg ggacaagcgc aacgagtacg aagacctgcg ccaggacgtc   1260
tacgccgacg cgccgccgcc gacctggaac acgatctggc acggcaacga caacgccctg   1320
ctgagcatct ccgccagtt cgacagcgcc tcggtgcgca agggcctgct ggcgaggta    1380 ccgcagaccc tgtggctgat ggactacccg ctgttcgagc gaacctacta cgggctggtg   1440
gtgaacttcg atgtcttcgg caacgtctcg caccaggcgc agacgcgcct gtacttcgac   1500
ctgatccgca acgcgccga gcagaacttc ctccgcttga tgccgatcga cgcgcgccag   1560
ccgttgctcg acgactggta ccagaacagc ggcaagctga agatgtggat ggactaccag   1620
gccttcgacg atgacacgcc gagcgcgctg ggattgccgg agaagcagcc gaagaaggcc   1680
ttcgccgaag aactgctgcg tcgctacggc gacctcaatg cgcgccccga cccgatcaac   1740
cgctgcctgg acggcaactg ctatcgaccg ggcatcgacc gcgaactgca ggacgccgag   1800
caggccttca gtcgcctggt gagccggccg gcggccggcc tcaaggtcat cgagcgcttc   1860
cccgaggcga ccatgctgcg gatacgtacg tccagcggca agcgcgaggt ctataccgtg   1920
ctgcgcaacc gcgcgcacag caatgtcgcc ttcatgctcg gcgagtcgct gcgctaccag   1980
ccgggcctgg acaccctgac gatctacccg ggcgtgctgt ccagctaccc gaacttcatg   2040
ttcgatctgc cggcgacgga tgccgaggcc ttcgtcggcg ccctggaggc ggcgaagagc   2100
ggcgaggact cgacaaggt ggtcgaacgc tggggcgtgc gccgcagcaa tccgcagttc   2160
tggagctact ccacgatct cgaggcgtac atccgcgaaa ccgagccggt cgaggcgggc   2220
gcactggaca tgaaccgcta cgagaacctc tga                              2253
```

<210> SEQ ID NO 104
<211> LENGTH: 750
<212> TYPE: PRT
<213> ORGANISM: Pseudomonas aeruginosa

<400> SEQUENCE: 104

Met Ser Ser Phe Ile Gln Ser Val Ser Ala Ala Glu Ile Ser Tyr Ser
1               5                   10                  15

Arg Asp Val Gln Pro Ile Phe Thr Ala Lys Cys Val Ala Cys His Ala
            20                  25                  30

Cys Tyr Asp Ser Pro Cys Gln Leu Asn Leu Ser Ser Ala Glu Gly Ala

```
                35                  40                  45
Gln Arg Gly Ala Asn Gln Leu Pro Val Tyr Asp Gly Thr Arg Thr Lys
 50                  55                  60

Ala Gln Glu Thr Thr Arg Leu Tyr Leu Asp Ala His Gly Ala Asp Ala
 65                  70                  75                  80

Trp Arg Arg Lys Asp Phe Trp Ser Val Leu Glu Pro Gln Asp Gly Gln
                 85                  90                  95

Ala Ala Leu Met Ala Arg Met Leu Glu Leu Gly His Ser Gln Pro Leu
                100                 105                 110

Gln Pro Asn Ala Lys Ile Pro Glu Gly Leu Asp Ile Ser Ile Asn Arg
                115                 120                 125

Ala Asn Gln Cys Pro Thr Pro Ala Ser Ile Asp Ala Phe Ile Arg Lys
130                 135                 140

Asn Pro Gly Ser Gly Met Pro Phe Ala Val Ala Gly Leu Ser Asp Asp
145                 150                 155                 160

Glu Tyr Ala Thr Leu Gln Lys Trp Leu Ala Ala Gly Ala Pro Val Asp
                165                 170                 175

Gln Gln Pro Leu Arg Pro Thr Ala Ala Glu Ala Arg Gln Val Ala Ser
                180                 185                 190

Trp Glu Arg Phe Leu Asn Gln Pro Gly Ala Lys Gln Ser Leu Val Ser
                195                 200                 205

Arg Trp Leu Tyr Glu His Leu Phe Leu Ala His Leu Tyr Phe Pro Glu
210                 215                 220

Gln Gly Ala Pro Gly His Phe Phe Gln Leu Val Arg Ser Arg Thr Pro
225                 230                 235                 240

Ser Gly Gln Pro Ile Asp Pro Ile Pro Thr Arg Arg Pro Asn Asp Asp
                245                 250                 255

Pro Gly Asn Ser Phe Tyr Tyr Arg Leu Trp Pro Ile Gln Gly Val Ile
                260                 265                 270

Val His Lys Thr His Ile Thr Tyr Pro Leu Thr Ala Lys Lys Leu Glu
                275                 280                 285

Arg Val Gln Glu Leu Phe Phe Gly Thr Gln Trp Asn Thr Asp Lys Val
290                 295                 300

Pro Gly Tyr Gly Val Gln Ser Arg Ala Asn Pro Phe Val Thr Phe Ala
305                 310                 315                 320

Ala Ile Pro Pro Arg Ala Arg Tyr Gln Phe Met Leu Asp Asn Ala Glu
                325                 330                 335

Tyr Phe Thr Arg Thr Phe Ile Arg Gly Pro Val Cys Arg Gly Gln Ile
                340                 345                 350

Ala Thr Asp Val Ile Arg Asp Asn Phe Trp Val Phe Gln Asp Pro
                355                 360                 365

Glu Gln Asp Leu Phe Val Thr Asp Ala Asn Phe Arg Ala Gln Ser Glu
                370                 375                 380

Pro Leu Leu Ala Leu Pro Gly Gln Ile Asp Glu Leu Lys Asn Leu Leu
385                 390                 395                 400

Gly Leu Trp Ser Ala Tyr Arg Asp Lys Arg Asn Glu Tyr Glu Asp Leu
                405                 410                 415

Arg Gln Asp Val Tyr Ala Asp Ala Pro Pro Thr Trp Asn Thr Ile
                420                 425                 430

Trp His Gly Asn Asp Asn Ala Leu Leu Ser Ile Phe Arg Gln Phe Asp
                435                 440                 445

Ser Ala Ser Val Arg Lys Gly Leu Leu Gly Glu Val Pro Gln Thr Leu
450                 455                 460
```

```
Trp Leu Met Asp Tyr Pro Leu Phe Glu Arg Thr Tyr Gly Leu Val
465                 470                 475                 480

Val Asn Phe Asp Val Phe Gly Asn Val Ser His Gln Ala Gln Thr Arg
                485                 490                 495

Leu Tyr Phe Asp Leu Ile Arg Asn Gly Ala Glu Gln Asn Phe Leu Arg
            500                 505                 510

Leu Met Pro Ile Asp Ala Arg Gln Pro Leu Leu Asp Asp Trp Tyr Gln
        515                 520                 525

Asn Ser Gly Lys Leu Lys Met Trp Met Asp Tyr Gln Ala Phe Asp Asp
    530                 535                 540

Asp Thr Pro Ser Ala Leu Gly Leu Pro Glu Lys Gln Pro Lys Lys Ala
545                 550                 555                 560

Phe Ala Glu Glu Leu Leu Arg Arg Tyr Gly Asp Leu Asn Ala Arg Pro
                565                 570                 575

Asp Pro Ile Asn Arg Cys Leu Asp Gly Asn Cys Tyr Arg Pro Gly Ile
            580                 585                 590

Asp Arg Glu Leu Gln Asp Ala Glu Gln Ala Phe Ser Arg Leu Val Ser
        595                 600                 605

Arg Pro Ala Ala Gly Leu Lys Val Ile Glu Arg Phe Pro Glu Ala Thr
610                 615                 620

Met Leu Arg Ile Arg Thr Ser Ser Gly Lys Arg Glu Val Tyr Thr Val
625                 630                 635                 640

Leu Arg Asn Arg Ala His Ser Asn Val Ala Phe Met Leu Gly Glu Ser
                645                 650                 655

Leu Arg Tyr Gln Pro Gly Leu Asp Thr Leu Thr Ile Tyr Pro Gly Val
            660                 665                 670

Leu Ser Ser Tyr Pro Asn Phe Met Phe Asp Leu Pro Ala Thr Asp Ala
        675                 680                 685

Glu Ala Phe Val Gly Ala Leu Glu Ala Ala Lys Ser Gly Glu Asp Phe
    690                 695                 700

Asp Lys Val Val Glu Arg Trp Gly Val Arg Arg Ser Asn Pro Gln Phe
705                 710                 715                 720

Trp Ser Tyr Phe His Asp Leu Glu Ala Tyr Ile Arg Glu Thr Glu Pro
                725                 730                 735

Val Glu Ala Gly Ala Leu Asp Met Asn Arg Tyr Glu Asn Leu
            740                 745                 750

<210> SEQ ID NO 105
<211> LENGTH: 1089
<212> TYPE: DNA
<213> ORGANISM: Pseudomonas aeruginosa

<400> SEQUENCE: 105
ttgccggggc agatcgacga gctgaagaac ctgctcggcc tgtggagcgc ctaccgggac      60
aagcgcaacg agtacgaaga cctgcgccag gacgtctacg ccgacgcgcc gccgccgacc     120
tggaacacgc tctggcacgg caacgacaac gccctgctga gcatcttccg ccagttcgac     180
agcgcctcgg tgcgcaaggg cctgcttggc gaggtaccgc agaccctgtg gctgatggac     240
tatccgctgt tcgagcgaac ctactacggg ctggtggtga acttcgatgt cttcggcaac     300
gtctcgcacc aggcgcagac gcggctgtac ttcgacctga tccgcaacgg cgccgagcag     360
aacttcctcc gcctgatgcc ggtcgacgcg cgccagccgt tgctcgacga ctggtaccag     420
aacagcggca agctgaagat gtggatggac taccaggtct cgacgacga cacgccgagc     480 gcgctgggat tgccggagaa gcagccgaag aaggccttcg ccgaagaact gctgcgtcgc     540
```

```
tacggcgacc tcaatgcgcg tcccgacccg atcaaccgct gcctggacgg caactgctat    600
cgaccgggca tcgaccgcga actgcaggac gccgagcagg ccttcagtcg cctggtgagc    660
cggccggcgg ccggcctcaa ggtcatcgag cgcttccccg aggcgaccat gctgcggata    720
cgtacgtcca gcggcaagcg cgaggtctat accgtgctgc gcaaccgcgc gcacagcaat    780
gtcgccttca tgctcggcga gtcgctgcgc taccagccgg gcctggacac cctgacgatc    840
tacccgggcg tgctgtccag ctacccgaac ttcatgttcg atctgccggc gacggatgcc    900
gaggccttcg tcggcgccct ggaggcggcg aagagcggcg aggacttcga caaggtggtc    960
gaacgctggg gcgtgcgccg cagcaatccg cagttctgga gctacttcca cgatctcgag   1020
gcgtacatcc gcgaaaccga gccggtcgag gcgggcgcac tggacatgaa ccgctacgag   1080
aacctctga                                                          1089

<210> SEQ ID NO 106
<211> LENGTH: 362
<212> TYPE: PRT
<213> ORGANISM: Pseudomonas aeruginosa

<400> SEQUENCE: 106

Met Pro Gly Gln Ile Asp Glu Leu Lys Asn Leu Leu Gly Leu Trp Ser
1               5                   10                  15

Ala Tyr Arg Asp Lys Arg Asn Glu Tyr Glu Asp Leu Arg Gln Asp Val
            20                  25                  30

Tyr Ala Asp Ala Pro Pro Thr Trp Asn Thr Leu Trp His Gly Asn
        35                  40                  45

Asp Asn Ala Leu Leu Ser Ile Phe Arg Gln Phe Asp Ser Ala Ser Val
    50                  55                  60

Arg Lys Gly Leu Leu Gly Glu Val Pro Gln Thr Leu Trp Leu Met Asp
65                  70                  75                  80

Tyr Pro Leu Phe Glu Arg Thr Tyr Tyr Gly Leu Val Val Asn Phe Asp
                85                  90                  95

Val Phe Gly Asn Val Ser His Gln Ala Gln Thr Arg Leu Tyr Phe Asp
            100                 105                 110

Leu Ile Arg Asn Gly Ala Glu Gln Asn Phe Leu Arg Leu Met Pro Val
        115                 120                 125

Asp Ala Arg Gln Pro Leu Leu Asp Asp Trp Tyr Gln Asn Ser Gly Lys
    130                 135                 140

Leu Lys Met Trp Met Asp Tyr Gln Val Phe Asp Asp Thr Pro Ser
145                 150                 155                 160

Ala Leu Gly Leu Pro Glu Lys Gln Pro Lys Lys Ala Phe Ala Glu Glu
                165                 170                 175

Leu Leu Arg Arg Tyr Gly Asp Leu Asn Ala Arg Pro Asp Pro Ile Asn
            180                 185                 190

Arg Cys Leu Asp Gly Asn Cys Tyr Arg Pro Gly Ile Asp Arg Glu Leu
        195                 200                 205

Gln Asp Ala Glu Gln Ala Phe Ser Arg Leu Val Ser Arg Pro Ala Ala
    210                 215                 220

Gly Leu Lys Val Ile Glu Arg Phe Pro Glu Ala Thr Met Leu Arg Ile
225                 230                 235                 240

Arg Thr Ser Ser Gly Lys Arg Glu Val Tyr Thr Val Leu Arg Asn Arg
                245                 250                 255

Ala His Ser Asn Val Ala Phe Met Leu Gly Glu Ser Leu Arg Tyr Gln
            260                 265                 270

Pro Gly Leu Asp Thr Leu Thr Ile Tyr Pro Gly Val Leu Ser Ser Tyr
```

```
            275                 280                 285
Pro Asn Phe Met Phe Asp Leu Pro Ala Thr Asp Ala Glu Ala Phe Val
            290                 295                 300

Gly Ala Leu Glu Ala Ala Lys Ser Gly Glu Asp Phe Asp Lys Val Val
305                 310                 315                 320

Glu Arg Trp Gly Val Arg Arg Ser Asn Pro Gln Phe Trp Ser Tyr Phe
                325                 330                 335

His Asp Leu Glu Ala Tyr Ile Arg Glu Thr Glu Pro Val Glu Ala Gly
                340                 345                 350

Ala Leu Asp Met Asn Arg Tyr Glu Asn Leu
                355                 360

<210> SEQ ID NO 107
<211> LENGTH: 2316
<212> TYPE: DNA
<213> ORGANISM: Vibrio cholerae

<400> SEQUENCE: 107
```

| | | | | | |
|---|---|---|---|---|---|
| ttgtttgctg | gctgcgcaac | ctatgcaggc | cttaactatg | accaactgtt | tggtccacag | 60 |
| ctcgttcgtg | aacgtacggc | ggacgtagct | acacctcaag | caaacttctt | ccaaagcgaa | 120 |
| gtcaaaccca | ttatggataa | ccgctgtgtc | gtctgtcatg | cgtgctacga | tgcaccatgt | 180 |
| cagcttaagc | tttcttccgt | tgagggtatt | gaccgtggcg | cgagcaaagc | actggtatat | 240 |
| gaaggaacaa | gactcactgc | cgcagcgcca | acacgcttat | tcgaagatgc | agaaacgacc | 300 |
| caagagtggc | gcgatgcggg | ttttcatccg | gtacttaacg | aacgtgatca | gagcatggtg | 360 |
| gccaacattg | atgcaggcct | cattgcacgt | tgctacaac | aaaaagaacg | ccacccgctg | 420 |
| cctgatcaag | tccagttaga | aggttttgat | ttttcgatag | accgagaaca | aacctgtcca | 480 |
| acaattgaag | agtacgaaca | gtacgaaaaa | gataacccaa | cctggggaat | gccttttggt | 540 |
| atgccaaacc | tatcaaacag | tgaataccac | acactaatga | cttggctgga | aaacggcgcg | 600 |
| ataatgaacg | ttcatcaacc | aattagtgaa | caagagcaag | ctcaaattga | caagtatgaa | 660 |
| actttactca | atcgcgctga | tctaaaaaat | caactgatgg | ctcgctatat | ttacgagcat | 720 |
| ttgttttgt | ctcacctcta | cttttcagaa | ctcactgaag | atcctcgatt | ctttacgtta | 780 |
| gttcgttctt | ctactccacc | ggggcaacca | gtaaaacgta | tttcaacacg | tcgcccgtac | 840 |
| gatgatcccg | gggttgagcg | cgtgttttat | cgaattattc | cagaacaagg | gacgattgta | 900 |
| gataaaacgc | acatgccgtt | cgcgttaaac | aagcaacgta | ttgaaaactg | gaacacatgg | 960 |
| tttatcgatg | ctgattacac | ggttaatcaa | ctaccgagtt | atgaacctga | agttgctgca | 1020 |
| aacccgatga | catcatttat | cgatcttccg | gttaaatcac | gcttcaagtt | tatgttggac | 1080 |
| aatgcgcaaa | acacgatcat | ggcttacatt | aaagggcctg | tttgtcgtgg | ccaacttgca | 1140 |
| ctgaatgtta | tcaatgatcg | cttttggata | ttctttctag | atccagataa | agcagatatc | 1200 |
| cctgaagtaa | atgagtttta | ccgatctcag | gctgataacc | taagactgcc | agcagagcag | 1260 |
| gaaagcaaca | cgctgcctgt | taccaactgg | gttaaatacg | cgcgtcagca | agctcgctac | 1320 |
| ctagaagcca | agtctgaatt | taccaataac | tggtttaagg | aaggcgaaaa | cctatccacc | 1380 |
| gacgtaattt | gggacggtaa | tggcaccaac | cacaatgcgg | cattaacgat | tttccgccac | 1440 |
| tttgacagcg | cgtctgtcgt | acaagggtta | gttggcgagc | agccgaaaac | ggtatggatt | 1500 |
| cttgactacg | cgttactaga | acgcatccac | tatttgctcg | ttgctgggtt | tgatgtgtat | 1560 |
| ggcaacttcg | gccaccaact | catgacacga | atgttcatgg | acttcttgcg | tctggaaggc | 1620 |
| gaaagtaact | ttatctcgtt | gctgccaacc | gacatgcgtc | atgaactgca | atcaagctgg | 1680 |

-continued

```
tataaagatc aaagcccaca gttaagtgac tttttacaac gcaacgtgaa gccatttaac    1740
caaccaacca gcgtcgagtt caaaactgac gatccaaaaa cagagttagt cgagttgctt    1800
agagaacgag tttcagatgt tcttcttccg cgctacgagg ttaaagatac tgagctttct    1860
gctcaaagtg aacaacagct ccaacgtatt ggccaagttc gtggagaagg cctgaaaacc    1920
gttccgcaaa tcaccatgct tatggtgaga agccagtctg gaaaagatga gttattcacc    1980
ctacttcaca ataatgcaca cacgaatatt tctagcttgt ttgatgaaga aagcaaccgc    2040
gactttgcta acgatgatat gaccatcgta cgtggcgttg tggggagcta cccagcggca    2100 ttttctcga  tcaacgaaaa tcaagtaaaa gaatttgtcg atcaatttag tgccatccaa    2160
aatgaatccg attacgttaa gttgttggat aattttgcga ttcgcagaag ctcagaaaaa    2220
ttctggccgt ttagcgatcg tctgcacaat tggtaccgta caaaacaacc gatcgaattt    2280
ggattacttg actataatcg ttttgagaat cgatga                              2316
```

<210> SEQ ID NO 108
<211> LENGTH: 771
<212> TYPE: PRT
<213> ORGANISM: Vibrio cholerae

<400> SEQUENCE: 108

```
Met Phe Ala Gly Cys Ala Thr Tyr Ala Gly Leu Asn Tyr Asp Gln Leu
1               5                   10                  15

Phe Gly Pro Gln Leu Val Arg Glu Arg Thr Ala Asp Val Ala Thr Pro
            20                  25                  30

Gln Ala Asn Phe Phe Gln Ser Glu Val Lys Pro Ile Met Asp Asn Arg
        35                  40                  45

Cys Val Cys His Ala Cys Tyr Asp Ala Pro Cys Gln Leu Lys Leu
    50                  55                  60

Ser Ser Val Glu Gly Ile Asp Arg Gly Ala Ser Lys Ala Leu Val Tyr
65                  70                  75                  80

Glu Gly Thr Arg Leu Thr Ala Ala Pro Thr Arg Leu Phe Glu Asp
                85                  90                  95

Ala Glu Thr Thr Gln Glu Trp Arg Asp Ala Gly Phe His Pro Val Leu
            100                 105                 110

Asn Glu Arg Asp Gln Ser Met Val Ala Asn Ile Asp Ala Gly Leu Ile
        115                 120                 125

Ala Arg Leu Leu Gln Gln Lys Glu Arg His Pro Leu Pro Asp Gln Val
    130                 135                 140

Gln Leu Glu Gly Phe Asp Phe Ser Ile Asp Arg Glu Gln Thr Cys Pro
145                 150                 155                 160

Thr Ile Glu Glu Tyr Glu Gln Tyr Glu Lys Asp Asn Pro Thr Trp Gly
                165                 170                 175

Met Pro Phe Gly Met Pro Asn Leu Ser Asn Ser Glu Tyr His Thr Leu
            180                 185                 190

Met Thr Trp Leu Glu Asn Gly Ala Ile Met Asn Val His Gln Pro Ile
        195                 200                 205

Ser Glu Gln Glu Gln Ala Gln Ile Asp Lys Tyr Glu Thr Leu Leu Asn
    210                 215                 220

Arg Ala Asp Leu Lys Asn Gln Leu Met Ala Arg Tyr Ile Tyr Glu His
225                 230                 235                 240

Leu Phe Leu Ser His Leu Tyr Phe Ser Glu Leu Thr Glu Asp Pro Arg
                245                 250                 255

Phe Phe Thr Leu Val Arg Ser Ser Thr Pro Pro Gly Gln Pro Val Lys
```

```
                    260             265             270
Arg Ile Ser Thr Arg Arg Pro Tyr Asp Asp Pro Gly Val Glu Arg Val
                275             280             285

Phe Tyr Arg Ile Ile Pro Glu Gln Gly Thr Ile Val Asp Lys Thr His
            290             295             300

Met Pro Phe Ala Leu Asn Lys Gln Arg Ile Glu Asn Trp Asn Thr Trp
305             310             315             320

Phe Ile Asp Ala Asp Tyr Thr Val Asn Gln Leu Pro Ser Tyr Glu Pro
                325             330             335

Glu Val Ala Ala Asn Pro Met Thr Ser Phe Ile Asp Leu Pro Val Lys
            340             345             350

Ser Arg Phe Lys Phe Met Leu Asp Asn Ala Gln Asn Thr Ile Met Ala
        355             360             365

Tyr Ile Lys Gly Pro Val Cys Arg Gly Gln Leu Ala Leu Asn Val Ile
    370             375             380

Asn Asp Arg Phe Trp Ile Phe Phe Leu Asp Pro Asp Lys Ala Asp Ile
385             390             395             400

Pro Glu Val Asn Glu Phe Tyr Arg Ser Gln Ala Asp Asn Leu Arg Leu
            405             410             415

Pro Ala Glu Gln Glu Ser Asn Thr Leu Pro Val Thr Asn Trp Val Lys
        420             425             430

Tyr Ala Arg Gln Gln Ala Arg Tyr Leu Glu Ala Lys Ser Glu Phe Thr
    435             440             445

Asn Asn Trp Phe Lys Glu Gly Glu Asn Leu Ser Thr Asp Val Ile Trp
450             455             460

Asp Gly Asn Gly Thr Asn His Asn Ala Ala Leu Thr Ile Phe Arg His
465             470             475             480

Phe Asp Ser Ala Ser Val Val Gln Gly Leu Val Gly Glu Gln Pro Lys
            485             490             495

Thr Val Trp Ile Leu Asp Tyr Ala Leu Leu Glu Arg Ile His Tyr Leu
        500             505             510

Leu Val Ala Gly Phe Asp Val Tyr Gly Asn Phe Gly His Gln Leu Met
    515             520             525

Thr Arg Met Phe Met Asp Phe Leu Arg Leu Glu Gly Glu Ser Asn Phe
530             535             540

Ile Ser Leu Leu Pro Thr Asp Met Arg His Glu Leu Gln Ser Ser Trp
545             550             555             560

Tyr Lys Asp Gln Ser Pro Gln Leu Ser Asp Phe Leu Gln Arg Asn Val
            565             570             575

Lys Pro Phe Asn Gln Pro Thr Ser Val Glu Phe Lys Thr Asp Asp Pro
        580             585             590

Lys Thr Glu Leu Val Glu Leu Leu Arg Glu Arg Val Ser Asp Val Leu
    595             600             605

Leu Pro Arg Tyr Glu Val Lys Asp Thr Glu Leu Ser Ala Gln Ser Glu
            610             615             620

Gln Gln Leu Gln Arg Ile Gly Gln Val Arg Gly Glu Gly Leu Lys Thr
625             630             635             640

Val Pro Gln Ile Thr Met Leu Met Val Arg Ser Gln Ser Gly Lys Asp
            645             650             655

Glu Leu Phe Thr Leu Leu His Asn Asn Ala His Thr Asn Ile Ser Ser
        660             665             670

Leu Phe Asp Glu Glu Ser Asn Arg Asp Phe Ala Asn Asp Asp Met Thr
    675             680             685
```

```
Ile Val Arg Gly Val Val Gly Ser Tyr Pro Ala Ala Phe Phe Ser Ile
        690                 695                 700

Asn Glu Asn Gln Val Lys Glu Phe Val Asp Gln Phe Ser Ala Ile Gln
705                 710                 715                 720

Asn Glu Ser Asp Tyr Val Lys Leu Leu Asp Asn Phe Ala Ile Arg Arg
                725                 730                 735

Ser Ser Glu Lys Phe Trp Pro Phe Ser Asp Arg Leu His Asn Trp Tyr
            740                 745                 750

Arg Thr Lys Gln Pro Ile Glu Phe Gly Leu Leu Asp Tyr Asn Arg Phe
        755                 760                 765

Glu Asn Arg
    770

<210> SEQ ID NO 109
<211> LENGTH: 2358
<212> TYPE: DNA
<213> ORGANISM: Vibrio cholerae

<400> SEQUENCE: 109
```

| | | | | | |
|---|---|---|---|---|---|
| atgaatttca | aatcttcgat | tctgttgctg | ctggccacgg | ttttctccgg | ttgcgccatg | 60 |
| tacgcaggca | tcaactatga | tcagctcttt | ggcacagagc | aggtacgtga | gcgacaatta | 120 |
| cctttgcact | ctagccaagc | tcagcatttt | ttaaacgaag | taaaacccat | cttagataac | 180 |
| cgctgtgtcg | tctgtcacgc | ctgttacgat | gcaccctgtc | agctcaaaat | gacctcggct | 240 |
| gaaggcattg | atcgcggggc | gagcaaagcg | ttggtttatc | agggaactcg | gctgacggcc | 300 |
| gctactccaa | ctcgtctcta | cgaagatgct | cagttaaccc | aagagtggcg | agctgctggt | 360 |
| tttcatcccg | tgctgaatga | gcgaaatcaa | accgcgcaag | ccaatcttga | tgctggggtg | 420 |
| atggcacgtt | tgctgatgca | gaaagagcgt | catccactac | cacagcaaga | tcagttacaa | 480 |
| ggatttgatt | tttcaattga | tcgtgagcaa | acctgcccaa | cgatcaacga | aatggatcac | 540 |
| ttcgaacaag | tgaatcctaa | ttggggaatg | ccctttggta | tgccgaattt | atccccaag | 600 |
| gagtacacta | ccctgctctc | ttggctacaa | gagggagccg | tgatgaatca | agcgctcccg | 660 |
| ctgagtgcgc | aagaacaagc | tttggttacg | gaatacgaag | ccttgttgaa | tcacagctcg | 720 |
| cgtaaaaatc | agctcgcagc | acgctatatc | tacgaacatc | tattcctctc | acatctgtac | 780 |
| ttttcagaga | tagcgcagga | gcggcctcgt | ttctttaaac | tcatccgctc | cagtactcca | 840 |
| ccgggtgagc | ctgtaaagcg | aatcgtgacg | cgtcgtccgt | acgatgatcc | gggcgttgag | 900 |
| cgagtctatt | atcgccttgt | gccagaacaa | gagacgattg | tcgataaaac | ccacatgcct | 960 |
| ttcgcactca | acaagcaacg | gattgcgaac | tggaaactct | ggtttattga | tgcggattat | 1020 |
| gaggttgccg | agcttccaag | ttatcgtccg | gatattgccg | caaacccgat | gtccgcgttc | 1080 |
| atcgaccttc | ccgtgaaagc | gcgctttaag | ttcttgctcg | ataatgcgca | aaatacggtg | 1140 |
| atggccttta | tcaaaggccc | agtgtgtcga | ggccagttgg | cgctgaatgt | gattaacgat | 1200 |
| agattctggg | tcttcttcct | cgatcctgag | aaagccgatc | ttccagaagt | caacgaattc | 1260 |
| tatcgctcac | aagtcaacaa | tttgaagcta | ccggctgaac | aagagaatac | ggcactgccg | 1320 |
| ctgagtaact | gggtacgtta | ttcgctacaa | caaagccgtt | atctcgaagc | aaaatctgaa | 1380 |
| tttattaatc | aatggtttaa | aaatggtacg | caccttacca | cggacatcat | tgggatgga | 1440 |
| gcgggcataa | accctaatgc | cgcattaacg | attttccgcc | atttcgatag | cgcatctgtc | 1500 |
| gtgcaaggat | tggtgggtga | gcctcccaaa | accgcttgga | taatggatta | tgcgctgctt | 1560 |
| gagcgcattc | attatctgct | tgttgctggt | tttgatgtat | atggcaattt | cggacatcag | 1620 |

```
ttgattactc gtatgttcat ggattttctg cgcatggagg gtgagagtaa ttttgttgcc    1680
ctgctaccac gcgatatgcg ccatcaggag ttatctagtt ggtaccaaaa tcaaagtgta    1740
cagttttccg atttcttgca acgtaacgta aaaccctttg atcagccaac cagcgttaac    1800
tatgtgactg ataacccgaa acaggagctg tttgctaaac tccgcaagca agtacagtcg    1860
gtattgagtg atcgatacgt gataactcaa acgggattca aagccgaaca tgagtttgct    1920
ttgcgccaaa tcgatcatct gcgtggtgaa ggtttgctgc ccattccgca attgatgatg    1980
ttgatgattg aaagtgaaca aggtaaaccg caactgttta cgctcatcca caacaatgcc    2040
cacaccaata tctcgagctt gtttgatgaa cagaacaacc gcgacccaa aaatgataat     2100 ttgactttag tgcgcggagt ggtcggcagt tatccatcgg cgtacttaac actgaaagaa    2160
aaccagatcc cggagctgta tcaacgcctt gcggcgatga agtcagagca agattatgtc    2220
gccctattgg atcgttttgc agtacgccgc agctcacccg aattttgggc atttagcgat    2280
cttgtgcatc aatggtatcg ccaagatcaa cccattgagt ttggtttgct cgattacaac    2340
cgtttcgaaa accgttga                                                   2358
```

<210> SEQ ID NO 110
<211> LENGTH: 785
<212> TYPE: PRT
<213> ORGANISM: Vibrio cholerae

<400> SEQUENCE: 110

```
Met Asn Phe Lys Ser Ser Ile Leu Leu Leu Ala Thr Val Phe Ser
1               5                   10                  15

Gly Cys Ala Met Tyr Ala Gly Ile Asn Tyr Asp Gln Leu Phe Gly Thr
            20                  25                  30

Glu Gln Val Arg Glu Arg Gln Leu Pro Leu His Ser Ser Gln Ala Gln
        35                  40                  45

His Phe Leu Asn Glu Val Lys Pro Ile Leu Asp Asn Arg Cys Val Val
    50                  55                  60

Cys His Ala Cys Tyr Asp Ala Pro Cys Gln Leu Lys Met Thr Ser Ala
65                  70                  75                  80

Glu Gly Ile Asp Arg Gly Ala Ser Lys Ala Leu Val Tyr Gln Gly Thr
                85                  90                  95

Arg Leu Thr Ala Ala Thr Pro Thr Arg Leu Tyr Glu Asp Ala Gln Leu
            100                 105                 110

Thr Gln Glu Trp Arg Ala Ala Gly Phe His Pro Val Leu Asn Glu Arg
        115                 120                 125

Asn Gln Thr Ala Gln Ala Asn Leu Asp Ala Gly Val Met Ala Arg Leu
    130                 135                 140

Leu Met Gln Lys Glu Arg His Pro Leu Pro Gln Asp Gln Leu Gln
145                 150                 155                 160

Gly Phe Asp Phe Ser Ile Asp Arg Glu Gln Thr Cys Pro Thr Ile Asn
                165                 170                 175

Glu Met Asp His Phe Glu Gln Val Asn Pro Asn Trp Gly Met Pro Phe
            180                 185                 190

Gly Met Pro Asn Leu Ser Pro Lys Glu Tyr Thr Thr Leu Leu Ser Trp
        195                 200                 205

Leu Gln Glu Gly Ala Val Met Asn Gln Ala Leu Pro Leu Ser Ala Gln
    210                 215                 220

Glu Gln Ala Leu Val Thr Glu Tyr Gly Ala Leu Leu Asn His Ser Ser
225                 230                 235                 240

Arg Lys Asn Gln Leu Ala Ala Arg Tyr Ile Tyr Glu His Leu Phe Leu
```

```
                    245                 250                 255
Ser His Leu Tyr Phe Ser Glu Ile Ala Gln Glu Arg Pro Arg Phe Phe
                260                 265                 270

Lys Leu Ile Arg Ser Ser Thr Pro Pro Gly Glu Pro Val Lys Arg Ile
            275                 280                 285

Val Thr Arg Arg Pro Tyr Asp Asp Pro Gly Val Glu Arg Val Tyr Tyr
        290                 295                 300

Arg Leu Val Pro Glu Gln Glu Thr Ile Val Asp Lys Thr His Met Pro
305                 310                 315                 320

Phe Ala Leu Asn Lys Gln Arg Ile Ala Asn Trp Lys Leu Trp Phe Ile
                325                 330                 335

Asp Ala Asp Tyr Glu Val Ala Glu Leu Pro Ser Tyr Arg Pro Asp Ile
            340                 345                 350

Ala Ala Asn Pro Met Ser Ala Phe Ile Asp Leu Pro Val Lys Ala Arg
        355                 360                 365

Phe Lys Phe Leu Leu Asp Asn Ala Gln Asn Thr Val Met Ala Phe Ile
    370                 375                 380

Lys Gly Pro Val Cys Arg Gly Gln Leu Ala Leu Asn Val Ile Asn Asp
385                 390                 395                 400

Arg Phe Trp Val Phe Phe Leu Asp Pro Glu Lys Ala Asp Leu Pro Glu
                405                 410                 415

Val Asn Glu Phe Tyr Arg Ser Gln Val Asn Asn Leu Lys Leu Pro Ala
            420                 425                 430

Glu Gln Glu Asn Thr Ala Leu Pro Leu Ser Asn Trp Val Arg Tyr Ser
        435                 440                 445

Leu Gln Gln Ser Arg Tyr Leu Glu Ala Lys Ser Glu Phe Ile Asn Gln
    450                 455                 460

Trp Phe Lys Asn Gly Thr His Leu Thr Thr Asp Ile Ile Trp Asp Gly
465                 470                 475                 480

Ala Gly Ile Asn Pro Asn Ala Ala Leu Thr Ile Phe Arg His Phe Asp
                485                 490                 495

Ser Ala Ser Val Val Gln Gly Leu Val Gly Glu Pro Pro Lys Thr Ala
            500                 505                 510

Trp Ile Met Asp Tyr Ala Leu Leu Glu Arg Ile His Tyr Leu Leu Val
        515                 520                 525

Ala Gly Phe Asp Val Tyr Gly Asn Phe Gly His Gln Leu Ile Thr Arg
    530                 535                 540

Met Phe Met Asp Phe Leu Arg Met Glu Gly Glu Ser Asn Phe Val Ala
545                 550                 555                 560

Leu Leu Pro Arg Asp Met Arg His Gln Glu Leu Ser Ser Trp Tyr Gln
                565                 570                 575

Asn Gln Ser Val Gln Phe Ser Asp Phe Leu Gln Arg Asn Val Lys Pro
            580                 585                 590

Phe Asp Gln Pro Thr Ser Val Asn Tyr Val Thr Asp Asn Pro Lys Gln
        595                 600                 605

Glu Leu Phe Ala Lys Leu Arg Lys Gln Val Gln Ser Val Leu Ser Asp
    610                 615                 620

Arg Tyr Val Ile Thr Gln Thr Gly Phe Lys Ala Glu His Glu Phe Ala
625                 630                 635                 640

Leu Arg Gln Ile Asp His Leu Arg Gly Glu Gly Leu Leu Pro Ile Pro
                645                 650                 655

Gln Leu Met Met Leu Met Ile Glu Ser Glu Gln Gly Lys Pro Gln Leu
            660                 665                 670
```

```
                Phe Thr Leu Ile His Asn Asn Ala His Thr Asn Ile Ser Ser Leu Phe
                            675                 680                 685

Asp Glu Gln Asn Asn Arg Asp Pro Lys Asn Asp Asn Leu Thr Leu Val
                        690                 695                 700

Arg Gly Val Val Gly Ser Tyr Pro Ser Ala Tyr Leu Thr Leu Lys Glu
                705                 710                 715                 720

Asn Gln Ile Pro Glu Leu Tyr Gln Arg Leu Ala Ala Met Lys Ser Glu
                            725                 730                 735

Gln Asp Tyr Val Ala Leu Leu Asp Arg Phe Ala Val Arg Arg Ser Ser
                        740                 745                 750

Pro Glu Phe Trp Ala Phe Ser Asp Leu Val His Gln Trp Tyr Arg Gln
                            755                 760                 765

Asp Gln Pro Ile Glu Phe Gly Leu Leu Asp Tyr Asn Arg Phe Glu Asn
                        770                 775                 780

Arg
                785

<210> SEQ ID NO 111
<211> LENGTH: 2394
<212> TYPE: DNA
<213> ORGANISM: Shewanella sp.

<400> SEQUENCE: 111
atgaatccga taaatgcagt ctggaaacgt tggctattgg ccctagtgtt agcggtcacg         60
ggttgtgcca gcgtcgctca agtggatttt gataatcttt acggtaaaag ctcgccgctg        120
acgcgggccg ataatcagcc aatccagagt gaactcacag cacaaacaaa gacttatcat        180
tcggctgttg aacctatcat caacggtcgc tgcgtggttt gccatgcctg ttacgatgcg        240
ccctgccaac ttaaaatgac ttccagtgag gggattgaac ggggcgcgaa caaggaaaaa        300
gtctatcagg gcacccgctt gatggcggca caccaaatc ggttatttgt cgatgcccac         360
acgcctgaag cttggcgcga acgcggtttt tatcccgtgc tcaatgagcg cgcccagacc        420
ccacaggcca atactcaggc ctcagtgctg gcgcggatgc taacgctaaa acaggcccat        480
cccctaccgg acactaaact gctcgataaa agtttcgact ttagcctcga tcgggttcag        540
caatgcgcca gcattgagga aatggacaaa tacgagcaat accaaccgct tgcgggcatg        600
ccctacggct tgcatgcgct caatcagcag gaacataagg tattgatgca atggctcgaa        660
cagggcgcag tgttgccgac gccacccgcg ctcagcgccg agtttaatca gaaaattgcc        720
cgctgggagc agttcttaaa tgccgacagc ctcaaggcgc aactgagcgc ccgttatatt        780
tacgagcact tatttgcctt tcacctgtat tttgagtcat taaccgcagc cgatgctccc        840
gcggcttact tcgagttagt cgctcacgc acgccgccgg gcaaaccgat tgatctgatt        900
gccagtcgtc gccccttcga cgatccgcaa gtgtcgcggg tgtattaccg ctttcagccc        960
tatcgcgcca cgatcgtcga taaacccat attccctaca ccttaaataa cactgtgctg       1020
caaaactggc agaagtggtt tatcgatgct aaataccaag tcagctcgct gcctagctat       1080
aaacctagcg tggcggccaa tcccttcgag gcctttattc agctgcccgc aggctcgcgt       1140
tatcgcttta tgcttacccg cgctcaagac accattatgg gctttatcaa gggaccagtt       1200
tgccgtggtc aggtcgccct caatgtgatc aacgatagat tgggtcta ctttgtcacc        1260 ccagaatata tggacgatag cgactttacc gatttctatc agggccaaat cgagaaccta       1320
cgcatgcccg ccgaggagga aagtaccgcc cttgccgtga cctgggtgaa atacgccgcc       1380
aaacagggcg agtatatgcg ggcgcgaaat cagttttaa atcataagtt taaaaatggt       1440
```

-continued

```
cgtcacctca ccatcgacgg tctatgggat ggcaacggca ataatgacaa tgccagcctg    1500
acggtattta gacatttcga taatgccact gtggtcaaag ggttagtggg agaatccccc    1560
aaaacggctt gggtgatcga ctatgccctg ctggagcgca ttcactatct cttggtcgcg    1620
ggtttcgatg tgtatggtaa ctatggccac cagctgctca ctcgcctgta tatggatttt    1680
ttacgcatgg agggcgagtc taacttcttg accttgttgc cccaagagga gcgccgtaag    1740
cagtttaagg attggtatca ggatgcaggt acccagctga ccgcctttat cgcggggggac   1800 attaatacct tcaatcaacc cacaggcgtg ctctactaca cggacgatct taaggccgag    1860
ctctaccaaa agttggccgc taaggtcggc gaggttcagc cccaacgtta tcaaatcgct    1920
ctcagtcagt tgcaacccaa tagcaaggct tgttgcagg cgctagggcg agtcaaaggt     1980
acgcaagcga ctcttttgcc cgagctgacg atgatcatga ttgagccgca accccaggc    2040 aaagcggaaa tcttcacctt agtgcgtaac agtgcccatc ggaatatttc gagcctattc    2100
aatgaggaaa gcaaccgcga gcccgctaag gatgatgtca cgctagtgcg cgggcttttg    2160
ggcagttacc ccgaagcctt ctggcatatc aaggagcagg acttagccaa agtcgtggct    2220
aaggtcgaag gcatgcaaac cgaaaaagac tacgaggcgt tattggattt ggcggcggtg    2280
cgccgtaccg atccgcggtt ctgggccttt agtgacaaac tcaaccaagc cttttcgac    2340 agtcatccga ttgaaagcgg ttggctggac tacaatcgac tgcaaaatcg ctaa          2394
```

<210> SEQ ID NO 112
<211> LENGTH: 797
<212> TYPE: PRT
<213> ORGANISM: Shewanella sp.

<400> SEQUENCE: 112

```
Met Asn Pro Ile Asn Ala Val Trp Lys Arg Trp Leu Leu Ala Leu Val
 1               5                  10                  15

Leu Ala Val Thr Gly Cys Ala Ser Val Ala Gln Val Asp Phe Asp Asn
             20                  25                  30

Leu Tyr Gly Lys Ser Ser Pro Leu Thr Arg Ala Asp Asn Gln Pro Ile
         35                  40                  45

Gln Ser Glu Leu Thr Ala Gln Thr Lys Thr Tyr His Ser Ala Val Glu
     50                  55                  60

Pro Ile Ile Asn Gly Arg Cys Val Val Cys His Ala Cys Tyr Asp Ala
 65                  70                  75                  80

Pro Cys Gln Leu Lys Met Thr Ser Ser Glu Gly Ile Glu Arg Gly Ala
                 85                  90                  95

Asn Lys Glu Lys Val Tyr Gln Gly Thr Arg Leu Met Ala Ala Thr Pro
            100                 105                 110

Asn Arg Leu Phe Val Asp Ala His Thr Pro Glu Ala Trp Arg Glu Arg
        115                 120                 125

Gly Phe Tyr Pro Val Leu Asn Glu Arg Ala Gln Thr Pro Gln Ala Asn
    130                 135                 140

Thr Gln Ala Ser Val Leu Ala Arg Met Leu Thr Leu Lys Gln Ala His
145                 150                 155                 160

Pro Leu Pro Asp Thr Lys Leu Leu Asp Lys Ser Phe Asp Phe Ser Leu
                165                 170                 175

Asp Arg Val Gln Gln Cys Ala Ser Ile Glu Glu Met Asp Lys Tyr Glu
            180                 185                 190

Gln Tyr Gln Pro Leu Ala Gly Met Pro Tyr Gly Leu His Ala Leu Asn
        195                 200                 205

Gln Gln Glu His Lys Val Leu Met Gln Trp Leu Glu Gln Gly Ala Val
```

```
                210                 215                 220
Leu Pro Thr Pro Pro Ala Leu Ser Ala Glu Phe Asn Gln Glu Ile Ala
225                 230                 235                 240

Arg Trp Glu Gln Phe Leu Asn Ala Asp Ser Leu Lys Ala Gln Leu Ser
                245                 250                 255

Ala Arg Tyr Ile Tyr Glu His Leu Phe Ala Phe His Leu Tyr Phe Glu
                260                 265                 270

Ser Leu Thr Ala Ala Asp Ala Pro Ala Tyr Phe Glu Leu Val Arg
                275                 280                 285

Ser Arg Thr Pro Pro Gly Lys Pro Ile Asp Leu Ile Ala Ser Arg Arg
                290                 295                 300

Pro Phe Asp Asp Pro Gln Val Ser Arg Val Tyr Tyr Arg Phe Gln Pro
305                 310                 315                 320

Tyr Arg Ala Thr Ile Val Asp Lys Thr His Ile Pro Tyr Thr Leu Asn
                325                 330                 335

Asn Thr Val Leu Gln Asn Trp Gln Lys Trp Phe Ile Asp Ala Lys Tyr
                340                 345                 350

Gln Val Ser Ser Leu Pro Ser Tyr Lys Pro Ser Val Ala Ala Asn Pro
                355                 360                 365

Phe Glu Ala Phe Ile Gln Leu Pro Ala Gly Ser Arg Tyr Arg Phe Met
370                 375                 380

Leu Thr Arg Ala Gln Asp Thr Ile Met Gly Phe Ile Lys Gly Pro Val
385                 390                 395                 400

Cys Arg Gly Gln Val Ala Leu Asn Val Ile Asn Asp Arg Phe Trp Val
                405                 410                 415

Tyr Phe Val Thr Pro Glu Tyr Met Asp Asp Ser Asp Phe Thr Asp Phe
                420                 425                 430

Tyr Gln Gly Gln Ile Glu Asn Leu Arg Met Pro Ala Glu Glu Ser
                435                 440                 445

Thr Ala Leu Ala Val Thr Trp Val Lys Tyr Ala Ala Lys Gln Gly Glu
                450                 455                 460

Tyr Met Arg Ala Arg Asn Gln Phe Leu Asn His Lys Phe Lys Asn Gly
465                 470                 475                 480

Arg His Leu Thr Ile Asp Gly Leu Trp Asp Gly Asn Gly Asn Asn Asp
                485                 490                 495

Asn Ala Ser Leu Thr Val Phe Arg His Phe Asp Asn Ala Thr Val Val
                500                 505                 510

Lys Gly Leu Val Gly Glu Ser Pro Lys Thr Ala Trp Val Ile Asp Tyr
                515                 520                 525

Ala Leu Leu Glu Arg Ile His Tyr Leu Leu Val Ala Gly Phe Asp Val
                530                 535                 540

Tyr Gly Asn Tyr Gly His Gln Leu Leu Thr Arg Leu Tyr Met Asp Phe
545                 550                 555                 560

Leu Arg Met Glu Gly Glu Ser Asn Phe Leu Thr Leu Pro Gln Glu
                565                 570                 575

Glu Arg Arg Lys Gln Phe Lys Asp Trp Tyr Gln Asp Ala Gly Thr Gln
                580                 585                 590

Leu Thr Ala Phe Ile Ala Gly Asp Ile Asn Thr Phe Asn Gln Pro Thr
                595                 600                 605

Gly Val Leu Tyr Tyr Thr Asp Asp Leu Lys Ala Glu Leu Tyr Gln Lys
                610                 615                 620

Leu Ala Ala Lys Val Gly Glu Val Gln Pro Gln Arg Tyr Gln Ile Ala
625                 630                 635                 640
```

```
Leu Ser Gln Leu Gln Pro Asn Ser Lys Ala Leu Leu Gln Ala Leu Gly
            645                 650                 655

Arg Val Lys Gly Thr Gln Ala Thr Leu Leu Pro Glu Leu Thr Met Ile
        660                 665                 670

Met Ile Glu Pro Gln Thr Pro Gly Lys Ala Glu Ile Phe Thr Leu Val
    675                 680                 685

Arg Asn Ser Ala His Arg Asn Ile Ser Ser Leu Phe Asn Glu Glu Ser
690                 695                 700

Asn Arg Glu Pro Ala Lys Asp Asp Val Thr Leu Val Arg Gly Leu Leu
705                 710                 715                 720

Gly Ser Tyr Pro Glu Ala Phe Trp His Ile Lys Glu Gln Asp Leu Ala
                725                 730                 735

Lys Val Ala Lys Val Glu Gly Met Gln Thr Glu Lys Asp Tyr Glu
        740                 745                 750

Ala Leu Leu Asp Leu Ala Ala Val Arg Arg Thr Asp Pro Arg Phe Trp
    755                 760                 765

Ala Phe Ser Asp Lys Leu Asn Gln Ala Phe Phe Asp Ser His Pro Ile
770                 775                 780

Glu Ser Gly Trp Leu Asp Tyr Asn Arg Leu Gln Asn Arg
785                 790                 795

<210> SEQ ID NO 113
<211> LENGTH: 2388
<212> TYPE: DNA
<213> ORGANISM: Pseudomonas putida

<400> SEQUENCE: 113
atgttgggcg gtggaggca gcgcaaggca cccaggacga ccaggcaaca aatcgtgatg        60
gctttcaaga accaggactt tccgcacatg gtgcatcgta tccttgccgg cgccttcgcc       120
ttgctcatca gcggcgcggt attcgggcag gcccccagt cgagcccggc tatttcctac       180
acccgggaca ttcaaccgat cttcaccgag aagtgcgtgg cctgccacgc ctgcaacgac      240
gccgcctgcc agctcaagct ggaaagccct gaaggcgcgg tacgcggggc cagcaaggtc      300
ccggtgtacc agggcgagcg gagcaaggcg gtgcccacca cgcggctgtt ctacgacgcc      360
cacagcgaag agcaatggcg caagaagggc ttctactcgg tgctcgacaa ccagggcggt      420
caggccgcgc tgatggcgcg catgctggaa ttgggccaca gaccccgct tacgcccaac       480
gccaagctgc ccgaagagat cgtcctgggc ctgagccgca acaacatgtg cccgttgccc      540
catgaattcg acgcctatgc cggcgcacac cccaaggagg gcatgccgct ggcggtgacc      600
gggctgaccg acgacgaata cgccaccctg cgccgctggc tggcggccgg tgcgccggtg      660
gagtaccagc cgatccagcc tagcgcggcc gaagccaggc agatcgcaga gtgggaagaa      720
ctgctcaacc gccgggttc accgaggcg ctggtgggcc gctggctgta cgagcacctg        780
tttttggcgc acatctattt cgcgggcggc gagcagggcc acttcttcca gtgggtgcgc      840
tcgcgcacgc caagtggcaa gccggtcgat atcattgcca cccgccgccc caacgaccca      900
ccgggcacgg acttctacta ccggttgatc ccggtgcagg gcgtgatcgt gcacaagacg      960
cacatcactt acccgatggg gccgcagaag ctcaagcgcg tgaagcagct gttctatgcc     1020
ggtgactggc atgctgccgc gcttccgggc tacggccccgc gccaccgggc caatccgttt     1080
gaaaccttcg aggcgatccc ggcggtggcg cgctaccagt tcatgctgga taacgccgag     1140
tacttcgtgc gcaccttcat ccgtggcccg gtgtgccgcg gcagattgc cactgacgtg      1200
atccgcgaca cttctgggc gctgttccag gagccggcct tcgatcgcta catcaccgat     1260
```

```
gccaagtacc gcggcgaggc taccccgctg ctggccatgc ctggtcagat cgatgacgtg    1320
ggcagtgtgc tgagcctgtg gcacgcctat cgtgacaagc gcaacgacta cgagaaactg    1380
cgccgtgaag cctatgccga aatgccggca ccgagatggt cgacgctgtg gccggtaac     1440 gacaatgcgc tgctgagcat cttccgtcac ttcgacagcg catcggtgac caagggcctg    1500 gtggggatg tgccgctgac cgtgtggctg ttcgactacc cgttgttcga gcgcacgtat     1560
taccagctgg cggtcaactt cgatgtgtat ggcaacgttt cgcaccagtt gcagacgcgc    1620
ctgtacttcg acctgatccg caacggcgcc gaggtcaact tcctgcgcct gatgccggcc    1680
gaccagcgca aggcgatcct tggcgactgg taccagaaca gtggcaaggt gaagatgtgg    1740
atggattatg aagacatcga caccgacacc ccgagtggca tcaagctcga cccgcgcaac    1800
cccaagcgcg actttggcct gaagctgctg cagcgcaccg gcagcctgaa tgccgcaccg    1860
gacccgatca accgctgcca gggcgcgttc tgctcacggc cgcagatgag cgaagaattc    1920
cgcaatgccg agcagtcgct cagccgtctg gtgtcgcgcc cggcggccgg gctgaaggtg    1980
atcaaccagt tgcccgaggc gaccatgctg cgtatcgaag ggcaggacgg ccaacgtcag    2040
gtgtacagcc tgctgcgcaa ccgcgcgcac agcaacgtgg cgttcctgct gggtgaggcg    2100
taccgctacc agccggggct ggatacactg accctgtacc cgggtgtgct ctccagctac    2160
ccgaacttca tcttcaacat cccgaccaag gatgtgccgg agttcgtcga ggacatggag    2220
tacgccaaag atgacgcggc gaagttcgag cgcattgtca tgcgctgggg tgtgcgccgc    2280
agtcacccgg cgttctggcg ctatttccat gacctgaaca gctatatcaa ggaaaccgaa    2340
ccggtcgagg cgggcgtgct ggacatgaac cggtacgaga acctctga                2388
```

<210> SEQ ID NO 114
<211> LENGTH: 795
<212> TYPE: PRT
<213> ORGANISM: Pseudomonas putida

<400> SEQUENCE: 114

```
Met Leu Gly Gly Trp Arg Gln Arg Lys Ala Pro Arg Thr Thr Arg Gln
1               5                   10                  15

Gln Ile Val Met Ala Phe Lys Asn Gln Asp Phe Pro His Met Val His
            20                  25                  30

Arg Ile Leu Ala Gly Ala Phe Ala Leu Leu Ile Ser Gly Ala Val Phe
        35                  40                  45

Gly Gln Ala Pro Gln Ser Ser Pro Ala Ile Ser Tyr Thr Arg Asp Ile
    50                  55                  60

Gln Pro Ile Phe Thr Glu Lys Cys Val Ala Cys His Ala Cys Asn Asp
65                  70                  75                  80

Ala Ala Cys Gln Leu Lys Leu Glu Ser Pro Glu Gly Ala Val Arg Gly
                85                  90                  95

Ala Ser Lys Val Pro Val Tyr Gln Gly Glu Arg Ser Lys Ala Val Pro
            100                 105                 110

Thr Thr Arg Leu Phe Tyr Asp Ala His Ser Glu Glu Gln Trp Arg Lys
        115                 120                 125

Lys Gly Phe Tyr Ser Val Leu Asp Asn Gln Gly Gln Ala Ala Leu
    130                 135                 140

Met Ala Arg Met Leu Glu Leu Gly His Lys Thr Pro Leu Thr Pro Asn
145                 150                 155                 160

Ala Lys Leu Pro Glu Glu Ile Val Leu Gly Leu Ser Arg Asn Asn Met
                165                 170                 175

Cys Pro Leu Pro His Glu Phe Asp Ala Tyr Ala Gly Ala His Pro Lys
```

```
                    180                 185                 190
Glu Gly Met Pro Leu Ala Val Thr Gly Leu Thr Asp Asp Glu Tyr Ala
                195                 200                 205
Thr Leu Arg Arg Trp Leu Ala Ala Gly Ala Pro Val Glu Tyr Gln Pro
            210                 215                 220
Ile Gln Pro Ser Ala Ala Glu Ala Arg Gln Ile Ala Glu Trp Glu Glu
225                 230                 235                 240
Leu Leu Asn Arg Pro Gly Ser Thr Glu Ala Leu Val Gly Arg Trp Leu
                245                 250                 255
Tyr Glu His Leu Phe Leu Ala His Ile Tyr Phe Ala Gly Gly Glu Gln
            260                 265                 270
Gly His Phe Phe Gln Trp Val Arg Ser Arg Thr Pro Ser Gly Lys Pro
        275                 280                 285
Val Asp Ile Ile Ala Thr Arg Arg Pro Asn Asp Pro Pro Gly Thr Asp
        290                 295                 300
Phe Tyr Tyr Arg Leu Ile Pro Val Gln Gly Val Ile Val His Lys Thr
305                 310                 315                 320
His Ile Thr Tyr Pro Met Gly Pro Gln Lys Leu Lys Arg Val Lys Gln
                325                 330                 335
Leu Phe Tyr Ala Gly Asp Trp His Ala Ala Leu Pro Gly Tyr Gly
            340                 345                 350
Pro Arg His Arg Ala Asn Pro Phe Glu Thr Phe Glu Ala Ile Pro Ala
        355                 360                 365
Val Ala Arg Tyr Gln Phe Met Leu Asp Asn Ala Glu Tyr Phe Val Arg
        370                 375                 380
Thr Phe Ile Arg Gly Pro Val Cys Arg Gly Gln Ile Ala Thr Asp Val
385                 390                 395                 400
Ile Arg Asp Asn Phe Trp Ala Leu Phe Gln Glu Pro Ala Phe Asp Arg
                405                 410                 415
Tyr Ile Thr Asp Ala Lys Tyr Arg Gly Glu Ala Thr Pro Leu Leu Ala
            420                 425                 430
Met Pro Gly Gln Ile Asp Asp Val Gly Ser Val Leu Ser Leu Trp His
        435                 440                 445
Ala Tyr Arg Asp Lys Arg Asn Asp Tyr Glu Lys Leu Arg Arg Glu Ala
        450                 455                 460
Tyr Ala Glu Met Pro Ala Pro Arg Trp Ser Thr Leu Trp Ala Gly Asn
465                 470                 475                 480
Asp Asn Ala Leu Leu Ser Ile Phe Arg His Phe Asp Ser Ala Ser Val
                485                 490                 495
Thr Lys Gly Leu Val Gly Asp Val Pro Leu Thr Val Trp Leu Phe Asp
            500                 505                 510
Tyr Pro Leu Phe Glu Arg Thr Tyr Tyr Gln Leu Ala Val Asn Phe Asp
        515                 520                 525
Val Tyr Gly Asn Val Ser His Gln Leu Gln Thr Arg Leu Tyr Phe Asp
        530                 535                 540
Leu Ile Arg Asn Gly Ala Glu Val Asn Phe Leu Arg Leu Met Pro Ala
545                 550                 555                 560
Asp Gln Arg Lys Ala Ile Leu Gly Asp Trp Tyr Gln Asn Ser Gly Lys
                565                 570                 575
Val Lys Met Trp Met Asp Tyr Glu Asp Ile Asp Thr Asp Thr Pro Ser
            580                 585                 590
Gly Ile Lys Leu Asp Pro Arg Asn Pro Lys Arg Asp Phe Gly Leu Lys
        595                 600                 605
```

| | | | | | | | | | | | | |
|---|---|---|---|---|---|---|---|---|---|---|---|---|
|Leu|Leu|Gln|Arg|Thr|Gly|Ser|Leu|Asn|Ala|Ala|Pro|Asp|Pro|Ile|Asn|
| |610| | | |615| | | |620| | | | | | |
|Arg|Cys|Gln|Gly|Ala|Phe|Cys|Ser|Arg|Pro|Gln|Met|Ser|Glu|Glu|Phe|
|625| | | | |630| | | | |635| | | | |640|
|Arg|Asn|Ala|Glu|Gln|Ser|Leu|Ser|Arg|Leu|Val|Ser|Arg|Pro|Ala|Ala|
| | | | |645| | | | |650| | | | |655| |
|Gly|Leu|Lys|Val|Ile|Asn|Gln|Leu|Pro|Glu|Ala|Thr|Met|Leu|Arg|Ile|
| | | | |660| | | | |665| | | | |670| |
|Glu|Gly|Gln|Asp|Gly|Gln|Arg|Gln|Val|Tyr|Ser|Leu|Leu|Arg|Asn|Arg|
| | | |675| | | | |680| | | | |685| | |
|Ala|His|Ser|Asn|Val|Ala|Phe|Leu|Leu|Gly|Glu|Ala|Tyr|Arg|Tyr|Gln|
| | | |690| | | | |695| | | | |700| | |
|Pro|Gly|Leu|Asp|Thr|Leu|Thr|Leu|Tyr|Pro|Gly|Val|Leu|Ser|Ser|Tyr|
|705| | | | |710| | | | |715| | | | |720|
|Pro|Asn|Phe|Ile|Phe|Asn|Ile|Pro|Thr|Lys|Asp|Val|Pro|Glu|Phe|Val|
| | | | |725| | | | |730| | | | |735| |
|Glu|Asp|Met|Glu|Tyr|Ala|Lys|Asp|Asp|Ala|Ala|Lys|Phe|Glu|Arg|Ile|
| | | |740| | | | |745| | | | |750| | |
|Val|Met|Arg|Trp|Gly|Val|Arg|Arg|Ser|His|Pro|Ala|Phe|Trp|Arg|Tyr|
| | | |755| | | | |760| | | | |765| | |
|Phe|His|Asp|Leu|Asn|Ser|Tyr|Ile|Lys|Glu|Thr|Glu|Pro|Val|Glu|Ala|
| | |770| | | | |775| | | | |780| | | |
|Gly|Val|Leu|Asp|Met|Asn|Arg|Tyr|Glu|Asn|Leu| | | | | |
|785| | | |790| | | | |795| | | | | | |

```
<210> SEQ ID NO 115
<211> LENGTH: 2355
<212> TYPE: DNA
<213> ORGANISM: Vibrio splendidus

<400> SEQUENCE: 115
atgaatttga aaaaactctt cattttagct tttgttagcg tcttctcagg ttgtgccgtc      60
tacgcgggtt taaacttcga cgacctgttt ggcaaacaac aagttcgcga tcgccaagcg     120
cctattctat cggctcaagc acagcacttc attgatgaag tgaagcccat cattgataac     180
cgatgtgtgg tttgtcacgc ttgctatgac gcaccttgcc agctcaaaat gtcttcggta     240
gaaggtatcg accgaggtgc gagcaaggca ctcgtttatc aaggcacccg tttaaccgcc     300
tcagccccta ctcgtttgtt tgaagatgct ttaaccacac aagagtggcg cgatgcggat     360
tttcatccag tcctcaacga acgtatgcag aattcaaggg ctaacctaga tgctggtctt     420
gtttctcgaa tgttgatcca gaaagagaac cacccacttc cagatcaaac ccagcttgaa     480
ggtttcgact ttcaaccgga tcgcgaccaa cagtgcccaa cgattgaaga atatgcccaa     540
tacgagagag attacccaac ttgggggatg ccttatggga tgccgaactt agataaaaca     600
gaatacgcga cttaatgag ttggttagaa aatggcgcgt taatgaatga ccacattcca     660
ctgaataatg cggagcaaga gctcgttaat gtctacgaaa gctttctcaa taagagcgac     720
aataaaagcc agctttcagc acgttacatc tatgagcacc tgtttctatc gcacgtctac     780
ttctctgatt tggcgcagcc aacgcgtttc ttcacccttg ttcgctctgc aacgcctcca     840
ggtgaagcgg tgcaacgcat cacgactcgt cgcccatacg acgatccaaa agtagaacgt     900
gtttactacc gcctgattcc agaacaaggc accatcgtcg acaaaacgca catgcctttc     960
gcactcaata agaacgact acaaaagtgg atcacttggt tgtcgatgc taattactct    1020 gtgaaacaac tccctagcta caacattgat gtcgcagcta accctatgac ttcatttgaa    1080
```

```
gcgctgccag taaactcgcg cttccatttc atgttggaca atgcgcaaaa caccatcatg   1140 gctttatca aagggccggt gtgtcgtggt caacttgcct tgaatgtgat taacgaccgt   1200
ttttgggttt tcttcattga tccagagaaa gccgatttac cagaaataaa cgcttttac   1260 gccagccaga agaaaaactt aaaactacct agcgagctaa aaagtaacac cgtaccagcg   1320
accaactggg tacgttactc taagcaacag gctcgatacc taaatgcgaa atcagacttc   1380
accaaccaat ggttcgatag tggcgtgaac ctagacaccg gtataatttg ggatggcgat   1440
ggcatcaacc caaatgccgc tctcaccatc tttagacact tcgatagcgc ttcggttgtt   1500
cagggtttag ttggttcaca gcctaagaca gcatggatcc ttgattacgc cttactagag   1560
cgcattcatt accttcttgt agcaggcttc gatgtgtacg gaaacttcgg ccaccagctg   1620
attacgcgta tgtttatgga cttcttgcgc cttgagggtg aaagtaactt cttaaccctt   1680
cttcctaaag atgttcgcca tattgaacac tcaagctggt acaaaaacca aagtgcacaa   1740
ctgagcgatt acttgcagcg caatatcgcc cctttcgacc aaccaacaag tgtggtttac   1800
aaaacggccg atcctaagcg tgaactgctc aatatgatca agataagct cgcgcctgtc   1860 ctcgatagtc gctttgatat tgtcgaaaca ggttttggtc gaaagaacga agcactgctt   1920
aaccaagtga atttgataaa gggagtcggc ctgcgtcatg ttcctcaatt agtgatgatc   1980
atgattgaag gcaaaaatag cgaagagcaa ttgttcacca tgattcacaa taacgcgcac   2040
agcaacattt ctagcttgtt taatgaagaa ggtaatcgcg attacgccaa tgatgactta   2100
acgctcgtac gaggcgttgt cggtagctac cctgccgctt acctgtcttt aaccgagagc   2160
gagataccga ctctggtgaa aatgctgcaa aatttaaaca cagaagaaga ttacgtggcg   2220
ctgctggata gtttgcggt acgacgcagt tctaacgagt tctggccgtt cagtgatcgt   2280
gtacatcgtt ggtatcaaca agaccaaccg attgagttcg gcttgttgga ttacaaccgc   2340
ttcgagaacc ggtag                                                    2355
```

<210> SEQ ID NO 116
<211> LENGTH: 784
<212> TYPE: PRT
<213> ORGANISM: Vibrio splendidus

<400> SEQUENCE: 116

```
Met Asn Leu Lys Lys Leu Phe Ile Leu Ala Phe Val Ser Val Phe Ser
1               5                   10                  15

Gly Cys Ala Val Tyr Ala Gly Leu Asn Phe Asp Asp Leu Phe Gly Lys
                20                  25                  30

Gln Gln Val Arg Asp Arg Gln Ala Pro Ile Leu Ser Ala Gln Ala Gln
        35                  40                  45

His Phe Ile Asp Glu Val Lys Pro Ile Ile Asp Asn Arg Cys Val Val
    50                  55                  60

Cys His Ala Cys Tyr Asp Ala Pro Cys Gln Leu Lys Met Ser Ser Val
65                  70                  75                  80

Glu Gly Ile Asp Arg Gly Ala Ser Lys Ala Leu Val Tyr Gln Gly Thr
                85                  90                  95

Arg Leu Thr Ala Ser Ala Pro Thr Arg Leu Phe Glu Asp Ala Leu Thr
            100                 105                 110

Thr Gln Glu Trp Arg Asp Ala Asp Phe His Pro Val Leu Asn Glu Arg
        115                 120                 125

Met Gln Asn Ser Arg Ala Asn Leu Asp Ala Gly Leu Val Ser Arg Met
    130                 135                 140

Leu Ile Gln Lys Glu Asn His Pro Leu Pro Asp Gln Thr Gln Leu Glu
```

```
                145                 150                 155                 160
Gly Phe Asp Phe Ser Thr Asp Arg Asp Gln Gln Cys Pro Thr Ile Glu
                    165                 170                 175

Glu Tyr Ala Gln Tyr Glu Arg Asp Tyr Pro Thr Trp Gly Met Pro Tyr
                    180                 185                 190

Gly Met Pro Asn Leu Asp Lys Thr Glu Tyr Ala Thr Leu Met Ser Trp
                    195                 200                 205

Leu Glu Asn Gly Ala Leu Met Asn Asp His Ile Pro Leu Asn Asn Ala
    210                 215                 220

Glu Gln Glu Leu Val Asn Val Tyr Glu Ser Phe Leu Asn Lys Ser Asp
225                 230                 235                 240

Asn Lys Ser Gln Leu Ser Ala Arg Tyr Ile Tyr Glu His Leu Phe Leu
                    245                 250                 255

Ser His Val Tyr Phe Ser Asp Leu Ala Gln Pro Thr Arg Phe Phe Thr
                    260                 265                 270

Leu Val Arg Ser Ala Thr Pro Pro Gly Glu Ala Val Gln Arg Ile Thr
                    275                 280                 285

Thr Arg Arg Pro Tyr Asp Asp Pro Lys Val Glu Arg Val Tyr Tyr Arg
    290                 295                 300

Leu Ile Pro Glu Gln Gly Thr Ile Val Asp Lys Thr His Met Pro Phe
305                 310                 315                 320

Ala Leu Asn Lys Glu Arg Leu Gln Lys Trp Ile Thr Trp Phe Val Asp
                    325                 330                 335

Ala Asn Tyr Ser Val Lys Gln Leu Pro Ser Tyr Asn Ile Asp Val Ala
                    340                 345                 350

Ala Asn Pro Met Thr Ser Phe Glu Ala Leu Pro Val Asn Ser Arg Phe
                    355                 360                 365

His Phe Met Leu Asp Asn Ala Gln Asn Thr Ile Met Ala Phe Ile Lys
                    370                 375                 380

Gly Pro Val Cys Arg Gly Gln Leu Ala Leu Asn Val Ile Asn Asp Arg
385                 390                 395                 400

Phe Trp Val Phe Phe Ile Asp Pro Glu Lys Ala Asp Leu Pro Glu Ile
                    405                 410                 415

Asn Ala Phe Tyr Ala Ser Gln Lys Lys Asn Leu Lys Leu Pro Ser Glu
                    420                 425                 430

Leu Lys Ser Asn Thr Val Pro Ala Thr Asn Trp Val Arg Tyr Ser Lys
                    435                 440                 445

Gln Gln Ala Arg Tyr Leu Asn Ala Lys Ser Asp Phe Thr Asn Gln Trp
    450                 455                 460

Phe Asp Ser Gly Val Asn Leu Asp Thr Gly Ile Ile Trp Asp Gly Asp
465                 470                 475                 480

Gly Ile Asn Pro Asn Ala Ala Leu Thr Ile Phe Arg His Phe Asp Ser
                    485                 490                 495

Ala Ser Val Val Gln Gly Leu Val Gly Ser Pro Lys Thr Ala Trp
                    500                 505                 510

Ile Leu Asp Tyr Ala Leu Leu Glu Arg Ile His Tyr Leu Leu Val Ala
    515                 520                 525

Gly Phe Asp Val Tyr Gly Asn Phe Gly His Gln Leu Ile Thr Arg Met
    530                 535                 540

Phe Met Asp Phe Leu Arg Leu Glu Gly Glu Ser Asn Phe Leu Thr Leu
545                 550                 555                 560

Leu Pro Lys Asp Val Arg His Ile Glu His Ser Ser Trp Tyr Lys Asn
                    565                 570                 575
```

-continued

```
Gln Ser Ala Gln Leu Ser Asp Tyr Leu Gln Arg Asn Ile Ala Pro Phe
            580                 585                 590

Asp Gln Pro Thr Ser Val Val Tyr Lys Thr Ala Asp Pro Lys Arg Glu
        595                 600                 605

Leu Leu Asn Met Ile Lys Asp Lys Leu Ala Pro Val Leu Asp Ser Arg
    610                 615                 620

Phe Asp Ile Val Glu Thr Gly Phe Gly Arg Lys Asn Glu Ala Leu Leu
625                 630                 635                 640

Asn Gln Val Asn Leu Ile Lys Gly Val Gly Leu Arg His Val Pro Gln
                645                 650                 655

Leu Val Met Ile Met Ile Glu Gly Lys Asn Ser Glu Glu Gln Leu Phe
            660                 665                 670

Thr Met Ile His Asn Asn Ala His Ser Asn Ile Ser Ser Leu Phe Asn
        675                 680                 685

Glu Gly Asn Arg Asp Tyr Ala Asn Asp Asp Leu Thr Leu Val Arg
    690                 695                 700

Gly Val Val Gly Ser Tyr Pro Ala Ala Tyr Leu Ser Leu Thr Glu Ser
705                 710                 715                 720

Glu Ile Pro Thr Leu Val Lys Met Leu Gln Asn Leu Asn Thr Glu Glu
                725                 730                 735

Asp Tyr Val Ala Leu Leu Asp Lys Phe Ala Val Arg Arg Ser Ser Asn
            740                 745                 750

Glu Phe Trp Pro Phe Ser Asp Arg Val His Arg Trp Tyr Gln Gln Asp
        755                 760                 765

Gln Pro Ile Glu Phe Gly Leu Leu Asp Tyr Asn Arg Phe Glu Asn Arg
    770                 775                 780

<210> SEQ ID NO 117
<211> LENGTH: 2301
<212> TYPE: DNA
<213> ORGANISM: Congregibacter litoralis

<400> SEQUENCE: 117
atgaacatgg tttttctttt cttccgtcgt agcgttgccc gtggctctcg tctgagcctg      60
ttgctggcaa tcttttttgt tcagggagcg caggtacatt cggaaacacc aacggcggag     120
gattaccccg caccgataaa gtccgtgatt gagcagcgct gcatggtctg tcacggttgc     180
tacgatgcgc cgtgccagct caagatggat gcctggatcg gctgcagcg  gggcgccagt     240 aaggacaagg tgtacaacgg cacccgatta ctaccggcca atctcacgcg tctttatgag     300
gatgctctta gcatcgagga atggcgggag aaggattttt atccggtgct ggatgattcc     360
gatcctcacc agggcgtgat gtaccagatg ctcaagctga acaggaaaa  cccatcgcca     420 agctcaggaa aactcccgga cagttttgat tttagtttgg accgtgatca aagctgcccg     480
aaagcggaag agtttgccga gtaccgcgag gagcggccgc tgcagggat  gccctacgga     540 tttcccggtc tggacgccga caggcaggcc ctcctgacgg agtggctgga ggccggtgcc     600
cccggcactc cgctgcctcc gcgccccgat gatgagttac gcgccatcga tgcctgggag     660
acattcctca cgcccccga  caataaatca cgattgatga gtcgctatat cttcgagcac     720
ctgtttatcg gtgatttgta ttttgaagat ctcggcgccg actcggcctg gtacaagctt     780
gttcgctcgc ggacagcacc ggggcagccc atcgattga  tcgcaacgcg acggccctac     840
gataagccgg gcacggacag cttctactac cgtctccaac gcgctatat  cagtcgactg     900 gcaaagcgcc acatgcccta tgcgctcagc gaagcgcgta tggagcgctg gaaagcactc     960
tttctggagc ccgactacga ggtgacatcg ctgccgggct ataaaggcaa gcacgctgcc    1020
```

-continued

```
aatcccttta tcaattttca gcagttgccc gtggaagcgc gttaccgttt tatgctcgag   1080
gaagcgcatt ttacgatcat ggcctacatc aagggccccg tctgtcgcgg ccaggtggcc   1140
ctcaatgtca tcgacgatca tttctgggtt gcctttgtcc gccccaacgc tgctgacccg   1200
gagcagaggg ccgactttt ggcggccgag gcgcaggaga tgcgtcttcc ccaggcgaaa   1260
ggtagtttgg ccatcacggc cttgcagtgg cggggctatg ccaaatccca gcagaagttc   1320
ttgaaggcgc aggcaaaagc gatagcaaag gttgtggatc agcagagtct tcagctggat   1380
atggacctga tctgggatgg cggtcccgaa gaaaacgaca atgcggcgtt gaccgtgttc   1440
cggcattttg acagtgccac ggtggttaaa ggctttgtgg gtcagcagcc ccagacaatg   1500
tgggtgatcg actactccct tctggagcgc attcattatc tcctcgtggc aggttttgat   1560
gtttacggtg ccgttggcca tcaactcgaa agccgccttt acatggactt tttgcgcatg   1620
gagggggaac aggcttttct gttgttcctc cccgagggcg agagggaagc tgtgcgcaac   1680
cactggtacc gcggtgcgac ggacgacgtc aaaaaataca tcatctcccc gaagctccag   1740
aaatttgagc ggccctcggc catcgagttt cagaccgatg atcccaagtc cgagctcatg   1800
gccatgttta aagcacgtat tcccgcggga cgcagagacc gctacgcggt gaatcaaaaa   1860
gcgctggagg cccttatgca ggggcagggt agggcttta gcttcatgcc cgaggtatcg   1920
tttctccgga tactcagtgc ccgcggtgat gacgctgttt acagcctcat cgccaacagg   1980
gctcacagca caacgcccca gcttttgcc gaggaggatc gtcgcctgcc tgaggaagat   2040
accctcacgg tgaccgaggg ctttgtgggc gcctatccca acatgttttt tcagattaac   2100
gagtcccagt taccgaagtt cagcgaggcc cttcgatccc tcgcaagcct ggaggattac   2160
accgccctgg tggatgcgtt cggggtgcga cgcacggcgc cgtggttctg gaagctcagc   2220
gacgacctca ccgcgcagta caaaagcagc catcccctgg aggccggcct gtttgatctc   2280
aaccgctatc agaatcgcta g                                             2301
```

<210> SEQ ID NO 118
<211> LENGTH: 766
<212> TYPE: PRT
<213> ORGANISM: Congregibacter litoralis

<400> SEQUENCE: 118

```
Met Asn Met Val Phe Leu Phe Phe Arg Arg Ser Val Ala Arg Gly Ser
1               5                   10                  15

Arg Leu Ser Leu Leu Leu Ala Ile Phe Phe Val Gln Gly Ala Gln Val
            20                  25                  30

His Ser Glu Thr Pro Thr Ala Glu Asp Tyr Pro Ala Pro Ile Lys Ser
        35                  40                  45

Val Ile Glu Gln Arg Cys Met Val Cys His Gly Cys Tyr Asp Ala Pro
    50                  55                  60

Cys Gln Leu Lys Met Asp Ala Trp Ile Gly Leu Gln Arg Gly Ala Ser
65                  70                  75                  80

Lys Asp Lys Val Tyr Asn Gly Thr Arg Leu Leu Pro Ala Asn Leu Thr
                85                  90                  95

Arg Leu Tyr Glu Asp Ala Leu Ser Ile Glu Glu Trp Arg Glu Lys Asp
            100                 105                 110

Phe Tyr Pro Val Leu Asp Asp Ser Asp Pro His Gln Gly Val Met Tyr
        115                 120                 125

Gln Met Leu Lys Leu Lys Gln Glu Asn Pro Ser Pro Ser Ser Gly Lys
    130                 135                 140
```

-continued

```
Leu Pro Asp Ser Phe Asp Phe Ser Leu Asp Arg Asp Gln Ser Cys Pro
145                 150                 155                 160

Lys Ala Glu Glu Phe Ala Glu Tyr Arg Glu Arg Pro Leu Gln Gly
            165                 170                 175

Met Pro Tyr Gly Phe Pro Gly Leu Asp Ala Asp Arg Gln Ala Leu Leu
            180                 185                 190

Thr Glu Trp Leu Glu Ala Gly Ala Pro Gly Thr Pro Leu Pro Pro Arg
            195                 200                 205

Pro Asp Asp Glu Leu Arg Ala Ile Asp Ala Trp Glu Thr Phe Leu Asn
210                 215                 220

Ala Pro Asp Asn Lys Ser Arg Leu Met Ser Arg Tyr Ile Phe Glu His
225                 230                 235                 240

Leu Phe Ile Gly Asp Leu Tyr Phe Glu Asp Leu Gly Ala Asp Ser Ala
            245                 250                 255

Trp Tyr Lys Leu Val Arg Ser Arg Thr Ala Pro Gly Gln Pro Ile Asp
            260                 265                 270

Leu Ile Ala Thr Arg Arg Pro Tyr Asp Lys Pro Gly Thr Asp Ser Phe
            275                 280                 285

Tyr Tyr Arg Leu Gln Pro Arg Tyr Ile Ser Arg Leu Ala Lys Arg His
            290                 295                 300

Met Pro Tyr Ala Leu Ser Glu Ala Arg Met Glu Arg Trp Lys Ala Leu
305                 310                 315                 320

Phe Leu Glu Pro Asp Tyr Glu Val Thr Ser Leu Pro Gly Tyr Lys Gly
            325                 330                 335

Lys His Ala Ala Asn Pro Phe Ile Asn Phe Gln Gln Leu Pro Val Glu
            340                 345                 350

Ala Arg Tyr Arg Phe Met Leu Glu Glu Ala His Phe Thr Ile Met Ala
            355                 360                 365

Tyr Ile Lys Gly Pro Val Cys Arg Gly Gln Val Ala Leu Asn Val Ile
            370                 375                 380

Asp Asp His Phe Trp Val Ala Phe Val Arg Pro Asn Ala Ala Asp Pro
385                 390                 395                 400

Glu Gln Arg Ala Asp Phe Leu Ala Ala Glu Ala Gln Glu Met Arg Leu
            405                 410                 415

Pro Gln Ala Lys Gly Ser Leu Ala Ile Thr Ala Leu Gln Trp Arg Gly
            420                 425                 430

Tyr Ala Lys Ser Gln Gln Lys Phe Leu Lys Ala Gln Ala Lys Ala Ile
            435                 440                 445

Ala Lys Val Val Asp Gln Gln Ser Leu Gln Leu Asp Met Asp Leu Ile
450                 455                 460

Trp Asp Gly Gly Pro Glu Glu Asn Asp Asn Ala Ala Leu Thr Val Phe
465                 470                 475                 480

Arg His Phe Asp Ser Ala Thr Val Val Lys Gly Phe Val Gly Gln Gln
            485                 490                 495

Pro Gln Thr Met Trp Val Ile Asp Tyr Ser Leu Leu Glu Arg Ile His
            500                 505                 510

Tyr Leu Leu Val Ala Gly Phe Asp Val Tyr Gly Ala Val Gly His Gln
            515                 520                 525

Leu Glu Ser Arg Leu Tyr Met Asp Phe Leu Arg Met Glu Gly Glu Gln
            530                 535                 540

Ala Phe Leu Leu Phe Leu Pro Glu Gly Glu Arg Glu Ala Val Arg Asn
545                 550                 555                 560

His Trp Tyr Arg Gly Ala Thr Asp Asp Val Lys Lys Tyr Ile Ile Ser
            565                 570                 575
```

Pro Lys Leu Gln Lys Phe Glu Arg Pro Ser Ala Ile Glu Phe Gln Thr
              580                 585                 590

Asp Asp Pro Lys Ser Glu Leu Met Ala Met Phe Lys Ala Arg Ile Pro
          595                 600                 605

Ala Gly Arg Arg Asp Arg Tyr Ala Val Asn Gln Lys Ala Leu Glu Ala
      610                 615                 620

Leu Met Gln Gly Gln Gly Arg Ala Phe Ser Phe Met Pro Glu Val Ser
625                 630                 635                 640

Phe Leu Arg Ile Leu Ser Ala Arg Gly Asp Asp Ala Val Tyr Ser Leu
              645                 650                 655

Ile Ala Asn Arg Ala His Ser Asn Asn Ala Gln Leu Phe Ala Glu Glu
          660                 665                 670

Asp Arg Arg Leu Pro Glu Glu Asp Thr Leu Thr Val Thr Glu Gly Phe
      675                 680                 685

Val Gly Ala Tyr Pro Asn Met Phe Phe Gln Ile Asn Glu Ser Gln Leu
690                 695                 700

Pro Lys Phe Ser Glu Ala Leu Arg Ser Leu Ala Ser Leu Glu Asp Tyr
705                 710                 715                 720

Thr Ala Leu Val Asp Ala Phe Gly Val Arg Arg Thr Ala Pro Trp Phe
                  725                 730                 735

Trp Lys Leu Ser Asp Asp Leu Thr Ala Gln Tyr Lys Ser Ser His Pro
              740                 745                 750

Leu Glu Ala Gly Leu Phe Asp Leu Asn Arg Tyr Gln Asn Arg
          755                 760                 765

<210> SEQ ID NO 119
<211> LENGTH: 2334
<212> TYPE: DNA
<213> ORGANISM: Pseudoalteromonas tunicata

<400> SEQUENCE: 119

| | | |
|---|---|---|
| atgtggcagc gactcggact gattgttatt ttttgctctt agctggctg tgctatttat | 60 |
| ggcgtaagcc aatatcagca acgctttgga gcgccgagcg ctgtagagcg tttagttgaa | 120 |
| tatccggctc gagaagctat ccactatttg acactgtta aacctataat tgagagtcgc | 180 |
| tgtgttgtgt gtcatggttg ttatgacgcg ccttgccagt taaagctttc ttcaccagaa | 240 |
| ggcattgacc gcggagtatc acagcaacta gtttatgatg gaactcgttt acttgcagcg | 300 |
| acgccgcaac gattatttat tgatgcgcag caaaccgttg agtggcgtga ccgtggtttt | 360 |
| aatcctgtcc tgaatgagtt ttcacaaacg cctgaagcaa accttgcagc cagtgtcatg | 420 |
| tataacagtt tgttattaaa acaagcgcac cctttaccaa atgttgcagt gcttggcgaa | 480 |
| gagttcgatt ttggtttaga ccgcagtcaa agctgtgcca gtatcgaaaa ttttgatgag | 540 |
| ctggctatca acaagcctca ttctggtatg ccttatgggt ttcctgcttt atcctctagc | 600 |
| gaatttaaaa cattagaagc atggatgcgc tctggcgcca ctatggcgca cagcccaaag | 660 |
| ccaagtgcct tcgaacttga gcaaatggcg cgttgggaag catttttaaa tcaagatgac | 720 |
| ttaaaagccc aattaatggc gcgctatata tatgagcatt ggttttttagc gcacatttat | 780 |
| tttggcattg agccgacaac acaattcttt aaattagtac gctccagtac acctcctggt | 840 |
| cagccaatta acaaattgc tacaactcgg ccatttgatg accccaaggt aaagcgggtt | 900 |
| tattatcgtt tatggcatga taaaaccacc attttagcaa aaacccattt acctctggcg | 960 |
| cttgatgatg acaagcttgc tcgtttatat cagcaatttc ttgcaccaca atatcaagtc | 1020 |
| acgcaattac caagttatga agctgcgatt gcctcaaatc ctttttaaatc gtttgagcag | 1080 |

```
cttccgactg cagctaaata ccagtttatg cttgatgagg cgcagttaat catcatgggg   1140
tttatcaagg gtcctgtttg tcgtggtcaa gtggcactga atgttattaa tgatcatttt   1200
tgggtatttt ttgtcgatcc gaaacaagat ggcagcgata aaatgggggc gttttagcg   1260 aaaaatcaag atgtgctcac tctaccagct caagatgaaa gcactgtttt acctgttgct   1320
tcatggttta aatatgccca agctcagata agatacttag cagcaaaaac taatttaatg   1380
aaccaagtct ttgctgataa ctcaaagcta aaccttaatt taatttggca aggcgagggc   1440
gtaaatacca atgccgcact aacaattttt cggcattttg acagtgctac ggtgacaaaa   1500
ggcttggttg gtcagccgcc taaaacagct tgggtgcttg attatgcttt atttgagcgg   1560
atccattatc tgctggtggc gggctttgat gtatacggca atgttgggca tcagctcaat   1620
acccgtttgt acatggattt tttacgtatt gaaggcgaaa ataacttttt agcgctattg   1680
ccagaggcta aacgagaaaa aattcgcgac ttttggtatc gtaatgcatc attaagttta   1740
attcgccatt ttcaagaaaa gcatccgttt tcacaagaaa ctggagtggt gtataaaacg   1800
gatgatcctc aagctgaact ttaccaaaaa ctacagcatc atctgaagca agttcttgat   1860
aattctcatg ctctacaatc acctgaagat ccgtctatct ggcatcaat agaacaaacc   1920 accagtcaag cggttggttt tttaccctcaa gtctcatttt tgttggttaa aatcgattct   1980
gagtaccgtg cattttcgat gattagaaat aatgctcatt taatattac cagtttgctt   2040 aatgaggcag cacaacgtgc gtatcaagaa gattcactta cgttagctaa aggctttatt   2100
ggtgattatc ccgcagttat ttggcatgtt gctaaagaag agctgccaaa ttttatctct   2160
caactgcact cactcaaaac tgaagctgat tatcatcaat taaaaaatcg ctatgctgtt   2220
cgtcgaacaa acaaggattt ttggcaatat agtgatttat tacatgacgt tgctaagcaa   2280
tatcaaggcg tagagtttgg tttattcgat tacaatcgct atgaaaataa ataa          2334

<210> SEQ ID NO 120
<211> LENGTH: 777
<212> TYPE: PRT
<213> ORGANISM: Pseudoalteromonas tunicata

<400> SEQUENCE: 120

Met Trp Gln Arg Leu Gly Leu Ile Val Ile Phe Cys Ser Leu Ala Gly
1               5                   10                  15

Cys Ala Ile Tyr Gly Val Ser Gln Tyr Gln Gln Arg Phe Gly Ala Pro
            20                  25                  30

Ser Ala Val Glu Arg Leu Val Glu Tyr Pro Ala Arg Glu Ala Ile His
        35                  40                  45

Tyr Leu Asp Thr Val Lys Pro Ile Ile Glu Ser Arg Cys Val Val Cys
    50                  55                  60

His Gly Cys Tyr Asp Ala Pro Cys Gln Leu Lys Leu Ser Ser Pro Glu
65                  70                  75                  80

Gly Ile Asp Arg Gly Val Ser Gln Gln Leu Val Tyr Asp Gly Thr Arg
                85                  90                  95

Leu Leu Ala Ala Thr Pro Gln Arg Leu Phe Ile Asp Ala Gln Gln Thr
            100                 105                 110

Val Glu Trp Arg Asp Arg Gly Phe Asn Pro Val Leu Asn Glu Phe Ser
        115                 120                 125

Gln Thr Pro Glu Ala Asn Leu Ala Ala Ser Val Met Tyr Asn Ser Leu
    130                 135                 140

Leu Leu Lys Gln Ala His Pro Leu Pro Asn Val Ala Val Leu Gly Glu
145                 150                 155                 160
```

```
Glu Phe Asp Phe Gly Leu Asp Arg Ser Gln Ser Cys Ala Ser Ile Glu
                165                 170                 175

Asn Phe Asp Glu Leu Ala Ile Asn Lys Pro His Ser Gly Met Pro Tyr
            180                 185                 190

Gly Phe Pro Ala Leu Ser Ser Ser Glu Phe Lys Thr Leu Glu Ala Trp
        195                 200                 205

Met Arg Ser Gly Ala Thr Met Ala His Ser Pro Lys Pro Ser Ala Phe
    210                 215                 220

Glu Leu Glu Gln Met Ala Arg Trp Glu Ala Phe Leu Asn Gln Asp Asp
225                 230                 235                 240

Leu Lys Ala Gln Leu Met Ala Arg Tyr Ile Tyr Glu His Trp Phe Leu
                245                 250                 255

Ala His Ile Tyr Phe Gly Ile Glu Pro Thr Thr Gln Phe Phe Lys Leu
            260                 265                 270

Val Arg Ser Ser Thr Pro Pro Gly Gln Pro Ile Lys Gln Ile Ala Thr
        275                 280                 285

Thr Arg Pro Phe Asp Asp Pro Lys Val Lys Arg Val Tyr Tyr Arg Leu
    290                 295                 300

Trp His Asp Lys Thr Thr Ile Leu Ala Lys Thr His Leu Pro Leu Ala
305                 310                 315                 320

Leu Asp Asp Lys Leu Ala Arg Leu Tyr Gln Gln Phe Leu Ala Pro
                325                 330                 335

Gln Tyr Gln Val Thr Gln Leu Pro Ser Tyr Glu Ala Ala Ile Ala Ser
                340                 345                 350

Asn Pro Phe Lys Ser Phe Glu Gln Leu Pro Thr Ala Ala Lys Tyr Gln
                355                 360                 365

Phe Met Leu Asp Glu Ala Gln Leu Ile Ile Met Gly Phe Ile Lys Gly
            370                 375                 380

Pro Val Cys Arg Gly Gln Val Ala Leu Asn Val Ile Asn Asp His Phe
385                 390                 395                 400

Trp Val Phe Phe Val Asp Pro Lys Gln Asp Gly Ser Asp Lys Met Gly
                405                 410                 415

Ala Phe Leu Ala Lys Asn Gln Asp Val Leu Thr Leu Pro Ala Gln Asp
            420                 425                 430

Glu Ser Thr Val Leu Pro Val Ala Ser Trp Phe Lys Tyr Ala Gln Ala
            435                 440                 445

Gln Ile Arg Tyr Leu Ala Ala Lys Thr Asn Leu Met Asn Gln Val Phe
    450                 455                 460

Ala Asp Asn Ser Lys Leu Asn Leu Asn Leu Ile Trp Gln Gly Glu Gly
465                 470                 475                 480

Val Asn Thr Asn Ala Ala Leu Thr Ile Phe Arg His Phe Asp Ser Ala
                485                 490                 495

Thr Val Thr Lys Gly Leu Val Gly Gln Pro Pro Lys Thr Ala Trp Val
            500                 505                 510

Leu Asp Tyr Ala Leu Phe Glu Arg Ile His Tyr Leu Leu Val Ala Gly
        515                 520                 525

Phe Asp Val Tyr Gly Asn Val Gly His Gln Leu Asn Thr Arg Leu Tyr
    530                 535                 540

Met Asp Phe Leu Arg Ile Glu Gly Glu Asn Asn Phe Leu Ala Leu Leu
545                 550                 555                 560

Pro Glu Ala Lys Arg Glu Lys Ile Arg Asp Phe Trp Tyr Arg Asn Ala
                565                 570                 575

Ser Leu Ser Leu Ile Arg His Phe Gln Glu Lys His Pro Phe Ser Gln
```

|     |     | 580 |     |     |     | 585 |     |     |     | 590 |     |
|-----|-----|-----|-----|-----|-----|-----|-----|-----|-----|-----|-----|
| Glu | Thr | Gly | Val | Val | Tyr | Lys | Thr | Asp | Asp | Pro | Gln | Ala | Glu | Leu | Tyr |
|     |     |     | 595 |     |     |     | 600 |     |     |     | 605 |

Glu Thr Gly Val Val Tyr Lys Thr Asp Asp Pro Gln Ala Glu Leu Tyr
            595                 600                 605

Gln Lys Leu Gln His His Leu Lys Gln Val Leu Asp Asn Ser His Ala
        610                 615                 620

Leu Gln Ser Pro Glu Asp Pro Ser Ile Leu Ala Ser Ile Glu Gln Thr
625                 630                 635                 640

Thr Ser Gln Ala Val Gly Phe Leu Pro Gln Val Ser Phe Leu Leu Val
                645                 650                 655

Lys Ile Asp Ser Glu Tyr Arg Ala Phe Ser Met Ile Arg Asn Asn Ala
            660                 665                 670

His Phe Asn Ile Thr Ser Leu Leu Asn Glu Ala Ala Gln Arg Ala Tyr
        675                 680                 685

Gln Glu Asp Ser Leu Thr Leu Ala Lys Gly Phe Ile Gly Asp Tyr Pro
    690                 695                 700

Ala Val Ile Trp His Val Ala Lys Glu Glu Leu Pro Asn Phe Ile Ser
705                 710                 715                 720

Gln Leu His Ser Leu Lys Thr Glu Ala Asp Tyr His Gln Leu Lys Asn
                725                 730                 735

Arg Tyr Ala Val Arg Arg Thr Asn Lys Asp Phe Trp Gln Tyr Ser Asp
            740                 745                 750

Leu Leu His Asp Val Ala Lys Gln Tyr Gln Gly Val Glu Phe Gly Leu
        755                 760                 765

Phe Asp Tyr Asn Arg Tyr Glu Asn Lys
770                 775

<210> SEQ ID NO 121
<211> LENGTH: 2355
<212> TYPE: DNA
<213> ORGANISM: Vibrio sp.

<400> SEQUENCE: 121
atgaatttga aaaaactctt cattttagct tttgttagcg tcttctcagg ttgtgccgtc      60
tacgcggggt tgaacttcga tcagctcttt ggtgaacaac aagtccgaga tcgccaagcg     120
cctattcttt catctcaagc acagcatttc attgacgaag taaagcctat cattgatagc     180
cgctgtgttg tttgccacgc ttgttatgat gcaccttgcc agctaaaaat gtcttcagtt     240
gaaggtatcg accgaggggc gagtaaggca ctcgtttatc aaggcacccg tttaaccgcc     300
tcagccccta cccgcctgtt tgaagacgcg ataaccacac aagagtggcg tgatgcggat     360
tttcatccag tgctaaacga acgtatgcag aattcaacgg ctaaccttga tgctgggctt     420
gtttctcgta tgttgatgca aaagaaaac caccctcttc cagatcaaac gcaacttgaa     480
ggcttcgact tttcaaccga tcgcgaccaa cagtgtccaa ccattgaaga gtacgctcaa     540
tacgaaagag attacccgac gtggggaatg cctatggca tgccgaactt agataaaacg     600
gaatacgcga ctttaatgag ttggttggaa acggcgcgt taatgaatga ccatattcca     660
ctgaatgatg cggaacaaga gctcgttgat atctacgagg ctttctcaa caagagtgac     720 aataaaagcc agctttcagc acgttatatc tatgaacatc tgtttctatc acacctctat     780
ttctctgatt tagctcagcc aacacgcttc tcaccttgg ttcgttctgc gacgcctcct     840
ggtgaagcgg ttcatcgcat cacgagtcgt cgaccttacg acgatccaaa agtggatcgg     900
gtttattatc gcctgattcc agagcaaggc accatcgtcc acaaaacaca catgcctttc     960
gcattaaatg aagaacgcct gaacaattgg aacacatggt ttgtggatgc tcgttacgct    1020

```
gtcaaacaac ttcctagcta cgcgattgac gtcgcggcga atccaatgac ttcgtttgaa    1080
gctcttccgg tgaactcgcg cttccatttc atgctggaca atgcacaaaa caccatcatg    1140
gcctttatca aggggccggt gtgtcgcggg cagctcgcac tcaacgtgat caatgataga    1200
ttctgggtac tattcatcga tcctgataaa gcagatctgc ctgaaattaa tcagttttat    1260
gccaaccaga agcaaaacct aaagctgcct agtgaactag aaagcaacac tgtccctgtc    1320
acaagctggg tgagctacgc gaagcaacaa gctcgatacc ttaatgcaaa atcagacttc    1380
accaatcaat ggtttgatag cggagtaaat ctagacacag atatcatttg ggatggcaat    1440
ggcacgaacc gtaatgccgc gcttactatc tttagacact tgatagcgc ttcagttgtt     1500 caaggtttag ttggcccaca acccaagaca gcgtggattc ttgattacgc ccttctagaa    1560
cgtatccatt accttctcgt tgctggtttt gatgtctacg gtaacttcgg ccaccaactg    1620
attacccgta tgtttatgga tttcttgcgc cttgagggtg agagtaactt cttgacccct    1680
cttccaaaag acgtacgaca cattgaacac tcaagttggt atgaaaacca aagctcacag    1740
ttgagcgact acttgcagcg taatattgca ccttttgacc agccaaccaa cgtgatatac    1800
aaaacgacaa atcctaagcg tgaactgctt aatatgatca agataagct cgcgccgatc     1860 ctcgataatc gctttgatat tgtcgaaaca ggtttcagtc ggaaaaacga agctctgctc    1920
aaacaagtga atttgattaa gggagttggt ctgcgtcatg tgcctcaatt agttacgatc    1980
atgattgaaa gcgagaacgg cgatgagcag ctgttcacca tgattcacaa taacgctcac    2040
agcaacattt caagcctgtt caatgaagag ggtaatcgag attacgccaa tgacgactta    2100
acactagtac gtggggttgt aggtagctac cctgccgctt atctgtcatt aactgagcgc    2160
aatataccga ctctggttaa agcactgcaa agcttggaca cagaaaaaga ttacgtcgcg    2220
ttgctggata agttttgcagt acgacgcagt tcgcctgagt tctggccatt cagcgaccga    2280
gttcaccgtt ggtatcaaca agatcaaccg attgagtttg gtttattgga ttacaaccgt    2340
tttgagaata gatag                                                    2355
```

<210> SEQ ID NO 122
<211> LENGTH: 784
<212> TYPE: PRT
<213> ORGANISM: Vibrio sp.

<400> SEQUENCE: 122

```
Met Asn Leu Lys Lys Leu Phe Ile Leu Ala Phe Val Ser Val Phe Ser
1               5                   10                  15

Gly Cys Ala Val Tyr Ala Gly Leu Asn Phe Asp Gln Leu Phe Gly Glu
            20                  25                  30

Gln Gln Val Arg Asp Arg Gln Ala Pro Ile Leu Ser Ser Gln Ala Gln
        35                  40                  45

His Phe Ile Asp Glu Val Lys Pro Ile Ile Asp Ser Arg Cys Val Val
    50                  55                  60

Cys His Ala Cys Tyr Asp Ala Pro Cys Gln Leu Lys Met Ser Ser Val
65                  70                  75                  80

Glu Gly Ile Asp Arg Gly Ala Ser Lys Ala Leu Val Tyr Gln Gly Thr
                85                  90                  95

Arg Leu Thr Ala Ser Ala Pro Thr Arg Leu Phe Glu Asp Ala Ile Thr
            100                 105                 110

Thr Gln Glu Trp Arg Asp Ala Asp Phe His Pro Val Leu Asn Glu Arg
        115                 120                 125

Met Gln Asn Ser Thr Ala Asn Leu Asp Ala Gly Leu Val Ser Arg Met
    130                 135                 140
```

```
Leu Met Gln Lys Glu Asn His Pro Leu Pro Asp Gln Thr Gln Leu Glu
145                 150                 155                 160

Gly Phe Asp Phe Ser Thr Asp Arg Asp Gln Gln Cys Pro Thr Ile Glu
                165                 170                 175

Glu Tyr Ala Gln Tyr Glu Arg Asp Tyr Pro Thr Trp Gly Met Pro Tyr
            180                 185                 190

Gly Met Pro Asn Leu Asp Lys Thr Glu Tyr Ala Thr Leu Met Ser Trp
            195                 200                 205

Leu Glu Asn Gly Ala Leu Met Asn Asp His Ile Pro Leu Asn Asp Ala
210                 215                 220

Glu Gln Glu Leu Val Asp Ile Tyr Glu Gly Phe Leu Asn Lys Ser Asp
225                 230                 235                 240

Asn Lys Ser Gln Leu Ser Ala Arg Tyr Ile Tyr Glu His Leu Phe Leu
                245                 250                 255

Ser His Leu Tyr Phe Ser Asp Leu Ala Gln Pro Thr Arg Phe Phe Thr
            260                 265                 270

Leu Val Arg Ser Ala Thr Pro Pro Gly Glu Ala Val His Arg Ile Thr
            275                 280                 285

Ser Arg Arg Pro Tyr Asp Asp Pro Lys Val Asp Arg Val Tyr Tyr Arg
290                 295                 300

Leu Ile Pro Glu Gln Gly Thr Ile Val His Lys Thr His Met Pro Phe
305                 310                 315                 320

Ala Leu Asn Glu Glu Arg Leu Asn Asn Trp Asn Thr Trp Phe Val Asp
                325                 330                 335

Ala Arg Tyr Ala Val Lys Gln Leu Pro Ser Tyr Ala Ile Asp Val Ala
            340                 345                 350

Ala Asn Pro Met Thr Ser Phe Glu Ala Leu Pro Val Asn Ser Arg Phe
            355                 360                 365

His Phe Met Leu Asp Asn Ala Gln Asn Thr Ile Met Ala Phe Ile Lys
370                 375                 380

Gly Pro Val Cys Arg Gly Gln Leu Ala Leu Asn Val Ile Asn Asp Arg
385                 390                 395                 400

Phe Trp Val Leu Phe Ile Asp Pro Asp Lys Ala Asp Leu Pro Glu Ile
                405                 410                 415

Asn Gln Phe Tyr Ala Asn Gln Lys Gln Asn Leu Lys Leu Pro Ser Glu
            420                 425                 430

Leu Glu Ser Asn Thr Val Pro Val Thr Ser Trp Val Ser Tyr Ala Lys
            435                 440                 445

Gln Gln Ala Arg Tyr Leu Asn Ala Lys Ser Asp Phe Thr Asn Gln Trp
450                 455                 460

Phe Asp Ser Gly Val Asn Leu Asp Thr Asp Ile Ile Trp Asp Gly Asn
465                 470                 475                 480

Gly Thr Asn Arg Asn Ala Ala Leu Thr Ile Phe Arg His Phe Asp Ser
                485                 490                 495

Ala Ser Val Val Gln Gly Leu Val Gly Pro Gln Pro Lys Thr Ala Trp
            500                 505                 510

Ile Leu Asp Tyr Ala Leu Leu Glu Arg Ile His Tyr Leu Leu Val Ala
            515                 520                 525

Gly Phe Asp Val Tyr Gly Asn Phe Gly His Gln Leu Ile Thr Arg Met
530                 535                 540

Phe Met Asp Phe Leu Arg Leu Glu Gly Glu Ser Asn Phe Leu Thr Leu
545                 550                 555                 560

Leu Pro Lys Asp Val Arg His Ile Glu His Ser Ser Trp Tyr Glu Asn
```

```
                    565                 570                 575
Gln Ser Ser Gln Leu Ser Asp Tyr Leu Gln Arg Asn Ile Ala Pro Phe
                580                 585                 590

Asp Gln Pro Thr Asn Val Ile Tyr Lys Thr Thr Asn Pro Lys Arg Glu
            595                 600                 605

Leu Leu Asn Met Ile Lys Asp Lys Leu Ala Pro Ile Leu Asp Asn Arg
        610                 615                 620

Phe Asp Ile Val Glu Thr Gly Phe Ser Arg Lys Asn Glu Ala Leu Leu
625                 630                 635                 640

Lys Gln Val Asn Leu Ile Lys Gly Val Gly Leu Arg His Val Pro Gln
                645                 650                 655

Leu Val Thr Ile Met Ile Glu Ser Glu Asn Gly Asp Glu Gln Leu Phe
            660                 665                 670

Thr Met Ile His Asn Asn Ala His Ser Asn Ile Ser Ser Leu Phe Asn
        675                 680                 685

Glu Glu Gly Asn Arg Asp Tyr Ala Asn Asp Asp Leu Thr Leu Val Arg
        690                 695                 700

Gly Val Val Gly Ser Tyr Pro Ala Ala Tyr Leu Ser Leu Thr Glu Arg
705                 710                 715                 720

Asn Ile Pro Thr Leu Val Lys Ala Leu Gln Ser Leu Asp Thr Glu Lys
                725                 730                 735

Asp Tyr Val Ala Leu Leu Asp Lys Phe Ala Val Arg Arg Ser Ser Pro
            740                 745                 750

Glu Phe Trp Pro Phe Ser Asp Arg Val His Arg Trp Tyr Gln Gln Asp
        755                 760                 765

Gln Pro Ile Glu Phe Gly Leu Leu Asp Tyr Asn Arg Phe Glu Asn Arg
        770                 775                 780

<210> SEQ ID NO 123
<211> LENGTH: 2355
<212> TYPE: DNA
<213> ORGANISM: Vibrio alginolyticus

<400> SEQUENCE: 123
atgaatttgc gcttaatttt tacactttgc attgctactt tgtttgccgg ctgtgcaacc      60
tatgctggtc ttaactatga ccaactgttt ggtccacagc tcgtgcgtga acgcacagtt     120
gacgtggaaa cccctcaagc aaacttcttc caaagcgaag ttaaacccat tatggataac     180
cgctgtgtcg tctgccacgc gtgctacgat gcaccatgcc aacttaagct ctcttctgtt     240
gagggcattg accgtggtgc gagtaaagca ctggtatatg aaggaacaag actcacagcc     300
gcagcaccaa cacgcttatt cgaagatgca gaaacaaccc aagagtggcg cgatgcgggt     360
tttcatccgg ttctcaacga acgtgatcaa agcatggcag ccaacattga tgcaggactt     420
atcgcacgtt tgctacaaca aaaagagcgc cacccattgc ctgaccaagt ccagttagaa     480
ggctttgact tttcgataga ccgagagcaa acctgtccga cgattgaaga atacgagcaa     540
tacgagaagg ataacccaac ctggggcatg ccttttggta tgccaaatct atcaaacagt     600
gaataccaca cactcatgac ttggttggaa cacggcgcaa taatgaacgt tcaccaacct     660
gttagtgaga atgagcaagc gcaaatagat aagtacgaaa cattacttaa ccactctgat     720
ttgaaaaatc agctgatggc taggtatata tatgagcatt tgttttatc tcatctctac     780 ttttcggaac tcgatgaaga tccccgattc ttcacgctcg tccgctctgc gacaccacca     840
ggacagcccg tcaaacgtat ttcaacgcgt cgcccgtacg atgatccagg ggttgaacgt     900
gtgttttatc gaattattcc agagcaaggg accatagtag ataaaactca catgccattc     960
```

```
gcgttaaaca agcaacgcat agagaactgg aaaacttggt ttattgatgc tgattacatg    1020
gttagtcagc taccgagtta tgaaccagaa gttgctgcaa acccgatgac atcattcatc    1080
gaccttccag tgaagtcgcg ctttaagttc atgctagata atgcacaaaa tacaataatg    1140
gcatacatca aaggcccagt tgtcgtggc caactggcat tgaatgttat caatgatcgc    1200
ttttgggtgt ttttccttga tccagataaa gcagacatcc cagaagtaaa tgagttttac    1260
cgatctcagg ctgataatct aaaactaccg gcagagcaag aaagtaacac gctacctgtt    1320
accaactggg tcaagtacgc gcgtcaacaa gctcgctacc tagaggctaa atctgagttc    1380
actaataact ggtttaaaga aggtgaaaac ctatccaccg atgtaatttg ggatggtaat    1440
ggcaccaacc ataatgcggc attaacgata ttccgccatt ttgatagtgc ttctgttgtt    1500
caagggttag ttggtgaaca gcctaaaaca gtgtggattc ttgactacgc gttactagag    1560
cgtatccact atttgcttgt tgctgggttt gacgtttacg gtaacttcgg ccaccagctc    1620
atgacacgaa tgtttatgga cttcttgcgt ctagaaggcg aaagtaactt tatctcgttg    1680
ttacccgccg atatgcgcca tgaacttcaa tctagctggt ataaagatca agcccgcag    1740 ttgagtgact ttttacaacg aaatgtgaag ccgtttaacc aaccaaccag cgttcagtat    1800
aagagtgacg atccaaaaac agagttggtg gagttgttga gcgaacatgt ttcagatgtg    1860
cttctgcctc gctacgaaat tcaagacacg gctctttctg cgagtagtga aaagcaacta    1920
aaacgtattg accacgttcg tggtgaaggc ctaaaaaccg ttccgcaaat cactatgctt    1980
atggtgagaa gtcaatcagg ggaagatgaa ctgttcacct tacttcacaa caatgcacac    2040
acaaacatct ctagcttgtt tgatgaagaa agtaaccgtg actttgctaa cgatgatatg    2100
accattgtac gcggcgttgt gggaagctac cctgcggcat ttttctcgat caacgaaaac    2160
caagtaaaag attttgtcga tcaatttagt gccatccaaa acgagtccga ttacgttaag    2220
ttattggata attttgcgat tcgtagaagc tcagaaaaat tctggtcatt tagcgatcgt    2280
ttacacaatt ggtaccgtac aaaacaaccg atcgaatttg gattacttga ctataatcgt    2340
tttgagaatc gatga                                                    2355
```

<210> SEQ ID NO 124
<211> LENGTH: 784
<212> TYPE: PRT
<213> ORGANISM: Vibrio alginolyticus

<400> SEQUENCE: 124

```
Met Asn Leu Arg Leu Ile Phe Thr Leu Cys Ile Ala Thr Leu Phe Ala
1               5                   10                  15

Gly Cys Ala Thr Tyr Ala Gly Leu Asn Tyr Asp Gln Leu Phe Gly Pro
            20                  25                  30

Gln Leu Val Arg Glu Arg Thr Val Asp Val Glu Thr Pro Gln Ala Asn
        35                  40                  45

Phe Phe Gln Ser Glu Val Lys Pro Ile Met Asp Asn Arg Cys Val Val
    50                  55                  60

Cys His Ala Cys Tyr Asp Ala Pro Cys Gln Leu Lys Leu Ser Ser Val
65                  70                  75                  80

Glu Gly Ile Asp Arg Gly Ala Ser Lys Ala Leu Val Tyr Glu Gly Thr
                85                  90                  95

Arg Leu Thr Ala Ala Ala Pro Thr Arg Leu Phe Glu Asp Ala Glu Thr
            100                 105                 110

Thr Gln Glu Trp Arg Asp Ala Gly Phe His Pro Val Leu Asn Glu Arg
        115                 120                 125
```

-continued

Asp Gln Ser Met Ala Ala Asn Ile Asp Ala Gly Leu Ile Ala Arg Leu
       130                 135                 140

Leu Gln Gln Lys Glu Arg His Pro Leu Pro Asp Gln Val Gln Leu Glu
145                 150                 155                 160

Gly Phe Asp Phe Ser Ile Asp Arg Glu Gln Thr Cys Pro Thr Ile Glu
                165                 170                 175

Glu Tyr Glu Gln Tyr Glu Lys Asp Asn Pro Thr Trp Gly Met Pro Phe
            180                 185                 190

Gly Met Pro Asn Leu Ser Asn Ser Glu Tyr His Thr Leu Met Thr Trp
        195                 200                 205

Leu Glu His Gly Ala Ile Met Asn Val His Gln Pro Val Ser Glu Asn
    210                 215                 220

Glu Gln Ala Gln Ile Asp Lys Tyr Glu Thr Leu Leu Asn His Ser Asp
225                 230                 235                 240

Leu Lys Asn Gln Leu Met Ala Arg Tyr Ile Tyr Glu His Leu Phe Leu
                245                 250                 255

Ser His Leu Tyr Phe Ser Glu Leu Asp Glu Asp Pro Arg Phe Phe Thr
            260                 265                 270

Leu Val Arg Ser Ala Thr Pro Pro Gly Gln Pro Val Lys Arg Ile Ser
        275                 280                 285

Thr Arg Arg Pro Tyr Asp Asp Pro Gly Val Glu Arg Val Phe Tyr Arg
    290                 295                 300

Ile Ile Pro Glu Gln Gly Thr Ile Val Asp Lys Thr His Met Pro Phe
305                 310                 315                 320

Ala Leu Asn Lys Gln Arg Ile Glu Asn Trp Lys Thr Trp Phe Ile Asp
                325                 330                 335

Ala Asp Tyr Met Val Ser Gln Leu Pro Ser Tyr Glu Pro Glu Val Ala
            340                 345                 350

Ala Asn Pro Met Thr Ser Phe Ile Asp Leu Pro Val Lys Ser Arg Phe
        355                 360                 365

Lys Phe Met Leu Asp Asn Ala Gln Asn Thr Ile Met Ala Tyr Ile Lys
    370                 375                 380

Gly Pro Val Cys Arg Gly Gln Leu Ala Leu Asn Val Ile Asn Asp Arg
385                 390                 395                 400

Phe Trp Val Phe Phe Leu Asp Pro Asp Lys Ala Asp Ile Pro Glu Val
                405                 410                 415

Asn Glu Phe Tyr Arg Ser Gln Ala Asp Asn Leu Lys Leu Pro Ala Glu
            420                 425                 430

Gln Glu Ser Asn Thr Leu Pro Val Thr Asn Trp Val Lys Tyr Ala Arg
        435                 440                 445

Gln Gln Ala Arg Tyr Leu Glu Ala Lys Ser Glu Phe Thr Asn Asn Trp
    450                 455                 460

Phe Lys Glu Gly Glu Asn Leu Ser Thr Asp Val Ile Trp Asp Gly Asn
465                 470                 475                 480

Gly Thr Asn His Asn Ala Ala Leu Thr Ile Phe Arg His Phe Asp Ser
                485                 490                 495

Ala Ser Val Val Gln Gly Leu Val Gly Glu Gln Pro Lys Thr Val Trp
            500                 505                 510

Ile Leu Asp Tyr Ala Leu Leu Glu Arg Ile His Tyr Leu Leu Val Ala
        515                 520                 525

Gly Phe Asp Val Tyr Gly Asn Phe Gly His Gln Leu Met Thr Arg Met
    530                 535                 540

Phe Met Asp Phe Leu Arg Leu Glu Gly Glu Ser Asn Phe Ile Ser Leu

```
                    545                550                555                560
Leu Pro Ala Asp Met Arg His Glu Leu Gln Ser Ser Trp Tyr Lys Asp
                565                570                575

Gln Ser Pro Gln Leu Ser Asp Phe Leu Gln Arg Asn Val Lys Pro Phe
                580                585                590

Asn Gln Pro Thr Ser Val Gln Tyr Lys Ser Asp Pro Lys Thr Glu
                595                600                605

Leu Val Glu Leu Leu Ser Glu His Val Ser Asp Val Leu Pro Arg
610                615                620

Tyr Glu Ile Gln Asp Thr Ala Leu Ser Ala Ser Glu Lys Gln Leu
625                630                635                640

Lys Arg Ile Asp His Val Arg Gly Glu Gly Leu Lys Thr Val Pro Gln
                645                650                655

Ile Thr Met Leu Met Val Arg Ser Gln Ser Gly Glu Asp Glu Leu Phe
                660                665                670

Thr Leu Leu His Asn Asn Ala His Thr Asn Ile Ser Ser Leu Phe Asp
                675                680                685

Glu Glu Ser Asn Arg Asp Phe Ala Asn Asp Asp Met Thr Ile Val Arg
690                695                700

Gly Val Val Gly Ser Tyr Pro Ala Ala Phe Phe Ser Ile Asn Glu Asn
705                710                715                720

Gln Val Lys Asp Phe Val Asp Gln Phe Ser Ala Ile Gln Asn Glu Ser
                725                730                735

Asp Tyr Val Lys Leu Leu Asp Asn Phe Ala Ile Arg Arg Ser Ser Glu
                740                745                750

Lys Phe Trp Ser Phe Ser Asp Arg Leu His Asn Trp Tyr Arg Thr Lys
                755                760                765

Gln Pro Ile Glu Phe Gly Leu Leu Asp Tyr Asn Arg Phe Glu Asn Arg
                770                775                780

<210> SEQ ID NO 125
<211> LENGTH: 2397
<212> TYPE: DNA
<213> ORGANISM: Photobacterium profundum

<400> SEQUENCE: 125
atgatgtata aaccttttt taagcactac acacgtgcaa ttttaatact agcttccatt        60
atattttctg gatgtgctgc ttacgcgggt ttaaattaca ataagctata tggtaaaccc       120
caacctcagc aacgtatgtt agatgcagat tattttcagg ctcaacacta tgttaatgat       180
gttaaaccga taatagacaa taggtgtgtc gtctgccacg cttgttatga tgcgccttgt       240
cagctgaaaa tgtcctcggc tgagggtata gaccgtggcg ccaataaaga taaagtctac       300
caaggcacac ggttactagc cgcaaataca actcgaatgt ttatagatgc acaaacaacc       360
acagagtggc gtaataaagg cttttcgcct gtcttgaatg aacgtttaca atcaccagaa       420
gccaatacac aagctggtgt tattgcccga atgcttcagt taaacaaaa ccaccctta        480 ccgaataatg aaattcttaa tgactcttgg gacttttctc tcgaccgtga tcaacagtgc       540
cctaccattg aagaaatgag cacctatgaa gaaaattacc ctaagtgggg aatgccttac       600
ggtttaccgc aaatatcaag cattgaaaat gatgttttga tgcagtgggt ttcggtaggt       660
gcaccaatga cgaccgtcgc tccccctcca agctctgaac ttgaagaagt ggaaaaatgg       720
gaaacattct taaatcgaga ttcgttaaaa caacaactaa caagccgtta tatatttgaa       780
catatttttg tttcacacat atatttcgat acagaagaaa tacgtaaaca aggaacgccg       840
```

-continued

```
accttcttca aattggtaag atctacaaca gcacccggta agccgattga tctggtcgcc    900
actcgccgac cttacggtga tcccaacgta gatcgcgtct actaccgctt agaacaagtg    960
cgcgaaacaa tcgttgataa aacacatatg ccatatgcac ttaataatga aaagcttgat   1020
cgaataaagt ctttgtttat tgcacctaat tacacaatat cggccttacc aagctacaaa   1080
cccaacgtag ctgcaaaccc gctaacagcc ttcactgaat tgccagttga ggcacgctat   1140
aagttcatgc ttgataatgc acaaaatacg attatgcgt atataaaagg cccagtatgt   1200
agaggacaac ttgcactcaa tgttattaat gaccgctttt gggtattttt tgttgatcct   1260
gatatgtcta atttcacgca agtaaactca ttttatcgtt cacaagcagc aaaccttcac   1320
cttccagctg aaaaggaaag taatactgtt tctattagta attggattcg gtattccaaa   1380
caacaaggtc gattttttgcg tgcaaaaaat gcattcatga atgaacggtt caaacaagga   1440
gagcacctaa ccactcaact catttgggat ggtgatggca caaacacaaa cgcaacttta   1500
acggtgttcc gccactttga cagtgcatca gttgttcaag cttaatagg agagcaaccg   1560
aaaacggcat gggttatcga ttattcactg ttagagcgca ttcattattt actcgtcgca   1620
ggttttgatg tttatggtaa ttatggtcat cagttaagta cacgtatgta catggatctt   1680
cttcggatgg aagggaatc aaatttctta tcattttac ctacaaaaaa tcgccatcaa   1740
gaacttgctg attggtatca aggagctaac caagacttaa ccaaatacct cgaaggtgat   1800
atcaataagt tcgaccaatt aacaggcgta acttatacaa caactaaccc taagcatgaa   1860
ttattacaaa tgctaaggaa acgcgtcgaa aatgtaacgc cgacacgtta ttcgctagaa   1920
tcaacactac tttcaaatga agtaaggag tctcttcata agatcagtaa attacgagga   1980
gaagatgcct ctatattccc tgagctcact tttattatgg ttgaaccaga agacgcttct   2040
ttagatcctc agctcttcac cttgataaga aatagtgccc ataaaaacat ctctagctta   2100
tttgatgaga aatcaaacag gcaatataaa cgcgatacag tgacaatcgt taacggacta   2160
ttgggaagct accccagcgc ttttggcta ataaaagaaa gtgaactacc agccttggta   2220
gatcaagtgc taaaagtgaa aaccaatggt gactatgaaa ggttattaga taaatatggg   2280
attcgtcgaa caaatccttc cttctggtct ttcagtgatg tactgattaa acagtacaag   2340
atcaactacc ctattgagtc aggcattctt gattacaacc gtattcaaaa cagatga      2397
```

<210> SEQ ID NO 126
<211> LENGTH: 798
<212> TYPE: PRT
<213> ORGANISM: Photobacterium profundum

<400> SEQUENCE: 126

```
Met Met Tyr Lys Pro Phe Phe Lys His Tyr Thr Arg Ala Ile Leu Ile
1               5                   10                  15

Leu Ala Ser Ile Ile Phe Ser Gly Cys Ala Ala Tyr Ala Gly Leu Asn
            20                  25                  30

Tyr Asn Lys Leu Tyr Gly Lys Pro Gln Pro Gln Gln Arg Met Leu Asp
        35                  40                  45

Ala Asp Tyr Phe Gln Ala Gln His Tyr Val Asn Asp Val Lys Pro Ile
    50                  55                  60

Ile Asp Asn Arg Cys Val Val Cys His Ala Cys Tyr Asp Ala Pro Cys
65                  70                  75                  80

Gln Leu Lys Met Ser Ser Ala Glu Gly Ile Asp Arg Gly Ala Asn Lys
                85                  90                  95

Asp Lys Val Tyr Gln Gly Thr Arg Leu Leu Ala Ala Asn Thr Thr Arg
            100                 105                 110
```

```
Met Phe Ile Asp Ala Gln Thr Thr Thr Glu Trp Arg Asn Lys Gly Phe
            115                 120                 125

Ser Pro Val Leu Asn Glu Arg Leu Gln Ser Pro Glu Ala Asn Thr Gln
130                 135                 140

Ala Gly Val Ile Ala Arg Met Leu Gln Leu Lys Gln Asn His Pro Leu
145                 150                 155                 160

Pro Asn Asn Glu Ile Leu Asn Asp Ser Trp Asp Phe Ser Leu Asp Arg
                165                 170                 175

Asp Gln Gln Cys Pro Thr Ile Glu Glu Met Ser Thr Tyr Glu Glu Asn
            180                 185                 190

Tyr Pro Lys Trp Gly Met Pro Tyr Gly Leu Pro Gln Ile Ser Ser Ile
        195                 200                 205

Glu Asn Asp Val Leu Met Gln Trp Val Ser Val Gly Ala Pro Met Thr
    210                 215                 220

Thr Val Ala Pro Pro Ser Ser Glu Leu Glu Glu Val Glu Lys Trp
225                 230                 235                 240

Glu Thr Phe Leu Asn Arg Asp Ser Leu Lys Gln Gln Leu Thr Ser Arg
                245                 250                 255

Tyr Ile Phe Glu His Ile Phe Val Ser His Ile Tyr Phe Asp Thr Glu
            260                 265                 270

Glu Ile Arg Lys Gln Gly Thr Pro Thr Phe Phe Lys Leu Val Arg Ser
        275                 280                 285

Thr Thr Ala Pro Gly Lys Pro Ile Asp Leu Val Ala Thr Arg Arg Pro
    290                 295                 300

Tyr Gly Asp Pro Asn Val Asp Arg Val Tyr Tyr Arg Leu Glu Gln Val
305                 310                 315                 320

Arg Glu Thr Ile Val Asp Lys Thr His Met Pro Tyr Ala Leu Asn Asn
                325                 330                 335

Glu Lys Leu Asp Arg Ile Lys Ser Leu Phe Ile Ala Pro Asn Tyr Thr
            340                 345                 350

Ile Ser Ala Leu Pro Ser Tyr Lys Pro Asn Val Ala Ala Asn Pro Leu
        355                 360                 365

Thr Ala Phe Thr Glu Leu Pro Val Glu Ala Arg Tyr Lys Phe Met Leu
    370                 375                 380

Asp Asn Ala Gln Asn Thr Ile Met Ala Tyr Ile Lys Gly Pro Val Cys
385                 390                 395                 400

Arg Gly Gln Leu Ala Leu Asn Val Ile Asn Asp Arg Phe Trp Val Phe
                405                 410                 415

Phe Val Asp Pro Asp Met Ser Asn Phe Thr Gln Val Asn Ser Phe Tyr
            420                 425                 430

Arg Ser Gln Ala Ala Asn Leu His Leu Pro Ala Glu Lys Glu Ser Asn
        435                 440                 445

Thr Val Ser Ile Ser Asn Trp Ile Arg Tyr Ser Lys Gln Gln Gly Arg
    450                 455                 460

Phe Leu Arg Ala Lys Asn Ala Phe Met Asn Glu Arg Phe Lys Gln Gly
465                 470                 475                 480

Glu His Leu Thr Thr Gln Leu Ile Trp Asp Gly Asp Gly Thr Asn Thr
                485                 490                 495

Asn Ala Thr Leu Thr Val Phe Arg His Phe Asp Ser Ala Ser Val Val
            500                 505                 510

Gln Gly Leu Ile Gly Glu Gln Pro Lys Thr Ala Trp Val Ile Asp Tyr
        515                 520                 525

Ser Leu Leu Glu Arg Ile His Tyr Leu Leu Val Ala Gly Phe Asp Val
```

```
                    530                 535                 540
Tyr Gly Asn Tyr Gly His Gln Leu Ser Thr Arg Met Tyr Met Asp Leu
545                 550                 555                 560

Leu Arg Met Glu Gly Glu Ser Asn Phe Leu Ser Phe Leu Pro Thr Lys
                565                 570                 575

Asn Arg His Gln Glu Leu Ala Asp Trp Tyr Gln Gly Ala Asn Gln Asp
                580                 585                 590

Leu Thr Lys Tyr Leu Glu Gly Asp Ile Asn Lys Phe Asp Gln Leu Thr
                595                 600                 605

Gly Val Thr Tyr Thr Thr Thr Asn Pro Lys His Glu Leu Leu Gln Met
610                 615                 620

Leu Arg Lys Arg Val Glu Asn Val Thr Pro Thr Arg Tyr Ser Leu Glu
625                 630                 635                 640

Ser Thr Leu Leu Ser Asn Glu Ser Lys Glu Ser Leu His Lys Ile Ser
                645                 650                 655

Lys Leu Arg Gly Glu Asp Ala Ser Ile Phe Pro Glu Leu Thr Phe Ile
                660                 665                 670

Met Val Glu Pro Glu Asp Ala Ser Leu Asp Pro Gln Leu Phe Thr Leu
                675                 680                 685

Ile Arg Asn Ser Ala His Lys Asn Ile Ser Ser Leu Phe Asp Glu Lys
                690                 695                 700

Ser Asn Arg Gln Tyr Lys Arg Asp Thr Val Thr Ile Val Asn Gly Leu
705                 710                 715                 720

Leu Gly Ser Tyr Pro Ser Ala Phe Trp Leu Ile Lys Glu Ser Glu Leu
                725                 730                 735

Pro Ala Leu Val Asp Gln Val Leu Lys Val Lys Thr Asn Gly Asp Tyr
                740                 745                 750

Glu Arg Leu Leu Asp Lys Tyr Gly Ile Arg Arg Thr Asn Pro Ser Phe
                755                 760                 765

Trp Ser Phe Ser Asp Val Leu Ile Lys Gln Tyr Lys Ile Asn Tyr Pro
                770                 775                 780

Ile Glu Ser Gly Ile Leu Asp Tyr Asn Arg Ile Gln Asn Arg
785                 790                 795
```

<210> SEQ ID NO 127
<211> LENGTH: 2253
<212> TYPE: DNA
<213> ORGANISM: Pseudomonas aeruginosa

<400> SEQUENCE: 127

```
ttgtcgtctt ttatccagtc tgtttgcgcc gctgaagtct cctatagccg cgacgtccag     60
ccgatcttca ctgccaagtg cgtcgcctgc cacgcctgct acgactcgcc ctgccagctc    120
aacctgagca gcgccgaagg cgcgcagcgc ggcgccaacc aactgccggt ctacgatggc    180
acgcggacca aggcgcagga gaccacccgc ctgtacctcg atgcgcacgg cgccgacgcc    240
tggcggcgca aggagttctg gtcggtgctc gaaccgcagg gcggccaggc ggcactgatg    300
gcgcggatgc tcgagcttgg ccacagccag ccgctgcagc cgaatgcgaa gatccctaaa    360
ggcctggaca tttcgatcaa ccgcgccaac cagtgcccga cgccggccag catcgacgag    420
ttcatccgca agaacccagg ttccggcatg ccttttcgcg gtggccgggct gagcgacgac    480
gaatacgcca ccttgcagaa gtggctggcc gcgggcgcgc cggtcgacga gcagccgttg    540
cgaccgaccg ccgccgagat cgccagggtg ccagctgggg agaacttcct caaccagccc    600
ggagccaagc agagcctggt atcgcgctgg ctctacgaac cctgttcct ggcacacctg    660
```

```
tatttcccgg agcagggcgc gcccggccac ttcttccagc tggttcgctc gcgtacgccc    720
agcggccagc cgatcgaccc gattcccacc cggcgcccca acgacgaccc gggcaatacc    780
ttctactacc ggctgtggcc gatccagggc gtgatcgtgc acaagacgca catcacctat    840
ccgctgacgg cgaagaagct ggaccatgtc caggagctgt tcttcggcac ccagtggaac    900
accgacaagg tccccggcta cggcctgcag agccgcgcca acccgttcac caccttcgcc    960
gcgatcccgg cgcgggcgcg ctaccagttc atgctggaca tgccgagta cttcacccgt    1020
accttcatcc gcggtccggt ctgccgcgga cagatcgcca ccgacgtgat ccgcgacaac    1080
ttctgggtgg tattccagga tccctcccag gacctgttcg tcaccgatgc caacttccgc    1140
gcgcagagcg agccgctgct ggccttgccg gggcagatcg acgagctgaa gaacctgctc    1200
ggcctgtgga cgccctaccg ggacaagcgc aacgagtacg aagacctgcg ccaggacgtc    1260
tacgccgacg cgccgccacc gacctggagc acgatctggc atggcaacga caacgccctg    1320
ctgagcatct ccgccagtt cgacagcgcc tcggtgcgca agggcctgct ggcgagata     1380
ccgcagacct tgtggctgat ggactacccg ctgttcgaac ggacctatta cgggctggtg    1440
gtgaacttcg atgtcttcgg caacgtctcg caccaggcgc agacgcgcct gtacttcgac    1500
ctgatccgca acggcgccga gcagaacttc ctccgcctga tgccggtcga cgcgcgccag    1560
ccgctgctcg acgactggta ccagaacagc ggcaagctga agatgtggct ggactaccag    1620
gccttcgacg acgacacgcc gagcgcgctg ggattgccgg agaagcagcc gaagaaggcc    1680
ttcgccgaag aactgctgcg tcgctacggc gacctcaatg cgcgtcccga cccgatcaat    1740
cgctgcctgg acggcaactg ctatcgaccg ggcatcgacc gcgaactgca ggacgccgag    1800
caggccttca gccgcctggt cagccggccg cggccggcc tcaaggtgat cgagcgcttc    1860
cccgaggcga ccatgctgcg gatacgtacg tccagcggca agcgcgaggt ctataccgtg    1920
ctgcgcaacc gcgcgcacag caatgtcgcc ttcatgctcg gcgagtcgct gcgctaccag    1980
ccgggcctgg acaccctgac gatctacccc ggcgtgctgt ccagctatcc gaacttcatg    2040
ttcgatctgc cggcgacgga tgccgaggcc ttcgtcggcg ccctggaggc ggcgaagagc    2100
ggcgaggact cgacaaggt ggtcgaacgc tggggcgtgc gccgcagcaa tccgcagttc    2160
tggagctact ccacgatct cgaggcgtac atccgcgaaa ccgagccggt cgaggcgggc    2220
gcactggaca tgaaccgcta cgagaacctc tga                                2253
```

<210> SEQ ID NO 128
<211> LENGTH: 750
<212> TYPE: PRT
<213> ORGANISM: Pseudomonas aeruginosa

<400> SEQUENCE: 128

Met Ser Ser Phe Ile Gln Ser Val Cys Ala Ala Glu Val Ser Tyr Ser
1               5                   10                  15

Arg Asp Val Gln Pro Ile Phe Thr Ala Lys Cys Val Ala Cys His Ala
            20                  25                  30

Cys Tyr Asp Ser Pro Cys Gln Leu Asn Leu Ser Ser Ala Glu Gly Ala
        35                  40                  45

Gln Arg Gly Ala Asn Gln Leu Pro Val Tyr Asp Gly Thr Arg Thr Lys
    50                  55                  60

Ala Gln Glu Thr Thr Arg Leu Tyr Leu Asp Ala His Gly Ala Asp Ala
65                  70                  75                  80

Trp Arg Arg Lys Glu Phe Trp Ser Val Leu Glu Pro Gln Gly Gly Gln
                85                  90                  95

-continued

```
Ala Ala Leu Met Ala Arg Met Leu Glu Leu Gly His Ser Gln Pro Leu
            100                 105                 110

Gln Pro Asn Ala Lys Ile Pro Lys Gly Leu Asp Ile Ser Ile Asn Arg
            115                 120                 125

Ala Asn Gln Cys Pro Thr Pro Ala Ser Ile Asp Glu Phe Ile Arg Lys
130                 135                 140

Asn Pro Gly Ser Gly Met Pro Phe Ala Val Ala Gly Leu Ser Asp Asp
145                 150                 155                 160

Glu Tyr Ala Thr Leu Gln Lys Trp Leu Ala Ala Gly Ala Pro Val Asp
                165                 170                 175

Glu Gln Pro Leu Arg Pro Thr Ala Ala Glu Met Arg Gln Val Ala Ser
            180                 185                 190

Trp Glu Asn Phe Leu Asn Gln Pro Gly Ala Lys Gln Ser Leu Val Ser
            195                 200                 205

Arg Trp Leu Tyr Glu His Leu Phe Leu Ala His Leu Tyr Phe Pro Glu
        210                 215                 220

Gln Gly Ala Pro Gly His Phe Phe Gln Leu Val Arg Ser Arg Thr Pro
225                 230                 235                 240

Ser Gly Gln Pro Ile Asp Pro Ile Pro Thr Arg Arg Pro Asn Asp Asp
                245                 250                 255

Pro Gly Asn Thr Phe Tyr Tyr Arg Leu Trp Pro Ile Gln Gly Val Ile
            260                 265                 270

Val His Lys Thr His Ile Thr Tyr Pro Leu Thr Ala Lys Lys Leu Asp
        275                 280                 285

His Val Gln Glu Leu Phe Phe Gly Thr Gln Trp Asn Thr Asp Lys Val
    290                 295                 300

Pro Gly Tyr Gly Leu Gln Ser Arg Ala Asn Pro Phe Thr Thr Phe Ala
305                 310                 315                 320

Ala Ile Pro Ala Arg Ala Arg Tyr Gln Phe Met Leu Asp Asn Ala Glu
                325                 330                 335

Tyr Phe Thr Arg Thr Phe Ile Arg Gly Pro Val Cys Arg Gly Gln Ile
            340                 345                 350

Ala Thr Asp Val Ile Arg Asp Asn Phe Trp Val Phe Gln Asp Pro
        355                 360                 365

Ser Gln Asp Leu Phe Val Thr Asp Ala Asn Phe Arg Ala Gln Ser Glu
    370                 375                 380

Pro Leu Leu Ala Leu Pro Gly Gln Ile Asp Glu Leu Lys Asn Leu Leu
385                 390                 395                 400

Gly Leu Trp Ser Ala Tyr Arg Asp Lys Arg Asn Glu Tyr Glu Asp Leu
                405                 410                 415

Arg Gln Asp Val Tyr Ala Asp Ala Pro Pro Thr Trp Ser Thr Ile
            420                 425                 430

Trp His Gly Asn Asp Asn Ala Leu Leu Ser Ile Phe Arg Gln Phe Asp
        435                 440                 445

Ser Ala Ser Val Arg Lys Gly Leu Leu Gly Glu Ile Pro Gln Thr Leu
    450                 455                 460

Trp Leu Met Asp Tyr Pro Leu Phe Glu Arg Thr Tyr Tyr Gly Leu Val
465                 470                 475                 480

Val Asn Phe Asp Val Phe Gly Asn Val Ser His Gln Ala Gln Thr Arg
                485                 490                 495

Leu Tyr Phe Asp Leu Ile Arg Asn Gly Ala Glu Gln Asn Phe Leu Arg
            500                 505                 510

Leu Met Pro Val Asp Ala Arg Gln Pro Leu Leu Asp Asp Trp Tyr Gln
        515                 520                 525
```

```
Asn Ser Gly Lys Leu Lys Met Trp Leu Asp Tyr Gln Ala Phe Asp
    530                 535                 540

Asp Thr Pro Ser Ala Leu Gly Leu Pro Glu Lys Gln Pro Lys Lys Ala
545                 550                 555                 560

Phe Ala Glu Glu Leu Leu Arg Arg Tyr Gly Asp Leu Asn Ala Arg Pro
                565                 570                 575

Asp Pro Ile Asn Arg Cys Leu Asp Gly Asn Cys Tyr Arg Pro Gly Ile
            580                 585                 590

Asp Arg Glu Leu Gln Asp Ala Glu Gln Ala Phe Ser Arg Leu Val Ser
        595                 600                 605

Arg Pro Ala Ala Gly Leu Lys Val Ile Glu Arg Phe Pro Glu Ala Thr
610                 615                 620

Met Leu Arg Ile Arg Thr Ser Ser Gly Lys Arg Glu Val Tyr Thr Val
625                 630                 635                 640

Leu Arg Asn Arg Ala His Ser Asn Val Ala Phe Met Leu Gly Glu Ser
                645                 650                 655

Leu Arg Tyr Gln Pro Gly Leu Asp Thr Leu Thr Ile Tyr Pro Gly Val
            660                 665                 670

Leu Ser Ser Tyr Pro Asn Phe Met Phe Asp Leu Pro Ala Thr Asp Ala
        675                 680                 685

Glu Ala Phe Val Gly Ala Leu Glu Ala Ala Lys Ser Gly Glu Asp Phe
690                 695                 700

Asp Lys Val Val Glu Arg Trp Gly Val Arg Arg Ser Asn Pro Gln Phe
705                 710                 715                 720

Trp Ser Tyr Phe His Asp Leu Glu Ala Tyr Ile Arg Glu Thr Glu Pro
                725                 730                 735

Val Glu Ala Gly Ala Leu Asp Met Asn Arg Tyr Glu Asn Leu
            740                 745                 750

<210> SEQ ID NO 129
<211> LENGTH: 2364
<212> TYPE: DNA
<213> ORGANISM: Oceanobacter sp.

<400> SEQUENCE: 129
atgctaagac ctactctgtt aattttattc ctagccggtt gtgccagtgt tggcattttg      60
caacccaacc taagtgagct gtatggagag gttgtagtct ctgatcgccg cgtcgacaac     120
gactccattg tcgcaagcaa ttaccacgaa caagtcgagc ctatcatcga gcaacgctgc     180
gttgtttgcc acggttgcta cgatgccccc tgtcagctaa agcttttcttc tagcgaaggc    240 attatgcgtg gtgccaccaa gcaaagagtt tatgatggta cccggattct tgccgtggac     300
ccgacacgta ttggtatcga tgccacatca accgaacaat ggcgtaataa agggtttttt     360
agcgtactaa acgatcgcac acaaaacgcg gaggtgaatt tagaaaatag tttgttctat     420
caaatgctgg aacaaaaaca gaacatcct ttgcccaaag ataaactgtt agatgaacgt       480
ttcccttggg gattagatcg ccctgaagtg tgtccgaccc cacaagaata tgctaattac     540
cgcagcaatc agccattgtg gggcatgcct tacgcattac ctgagttgaa gcagcaagag     600
catgaaatat tgaaagaatg gattagaaaa ggcgcgcctt taccgaagct acctgagttg    660
cctgatgata ttaagcaaca gatcaccact tgggagacct tttaaataa gcctgacaat     720 aaacatcaat taaccgcgcg ctatgtattt gagcatacat acctagcaaa cctgtatttt     780
tcagacctgc ctttattcaa aaatattgaa cctgaacagc aaccaaagtt cttttttcaaa   840 atggtacgat ccgctacacc accaggtttt cctattaaac cggttaacgc tcgacgtccc    900
```

-continued

```
tatgacaagc caaatgtaca acaaatttat tatcgcttaa tgcaaataga tcgctcgatt    960
gtgcacaaga cccacatgcc gtatcgatta aatcaagaac gtttagattg gattaacgaa   1020
ttatttatcg agcctgaata cacagtagat aaattaccaa gttatgaacc tgaagtggct   1080
gctaacccat ttattgcatt cgaacaatta ccagttgaag cacgctatcg ttttatgttg   1140
caagaaagcg agtttattgt tcaaggtttt ataaaaggac cggtatgccg tgggcaaatt   1200
gctctcaatg ttattgatga tcatttctgg gttgcctttg ttgatccaga ttatcaagac   1260
gatccggcct tggctgagtt tttaagtgaa caaagcaata atttgcgatt accgggtgaa   1320
gcgcaaagta actcgggaat tgccactaac tggttgcgct atagctcgct gcatgctgat   1380
tacttaaaag caaaaaacaa agctatcgaa gaaaacctttt tagatcaaaa gcgtatgaca   1440
acggatattg tttgggacgg tgacggtcat aatcccaatg ccgctttaac catcatgcgt   1500
cattttgata gttcgactgt ggtgaaaggt tgggttggtc aagaaccaaa aaccgcgtgg   1560
cttatttctt atccattatt agagcgtatt cactatctac tggtggctga gtttgatgtt   1620
tatgggaaca ttggccatca gttaatgaca cgtttatata tggactttttt gcgtatggaa   1680
ggcgaagcca acttcttagc tttattacca caacatgaac gtaaacgact atcggaatat   1740
tggtatcgcg acgctggcga taaagttaaa gagtatttgg aaattaatga aaaacacatg   1800
ctttccgaac caaatatcca atacaaaagt gagcaaccta atccgagct attagctcgc    1860
ttacataaaa aactgagccc tgcaatgagc gataagttta aacttgagag ccagctacct   1920
agtgatatta gtgacttaaa ttcgattaat gcagtaagag gaaaaacggc ctctattatg   1980
cccgaagcaa gtatcctata tattgaagat acacaaaaac tctacacaat acttcgtgcc   2040
agtggacata gtaatttgac aggattgttg tatgaagagt aaatcgtct accagaagag    2100
gattacttaa caatattacc taacatcgct accgcttatc ccaatgcctt ctatcgcatt   2160
cagagtcagc aagcagaacg ctttgctaaa acagttgcta gcattcaaac cgagcaagac   2220
tacgaagcac tgatcgacca gttcggtgtg cgtcgaaccg atccgaagtt ctggcaatat   2280
agcgacgcga ttcataaatc attttctaaa cttgacccttt tgaattatgg tcttttagat   2340
tataaccgtt tagaaaatcg ctaa                                          2364
```

<210> SEQ ID NO 130
<211> LENGTH: 787
<212> TYPE: PRT
<213> ORGANISM: Oceanobacter sp.

<400> SEQUENCE: 130

```
Met Leu Arg Pro Thr Leu Leu Ile Leu Phe Leu Ala Gly Cys Ala Ser
1               5                   10                  15

Val Gly Ile Leu Gln Pro Asn Leu Ser Glu Leu Tyr Gly Glu Val Val
            20                  25                  30

Val Ser Asp Arg Arg Val Asp Asn Asp Ser Ile Val Ala Ser Asn Tyr
        35                  40                  45

His Glu Gln Val Glu Pro Ile Ile Glu Gln Arg Cys Val Val Cys His
    50                  55                  60

Gly Cys Tyr Asp Ala Pro Cys Gln Leu Lys Leu Ser Ser Ser Glu Gly
65                  70                  75                  80

Ile Met Arg Gly Ala Thr Lys Gln Arg Val Tyr Asp Gly Thr Arg Ile
                85                  90                  95

Leu Ala Val Asp Pro Thr Arg Ile Gly Ile Asp Ala Thr Ser Thr Glu
            100                 105                 110
```

-continued

```
Gln Trp Arg Asn Lys Gly Phe Phe Ser Val Leu Asn Asp Arg Thr Gln
            115                 120                 125

Asn Ala Glu Val Asn Leu Glu Asn Ser Leu Phe Tyr Gln Met Leu Glu
        130                 135                 140

Gln Lys Gln Glu His Pro Leu Pro Lys Asp Lys Leu Leu Asp Glu Arg
145                 150                 155                 160

Phe Pro Leu Gly Leu Asp Arg Pro Glu Val Cys Pro Thr Pro Gln Glu
                165                 170                 175

Tyr Ala Asn Tyr Arg Ser Asn Gln Pro Leu Trp Gly Met Pro Tyr Ala
                180                 185                 190

Leu Pro Glu Leu Lys Gln Gln Glu His Glu Ile Leu Lys Glu Trp Ile
            195                 200                 205

Arg Lys Gly Ala Pro Leu Pro Lys Leu Pro Glu Leu Pro Asp Asp Ile
        210                 215                 220

Lys Gln Gln Ile Thr Thr Trp Glu Thr Phe Leu Asn Lys Pro Asp Asn
225                 230                 235                 240

Lys His Gln Leu Thr Ala Arg Tyr Val Phe Glu His Thr Tyr Leu Ala
                245                 250                 255

Asn Leu Tyr Phe Ser Asp Leu Pro Leu Phe Lys Asn Ile Glu Pro Glu
            260                 265                 270

Gln Gln Pro Lys Phe Phe Lys Met Val Arg Ser Ala Thr Pro Pro
        275                 280                 285

Gly Phe Pro Ile Lys Pro Val Asn Ala Arg Arg Pro Tyr Asp Lys Pro
290                 295                 300

Asn Val Gln Gln Ile Tyr Tyr Arg Leu Met Gln Ile Asp Arg Ser Ile
305                 310                 315                 320

Val His Lys Thr His Met Pro Tyr Arg Leu Asn Gln Glu Arg Leu Asp
                325                 330                 335

Trp Ile Asn Glu Leu Phe Ile Glu Pro Glu Tyr Thr Val Asp Lys Leu
            340                 345                 350

Pro Ser Tyr Glu Pro Glu Val Ala Ala Asn Pro Phe Ile Ala Phe Glu
        355                 360                 365

Gln Leu Pro Val Glu Ala Arg Tyr Arg Phe Met Leu Gln Glu Ser Glu
    370                 375                 380

Phe Ile Val Gln Gly Phe Ile Lys Gly Pro Val Cys Arg Gly Gln Ile
385                 390                 395                 400

Ala Leu Asn Val Ile Asp Asp His Phe Trp Val Ala Phe Val Asp Pro
                405                 410                 415

Asp Tyr Gln Asp Asp Pro Ala Leu Ala Glu Phe Leu Ser Glu Gln Ser
            420                 425                 430

Asn Asn Leu Arg Leu Pro Gly Glu Ala Gln Ser Asn Ser Gly Ile Ala
        435                 440                 445

Thr Asn Trp Leu Arg Tyr Ser Ser Leu His Ala Asp Tyr Leu Lys Ala
    450                 455                 460

Lys Asn Lys Ala Ile Glu Glu Asn Leu Leu Asp Gln Lys Arg Met Thr
465                 470                 475                 480

Thr Asp Ile Val Trp Asp Gly Asp Gly His Asn Pro Asn Ala Ala Leu
                485                 490                 495

Thr Ile Met Arg His Phe Asp Ser Ser Thr Val Val Lys Gly Trp Val
            500                 505                 510

Gly Gln Glu Pro Lys Thr Ala Trp Leu Ile Ser Tyr Pro Leu Leu Glu
        515                 520                 525

Arg Ile His Tyr Leu Leu Val Ala Glu Phe Asp Val Tyr Gly Asn Ile
    530                 535                 540
```

| | | | | | | | | | | | |
|---|---|---|---|---|---|---|---|---|---|---|---|
|Gly|His|Gln|Leu|Met|Thr|Arg|Leu|Tyr|Met|Asp|Phe|Leu|Arg|Met|Glu|
|545| | | | |550| | | | |555| | | | |560|

Gly His Gln Leu Met Thr Arg Leu Tyr Met Asp Phe Leu Arg Met Glu
545                 550                 555                 560

Gly Glu Ala Asn Phe Leu Ala Leu Leu Pro Gln His Glu Arg Lys Arg
                565                 570                 575

Leu Ser Glu Tyr Trp Tyr Arg Asp Ala Gly Asp Lys Val Lys Glu Tyr
            580                 585                 590

Leu Glu Ile Asn Glu Lys His Met Leu Ser Glu Pro Asn Ile Gln Tyr
        595                 600                 605

Lys Ser Glu Gln Pro Lys Ser Glu Leu Leu Ala Arg Leu His Lys Lys
    610                 615                 620

Leu Ser Pro Ala Met Ser Asp Lys Phe Lys Leu Glu Ser Gln Leu Pro
625                 630                 635                 640

Ser Asp Ile Ser Asp Leu Asn Ser Ile Asn Ala Val Arg Gly Lys Thr
                645                 650                 655

Ala Ser Ile Met Pro Glu Ala Ser Ile Leu Tyr Ile Glu Asp Thr Gln
                660                 665                 670

Lys Leu Tyr Thr Ile Leu Arg Ala Ser Gly His Ser Asn Leu Thr Gly
            675                 680                 685

Leu Leu Tyr Glu Glu Leu Asn Arg Leu Pro Glu Glu Asp Tyr Leu Thr
690                 695                 700

Ile Leu Pro Asn Ile Ala Thr Ala Tyr Pro Asn Ala Phe Tyr Arg Ile
705                 710                 715                 720

Gln Ser Gln Gln Ala Glu Arg Phe Ala Lys Thr Val Ala Ser Ile Gln
                725                 730                 735

Thr Glu Gln Asp Tyr Glu Ala Leu Ile Asp Gln Phe Gly Val Arg Arg
            740                 745                 750

Thr Asp Pro Lys Phe Trp Gln Tyr Ser Asp Ala Ile His Lys Ser Phe
        755                 760                 765

Ser Lys Leu Asp Pro Leu Asn Tyr Gly Leu Leu Asp Tyr Asn Arg Leu
    770                 775                 780

Glu Asn Arg
785

<210> SEQ ID NO 131
<211> LENGTH: 2394
<212> TYPE: DNA
<213> ORGANISM: Shewanella baltica

<400> SEQUENCE: 131

```
atggacgcga taaaaagaat atggaaaagg ttgttattgg ccacagtgct gttggcgacg      60
ggttgtgcca gtagcgcaa atcgatttc aatgctctgt ttggcactag ctcaccgcaa       120
aagcgcgtcg agaatgcaca gcttaacaac caatttgttc aacaggccga atttgtgcac    180
aaagaagttg agccaatcct caatagccgc tgcgtggtgt gccatgcctg ctacgatgct    240
ccctgccagc tcaaaatgac ctcaagcgaa ggcatagaac gcggagcgag taaggaaaaa    300
gtctatcaag gcacacgttt agtcgccgcc acgcccaatc gcttatttgt cgatgccttt    360
accccagaag cttggcgtca acgcgggttt taccccatgt aaacgagcg caatcaaact    420
ccagaagcca tacccaagc ctcagtatta gccagaatgc tcacacttaa gcaaatgcat    480
cccctgcccg aagacaagat tttagataag cgttttgatt tcagcctcga cagagttcaa    540
caatgcgcca acctagagga aatggacaaa tacgagcaaa gccaaccgtt tgcgggtatg    600
ccctatggct tgccagcatt gaatgcgaat gaacatcaag tgttgatgca ctggctcgaa    660
caaggtgcgc cattgccatt cgcgccatcg ctagcccctg aatttataac ggaaatcacc    720
```

```
cattgggagc aattttaaa cggcgacagt ttaaaaagcc aattaagcgc acgctacatc      780
tacgagcatt tgtttgcctt ccatttatat tttgaatctt taaatcagcc gaacgcccag      840
cctctatttt tcgagttagt ccgttcgagg acgccgccgg ggcaagcgct ggatattatc      900
gcctcccgtc gtcccttcga cgatcctaag gtggaacgtg tctattaccg ttttcgacct      960
tatcgggcga ccatagtcga taaaacccat atccccatg ccttaaatac cggcttgctg     1020
cacgactggc agcaatggtt tatcgatgcg gattactcag tgactcagct gccgagctac     1080
cagccgagca ttgcggccaa tcccttcgaa gcctttattc aaattcctgc cggtgcgcgc     1140
tatcgcttta tgctgacccg cgcccaagac accattatgg gctttattaa aggcccagtg     1200
tgccgtggtc aggtggcgct caatgtgatt aacgacagat tctgggtgta ctttgttacc     1260
ccagattata tggacgacac ggattttagg accttctacc attcccagat gaaaaccta     1320 cgaatgcctg cggaggaaga aagcactgca ctcgccgtaa cttgggtgaa atatgccgcc     1380
aagcaaggcc agtacatgcg ggcacgtaat cagttcttga acgagaagtt taaaaacggc     1440
caacacctca ccatagacgg gctctgggat ggcgacgaca acaatgataa tgctagcctg     1500
acagtgtttc gccatttcga taatgccact gtggtcaaag gtttagtcgg tgagccgccc     1560
aaaaccgctt ggattatcga ttacgcctta ttggagcgta tccactattt actggtcgca     1620
ggtttcgatg tgtatggtaa ctacggccac cagctattaa ctcgcttata catggatttt     1680
ttacgcatgg agggggaatc aaatttccta actttgttac cgcaggagga aaggcgcaaa     1740
cagtttagtg attggtatca aggggctggc actcaactca cagcgtttat cgcgggggat     1800
atcaacacct ttaatcagcc cacgggcgtg ctctactata gcgatgacct caagggcgaa     1860
ctgtatcaaa aactcgggca gaaagtcgct aaggtacagc caaatagata tcaaatagaa     1920
aacagtcact tgcaagccaa cagcaaggca ctgttgcagg ctttaggtcg attaaaaggc     1980
acccaagcga ccctgttacc tgagctgacg atgatcatgg tcgagcccga aaaagcaggt     2040
aaagctgagg tctttacctt agttcgcaat agtgcccatc gtaatatttc gagcctgttt     2100
aatgaggcca gtaaccgcga acccgcaaag gatgatgtca ccttagtgca tggtttattg     2160
ggcagttacc cagaagcctt ctggctggtg aaagaacagg acttacctaa aatcgtcgcg     2220
gcggtagagc aaatgcaaac cgagaaagac tatgaggcac tgctcgatat tgcggctgta     2280
cgccgtagcg atcccacatt tgggcctttt agtgacaaac tcaatcagat attttcgac      2340 aatcatccaa tagaaagtgg ttggctggat tataaccgtc tgcaaaatcg ttaa           2394

<210> SEQ ID NO 132
<211> LENGTH: 797
<212> TYPE: PRT
<213> ORGANISM: Shewanella baltica

<400> SEQUENCE: 132

Met Asp Ala Ile Lys Arg Ile Trp Lys Arg Leu Leu Leu Ala Thr Val
1               5                   10                  15

Leu Leu Ala Thr Gly Cys Ala Ser Val Ala Gln Ile Asp Phe Asn Ala
            20                  25                  30

Leu Phe Gly Thr Ser Ser Pro Gln Lys Arg Val Glu Asn Ala Gln Leu
        35                  40                  45

Asn Asn Gln Phe Val Gln Gln Ala Glu Phe Val His Lys Glu Val Glu
    50                  55                  60

Pro Ile Leu Asn Ser Arg Cys Val Val Cys His Ala Cys Tyr Asp Ala
65                  70                  75                  80
```

-continued

Pro Cys Gln Leu Lys Met Thr Ser Ser Glu Ile Glu Arg Gly Ala
                85                  90                  95

Ser Lys Glu Lys Val Tyr Gln Gly Thr Arg Leu Val Ala Ala Thr Pro
                100                 105                 110

Asn Arg Leu Phe Val Asp Ala Phe Thr Pro Glu Ala Trp Arg Gln Arg
                115                 120                 125

Gly Phe Tyr Pro Met Leu Asn Glu Arg Asn Gln Thr Pro Glu Ala Asn
        130                 135                 140

Thr Gln Ala Ser Val Leu Ala Arg Met Leu Thr Leu Lys Gln Met His
145                 150                 155                 160

Pro Leu Pro Glu Asp Lys Ile Leu Asp Lys Arg Phe Asp Phe Ser Leu
                165                 170                 175

Asp Arg Val Gln Gln Cys Ala Asn Leu Glu Glu Met Asp Lys Tyr Glu
                180                 185                 190

Gln Ser Gln Pro Phe Ala Gly Met Pro Tyr Gly Leu Pro Ala Leu Asn
        195                 200                 205

Ala Asn Glu His Gln Val Leu Met His Trp Leu Glu Gln Gly Ala Pro
210                 215                 220

Leu Pro Phe Ala Pro Ser Leu Ala Pro Glu Phe Ile Thr Glu Ile Thr
225                 230                 235                 240

His Trp Glu Gln Phe Leu Asn Gly Asp Ser Leu Lys Ser Gln Leu Ser
                245                 250                 255

Ala Arg Tyr Ile Tyr Glu His Leu Phe Ala Phe His Leu Tyr Phe Glu
                260                 265                 270

Ser Leu Asn Gln Pro Asn Ala Gln Pro Leu Phe Glu Leu Val Arg
                275                 280                 285

Ser Arg Thr Pro Pro Gly Gln Ala Leu Asp Ile Ile Ala Ser Arg Arg
                290                 295                 300

Pro Phe Asp Asp Pro Lys Val Glu Arg Val Tyr Tyr Arg Phe Arg Pro
305                 310                 315                 320

Tyr Arg Ala Thr Ile Val Asp Lys Thr His Ile Pro Tyr Ala Leu Asn
                325                 330                 335

Thr Gly Leu Leu His Asp Trp Gln Trp Phe Ile Asp Ala Asp Tyr
        340                 345                 350

Ser Val Thr Gln Leu Pro Ser Tyr Gln Pro Ser Ile Ala Ala Asn Pro
                355                 360                 365

Phe Glu Ala Phe Ile Gln Ile Pro Ala Gly Ala Arg Tyr Arg Phe Met
        370                 375                 380

Leu Thr Arg Ala Gln Asp Thr Ile Met Gly Phe Ile Lys Gly Pro Val
385                 390                 395                 400

Cys Arg Gly Gln Val Ala Leu Asn Val Ile Asn Asp Arg Phe Trp Val
                405                 410                 415

Tyr Phe Val Thr Pro Asp Tyr Met Asp Asp Thr Asp Phe Arg Thr Phe
                420                 425                 430

Tyr His Ser Gln Ile Glu Asn Leu Arg Met Pro Ala Glu Glu Ser
        435                 440                 445

Thr Ala Leu Ala Val Thr Trp Val Lys Tyr Ala Ala Lys Gln Gly Gln
        450                 455                 460

Tyr Met Arg Ala Arg Asn Gln Phe Leu Asn Glu Lys Phe Lys Asn Gly
465                 470                 475                 480

Gln His Leu Thr Ile Asp Gly Leu Trp Asp Gly Asp Asn Asn Asp
        485                 490                 495

Asn Ala Ser Leu Thr Val Phe Arg His Phe Asp Asn Ala Thr Val Val
                500                 505                 510

```
Lys Gly Leu Val Gly Glu Pro Pro Lys Thr Ala Trp Ile Ile Asp Tyr
            515                 520                 525

Ala Leu Leu Glu Arg Ile His Tyr Leu Leu Val Ala Gly Phe Asp Val
            530                 535                 540

Tyr Gly Asn Tyr Gly His Gln Leu Leu Thr Arg Leu Tyr Met Asp Phe
545                 550                 555                 560

Leu Arg Met Glu Gly Glu Ser Asn Phe Leu Thr Leu Pro Gln Glu
                565                 570                 575

Glu Arg Arg Lys Gln Phe Ser Asp Trp Tyr Gln Gly Ala Gly Thr Gln
            580                 585                 590

Leu Thr Ala Phe Ile Ala Gly Asp Ile Asn Thr Phe Asn Gln Pro Thr
            595                 600                 605

Gly Val Leu Tyr Tyr Ser Asp Asp Leu Lys Gly Glu Leu Tyr Gln Lys
            610                 615                 620

Leu Gly Gln Lys Val Ala Lys Val Gln Pro Asn Arg Tyr Gln Ile Glu
625                 630                 635                 640

Asn Ser His Leu Gln Ala Asn Ser Lys Ala Leu Leu Gln Ala Leu Gly
                645                 650                 655

Arg Leu Lys Gly Thr Gln Ala Thr Leu Leu Pro Glu Leu Thr Met Ile
            660                 665                 670

Met Val Glu Pro Glu Lys Ala Gly Lys Ala Glu Val Phe Thr Leu Val
            675                 680                 685

Arg Asn Ser Ala His Arg Asn Ile Ser Ser Leu Phe Asn Glu Ala Ser
690                 695                 700

Asn Arg Glu Pro Ala Lys Asp Asp Val Thr Leu Val His Gly Leu Leu
705                 710                 715                 720

Gly Ser Tyr Pro Glu Ala Phe Trp Leu Val Lys Glu Gln Asp Leu Pro
                725                 730                 735

Lys Ile Val Ala Ala Val Glu Gln Met Gln Thr Glu Lys Asp Tyr Glu
            740                 745                 750

Ala Leu Leu Asp Ile Ala Ala Val Arg Arg Ser Asp Pro Thr Phe Trp
            755                 760                 765

Ala Phe Ser Asp Lys Leu Asn Gln Ile Phe Phe Asp Asn His Pro Ile
            770                 775                 780

Glu Ser Gly Trp Leu Asp Tyr Asn Arg Leu Gln Asn Arg
785                 790                 795

<210> SEQ ID NO 133
<211> LENGTH: 2253
<212> TYPE: DNA
<213> ORGANISM: Pseudomonas aeruginosa

<400> SEQUENCE: 133
ttgtcgtctt ttatccagtc tgtttccgct gctgaaattt cctatagccg tgacgtccag    60
ccgatcttta ccgccaaatg cgtcgcctgc cacgcctgct acgattcgcc ctgccagctc   120
aacctgagca gcgccgaggg cgcgcagcgc ggcgccaacc agctgccggt ctacgacggc   180
actcggacca aggcgcagga aaccacccgc ctgtacctcg atgcgcacgg tgccgacgcc   240
tgccggcgca aggacttctg gtcggtgctc gaatcgcagg acggccaggc cgcactgatg   300
gcgcggatgc tcgagcttgg ccacagccag ccgttgcagc gaatgcgaa gatccccgaa   360
ggcctggaca tttcgatcaa ccgcgccaac cagtgcccga cgccggccag catcgatgcg   420
ttcatccgca gaaccccagg ttccggcatg cctttcgcgg tggccgggct gagcgacgac   480
gaatacgcca ccttgcagaa gtggctggcc gcgggcgccc cggtcgacca gcagccgttg   540
```

```
cggccgaccg ccgccgaggc gcgccaggtg gccagctggg agcgtttcct caaccagcct      600
ggggccaagc agagcctggt ctcgcgctgg ctctacgagc acctgttcct ggcgcacctg      660
tatttcccgg agcagggcgc gcccggccac ttcttccagc tggtgcgttc gcgcacgccc      720
agcggccagc cgatcgaccc gatcccgacc cggcgtccca cgacgatcc gggcaacagc      780 ttctattacc gcctctggcc gatccagggc gtgatcgtac acaagacgca catcacctat      840
ccgctgacgg cgaagaagct ggaacgcgtc caggagctgt tcttcggcac ccagtggaac      900
accgacaagg ttcccggcta cggcgtgcag agccgcgcca cccgttcgc caccttcgcc      960 gcgatcccgc cacgggcgcg ctaccagttc atgctggata cgccgaata cttcacccgt     1020 accttcatcc gcgggccggt gtgccgtgga cagatcgcca ccgacgtgat ccgcgacaac     1080 ttctggtgg tattccagga ccccgatcag gacctgttcg tcaccgacgc caacttccgc     1140
gcgcagagcg agccgctgct ggccttgccg gggcagatcg acgagctgaa gaacctgctc     1200
ggcctgtgga gcgcctaccg ggacaagcgc aacgagtacg aagacctgcg ccaggacgtc     1260
tacgccgacg cgccgccgcc gacctggaac acgctctggc acggcaacga caacgccctg     1320
ctgagcatct ccgccagtt cgacagcgcc tcggtgcgca agggcctgct ggcgaggta     1380 ccgcagaccc tgtggctgat ggactatccg ctgttcgagc gaacctacta cgggctggtg     1440
gtgaacttcg atgtcttcgg caacgtctcg caccaggcgc agacgcggct gtacttcgac     1500
ctgatccgca acggcgccga gcagaacttc ctccgcctga tgccggtcga cgcgcgccag     1560
ccgttgctcg acgactggta ccagaacagc ggcaagctga agatgtggat ggactaccag     1620
gccttcgacg acgacacgcc gagcgcgctg ggattgccgg agaagcagcc gaagaaggcc     1680
ttcgccgaag aactgctgcg tcgctacggc gacctcaatg cgcgtcccga cccgatcaac     1740
cgctgcctgg acggcaactg ctatcgaccg ggcatcgacc gcgaactgca ggacgccgag     1800
caggccttca gtcgcctggt gagccggccg cggccggcc tcaaggtcat cgagcgcttc     1860
cccgaggcga ccatgctgcg gatacgtacg tccagcggca agcgcgaggt ctataccgtg     1920
ctgcgcaacc gcgcgcacag caatgtcgcc ttcatgctcg gcgagtcgct gcgctaccag     1980
ccgggcctgg acaccctgac gatctacccg ggcgtgctgt ccagctaccc gaacttcatg     2040
ttcgatctgc cggcgacgga tgccgagtcc ttcgtcggcg ccctggaggc ggcgaagagc     2100
ggcgaggact cgacaaggt ggtcgaacgc tggggcgtgc gccgcagcaa tcctcagttc     2160
tggagctact ccacgatct cgaggcgtac atccgcgaaa ccgagccggt cgaggcgggc     2220
gcactggaca tgaaccgcta cgagaacctc tga                                  2253
```

<210> SEQ ID NO 134
<211> LENGTH: 750
<212> TYPE: PRT
<213> ORGANISM: Pseudomonas aeruginosa

<400> SEQUENCE: 134

```
Met Ser Ser Phe Ile Gln Ser Val Ser Ala Ala Glu Ile Ser Tyr Ser
1               5                  10                  15

Arg Asp Val Gln Pro Ile Phe Thr Ala Lys Cys Val Ala Cys His Ala
            20                  25                  30

Cys Tyr Asp Ser Pro Cys Gln Leu Asn Leu Ser Ser Ala Glu Gly Ala
        35                  40                  45

Gln Arg Gly Ala Asn Gln Leu Pro Val Tyr Asp Gly Thr Arg Thr Lys
    50                  55                  60

Ala Gln Glu Thr Thr Arg Leu Tyr Leu Asp Ala His Gly Ala Asp Ala
```

-continued

```
             65                  70                  75                  80
Trp Arg Arg Lys Asp Phe Trp Ser Val Leu Glu Ser Gln Asp Gly Gln
                     85                  90                  95

Ala Ala Leu Met Ala Arg Met Leu Glu Leu Gly His Ser Gln Pro Leu
                100                 105                 110

Gln Pro Asn Ala Lys Ile Pro Glu Gly Leu Asp Ile Ser Ile Asn Arg
            115                 120                 125

Ala Asn Gln Cys Pro Thr Pro Ala Ser Ile Asp Ala Phe Ile Arg Lys
        130                 135                 140

Asn Pro Gly Ser Gly Met Pro Phe Ala Val Ala Gly Leu Ser Asp Asp
145                 150                 155                 160

Glu Tyr Ala Thr Leu Gln Lys Trp Leu Ala Ala Gly Ala Pro Val Asp
                165                 170                 175

Gln Gln Pro Leu Arg Pro Thr Ala Ala Glu Ala Arg Gln Val Ala Ser
            180                 185                 190

Trp Glu Arg Phe Leu Asn Gln Pro Gly Ala Lys Gln Ser Leu Val Ser
        195                 200                 205

Arg Trp Leu Tyr Glu His Leu Phe Leu Ala His Leu Tyr Phe Pro Glu
210                 215                 220

Gln Gly Ala Pro Gly His Phe Phe Gln Leu Val Arg Ser Arg Thr Pro
225                 230                 235                 240

Ser Gly Gln Pro Ile Asp Pro Ile Pro Thr Arg Arg Pro Asn Asp Asp
                245                 250                 255

Pro Gly Asn Ser Phe Tyr Tyr Arg Leu Trp Pro Ile Gln Gly Val Ile
            260                 265                 270

Val His Lys Thr His Ile Thr Tyr Pro Leu Thr Ala Lys Lys Leu Glu
        275                 280                 285

Arg Val Gln Glu Leu Phe Phe Gly Thr Gln Trp Asn Thr Asp Lys Val
    290                 295                 300

Pro Gly Tyr Gly Val Gln Ser Arg Ala Asn Pro Phe Ala Thr Phe Ala
305                 310                 315                 320

Ala Ile Pro Pro Arg Ala Arg Tyr Gln Phe Met Leu Asp Asn Ala Glu
                325                 330                 335

Tyr Phe Thr Arg Thr Phe Ile Arg Gly Pro Val Cys Arg Gly Gln Ile
            340                 345                 350

Ala Thr Asp Val Ile Arg Asp Asn Phe Trp Val Val Phe Gln Asp Pro
        355                 360                 365

Asp Gln Asp Leu Phe Val Thr Asp Ala Asn Phe Arg Ala Gln Ser Glu
    370                 375                 380

Pro Leu Leu Ala Leu Pro Gly Gln Ile Asp Glu Leu Lys Asn Leu Leu
385                 390                 395                 400

Gly Leu Trp Ser Ala Tyr Arg Asp Lys Arg Asn Glu Tyr Glu Asp Leu
                405                 410                 415

Arg Gln Asp Val Tyr Ala Asp Ala Pro Pro Thr Trp Asn Thr Leu
            420                 425                 430

Trp His Gly Asn Asp Asn Ala Leu Leu Ser Ile Phe Arg Gln Phe Asp
        435                 440                 445

Ser Ala Ser Val Arg Lys Gly Leu Leu Gly Glu Val Pro Gln Thr Leu
    450                 455                 460

Trp Leu Met Asp Tyr Pro Leu Phe Glu Arg Thr Tyr Tyr Gly Leu Val
465                 470                 475                 480

Val Asn Phe Asp Val Phe Gly Asn Val Ser His Gln Ala Gln Thr Arg
                485                 490                 495
```

```
Leu Tyr Phe Asp Leu Ile Arg Asn Gly Ala Glu Gln Asn Phe Leu Arg
            500                 505                 510

Leu Met Pro Val Asp Ala Arg Gln Pro Leu Leu Asp Asp Trp Tyr Gln
            515                 520                 525

Asn Ser Gly Lys Leu Lys Met Trp Met Asp Tyr Gln Ala Phe Asp Asp
        530                 535                 540

Asp Thr Pro Ser Ala Leu Gly Leu Pro Glu Lys Gln Pro Lys Lys Ala
545                 550                 555                 560

Phe Ala Glu Glu Leu Leu Arg Arg Tyr Gly Asp Leu Asn Ala Arg Pro
                565                 570                 575

Asp Pro Ile Asn Arg Cys Leu Asp Gly Asn Cys Tyr Arg Pro Gly Ile
            580                 585                 590

Asp Arg Glu Leu Gln Asp Ala Glu Gln Ala Phe Ser Arg Leu Val Ser
        595                 600                 605

Arg Pro Ala Ala Gly Leu Lys Val Ile Glu Arg Phe Pro Glu Ala Thr
610                 615                 620

Met Leu Arg Ile Arg Thr Ser Ser Gly Lys Arg Glu Val Tyr Thr Val
625                 630                 635                 640

Leu Arg Asn Arg Ala His Ser Asn Val Ala Phe Met Leu Gly Glu Ser
                645                 650                 655

Leu Arg Tyr Gln Pro Gly Leu Asp Thr Leu Thr Ile Tyr Pro Gly Val
            660                 665                 670

Leu Ser Ser Tyr Pro Asn Phe Met Phe Asp Leu Pro Ala Thr Asp Ala
        675                 680                 685

Glu Ser Phe Val Gly Ala Leu Glu Ala Ala Lys Ser Gly Glu Asp Phe
690                 695                 700

Asp Lys Val Val Glu Arg Trp Gly Val Arg Arg Ser Asn Pro Gln Phe
705                 710                 715                 720

Trp Ser Tyr Phe His Asp Leu Glu Ala Tyr Ile Arg Glu Thr Glu Pro
                725                 730                 735

Val Glu Ala Gly Ala Leu Asp Met Asn Arg Tyr Glu Asn Leu
            740                 745                 750

<210> SEQ ID NO 135
<211> LENGTH: 2301
<212> TYPE: DNA
<213> ORGANISM: Pseucomonas putida

<400> SEQUENCE: 135
atggtgcatc gtatccttgc cggcgccttc gccctgctca tcagcggcgc ggtattcggg    60
caggccccca gtcgagccc ggctatttcc tacacccggg acattcaacc gatcttcacc   120
gagaagtgcg tggcctgcca cgcctgcaac gacgccgcct gccagctcaa gctggaaagc   180
cctgaaggcg cggtacgcgg ggccagcaag gtcccggtgt accagggcga gcggagcaag   240
gcagtcccca ccacgcggct gttctacgac gcacacagcg aagagcaatg gcgcaagaag   300
ggcttctact cggtgctcga caaccagggc ggtcaggccg cgttgatggc gcgcatgctg   360
gagttgggcc acaagacccc gcttacgccc aacgccaagc tgcccgaaga gatcgtcctg   420
ggcctgagcc gcaacaacat gtgcccgttg ccccatgaat cgacgcctca tgccggcgca   480
caccccaagg agggcatgcc gctggcggtg accgggctga ccgacaagga atatgacacc   540
atgcgccgct ggctggccgc tggtgcgccg gtggagtacc agccgatcca gccgagcgcg   600
gccgaagcca ggcagatcgc agagtgggaa gaactgctca accgcccggg ttccaccgag   660
gcgctggtgg gacgctggct gtacgagcac ctgttttttgg cgcacatcca tttcgctggc   720
```

-continued

```
ggcgagcagg gccacttctt ccagtgggtg cgctcgcgca cgccaagtgg caagccggtc      780
gatatcattg ccacccgccg ccccaacgac ccaccgggca cggacttcta ctaccggttg      840
atcccggtgc agggcgtgat cgtgcacaag acgcacatca cctacccgat ggggccgcag      900
aagctcaagc gcgtgaagca gctgttctat gccggtgact ggcatgctgc cgcgcttccg      960
ggctacggcc cgcgccaccg ggccaatccg tttgaaacct tcgaggcgat cccggcggtg     1020
gcgcgctacc agttcatgct ggataacgcc gagtacttcg tgcgcacctt catccgtggc     1080
ccggtgtgcc gcgggcagat tgccaccgac gtgatccgcg acaacttctg ggcgctgttc     1140
caggagccgg ccttcgatcg ctacatcacc gatgccaagt accgcggcga ggctaccccg     1200
ctgctggcca tgcctggtca gatcgatgac gtgggcagtg tgctgagcct gtggcacgcc     1260
tatcgtgaca agcgcaacga ctacgagaaa ctgcgccgtg aagcctatgc cgaaatgccg     1320
gcaccgagat ggtcgacgct gtgggccggt aacgacaatg cgctgctgag catcttccgt     1380
cacttcgaca cgcatcggt gaccaagggc ctggtggggg atgtgccgct gaccgtgtgg     1440
ctgttcgact acccgttgtt cgagcgcacg tattaccagc tggcggtcaa cttcgatgtg     1500
tatggcaacg tttcgcacca gttgcagacg cgcctgtatt cgacctgat ccgcaacggc     1560
gccgaggtca acttcctgcg cctgatgccg gccgaccagc gcaaggcgat ccttggcgac     1620
tggtaccaga acagtggcaa ggtgaagatg tggatggatt atgaagacat cgacaccgac     1680
accccgagtg gcatcaagct cgacccgcgc aaccccaaac gcgactttgg actgaagctg     1740
ctgcagcgca ccggcagcct gaatgccgca ccggacccga tcaaccgctg ccagggcgcg     1800
ttctgctcac ggccgcagat gagcgaagaa ttccgcaatg ccgagcagtc gctcagccga     1860
ctggtgtcac gcccggcggc cgggctgaag gtgatcaacc agttgcccga ggcgaccatg     1920
ctgcgtatcg aagggcagga cggccagcgt caggtgtaca gcctgctgcg caaccgcgcg     1980
cacagcaacg tggcgttcct gctgggtgag gcgtaccgct accagccggg gctggatacc     2040
ctgaccctgt acccgggggt gctctccagc tacccgaact tcatcttcaa catcccgacc     2100
aaggatgtgc cggagttcgt cgaggacatg gagtacgcca agatgacgc ggcgaagttc     2160
gagcgcattg tcatgcgctg gggtgtgcgc cgcagtcacc cggccttctg gcgctatttc     2220
catgacctga acagctatat caaggagacc gaaccggtcg aggcgggcgt gctggacatg     2280
aaccgctacg agaacctctg a                                               2301
```

<210> SEQ ID NO 136
<211> LENGTH: 766
<212> TYPE: PRT
<213> ORGANISM: Pseudomonas putida

<400> SEQUENCE: 136

```
Met Val His Arg Ile Leu Ala Gly Ala Phe Ala Leu Leu Ile Ser Gly
1               5                   10                  15

Ala Val Phe Gly Gln Ala Pro Gln Ser Ser Pro Ala Ile Ser Tyr Thr
            20                  25                  30

Arg Asp Ile Gln Pro Ile Phe Thr Glu Lys Cys Val Ala Cys His Ala
        35                  40                  45

Cys Asn Asp Ala Ala Cys Gln Leu Lys Leu Glu Ser Pro Glu Gly Ala
    50                  55                  60

Val Arg Gly Ala Ser Lys Val Pro Val Tyr Gln Gly Glu Arg Ser Lys
65                  70                  75                  80

Ala Val Pro Thr Thr Arg Leu Phe Tyr Asp Ala His Ser Glu Glu Gln
                85                  90                  95
```

```
Trp Arg Lys Lys Gly Phe Tyr Ser Val Leu Asp Asn Gln Gly Gly Gln
            100                 105                 110

Ala Ala Leu Met Ala Arg Met Leu Glu Leu Gly His Lys Thr Pro Leu
        115                 120                 125

Thr Pro Asn Ala Lys Leu Pro Glu Glu Ile Val Leu Gly Leu Ser Arg
    130                 135                 140

Asn Asn Met Cys Pro Leu Pro His Glu Phe Asp Ala Tyr Ala Gly Ala
145                 150                 155                 160

His Pro Lys Glu Gly Met Pro Leu Ala Val Thr Gly Leu Thr Asp Lys
                165                 170                 175

Glu Tyr Asp Thr Met Arg Arg Trp Leu Ala Ala Gly Ala Pro Val Glu
            180                 185                 190

Tyr Gln Pro Ile Gln Pro Ser Ala Ala Glu Ala Arg Gln Ile Ala Glu
        195                 200                 205

Trp Glu Glu Leu Leu Asn Arg Pro Gly Ser Thr Glu Ala Leu Val Gly
    210                 215                 220

Arg Trp Leu Tyr Glu His Leu Phe Leu Ala His Ile His Phe Ala Gly
225                 230                 235                 240

Gly Glu Gln Gly His Phe Phe Gln Trp Val Arg Ser Arg Thr Pro Ser
                245                 250                 255

Gly Lys Pro Val Asp Ile Ile Ala Thr Arg Arg Pro Asn Asp Pro Pro
            260                 265                 270

Gly Thr Asp Phe Tyr Tyr Arg Leu Ile Pro Val Gln Gly Val Ile Val
        275                 280                 285

His Lys Thr His Ile Thr Tyr Pro Met Gly Pro Gln Lys Leu Lys Arg
    290                 295                 300

Val Lys Gln Leu Phe Tyr Ala Gly Asp Trp His Ala Ala Ala Leu Pro
305                 310                 315                 320

Gly Tyr Gly Pro Arg His Arg Ala Asn Pro Phe Glu Thr Phe Glu Ala
                325                 330                 335

Ile Pro Ala Val Ala Arg Tyr Gln Phe Met Leu Asp Asn Ala Glu Tyr
            340                 345                 350

Phe Val Arg Thr Phe Ile Arg Gly Pro Val Cys Arg Gly Gln Ile Ala
        355                 360                 365

Thr Asp Val Ile Arg Asp Asn Phe Trp Ala Leu Phe Gln Glu Pro Ala
    370                 375                 380

Phe Asp Arg Tyr Ile Thr Asp Ala Lys Tyr Arg Gly Glu Ala Thr Pro
385                 390                 395                 400

Leu Leu Ala Met Pro Gly Gln Ile Asp Asp Val Gly Ser Val Leu Ser
                405                 410                 415

Leu Trp His Ala Tyr Arg Asp Lys Arg Asn Asp Tyr Glu Lys Leu Arg
            420                 425                 430

Arg Glu Ala Tyr Ala Glu Met Pro Ala Pro Arg Trp Ser Thr Leu Trp
        435                 440                 445

Ala Gly Asn Asp Asn Ala Leu Leu Ser Ile Phe Arg His Phe Asp Ser
    450                 455                 460

Ala Ser Val Thr Lys Gly Leu Val Gly Asp Val Pro Leu Thr Val Trp
465                 470                 475                 480

Leu Phe Asp Tyr Pro Leu Phe Glu Arg Thr Tyr Tyr Gln Leu Ala Val
                485                 490                 495

Asn Phe Asp Val Tyr Gly Asn Val Ser His Gln Leu Gln Thr Arg Leu
            500                 505                 510

Tyr Phe Asp Leu Ile Arg Asn Gly Ala Glu Val Asn Phe Leu Arg Leu
        515                 520                 525
```

```
Met Pro Ala Asp Gln Arg Lys Ala Ile Leu Gly Asp Trp Tyr Gln Asn
    530                 535                 540
Ser Gly Lys Val Lys Met Trp Met Asp Tyr Glu Asp Ile Asp Thr Asp
545                 550                 555                 560
Thr Pro Ser Gly Ile Lys Leu Asp Pro Arg Asn Pro Lys Arg Asp Phe
                565                 570                 575
Gly Leu Lys Leu Leu Gln Arg Thr Gly Ser Leu Asn Ala Ala Pro Asp
            580                 585                 590
Pro Ile Asn Arg Cys Gln Gly Ala Phe Cys Ser Arg Pro Gln Met Ser
        595                 600                 605
Glu Glu Phe Arg Asn Ala Glu Gln Ser Leu Ser Arg Leu Val Ser Arg
610                 615                 620
Pro Ala Ala Gly Leu Lys Val Ile Asn Gln Leu Pro Glu Ala Thr Met
625                 630                 635                 640
Leu Arg Ile Glu Gly Gln Asp Gly Gln Arg Gln Val Tyr Ser Leu Leu
                645                 650                 655
Arg Asn Arg Ala His Ser Asn Val Ala Phe Leu Leu Gly Glu Ala Tyr
            660                 665                 670
Arg Tyr Gln Pro Gly Leu Asp Thr Leu Thr Leu Tyr Pro Gly Val Leu
        675                 680                 685
Ser Ser Tyr Pro Asn Phe Ile Phe Asn Ile Pro Thr Lys Asp Val Pro
690                 695                 700
Glu Phe Val Glu Asp Met Glu Tyr Ala Lys Asp Ala Ala Lys Phe
705                 710                 715                 720
Glu Arg Ile Val Met Arg Trp Gly Val Arg Arg Ser His Pro Ala Phe
                725                 730                 735
Trp Arg Tyr Phe His Asp Leu Asn Ser Tyr Ile Lys Glu Thr Glu Pro
            740                 745                 750
Val Glu Ala Gly Val Leu Asp Met Asn Arg Tyr Glu Asn Leu
        755                 760                 765

<210> SEQ ID NO 137
<211> LENGTH: 282
<212> TYPE: DNA
<213> ORGANISM: Lactobacillus plantarum

<400> SEQUENCE: 137
gtaaatgaga agtaggccgt cattgcgcgt gccaagaatg aaaataaagt caaaataatg      60
aaaatccaac gatttgaaag cttaatgaaa gcttgatatt gttggatttt tattgattga     120
cgaaatgttg aaattatttt caattttttc gacggtggtg gtattattac ctttgtattt     180
tgattagggg tgtctctaat ctaccatttc aggttacgat aaaattgacg ttgactagct     240
caaaggttaa ggttatcgta gcaccgaaat taaggaaag ag                         282

<210> SEQ ID NO 138
<211> LENGTH: 51
<212> TYPE: DNA
<213> ORGANISM: artificial sequence
<220> FEATURE:
<223> OTHER INFORMATION: primer

<400> SEQUENCE: 138
tactcgagct taagacgcgt gtaaatgaga agtaggccgt cattgcgcgt g               51

<210> SEQ ID NO 139
<211> LENGTH: 42
<212> TYPE: DNA
```

<213> ORGANISM: artificial sequence
<220> FEATURE:
<223> OTHER INFORMATION: primer

<400> SEQUENCE: 139
taggatccac tagtctcttt cctttaattt cggtgctacg at                    42

<210> SEQ ID NO 140
<211> LENGTH: 29
<212> TYPE: DNA
<213> ORGANISM: Artificial Sequence
<220> FEATURE:
<223> OTHER INFORMATION: Primer LDH EcoRV F

<400> SEQUENCE: 140
gacgtcatga ccacccgccg atcccttttt                                  29

<210> SEQ ID NO 141
<211> LENGTH: 30
<212> TYPE: DNA
<213> ORGANISM: Artificial Sequence
<220> FEATURE:
<223> OTHER INFORMATION: Primer LDH AatIIR

<400> SEQUENCE: 141
gatatccaac accagcgacc gacgtattac                                  30

<210> SEQ ID NO 142
<211> LENGTH: 6509
<212> TYPE: DNA
<213> ORGANISM: Artificial Sequence
<220> FEATURE:
<223> OTHER INFORMATION: Vector pFP988

<400> SEQUENCE: 142
tcgaggcccc gcacatacga aaagactggc tgaaaacatt gagcctttga tgactgatga     60
tttggctgaa gaagtggatc gattgtttga gaaagaaga agaccataaa atacccttgt    120
ctgtcatcag acagggtatt ttttatgctg tccagactgt ccgctgtgta aaaatagga    180
ataaggggg gttgttatta ttttactgat atgtaaaata taatttgtat aaggaattgt    240
gagcggataa caattcctac gaaaatgaga gggagaggaa acatgattca aaaacgaaag    300
cggacagttt cgttcagact tgtgcttatg tgcacgctgt tattgtcag tttgccgatt    360
acaaaaacat cagccggatc ccaccatcac catcaccatt aagaattcct agaaactcca    420
agctatcttt aaaaaatcta gtaaatgcac gagcaacatc ttttgttgct cagtgcattt    480
tttattttgt acactagata tttcttctcc gcttaaatca tcaagaaaat ctttatcact    540
tgtaaccagt ccgtccacat gtcgaattgc atctgaccga attttacgtt tccctgaata    600
attctcatca atcgtttcat caattttatc tttatacttt atatttttgtg cgttaatcaa    660
atcataattt ttatatgttt cctcatgatt tatgtcttta ttattatagt ttttattctc    720
tcttgattga tgtcttttgta tccgtttgt attacttgat cctttaactc tggcaaccct    780
caaaattgaa tgagacatgc tacacctccg gataataaat atatataaac gtatatagat    840
ttcataagt ctaacacact agacttattt acttcgtaat taagtcgtta aaccgtgtgc    900
tctacgacca aaactataaa acctttaaga actttctttt tttacaagaa aaagaaatt    960
agataaatct ctcatatctt ttattcaata atcgcatccg attgcagtat aaatttaacg   1020
atcactcatc atgttcatat ttatcagagc tcgtgctata attatactaa ttttataagg   1080
aggaaaaaat atgggcattt ttagtatttt tgtaatcagc acagttcatt atcaaccaaa   1140

```
caaaaaataa gtggttataa tgaatcgtta ataagcaaaa ttcatataac caaattaaag    1200
agggttataa tgaacgagaa aaatataaaa cacagtcaaa actttattac ttcaaaacat    1260
aatatagata aaataatgac aaatataaga ttaaatgaac atgataatat ctttgaaatc    1320
ggctcaggaa aaggccattt tacccttgaa ttagtaaaga ggtgtaattt cgtaactgcc    1380
attgaaatag accataaatt atgcaaaact acagaaaata aacttgttga tcacgataat    1440
ttccaagttt taaacaagga tatattgcag tttaaatttc ctaaaaacca atcctataaa    1500
atatatggta atatacctta taacataagt acggatataa tacgcaaaat tgtttttgat    1560
agtatagcta atgagattta tttaatcgtg gaatacgggt ttgctaaaag attattaaat    1620
acaaaacgct cattggcatt acttttaatg gcagaagttg atatttctat attaagtatg    1680
gttccaagag aatattttca tcctaaacct aaagtgaata gctcacttat cagattaagt    1740
agaaaaaaat caagaatatc acacaaagat aaacaaaagt ataattattt cgttatgaaa    1800
tgggttaaca aagaatacaa gaaaatattt acaaaaaatc aatttaacaa ttccttaaaa    1860
catgcaggaa ttgacgattt aaacaatatt agctttgaac aattcttatc tcttttcaat    1920
agctataaat tatttaataa gtaagttaag ggatgcagtt catcgatgaa ggcaactaca    1980
gctcaggcga caaccatacg ctgagagatc ctcactacgt agaagataaa ggccacaaat    2040
acttagtatt tgaagcaaac actggaactg aagatggcta ccaaggcgaa gaatctttat    2100
ttaacaaagc atactatggc aaaagcacat cattcttccg tcaagaaagt caaaaacttc    2160
tgcaaagcga taaaaacgc acggctgagt tagcaacgg cgctctcggt atgattgagc    2220
taaacgatga ttacacactg aaaaaagtga tgaaaccgct gattgcatct aacacagtaa    2280
cagatgaaat tgaacgcgcg aacgtcttta aaatgaacgg caaatggtac ctgttcactg    2340
actcccgcgg atcaaaaatg acgattgacg gcattacgtc taacgatatt tacatgcttg    2400
gttatgtttc taattcttta actggcccat acaagccgct gaacaaaact ggccttgtgt    2460
taaaaatgga tcttgatcct aacgatgtaa cctttactta ctcacacttc gctgtacctc    2520
aagcgaaagg aaacaatgtc gtgattacaa gctatatgac aaacagagga ttctacgcag    2580
acaaacaatc aacgtttgcg ccaagcttgc atgcgagagt agggaactgc caggcatcaa    2640
ataaaacgaa aggctcagtc gaaagactgg gcctttcgtt ttatctgttg tttgtcggtg    2700
aacgctctcc tgagtaggac aaatccgccg ggagcggatt tgaacgttgc gaagcaacgg    2760
cccggagggt ggcgggcagg acgcccgcca taaactgcca ggcatcaaat taagcagaag    2820
gccatcctga cggatggcct ttttgcgttt ctacaaactc tttttgttta tttttctaaa    2880
tacattcaaa tatgtatccg ctcatgctcc ggatctgcat cgcaggatgc tgctggctac    2940
cctgtggaac acctacatct gtattaacga agcgctggca ttgaccctga gtgatttttc    3000
tctggtcccg ccgcatccat accgccagtt gtttaccctc acaacgttcc agtaaccggg    3060
catgttcatc atcagtaacc cgtatcgtga gcatcctctc tcgtttcatc ggtatcatta    3120
cccccatgaa cagaaattcc cccttacacg gaggcatcaa gtgaccaaac aggaaaaaac    3180
cgcccttaac atggcccgct ttatcagaag ccagacatta acgcttctgg agaaactcaa    3240
cgagctggac gcggatgaac aggcagacat ctgtgaatcg cttcacgacc acgctgatga    3300
gctttaccgc agctgcctcg cgcgtttcgg tgatgacggt gaaaacctct gacacatgca    3360
gctcccggag acggtcacag cttgtctgta agcggatgcc gggagcagac aagcccgtca    3420
gggcgcgtca gcgggtgttg gcgggtgtcg ggcgcagcc atgacccagt cacgtagcga    3480
tagcggagtg tatactggct taactatgcg gcatcagagc agattgtact gagagtgcac    3540
```

```
catatgcggt gtgaaatacc gcacagatgc gtaaggagaa ataccgcat caggcgctct    3600
tccgcttcct cgctcactga ctcgctgcgc tcggtcgttc ggctgcggcg agcggtatca    3660
gctcactcaa aggcggtaat acggttatcc acagaatcag gggataacgc aggaaagaac    3720
atgtgagcaa aaggccagca aaaggccagg aaccgtaaaa aggccgcgtt gctggcgttt    3780
ttccataggc tccgcccccc tgacgagcat cacaaaaatc gacgctcaag tcagaggtgg    3840
cgaaacccga caggactata aagataccag gcgtttcccc ctggaagctc cctcgtgcgc    3900
tctcctgttc cgaccctgcc gcttaccgga tacctgtccg cctttctccc ttcgggaagc    3960
gtggcgcttt ctcaatgctc acgctgtagg tatctcagtt cggtgtaggt cgttcgctcc    4020
aagctgggct gtgtgcacga accccccgtt cagcccgacc gctgcgcctt atccggtaac    4080
tatcgtcttg agtccaaccc ggtaagacac gacttatcgc cactggcagc agccactggt    4140
aacaggatta gcagagcgag gtatgtaggc ggtgctacag agttcttgaa gtggtggcct    4200
aactacggct acactagaag gacagtattt ggtatctgcg ctctgctgaa gccagttacc    4260
ttcggaaaaa gagttggtag ctcttgatcc ggcaaacaaa ccaccgctgg tagcggtggt    4320
ttttttgttt gcaagcagca gattacgcgc agaaaaaaag gatctcaaga agatcctttg    4380
atcttttcta cggggtctga cgctcagtgg aacgaaaact cacgttaagg gattttggtc    4440
atgagattat caaaaaggat cttcacctag atccttttaa attaaaaatg aagttttaaa    4500
tcaatctaaa gtatatatga gtaaacttgg tctgacagtt accaatgctt aatcagtgag    4560
gcacctatct cagcgatctg tctatttcgt tcatccatag ttgcctgact ccccgtcgtg    4620
tagataacta cgatacggga gggcttacca tctggcccca gtgctgcaat gataccgcga    4680
gacccacgct caccggctcc agatttatca gcaataaacc agccagccgg aagggccgag    4740
cgcagaagtg gtcctgcaac tttatccgcc tccatccagt ctattaattg ttgccgggaa    4800
gctagagtaa gtagttcgcc agttaatagt ttgcgcaacg ttgttgccat tgctgcaggc    4860
atcgtggtgt cacgctcgtc gtttggtatg gcttcattca gctccggttc ccaacgatca    4920
aggcgagtta catgatcccc catgttgtgc aaaaaagcgg ttagctcctt cggtcctccg    4980
atcgttgtca gaagtaagtt ggccgcagtg ttatcactca tggttatggc agcactgcat    5040
aattctctta ctgtcatgcc atccgtaaga tgcttttctg tgactggtga gtactcaacc    5100
aagtcattct gagaatagtg tatgcggcga ccgagttgct cttgcccggc gtcaatacgg    5160
gataataccg cgccacatag cagaacttta aaagtgctca tcattggaaa acgttcttcg    5220
gggcgaaaac tctcaaggat cttaccgctg ttgagatcca gttcgatgta acccactcgt    5280
gcacccaact gatcttcagc atcttttact ttcaccagcg tttctgggtg agcaaaaaca    5340
ggaaggcaaa atgccgcaaa aaagggaata agggcgacac ggaaatgttg aatactcata    5400
ctcttccttt ttcaatatta ttgaagcatt tatcagggtt attgtctcat gagcggatac    5460
atatttgaat gtatttagaa aaataaacaa ataggggttc cgcgcacatt tccccgaaaa    5520
gtgccacctg acgtctaaga aaccattatt atcatgacat taacctataa aaataggcgt    5580
atcacgaggc cctttcgtct cgcgcgtttc ggtgatgacg gtgaaaacct ctgacacatg    5640
cagctcccgg agacggtcac agcttgtctg taagcggatg ccgggagcag acaagcccgt    5700
cagggcgcgt cagcgggtgt tcatgtgcgt aactaacttg ccatcttcaa acaggagggc    5760
tggaagaagc agaccgctaa cacagtacat aaaaaaggag acatgaacga tgaacatcaa    5820
aaagtttgca aaacaagcaa cagtattaac ctttactacc gcactgctgg caggaggcgc    5880
aactcaagcg tttgcgaaag aaacgaacca aaagccatat aaggaaacat acggcatttc    5940
```

```
ccatattaca cgccatgata tgctgcaaat ccctgaacag caaaaaaatg aaaaatatca    6000
agttcctgaa ttcgattcgt ccacaattaa aaatatctct tctgcaaaag gcctggacgt    6060
ttgggacagc tggccattac aaaacgctga cggcactgtc gcaaactatc acggctacca    6120
catcgtcttt gcattagccg gagatcctaa aaatgcggat gacacatcga tttacatgtt    6180
ctatcaaaaa gtcggcgaaa cttctattga cagctggaaa aacgctggcc gcgtctttaa    6240
agacagcgac aaattcgatg caaatgattc tatcctaaaa gaccaaacac aagaatggtc    6300
aggttcagcc acatttacat ctgacggaaa aatccgttta ttctacactg atttctccgg    6360
taaacattac ggcaaacaaa cactgacaac tgcacaagtt aacgtatcag catcagacag    6420
ctctttgaac atcaacggtg tagaggatta taaatcaatc tttgacggtg acggaaaaac    6480
gtatcaaaat gtacagcatg ccacgcgtc                                      6509

<210> SEQ ID NO 143
<211> LENGTH: 47
<212> TYPE: DNA
<213> ORGANISM: Artificial Sequence
<220> FEATURE:
<223> OTHER INFORMATION: Primer Cm F

<400> SEQUENCE: 143
atttaaatct cgagtagagg atcccaacaa acgaaaattg gataaag                   47

<210> SEQ ID NO 144
<211> LENGTH: 29
<212> TYPE: DNA
<213> ORGANISM: Artificial Sequence
<220> FEATURE:
<223> OTHER INFORMATION: Primer Cm R

<400> SEQUENCE: 144
acgcgttatt ataaaagcca gtcattagg                                      29

<210> SEQ ID NO 145
<211> LENGTH: 58
<212> TYPE: DNA
<213> ORGANISM: Artificial Sequence
<220> FEATURE:
<223> OTHER INFORMATION: Primer P11 F-StuI

<400> SEQUENCE: 145
cctagcgcta tagttgttga cagaatggac atactatgat atattgttgc tatagcga      58

<210> SEQ ID NO 146
<211> LENGTH: 62
<212> TYPE: DNA
<213> ORGANISM: Artificial Sequence
<220> FEATURE:
<223> OTHER INFORMATION: Primer P11 R-SpeI

<400> SEQUENCE: 146
ctagtcgcta tagcaacaat atatcatagt atgtccattc tgtcaacaac tatagcgcta    60
gg                                                                   62

<210> SEQ ID NO 147
<211> LENGTH: 38
<212> TYPE: DNA
<213> ORGANISM: Artificial Sequence
<220> FEATURE:
<223> OTHER INFORMATION: Primer PldhL F-HindIII

<400> SEQUENCE: 147
```

-continued

```
aagcttgtcg acaaaccaac attatgacgt gtctgggc                              38
```

<210> SEQ ID NO 148
<211> LENGTH: 28
<212> TYPE: DNA
<213> ORGANISM: Artificial Sequence
<220> FEATURE:
<223> OTHER INFORMATION: Primer PldhL R-BamHI

<400> SEQUENCE: 148

```
ggatcctcat cctctcgtag tgaaaatt                                        28
```

<210> SEQ ID NO 149
<211> LENGTH: 62
<212> TYPE: DNA
<213> ORGANISM: Artificial Sequence
<220> FEATURE:
<223> OTHER INFORMATION: Primer P11 F

<400> SEQUENCE: 149

```
tcgagagcgc tatagttgtt gacagaatgg acatactatg atatattgtt gctatagcgc     60
cc                                                                    62
```

<210> SEQ ID NO 150
<211> LENGTH: 58
<212> TYPE: DNA
<213> ORGANISM: Artificial Sequence
<220> FEATURE:
<223> OTHER INFORMATION: Primer P11 R

<400> SEQUENCE: 150

```
gggcgctata gcaacaatat atcatagtat gtccattctg tcaacaacta tagcgctc       58
```

<210> SEQ ID NO 151
<211> LENGTH: 38
<212> TYPE: DNA
<213> ORGANISM: Artificial Sequence
<220> FEATURE:
<223> OTHER INFORMATION: Primer PldhL F

<400> SEQUENCE: 151

```
gagctcgtcg acaaaccaac attatgacgt gtctgggc                             38
```

<210> SEQ ID NO 152
<211> LENGTH: 30
<212> TYPE: DNA
<213> ORGANISM: Artificial Sequence
<220> FEATURE:
<223> OTHER INFORMATION: Primer PldhL R

<400> SEQUENCE: 152

```
ggatcctacc atgtttgtgc aaaataagtg                                      30
```

<210> SEQ ID NO 153
<211> LENGTH: 37
<212> TYPE: DNA
<213> ORGANISM: artificial sequence
<220> FEATURE:
<223> OTHER INFORMATION: primer

<400> SEQUENCE: 153

```
acaggagaat gaattcatgg tgcatcgtat ccttgcc                              37
```

<210> SEQ ID NO 154
<211> LENGTH: 20
<212> TYPE: DNA

```
<213> ORGANISM: artificial sequence
<220> FEATURE:
<223> OTHER INFORMATION: primer

<400> SEQUENCE: 154
tcagaggttc tcgtagcggt                                              20

<210> SEQ ID NO 155
<211> LENGTH: 27
<212> TYPE: DNA
<213> ORGANISM: artificial sequence
<220> FEATURE:
<223> OTHER INFORMATION: primer

<400> SEQUENCE: 155
gcaatggttt gacagcttat catcgac                                      27

<210> SEQ ID NO 156
<211> LENGTH: 26
<212> TYPE: DNA
<213> ORGANISM: artificial sequence
<220> FEATURE:
<223> OTHER INFORMATION: primer

<400> SEQUENCE: 156
gcaatggagg ttctcgtagc ggttca                                       26
```